US007053177B1

(12) United States Patent
Alvarez et al.

(10) Patent No.: US 7,053,177 B1
(45) Date of Patent: May 30, 2006

(54) RANDOM PEPTIDES THAT BIND TO GASTRO-INTESTINAL TRACT (GIT) TRANSPORT RECEPTORS AND RELATED METHODS

(75) Inventors: Vernon L. Alvarez, Morrisville, PA (US); Daniel J. O'Mahony, Dublin (IE); Imelda J. Lambkin, Dublin (IE); Catherine A. Patterson, Dublin (IE); Judith Singleton, Rocky Hill, NJ (US); Benjamin A. Belinka, Jr., Kendall Park, NJ (US); John M. Carter, Trenton, NJ (US); Gerard M. Cagney, Seattle, WA (US)

(73) Assignee: Cytogen Corporation, Princeton, NJ (US)

( * ) Notice: Subject to any disclaimer, the term of this patent is extended or adjusted under 35 U.S.C. 154(b) by 0 days.

(21) Appl. No.: 09/079,678

(22) Filed: May 15, 1998

Related U.S. Application Data

(60) Provisional application No. 60/046,595, filed on May 15, 1997.

(51) Int. Cl.
*A61K 38/00* (2006.01)
(52) U.S. Cl. ...................... 530/324; 514/21; 424/185.1
(58) Field of Classification Search ................ 530/300, 530/350, 324, 345, 387; 514/12, 21; 424/184.7, 424/185.1, 400; 435/69.1, 6, 91.2; 436/86
See application file for complete search history.

(56) References Cited

U.S. PATENT DOCUMENTS

| 5,338,665 A | | 8/1994 | Schatz et al. |
| 5,498,538 A | | 3/1996 | Kay et al. |
| 5,620,855 A | * | 4/1997 | Dantzig ......................... 435/6 |
| 6,117,632 A | * | 9/2000 | O'Mahony ..................... 435/6 |

FOREIGN PATENT DOCUMENTS

| WO | WO 91/19818 | 12/1991 |
| WO | WO 94/07530 | 4/1994 |
| WO | WO 94/18318 | 8/1994 |
| WO | WO 95/29938 | 11/1995 |

OTHER PUBLICATIONS

Balass et al., 1993, "Identification of a hexapeptide that mimics a conformation-dependent binding site of acetylcholine receptor by use of a phage-epitope library", Proc. Natl. Acad. Sci. USA 90:10638-10642.
Bass et al., 1990, "Hormone phage: an enrichment method for variant proteins with altered binding properties", Proteins: Struct. Func. Genet. 8:309-314.
Cesareni, 1992, "Peptide display on filamentous phage capsids", FEBS Lett. 307:66-70.

Christian et al., 1992, "Simplified methods for construction, assessment and rapid screening of peptide libraries in bacteriophage", J. Mol. Biol. 227:711-718.
Cwirla et al., 1990, "Peptides on phage: A vast library of peptides for identifying ligands", Proc. Natl. Acad. Sci. USA 87:6378-6382.
Davis and Jllum, 1994, "Particulate systems for site specific drug delivery", In: Targeting of Drugs 4 (Eds), Gregoriadis, McCormack and Poste, 183-194.
De la Cruz et al., 1988, "Immunogenicity and epitope mapping of foreign sequences via genetically engineered filamentous phage", J. Biol. Chem. 263:4318-4322.
Devlin et al., 1990, "Random peptide libraries: a source of specific protein binding molecules", Science 249:404-406.
Evers, 1995, Developments in Drug Delivery: Technology and Markets, Financial Times Management Report, p. 1-26.
Fix, 1996, "Strategies for delivery of peptides utilizing absorption-enhancing agents", J. Pharmac. Sci. 85:1282-1285.
Fodor et al., 1991, "Light-directed, spatially addressable parallel chemical synthesis", Science 251:767-773.
Fong et al., 1994, "Scanning whole cells with phage-display libraries: identification of peptide ligands that modulate cell function", Drug Development Research 33:64-70.
Gallop et al., 1994, "Applications of combinatorial technologies to drug discovery. 1. Background and peptide combinatorial libraries", J. Med. Chem. 37:1233-1251.
Greenwood et al., 1991, "Multiple display of foreign peptides on a filamentous bacteriophage", J. Mol. Biol. 220:821-827.
Houghten et al., 1991, "Generation and use of synthetic peptide combinatorial libraries for basic research and drug discovery", Nature 354:84-86.
Hoogenboom et al., 1991, "Multi-subunit proteins on the surface of filamentous phage: methodologies for displaying antibody (Fab) haevy and light chains", Nucleic Acids Res. 19:4133-4137.

(Continued)

*Primary Examiner*—Bruce R. Campell
*Assistant Examiner*—Roy Teller
(74) *Attorney, Agent, or Firm*—Morgan, Lewis & Bockius

(57) ABSTRACT

This invention relates to proteins (e.g., peptides) that are capable of facilitating transport of an active agent through a human or animal gastrointestinal tissue, and derivatives (e.g., fragments) and analogs thereof, and nucleotide sequences coding for said proteins and derivatives. The proteins of the invention have use in facilitating transport of active agents from the lumenal side of the GIT into the systemic blood system, and/or in targeting active agents to the GIT. Thus, for example, by binding (covalently or noncovalently) a protein of the invention to an orally administered drug, the drug can be targeted to specific receptor sites or transport pathways which are known to operate in the human gastrointestinal tract, thus facilitating its absorption into the systemic system.

10 Claims, 38 Drawing Sheets

OTHER PUBLICATIONS

Figure 5A:
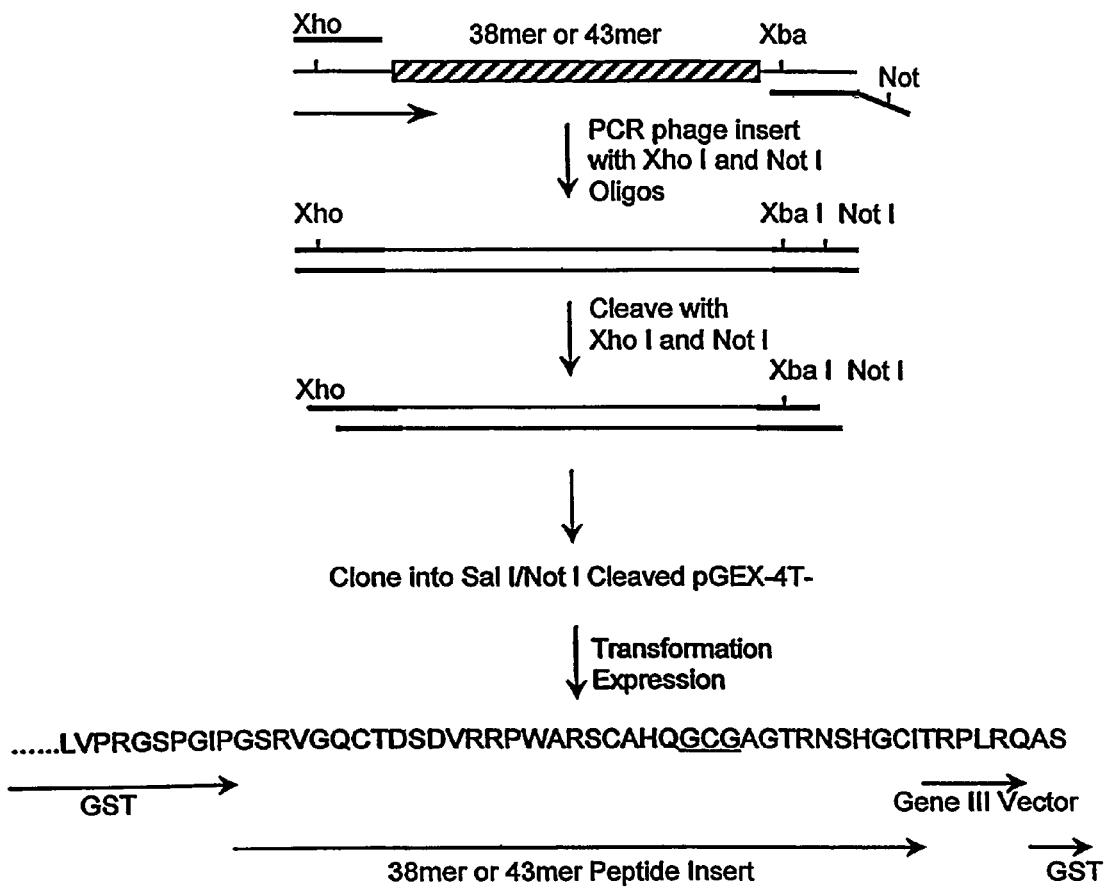

Kang et al., 1991, "Linkage of recognition and replication functions by assembling combinatorial antibody Fab libraries along phage surfaces", Proc. Natl. Acad. Sci. USA 88:4363-4366.

Kay et al., 1993, "An M13 phage library displaying random 38-amino-acid peptides as a source of novel sequences with affinity to select targets", Gene 128:59-65.

Lam et al, "A new type of synthetic peptide library for identifying ligand-binding activity", Nature 354:82-84.

Liang et al., 1995, "Human intestinal $H^+$/peptide cotransporter: cloning, functional expression, and chromosomal localization," J. Biol. Chem. 270:6456-6463.

Lowman et al., 1991, "Selecting high-affinity binding proteins by monovalent phage display", Biochemistry 30:10832-10838.

Marks et al., 1991, "By-passing immunization: human antibodies from V-gene libraries displayed on phage", J. Mol. Biol. 222:581-597.

McCafferty et al., 1990, "Phage antibodies: filamentous phage displaying antibody variable domains", Nature 348:552-554.

Parmley and Smith, 1988, "Antibody-selectable filamentous fd phage vectors: affinity purification of target genes", Gene 73:305-318.

Parmley and Smith, 1989, "Filamentous fusion phage cloning vectors for the study of epitopes and design of vaccines", Adv. Exp. Med. Biol. 251:215-218.

Peterson and Mooseker, 1992, "Characterization of the enterocyte-like brush border cytoskeleton of the $C2_{BBe}$ clones of the human intestinal cell line, Caco-2", J. Cell Science 102:581-600.

Pietersz, 1990, "The linkage of cytotoxic drugs to monoclonal antibodies for the treatment of cancer", Bioconjugate Chem. 1:89-95.

Saito et al., 1997, "Cloning and characterization of a pH-sensing regulatory factor that modulates transport activity of the human H+/peptide cotransporter, PEPT1," Biochem. and Biophys. Res. Commun. 237:577-582.

Scott and Smith, 1990, "Searching for peptide ligands with an epitope library", Science 249:386-390.

Smith, 1985, "Filamentous fusion phage: novel expression vectors that display cloned antigens on the virion surface", Science 228:1315-1317.

Stevenson et al., 1995, "Permeability screen for synthetic peptide combinatorial libraries using CACO-2 cell monolayers and LC/MS/MS", Pharmaceutical Res. 12(9), S94.

Yayon et al., 1993, "Isolation of peptides that inhibit binding of basic fibroblast growth factor to its receptor from a random phage-epitope library", Proc. Natl. Acad. Sci. USA 90:10643-10647.

\* cited by examiner

```
                    20                            40                               60
MGMSKSHSFFGYPLSIFFIV   VNEFCERFSYYGMRAILILY   FTNFISWDDNLSTAIYHTFV
                    80                           100                              120
ALCYLTPILGALIADSWLGK   FKTIVSLSIVYTIGQAVTSV   SSINDLTDHNHDGTPDSLPV
                   140                           160                              180
HVVLSLIGLALIALGTGGIK   PCVSAFGGDQFEEGQEKQRN   RFFSIFYLAINAGSLLSTII
                   200                           220                              240
TPMLRVQQCGIHSKQACYPL   AFGVPAALMAVALIVFVLGS   GMYKKFKPQGNIMGKVAKCI
                   260                           280                              300
GFAIKNRFRHRSKAFPKREH   WLDWAKEKYDERLISQIKMV   TRVMFLYIPLPMFWALFDQQ
                   320                           340                              360
GSRWTLQATTMSGKIGALEI   QPDQMQTVNAILIVIMVPIF   DAVLYPLIAKCGFNFTSLKK
                   380                           400                              420
MAVGMVLASMAFVVAAIVQV   EIDKTLPVFPKGNEVQIKVL   NIGNNTMNISLPGEMVTLGP
                   440                           460                              480
MSQTNAFMTFDVNKLTRINI   SSPGSPVTAVTDDFKQGQRH   TLLVWAPNHYQVVKDGLNQK
                   500                           520                              540
PEKGENGIRFVNTFNELITI   TMSGKVYANISSYNASTYQF   FPSGIKGFTISSTEIPPQCQ
                   560                           580                              600
PNFNTFYLEFGSAYTYIVQR   KNDSCPEVKVFEDISANTVN   MALQIPQYFLLTCGEVVFSV
                   620                           640                              660
TGLEFSYSQAPSNMKSVLQA   GWLLTVAVGNIIVLIVAGAG   QFSKQWAEYILFAALLLVVC
                   680                           700      708
VIFAIMARFYTYINPAEIEA   QFDEDEKKNRLEKSNPYFMS   GANSQKQM
```

Fig. 1

```
   1 gaattccgtc tcgaccactg aatggaagaa aaggactttt aaccaccatt ttgtgactta
  61 cagaaaggaa tttgaataaa gaaaactatg atacttcagg cccatcttca ctccctgtgt
                                   M  I  L  Q   A  H  L    H  S  L  C
 121 cttcttatgc tttatttggc aactggatat ggccaagagg ggaagtttag tggacccctg
      L  L  M   L  Y  L    A  T  G  Y  G  Q  E   G  K  F    S  G  P  L
 181 aaacccatga catttctat ttatgaaggc caagaaccga gtcaaattat attccagttt
      K  P  M   T  F  S    I  Y  E  G  Q  E  P   S  Q  I   I  F  Q  F
 241 aaggccaatc ctcctgctgt gactttgaa ctaactgggg agacagacaa catatttgtg
      K  A  N   P  P  A   V  T  F  E   L  T  G   E  T  D   N  I  F  V
 301 atagaacggg agggacttct gtattacaac agagccttgg acagggaaac aagatctact
      I  E  R   E  G  L    L  Y  Y  N  R  A  L   D  R  E    T  R  S  T
 361 cacaatctcc aggttgcagc cctggacgct aatggaatta tagtggaggg tccagtccct
      H  N  L   Q  V  A    A  L  D  A  N  G  I   I  V  E    G  P  V  P
 421 atcaccatag aagtgaagga catcaacgac aatcgaccca cgtttctcca gtcaaagtac
      I  T  I   E  V  K    D  I  N  D  N  R  P   T  F  L    Q  S  K  Y
 481 gaaggctcag taaggcagaa ctctcgccca ggaaagccct tcttgtatgt caatgccaca
      E  G  S   V  R  Q    N  S  R  P  G  K  P   F  L  Y    V  N  A  T
 541 gacctggatg atccggccac tcccaatggc cagctttatt accagattgt catccagctt
      D  L  D   D  P  A    T  P  N  G  Q  L  Y   Y  Q  I    V  I  Q  L
 601 cccatgatca acaatgtcat gtactttcag atcaacaaca aaacgggagc catctctctt
      P  M  I   N  N  V    M  Y  F  Q  I  N  N   K  T  G    A  I  S  L
 661 acccgagagg gatctcagga attgaatcct gctaagaatc cttcctataa tctggtgatc
      T  R  E   G  S  Q    E  L  N  P  A  K  N   P  S  Y    N  L  V  I
 721 tcagtgaagg acatgggagg ccagagtgag aattccttca gtgataccac atctgtggat
      S  V  K   D  M  G    G  Q  S  E  N  S  F   S  D  T    T  S  V  D
 781 atcatagtga cagagaatat ttggaaagca ccaaaacctg tggagatggt ggaaaactca
      I  I  V   T  E  N    I  W  K  A  P  K  P   V  E  M    V  E  N  S
 841 actgatcctc accccatcaa aatcactcag gtgcggtgga atgatcccgg tgcacaatat
      T  D  P   H  P  I    K  I  T  Q  V  R  W   N  D  P    G  A  Q  Y
 901 tccttagttg acaaagagaa gctgccaaga ttcccatttt caattgacca ggaaggagat
      S  L  V   D  K  E    K  L  P  R  F  P  F   S  I  D    Q  E  G  D
 961 atttacgtga ctcagccctt ggaccgagaa gaaaaggatg catatgtttt ttatgcagtt
      I  Y  V   T  Q  P    L  D  R  E  E  K  D   A  Y  V    F  Y  A  V
1021 gcaaaggatg agtacggaaa accactttca tatccgctgg aaattcatgt aaaagttaaa
      A  K  D   E  Y  G    K  P  L  S  Y  P  L   E  I  H    V  K  V  K
1081 gatattaatg ataatccacc tacatgtccg tcaccagtaa ccgtatttga ggtccaggag
      D  I  N   D  N  P    P  T  C  P  S  P  V   T  V  F    E  V  Q  E
1141 aatgaacgac tgggtaacag tatcgggacc cttactgcac atgacaggga tgaagaaaat
      N  E  R   L  G  N    S  I  G  T  L  T  A   H  D  R    D  E  E  N
1201 actgccaaca gttttctaaa ctacaggatt gtggagcaaa ctcccaaact tcccatggat
      T  A  N   S  F  L    N  Y  R  I  V  E  Q   T  P  K    L  P  M  D
```

Fig. 2A

```
1261 ggactcttcc taatccaaac ctatgctgga atgttacagt tagctaaaca gtccttgaag
      G  L  F   L  I  Q   T  Y  A   M  L  Q   L  A  K   Q  S  L  K
1321 aagcaagata ctcctcagta caacttaacg atagaggtgt ctgacaaaga tttcaagacc
      K  Q  D   T  P  Q   Y  N  L   T  I  E  V  S  D  K   D  F  K  T
1381 ctttgttttg tgcaaatcaa cgttattgat atcaatgatc agatccccat ctttgaaaaa
      L  C  F   V  Q  I   N  V  I  D  I  N  D   Q  I  P   I  F  E  K
1441 tcagattatg gaaacctgac tcttgctgaa gacacaaaca ttgggtccac catcttaacc
      S  D  Y   G  N  L   T  L  A  E  D  T  N   I  G  S   T  I  L  T
1501 atccaggcca ctgatgctga tgagccattt actggagtt ctagaattct gtatcatatc
      I  Q  A   T  D  A   D  E  P  F  T  G  S   S  R  I   L  Y  H  I
1561 ataaagggag acagtgaggg acgcctgggg gttgacacag atccccatac caacaccgga
      I  K  G   D  S  E   G  R  L  G  V  D  T   D  P  H   T  N  T  G
1621 tatgtcataa ttaaaaagcc tcttgatttt gaaacagcag ctgtttccaa cattgtgttc
      Y  V  I   I  K  K   P  L  D  F  E  T  A   A  V  S   N  I  V  F
1681 aaagcagaaa atcctgagcc tctagtgttt ggtgtgaagt acaatgcaag ttcttttgcc
      K  A  E   N  P  E   P  L  V  F  G  V  K   Y  N  A   S  S  F  A
1741 aagttcacgc ttattgtgac agatgtgaat gaagcacctc aatttcccca acacgtattc
      K  F  T   L  I  V   T  D  V  N  E  A  P   Q  F  S   Q  H  V  F
1801 caagcgaaag tcagtgagga tgtagctata ggcactaaag tgggcaatgt gactgccaag
      Q  A  K   V  S  E   D  V  A  I  G  T  K   V  G  N   V  T  A  K
1861 gatccagaag gtctggacat aagctattca ctgaggggag acacaagagg ttggcttaaa
      D  P  E   G  L  D   I  S  Y  S  L  R  G   D  T  R   G  W  L  K
1921 attgaccacg tgactggtga gatctttagt gtggctccat ggacagaga agccggaagt
      I  D  H   V  T  G   E  I  F  S  V  A  P   L  D  R   E  A  G  S
1981 ccatatcggg tacaagtggt ggccacagaa gtaggggggt cttccttaag ctctgtgtca
      P  Y  R   V  Q  V   V  A  T  E  V  G  G   S  S  L   S  S  V  S
2041 gagttccacc tgatccttat ggatgtgaat gacaaccctc ccaggctagc caaggactac
      E  F  H   L  I  L   M  D  V  N  D  N  P   P  R  L   A  K  D  Y
2101 acgggcttgt tcttctgcca tcccctcagt gcacctggaa gtctcatttt cgaggctact
      T  G  L   F  F  C   H  P  L  S  A  P  G   S  L  I   F  E  A  T
2161 gatgatgatc agcacttatt tcggggtccc catttttacat tttccctcgg cagtggaagc
      D  D  D   Q  H  L   F  R  G  P  H  F  T   F  S  L   G  S  G  S
2221 ttacaaaacg actgggaagt ttccaaaatc aatggtactc atgcccgact gtctaccagg
      L  Q  N   D  W  E   V  S  K  I  N  G  T   H  A  R   L  S  T  R
2281 cacacagact ttgaggagag ggcgtatgtc gtcttgatcc gcatcaatga tggggggtcgg
      H  T  D   F  E  E   R  A  Y  V  V  L  I   R  I  N   D  G  G  R
2341 ccacccttgg aaggcattgt ttctttacca gttacattct gcagttgtgt ggaaggaagt
      P  P  L   E  G  I   V  S  L  P  V  T  F   C  S  C   V  E  G  S
2401 tgtttccggc cagcaggtca ccagactggg atacccactg tgggcatggc agttggtata
      C  F  R   P  A  G   H  Q  T  G  I  P  T   V  G  M   A  V  G  I
```

Fig. 2B

```
2461 ctgctgacca cccttctggt gattggtata attttagcag ttgtgtttat ccgcataaag
      L   L   T    T   L    V  I  G  I   I  L  A    V  V  F    I  R   I  K
2521 aaggataaag gcaaagataa tgttgaaagt gctcaagcat ctgaagtcaa acctctgaga
      K  D  K    G  K  D   N  V  E  S   A  Q  A    S  E  V    K  P  L  R
2581 agctgaattt gaaaaggaat gtttgaattt atatagcaag tgctatttca gcaacaacca
      S
2641 tctcatccta ttacttttca tctaacgtgc attataattt tttaaacaga tattccctct
2701 tgtcctttaa tatttgctaa atatttcttt tttgaggtgg agtcttgctc tgtcgcccag
2761 gctggagtac agtggtgtga tcccagctca ctgcaacctc cgcctcctgg gttcacatga
2821 ttctcctgcc tcagcttcct aagtagctgg gttacaggc acccaccacc atgcccagct
2881 aattttgta tttttaatag gacggggtt tcgccatttg gccaggctgg tcttgaactc
2941 ctgacgtcaa gtgatctgcc tgccttggtc tcccaataca ggcatgaacc actgcaccca
3001 cctacttaga tatttcatgt gctatagaca ttagagagat ttttcatttt tccatgacat
3061 ttttcctctc tgcaaatggc ttagctactt gtgttttcc cttttggggc aagacagact
3121 cattaaatat tctgtacatt tttctttat caaggagata tatcagtgtt gtctcataga
3181 actgcctgga ttccatttat gttttttctg attccatcct gtgtccctt catccttgac
3241 tcctttggta tttcactgaa tttcaaacat ttgtcagaga agaaaaagt gaggactcag
3301 gaaaaataaa taaataaaag aacagccttt tgcggccgcg aattc
```

Fig. 2C

```
                    20                          40                          60
MARKKFSGLEISLIVLFVIV    TIIAIALIVVLATKTPAVDE    ISDSTSTPATTRVTTNPSDS
                    80                         100                         120
GKCPNVLNDPVNVRINCIPE    QFPTEGICAQRGCCWRPWND    SLIPWCFFVDNHGYNVQDMT
                   140                         160                         180
TTSIGVEAKLNRIPSPTLFG    NDINSVLFTTQNQTPNRFRF    KITDPNNRRYEVPHQYVKEF
                   200                         220                         240
TGPTVSDTLYDVKVAQNPFS    IQVIRKSNGKTLFDTSIGPL    VYSDQYLQISARLPSDYIYG
                   260                         280                         300
IGEQVHKRFRHDLSWKTWPI    FTRDQLPGDNNNNLYGHQTF    FMCIEDTSGKSFGVFLMNSN
                   320                         340                         360
AMEIFIQPTPIVTYRVTGGI    LDFYILLGDTPEQVVQQYQQ    LVGLPAMPAYWNLGFQLSRW
                   380                         400                         420
NYKSLDVVKEVVRRNREAGI    PFDTQVTDIDYMEDKKDFTY    DQVAFNGLPQFVQDLHDHGQ
                   440                         460                         480
KYVIILDPAISIGRRANGTT    YATYERGNTQHVWINESDGS    TPIIGEVWPGLTVYPDFTNP
                   500                         520                         540
NCIDWWANECSIFHQEVQYD    GLWIDMNEVSSFIQGSTKGC    NVNKLNYPPFTPDILDKLMY
                   560                         580                         600
SKTICMDAVQNWGKQYDVHS    LYGYSMAIATEQAVQKVFPN    KRSFILTRSTFAGSGRHAAH
                   620                         640                         660
WLGDNTASWEQMEWSITGML    EFSLFGIPLVGADICGFVAE    TTEELCRRWMQLGAFYPFSR
                   680                         700                         720
NHNSDGYEHQDPAFFGQNSL    LVKSSRQYLTIRYTLLPFLY    TLFYKAHVFGETVARPVLHE
                   740                         760                         780
FYEDTNSWIEDTEFLWGPAL    LITPVLKQGADTVSAYIPDA    IWYDYESGAKRPWRKQRVDM
                   800                         820                         840
YLPADKIGLHLRGGYIIPIQ    EPDVTTTASRKNPLGLIVAL    GENNTAKGDFFWDDGETKDT
                   860                         880                         900
IQNGNYILYTFSVSNNTLDI    VCTHSSYQEGTTLAFQTVKI    LGLTDSVTEVRVAENNQPMN
                   920                         940                         960
AHSNFTYDASNQVLLIADLK    LNLGRNFSVQWNQIFSENER    FNCYPDADLATEQKCTQRGC
                   980                        1000                        1020
VWRTGSSLSKAPECYFPRQD    NSYSVNSARYSSMGITADLQ    LNTANARIKLPSDPISTLRV
                  1040                        1060                        1080
EVKYHKNDMLQFKIYDPQKK    RYEVPVPLNIPTTPISTYED    RLYDVEIKENPFGIQIRRRS
                  1100                        1120                        1140
SGRVIWDSWLPGFAFNDQFI    QISTRLPSEYIYGFGEVEHT    AFKRDLNWNTWGMFTRDQPP
                  1160                        1180                        1200
GYKLNSYGFHPYYMALEEEG    NAHGVFLLNSNAMDVTFQPT    PALTYRTVGGILDFYMFLGP
                  1220                        1240                        1260
TPQVATKQYHEVIGHPVMPA    YWALGFQLCRYGYANTSEVR    ELYDAMVAANIPYDVQYTDI
```

Fig. 3A

```
            1280                    1300                        1320
DYMERQLDFTIGEAFQDLPQ  FVDKIRGEGMRYIIILDPAI  SGNETKTYPAFERGQQNDVF
            1340                    1360                        1380
VKWPNTNDICWAKVWPDLPN  ITIDKTLTEDEAVNASRAHV  AFPDFFRTSTAEWWAREIVD
            1400                    1420                        1440
FYNEKMKFDGLWIDMNEPSS  FVNGTTTNQCRNDELNYPPY  FPELTKRTDGLHFRTICMEA
            1460                    1480                        1500
EQILSDGTSVLHYDVHNLYG  WSQMKPTHDALQKTTGKRGI  VISRSTYPTSGRWGGHWLGD
            1520                    1540                        1560
NYARWDNMDKSIIGMMEFSL  FGISYTGADICGFFNNSEYH  LCTRWMQLGAFYPYSRNHNI
            1580                    1600                        1620
ANTRRQDPASWNETFAEMSR  NILNIRYTLLPYFYTQMHEI  HANGGTVIRPLLHEFFDEKP
            1640                    1660                        1680
TWDIFKQFLWGPAFMVTPVL  EPYVQTVNAYVPNARWFDYH  TGKDIGVRGQFQTFNASYDT
            1700                    1720                        1740
INLHVRGGHILPCQEPAQNT  FYSRQKHMKLIVAADDNQMA  QGSLFWDDGESIDTYERDLY
            1760                    1780                        1800
LSVQFNLNQTTLTSTILKRG  YINKSETRLGSLHVWGKGTT  PVNAVTLTYNGNKNSLPFNE
            1820       1827
DTTNMILRIDLTTHNVTLEE  PIEINWS
```

Fig. 3B

```
  1 gccttactgc aggaaggcac tccgaagaca taagtcggtg agacatggct gaagataaaa
                                                          M A  E D K
 61 gcaagagaga ctccatcgag atgagtatga agggatgcca gacaaacaac gggtttgtcc
     S K R     D S I E    M S M      K G C      Q T N N    G F V
121 ataatgaaga cattctggag cagaccccgg atccaggcag ctcaacagac aacctgaagc
     H N E     D I L E    Q T P      D P G      S S T D    N L K
181 acagcaccag gggcatcctt ggctcccagg agcccgactt caagggcgtc cagccctatg
     H S T     R G I L    G S Q      E P D      F K G V    Q P Y
241 cggggatgcc caaggaggtg ctgttccagt tctctggcca ggcccgctac cgcatacctc
     A G M     P K E V    L F Q      F S G      Q A R Y    R I P
301 gggagatcct cttctggctc acagtggctt ctgtgctggt gctcatcgcg gccaccatag
     R E I     L F W L    T V A      S V L      V L I A    A T I
361 ccatcattgc cctctctcca aagtgcctag actggtggca ggagggccc  atgtaccaga
     A I I     A L S P    K C L      D W W      Q E G P    M Y Q
421 tctacccaag gtctttcaag gacagtaaca aggatgggaa cggagatctg aaaggtattc
     I Y P     R S F K    D S N      K D G      N G D L    K G I
481 aagataaact ggactacatc acagctttaa atataaaaac tgtttggatt acttcatttt
     Q D K     L D Y I    T A L      N I K      T V W I    T S F
541 ataaatcgtc ccttaaagat ttcagatatg gtgttgaaga tttccgggaa gttgatccca
     Y K S     L K D      F R Y      G V E      D F R E    V D P
601 tttttggaac gatggaagat tttgagaatc tggttgcagc catacatgat aaaggtttaa
     I F G     T M E D    F E N      L V A      A I H D    K G L
661 aattaatcat cgatttcata ccaaaccaca cgagtgataa acatatttgg tttcaattga
     K L I     I D F I    P N H      T S D      K H I W    F Q L
721 gtcggacacg gacaggaaaa tatactgatt attatatctg gcatgactgt acccatgaaa
     S R T     R T G K    Y T D      Y Y I      W H D C    T H E
781 atggcaaaac cattccaccc aacaactggt taagtgtgta tggaaactcc agttggcact
     N G K     T I P P    N N W      L S V      Y G N S    S W H
841 ttgacgaagt gcgaaaccaa tgttattttc atcagtttat gaaagagcaa cctgatttaa
     F D E     V R N Q    C Y F      H Q F      M K E Q    P D L
901 atttccgcaa tcctgatgtt caagaagaaa taaaagaaat tttacggttc tggctcacaa
     N F R     N P D V    Q E E      I K E      I L R F    W L T
961 agggtgttga tggttttagt ttggatgctg ttaaattcct cctagaagca aagcacctga
     K G V     D G F S    L D A      V K F      L L E A    K H L
```

Fig. 4A

```
1021 gagatgagat ccaagtaaat aagacccaaa tcccggacac ggtcacacaa tactcggagc
      R  D  E    I  Q  V  N    K  T  Q    I  P  D    T  V  T  Q    Y  S  E
1081 tgtaccatga cttcaccacc acgcaggtgg gaatgcacga cattgtccgc agcttccggc
      L  Y  H    D  F  T  T    T  Q  V    G  M  H    D  I  V  R    S  F  R
1141 agaccatgga ccaatacagc acggagcccg gcagatacag gttcatgggg actgaagcct
      Q  T  M    D  Q  Y  S    T  E  P    G  R  Y    R  F  M  G    T  E  A
1201 atgcagagag tattgacagg accgtgatgt actatggatt gccatttatc caagaagctg
      Y  A  E    S  I  D  R    T  V  M    Y  Y  G    L  P  F  I    Q  E  A
1261 attttccctt caacaattac ctcagcatgc tagacactgt ttctgggaac agcgtgtatg
      D  F  P    F  N  N  Y    L  S  M    L  D  T    V  S  G  N    S  V  Y
1321 aggttatcac atcctggatg gaaaacatgc cagaaggaaa atggcctaac tggatgattg
      E  V  I    T  S  W  M    E  N  M    P  E  G    K  W  P  N    W  M  I
1381 gtggaccaga cagttcacgg ctgacttcgc gtttggggaa tcagtatgtc aacgtgatga
      G  G  P    D  S  S  R    L  T  S    R  L  G    N  Q  Y  V    N  V  M
1441 acatgcttct tttcacactc cctggaactc ctataactta ctatggagaa gaaattggaa
      N  M  L    L  F  T  L    P  G  T    P  I  T    Y  Y  G  E    E  I  G
1501 tgggaaatat tgtagccgca aatctcaatg aaagctatga tattaatacc cttcgctcaa
      M  G  N    I  V  A  A    N  L  N    E  S  Y    D  I  N  T    L  R  S
1561 agtcaccaat gcagtgggac aatagttcaa atgctggttt ttctgaagct agtaacacct
      K  S  P    M  Q  W  D    N  S  S    N  A  G    F  S  E  A    S  N  T
1621 ggttacctac caattcagat taccacactg tgaatgttga tgtccaaaag actcagccca
      W  L  P    T  N  S  D    Y  H  T    V  N  V    D  V  Q  K    T  Q  P
1681 gatcggcttt gaagttatat caagatttaa gtctacttca tgccaatgag ctactcctca
      R  S  A    L  K  L  Y    Q  D  L    S  L  L    H  A  N  E    L  L  L
1741 acaggggctg gttttgccat tgaggaatg acagccacta tgttgtgtac acaagagagc
      N  R  G    W  F  C  H    L  R  N    D  S  H    Y  V  V  Y    T  R  E
1801 tggatggcat cgacagaatc tttatcgtgg ttctgaattt tggagaatca acactgttaa
      L  D  G    I  D  R  I    F  I  V    V  L  N    F  G  E  S    T  L  L
1861 atctacataa tatgatttcg ggccttcccg ctaaaataag aataaggtta agtaccaatt
      N  L  H    N  M  I  S    G  L  P    A  K  I    R  I  R  L    S  T  N
1921 ctgccgacaa aggcagtaaa gttgatacaa gtggcatttt tctggacaag ggagagggac
      S  A  D    K  G  S  K    V  D  T    S  G  I    F  L  D  K    G  E  G
1981 tcatctttga acacaacacg aagaatctcc ttcatcgcca aacagctttc agagatagat
      L  I  F    E  H  N  T    K  N  L    L  H  R    Q  T  A  F    R  D  R
2041 gctttgtttc caatcgagca tgctattcca gtgtactgaa catactgtat acctcgtgtt
      C  F  V    S  N  R  A    C  Y  S    S  V  L    N  I  L  Y    T  S  C
2101 aggcacctt atgaagagat gaagacactg gcatttcagt gggattgtaa gcatttgtaa
2161 tagcttcatg tacagcatgc tgcttggtga acaatcatta attcttcgat atttctgtag
2221 cttgaatgta accgctttaa gaaggttct caaatgtttt gaaaaaaata aatgtttaa
2281 aagt
```

Fig. 4B

| | | | | | |
|---|---|---|---|---|---|
| P31 | 1 | 10 | 20 | 30 | Clone # |

```
SARDSGPAEDGSRAVRLNGVENANTRKSSRSNPRGRRHP
SARDSGPAEDGSRAVRLNG                        101
        DGSRAVRLNGVENANTRKSSR              102
                    ENANTRKSSRSNPRGRRHP    103
                        TRKSSRSNPRG        119
```

| | | | | | |
|---|---|---|---|---|---|
| Pax2 | 1 | 10 | 20 | 30 | Clone # |

```
STPPSREAYSRPYSVDSDSDTNAKHSSHNRRLRTRSRPN
STPPSREAYSRPYSVDSDSD                       104
        SRPYSVDSDSDTNAKHSSHNR              105
                    TNAKHSSHNRRLRTRSRPN    106
```

| | | | | | |
|---|---|---|---|---|---|
| DCX8 | 1 | 10 | 20 | 30 | Clone # |

```
RYKHDIGCDAGVDKKSSSVRGGCGAHSSPPRAGRGPRGTMVSRL
RYKHDIGCDAGVDKKSSSVRGGCG                   107
        GCDAGVDKKSSSVRGGCGAHSSPPRA         108
                    GAHSSPPRAGRGPRGTMVSRL  109
```

Fig. 5B

| P31 | 1 | 10 | 20 | 30 | | Clone # |
|---|---|---|---|---|---|---|
| | SARDSGPAEDGSRAVRLNGVENANTRKSSRSNPRGRRHP | | | | | |
| | | ENANTRKSSRSNPRGRRHP | | | | 103 |
| | | ENANTRKSSR | | | | 110 |
| | | | TRKSSRSNPRG | | | 119 |
| | | | RKSSRSNPRG | | | 111 |
| | | | | SNPRGRRHP | | 112 |

| Pax2 | 1 | 10 | 20 | 30 | | Clone # |
|---|---|---|---|---|---|---|
| | STPPSREAYSRPYSVDSDSDTNAKHSSHNRRLRTRSRPN | | | | | |
| | | TNAKHSSHNRRLRTRSRPN | | | | 106 |
| | | TNAKHSSHN | | | | 113 |
| | | | SSHNRRLRTR | | | 114 |
| | | | | RRLRTRSRPN | | 115 |

| SNi10 | 1 | 10 | 20 | 30 | | Cl ne # |
|---|---|---|---|---|---|---|
| | RVGQCTDSDVRRPWARSCAHQGCGAGTRNSHGCITRPLRQASAH | | | | | |
| | RVGQCTDSDVRRPWARSCA | | | | | 116 |
| | | VRRPWARSCAHQGCGAGTRNS | | | | 117 |
| | | | | GTRNSHGCITRPLRQASAH | | 118 |

Fig. 5C

A
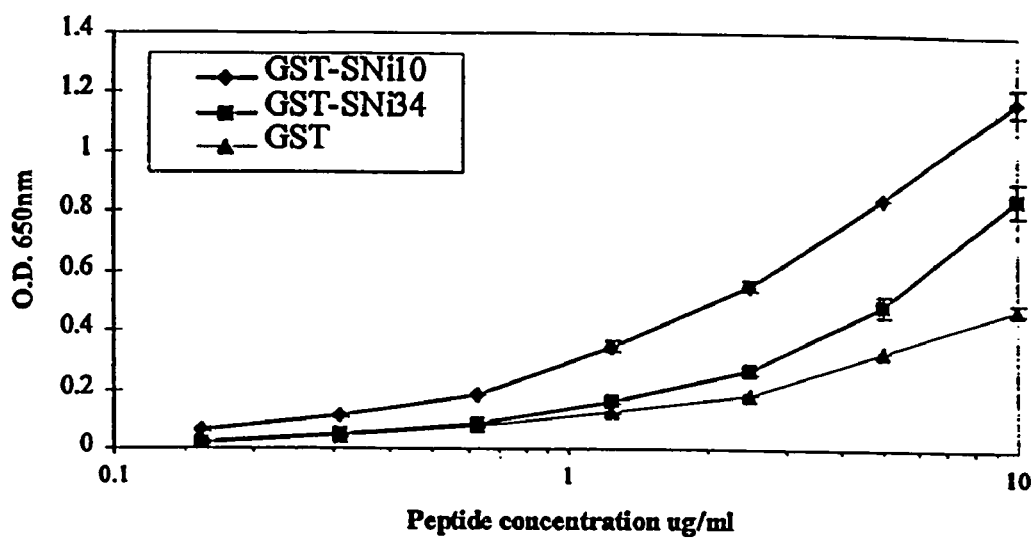
B
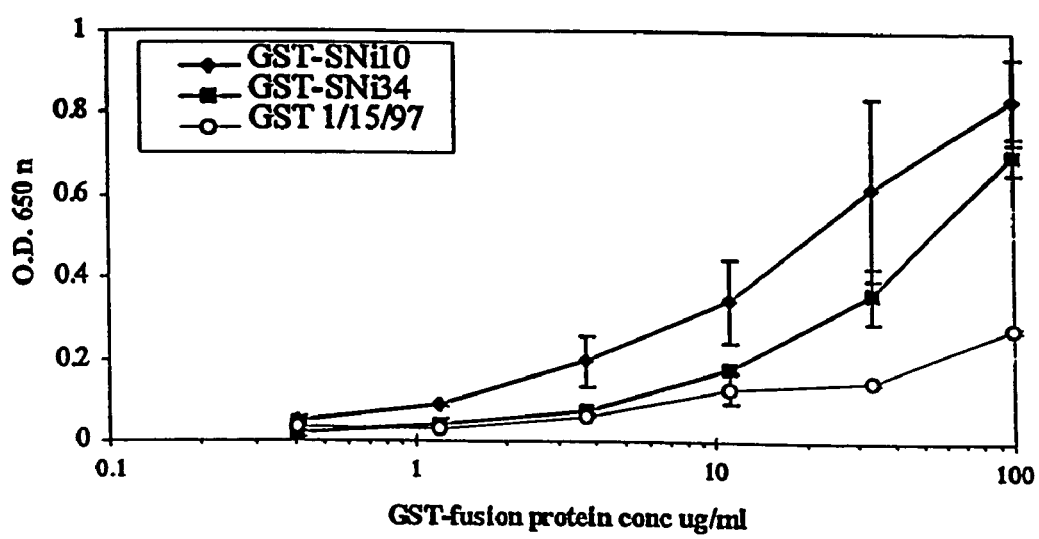
Fig. 6

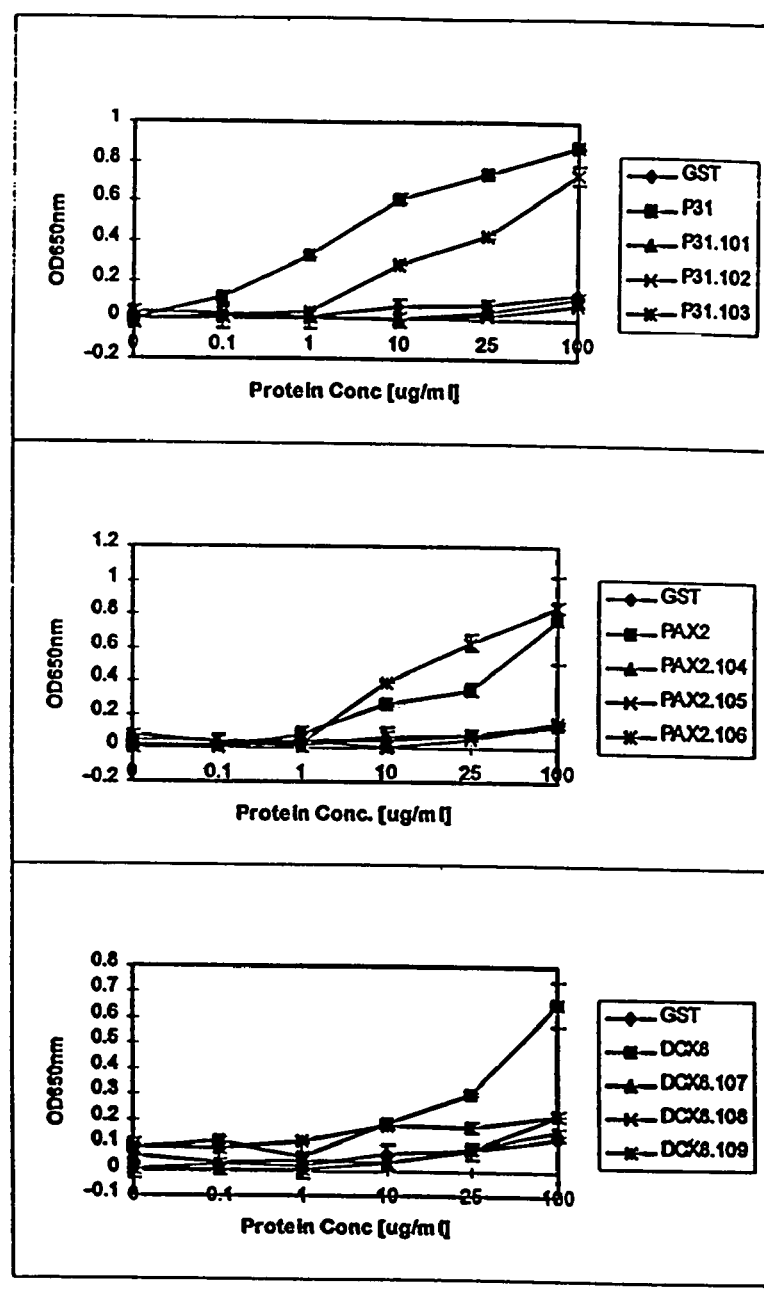
Fig. 7A-C

D
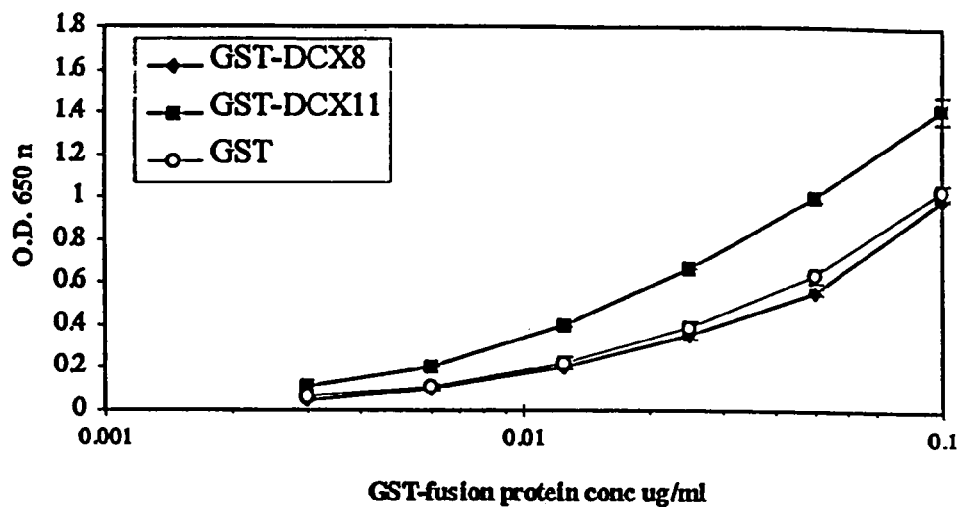
E
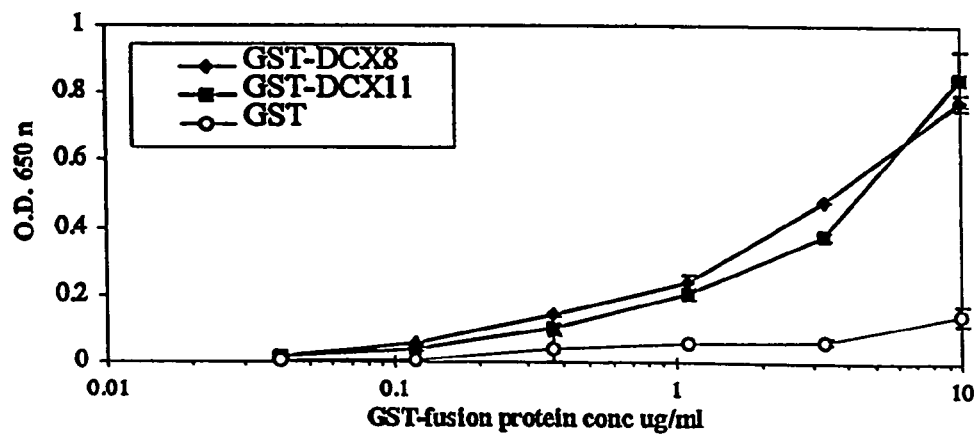
Fig. 7 D-E

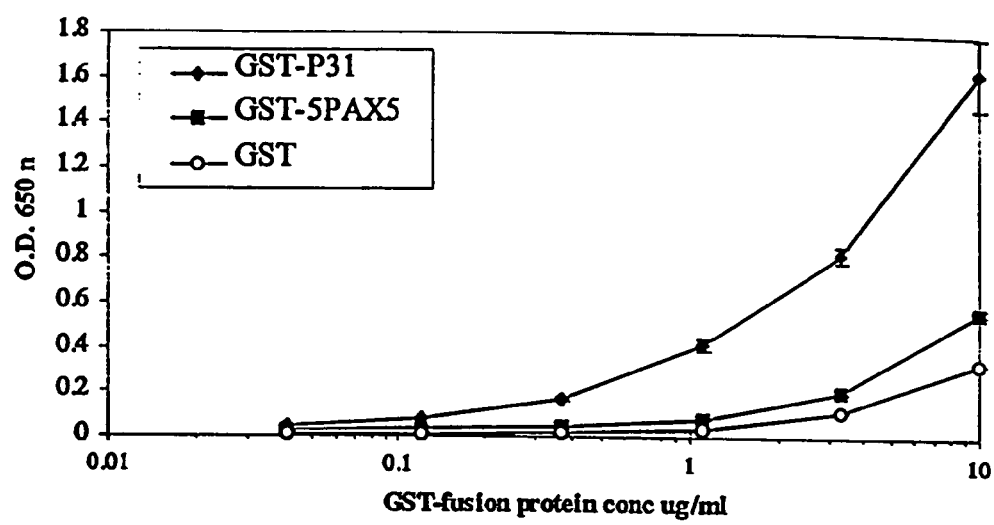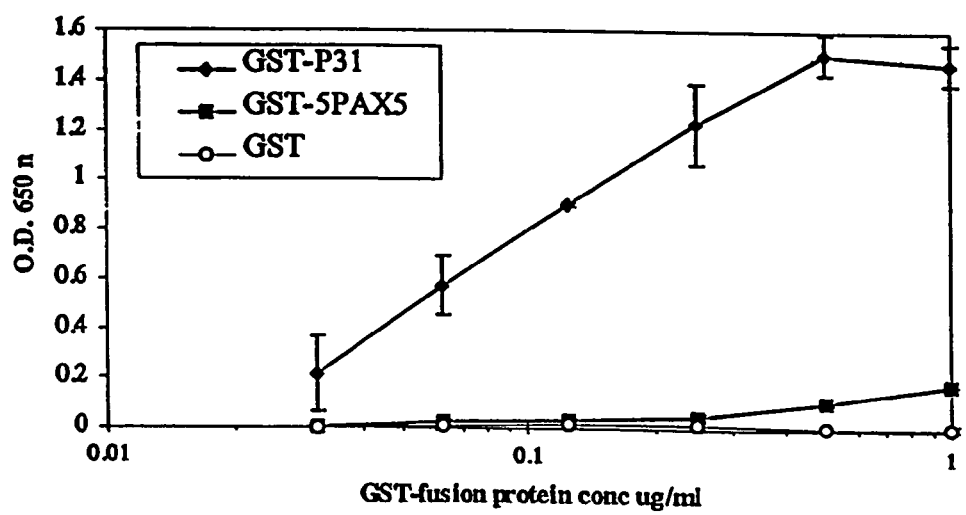
Fig. 7 F-G

H
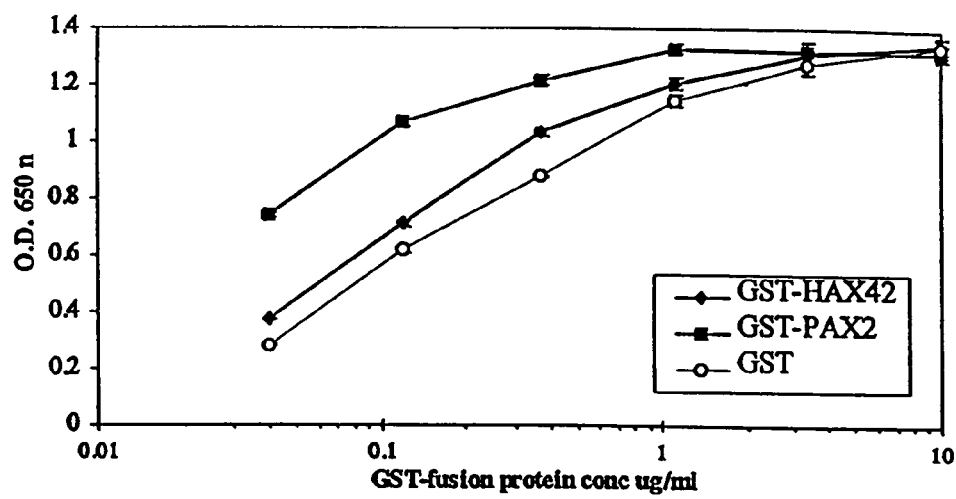
I
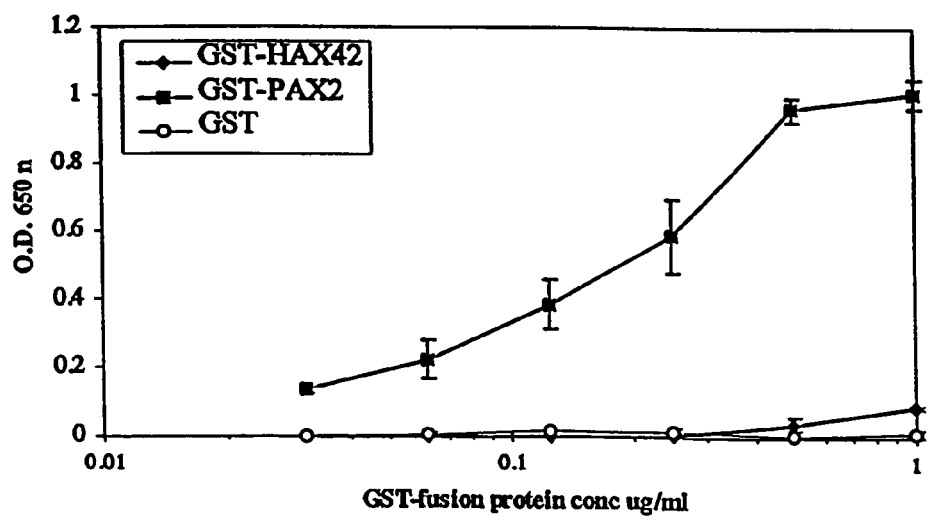
Fig. 7 H-I

J
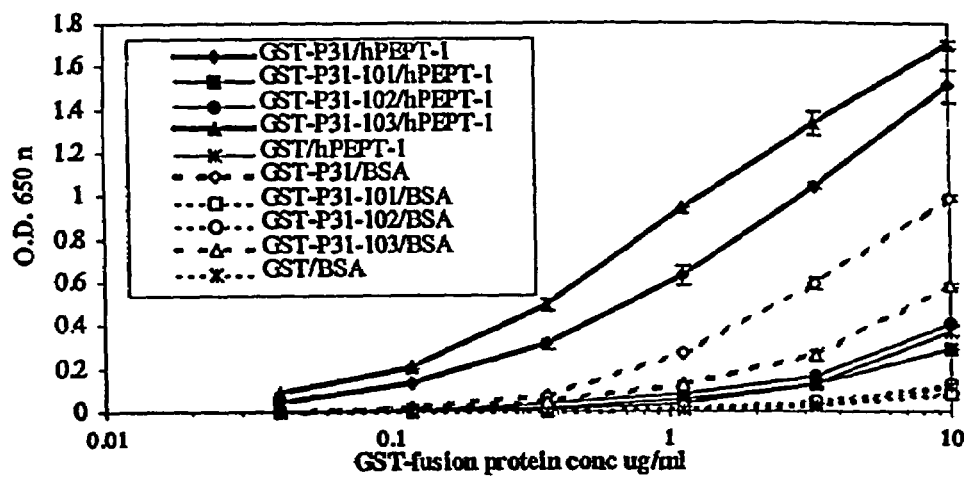
K
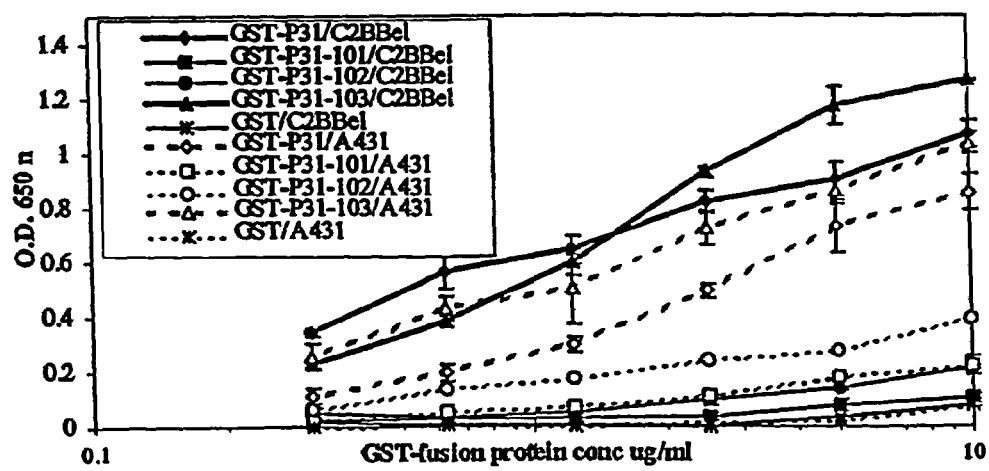
Fig. 7 J-K

L
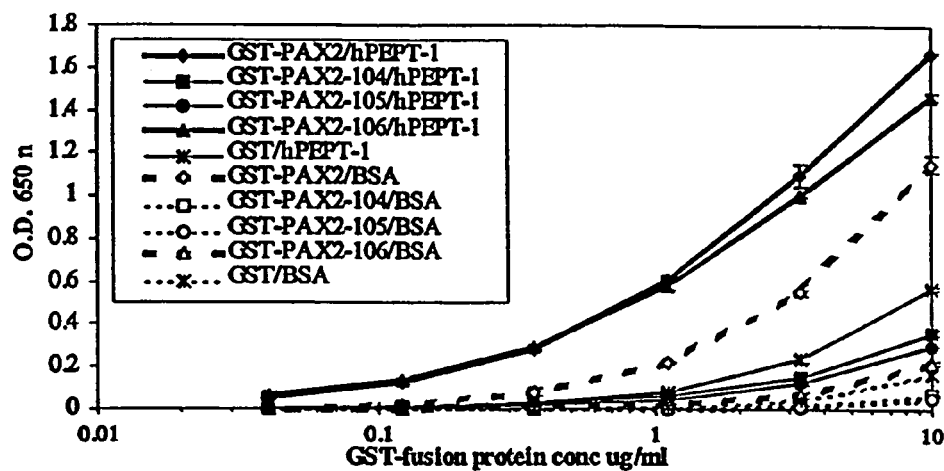
M
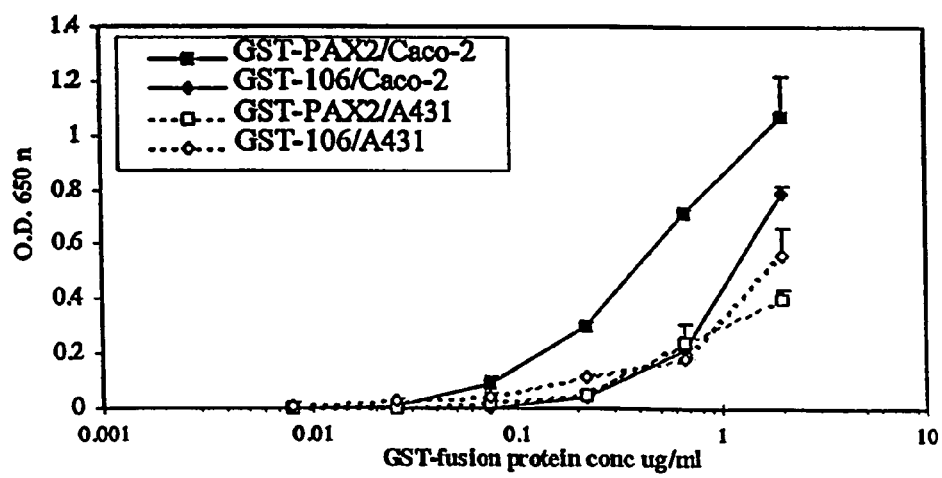
Fig. 7 L-M

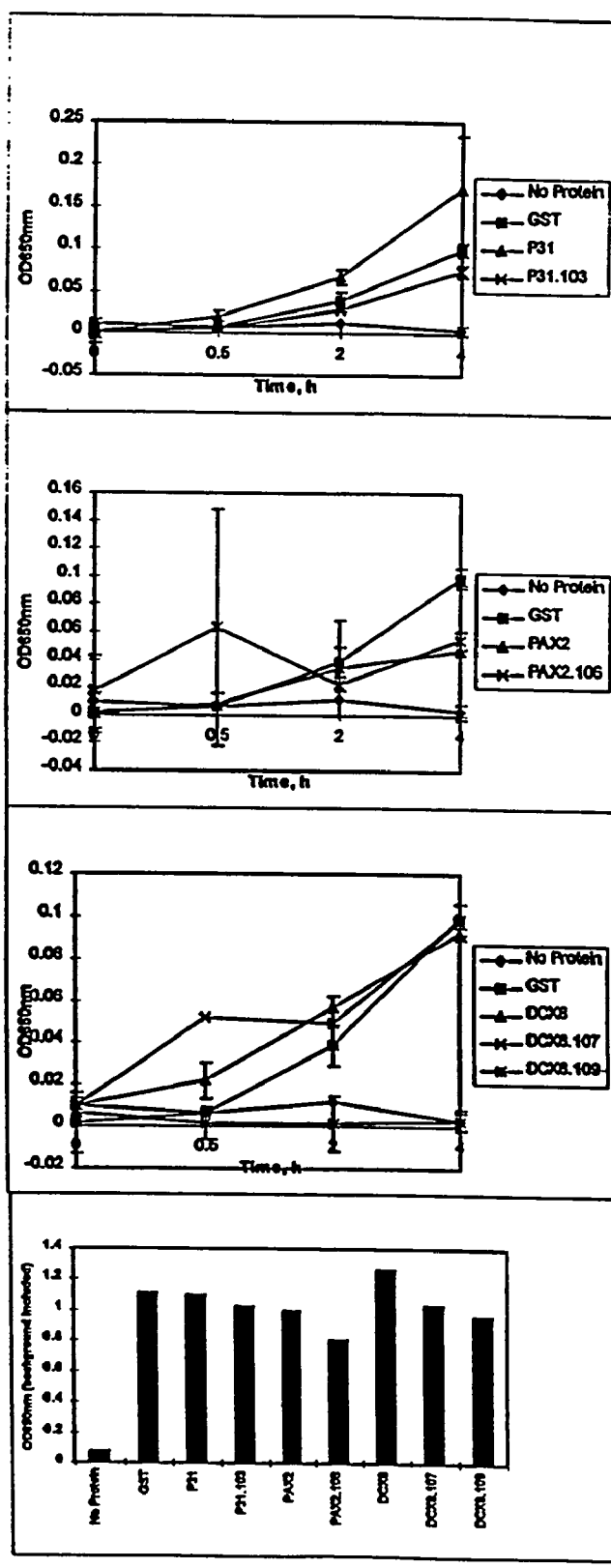
Figs. 8 A-D

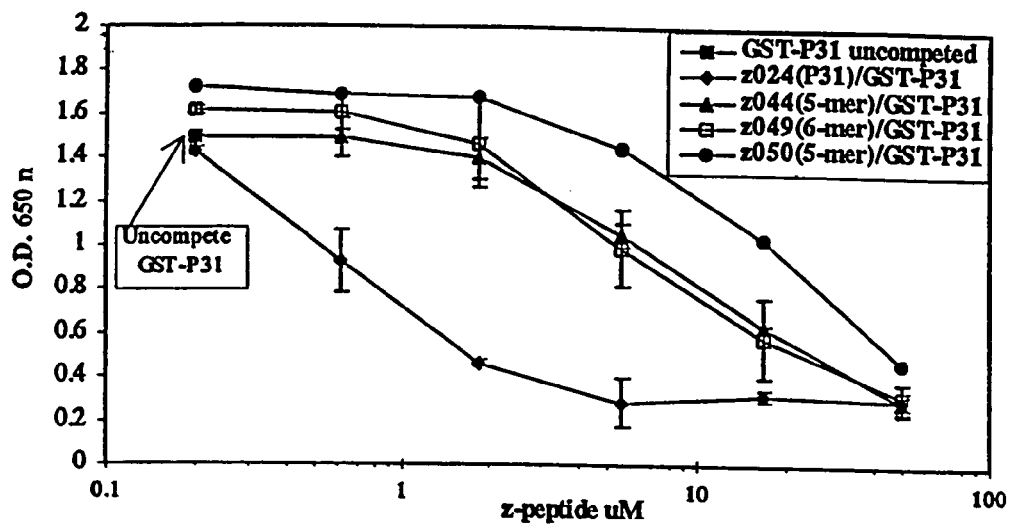
A
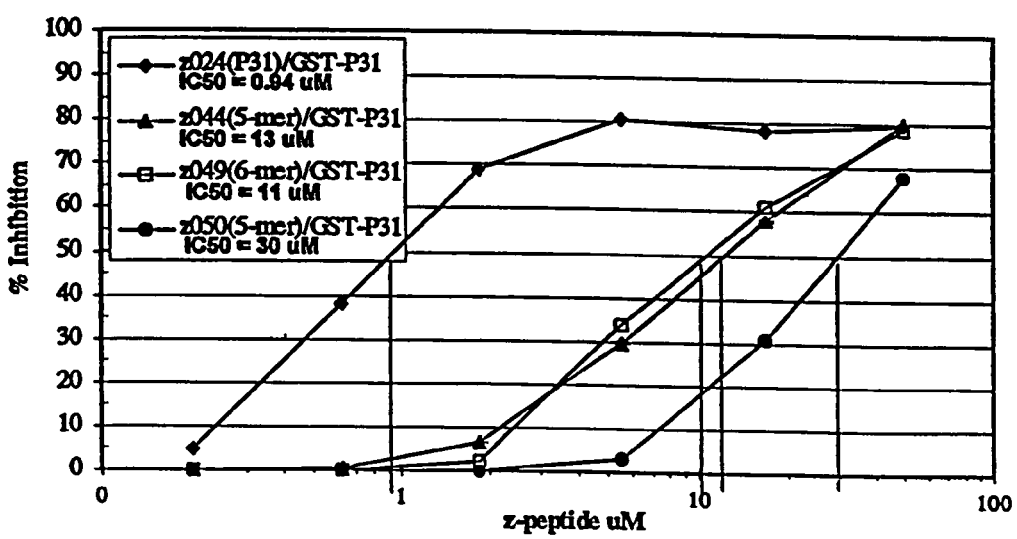
B
Fig. 9

P31

| Peptide Name | Sequence | | | | pI | IC₅₀ | GST/C2BBe1 |
|---|---|---|---|---|---|---|---|
| | 1 | 10 | 20 | 30 | 40 | | |
| ELAN024 (P31) | SARDSGPAEDGSRAVRLNGVENANTRKSSRSNPRGRRHPG | | | | 11.88 | 0.5-2.2 | +++ |
| 101 | SARDSGPAEDGSRAVRLNG | | | | | | |
| 102 | DGSRAVRLNGVENANTRKSSR | | | | | | |
| 103 | ENANTRKSSRSNPRGRRHP | | | | | | |
| 110 | ENANTRKSSR | | | | | | |
| 111 | RKSSRSNPRG | | | | | | |
| 112 | SNPRGRRHP | | | | | | |
| 119 | TRKSSRSNPRG | | | | | | |
| Z28 | ZENANTRKSSRSNPRGRRHPG | | | | 12.28 | 0.5-1.7 | |
| Z29 | ZTRKSSRSNPRG | | | | 12.40 | 5.5-15 | |
| Z30 | ZENANTRKSSRSNPRG | | | | 11.81 | >50 | |
| Z31 | ZTRKSSRSNPRGRRHPG | | | | 12.70 | 0.6-3.2 | |
| Z39 | ZENANTRKSSR | | | | 10.89 | >50 | |
| Z40 | ZSNPRGRRHPG | | | | 12.40 | 5.9-29 | |
| Z41 | ZENANT | | | | 3.75 | >50 | |
| Z42 | ZANTRKS | | | | 11.05 | >50 | |
| Z43 | ZTRKSS | | | | 11.05 | >50 | |
| Z44 | ZRKSSR | | | | 12.11 | 13->50 | |
| Z45 | ZKSSRSN | | | | 11.05 | 40-48 | |
| Z46 | ZSSRSNPG | | | | 10.04 | >50 | |
| Z47 | ZSRSNPRG | | | | 12.40 | >50 | |
| Z48 | ZSNPRG | | | | 10.04 | >50 | |
| Z49 | ZPRGRRH | | | | 12.40 | 11-20 | |
| Z50 | ZRRHPG | | | | 12.10 | 30 | |
| Z51 (HepC core) | ZKSSRGN | | | | 12.40 | >50 | |
| Z52 (HepC P26664) | ZTLKSSISNPIGIIHPG | | | | 12.10 | 9.8 | |
| Z53 | ZTRKSSISNPRGIIHPG | | | | | 1.6 | |
| Z54 | ZTRKSSISNPRGIRHPG | | | | | 1.6 | |
| Z21 (HAX42) | SDHALGTNLRSDNAKEPGDYNCCGNGNSTGRKVENRRPSAIPT | | | | 11.27 | 1.7 | |

Fig. 10A

PAX2

| Peptide Name | Sequence (1-10-20-30-40) | pI | IC₅₀ | GST/C2BBe1 |
|---|---|---|---|---|
| ELAN018 (PAX2) | STPPSREAISRPISVDSDSDTNAKHSSHNRRLRTRSRPNG | 10.88 | 0.6-0.9, 1 | +++ |
| 104 | STPPSREAISRPISVDSDSD | | | |
| 105 | SRPISVDSDTNAKHSSHNR | | | — |
| 106 | TNAKHSSHNRRLRTRSRPN | | | — |
| 113 | TNAKHSSHN | | | |
| 114 | SSHNRRLRTR | | | +/— |
| 115 | RRLRTRSRPN | | | +/— |
| Z32 | ZTNAKHSSHNRRLRTRSRPN | 12.7 | 1.2 | |
| Z33 | ZTNAKHSSHNRRLRTR | 12.58 1.6 | | |
| Z34 | ZSSHNRRLRTRSRPN | 12.7 | 1.6, 1.3, 0.68, 1.5 | |
| Z35 | ZSSHNRRLRTR | 12.58 0.38 - 1.8, 2.7 | | |
| Z26 | ZSEANLDGRKSRISSPRRNSSTRPRTSPNSVHARYPSTDHD | 10.88 7-8, 3 | | |
| Z38 | ZSRANTDGRKSRISSPRRNSSTEPRLSPNSVHARYPSTDED | 10.88 1.7, 0.9 | | |
| Z55 | ZTNAKHSSHN | | 42 | |
| Z56 | ZRRLRTRSRPN | | 1.7 | |
| Z57 | ZRRLRTRSR | | 1.9 | |
| Z58 | ZRRLRTR | | | |
| Z59 | ZRRLRTRSRPN | 3.4 | NOT DONE | |
| Z73 | ZASHNRRLRTR | 1.5, 5.5 | | |
| Z74 | ZSAHNRRLRTR | 6.2 | | |
| Z75 | ZSSANRRLRTR | 1.6 | | |
| Z76 | ZSHARRLRTR | 1.8 | | |
| Z77 | ZSSHNARLRTR | 3.9, 5.2 | | |
| Z78 | ZSSHNRALRTR | 4.5, 4.6 | | |
| Z79 | ZSSHNRRARTR | 1.4 | | |
| Z80 | ZSSHNRRLATR | 3.4, 5.2 | | |
| Z81 | ZSSHNRRLRAR | 2.2 | | |
| Z82 | ZSSHNRRLRTA | 3.4 | | |
| Z21 (HAX42) | ZSDHALGTNLRSDNAKEPGDINCCGNGNSTGRKVFNRRRPSAIPT | 11.27 0.7 | | |

Fig. 10B

SN110

| Peptide Name | Sequence | | | | pI | IC$_{50}$ | GST/C2BBe1 |
|---|---|---|---|---|---|---|---|
| | 1 | 10 | 20 | 30 | 40 | | |
| ELAN016(SN110) | RVGQCTDSDVRRPWARSCAHQGCGAGTRNSHGCITRPLRQASAH | | | | 10.19 | 0.22 | ++ |
| 116 | RVGQCTDSDVRRPWARSCA | | | | 8.66 | 3.6 | − |
| 117 | VRRPWARSCAHQGCGAGTRNS | | | | 9.03 | 0.7 | + |
| 118 | GTRNSHGCITRPLRQASAH | | | | 11.62 | 0.27 | +/− |
| Z17 | ZRVGQCTDSDVRRPWARSCAH | | | | 8.01 | 3 | |
| Z16C23 | ZCGAGTRNSHGCITRPLRQASAH | | | | | | |
| Z36 | ZVRRPWARSCAHQGCGAGTRNS | | | | | | |
| Z37 | ZCTDSDVRRPWARSC | | | | | | |

HAX42

| Peptide Name | Sequence | | | | pI | IC$_{50}$ | GST/C2BBe1 |
|---|---|---|---|---|---|---|---|
| | 1 | 10 | 20 | 30 | 40 | | |
| ELAN021(HAX42) | SDHALGTNLRSDNAKEPGDINCCGNGNSTGRKVFNRRRPSAIPT | | | | 11.27 | 5.5 | ++ |
| ELAN018(PAX2) | STPPSREAYSRPISVDSDTNAKHSSHNRRLRTRSRPNG | | | | 10.88 | 0.23 | +++ |
| Z26 | ZSEANLDGRKSRISSPRRNSSTRPRTSPNSVHARYPSTDHD | | | | 10.88 | <0.2 | |
| Z38 | ZSRANTDGRKSRISSPRRNSSTEPRLSPNSVHARYPSTDHD | | | | 10.88 | <0.2 | |
| Z34 (PAX2 14mer) | ZSSHNRRLRTRSRPN | | | | 12.7 | 0.33 | |

Fig. 10C

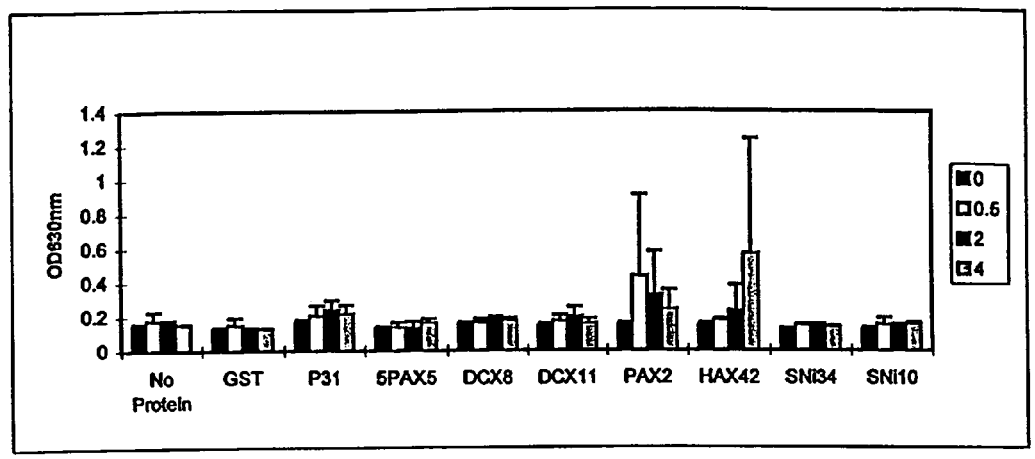
A
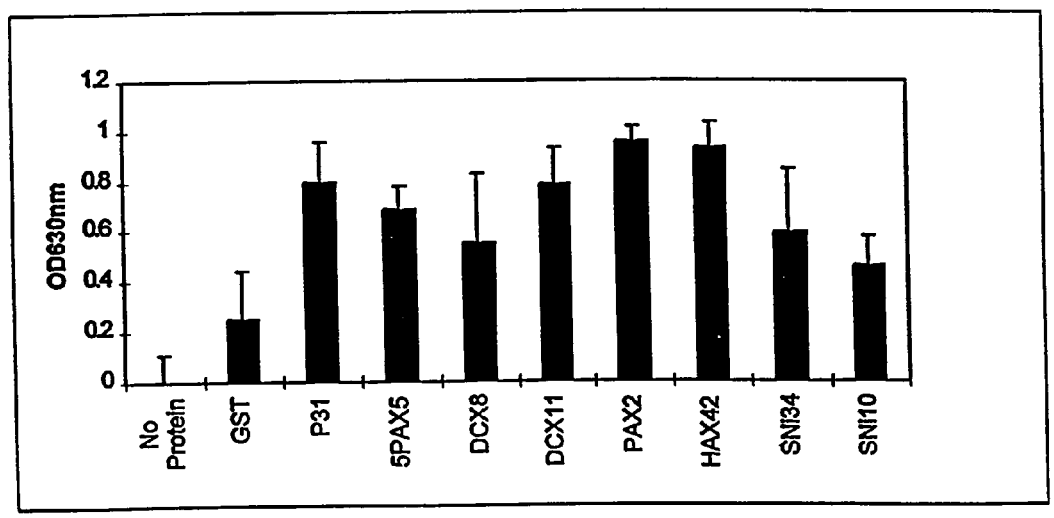
B
Fig. 11

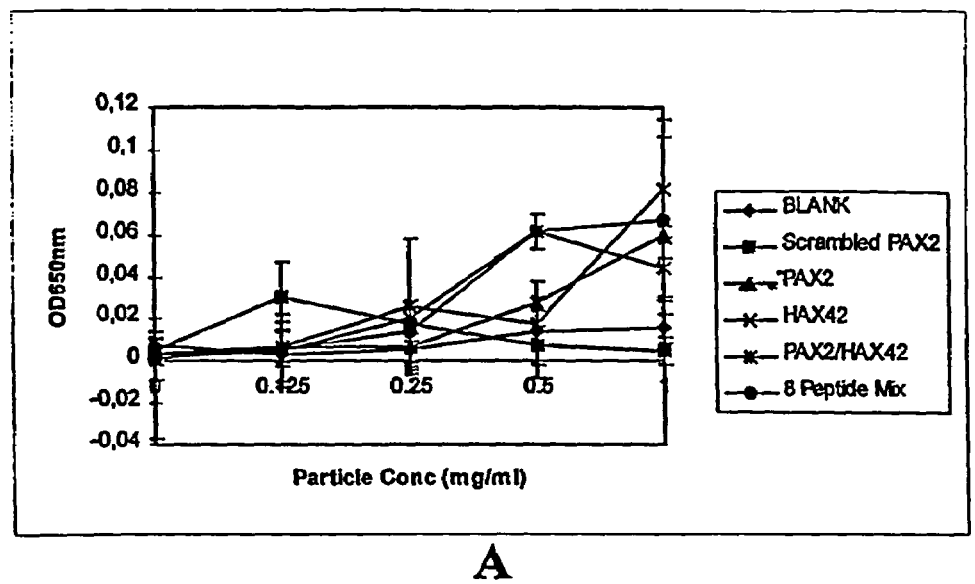
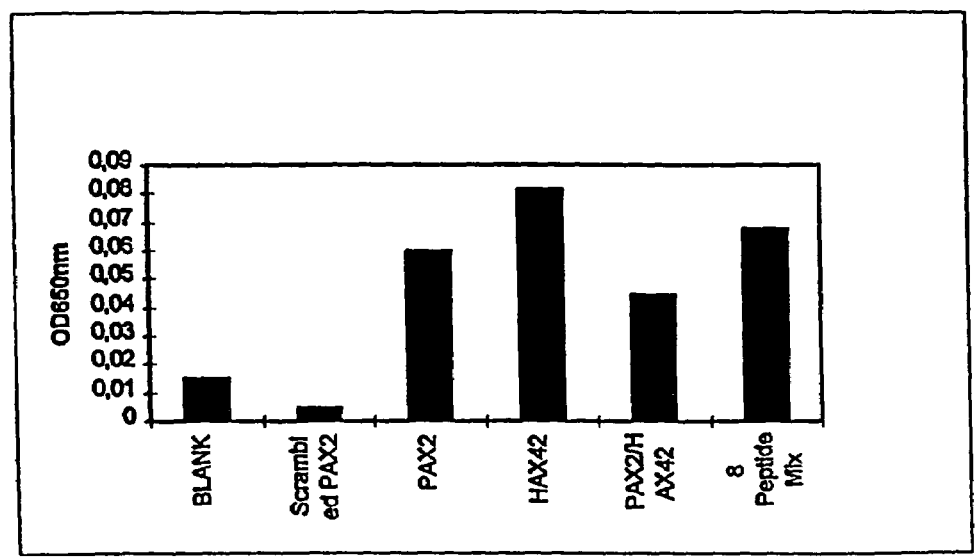
Fig. 13

A
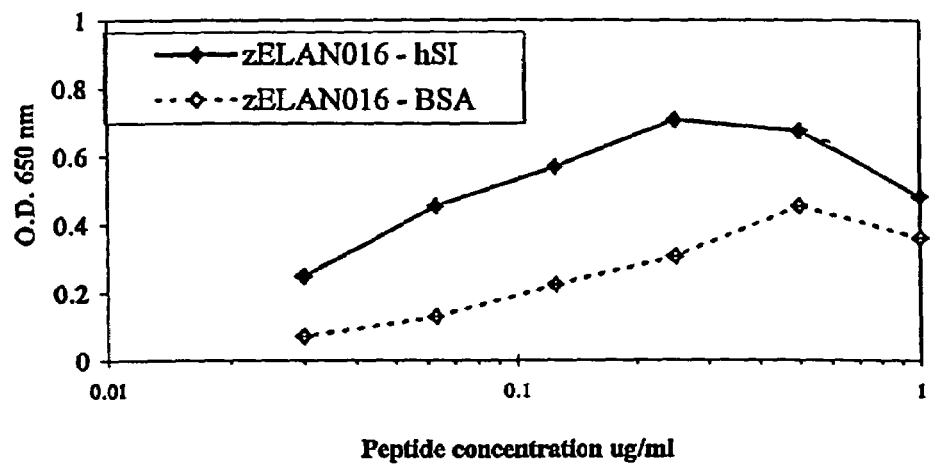
B
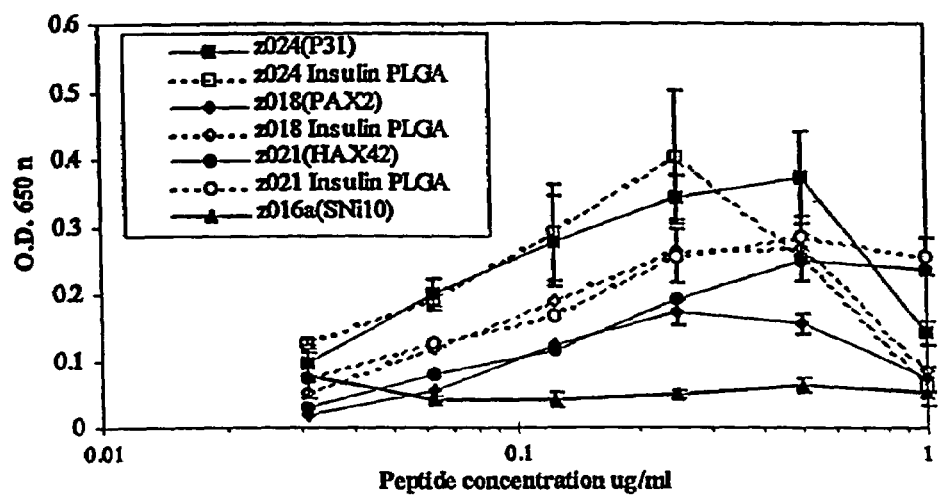
Fig. 14

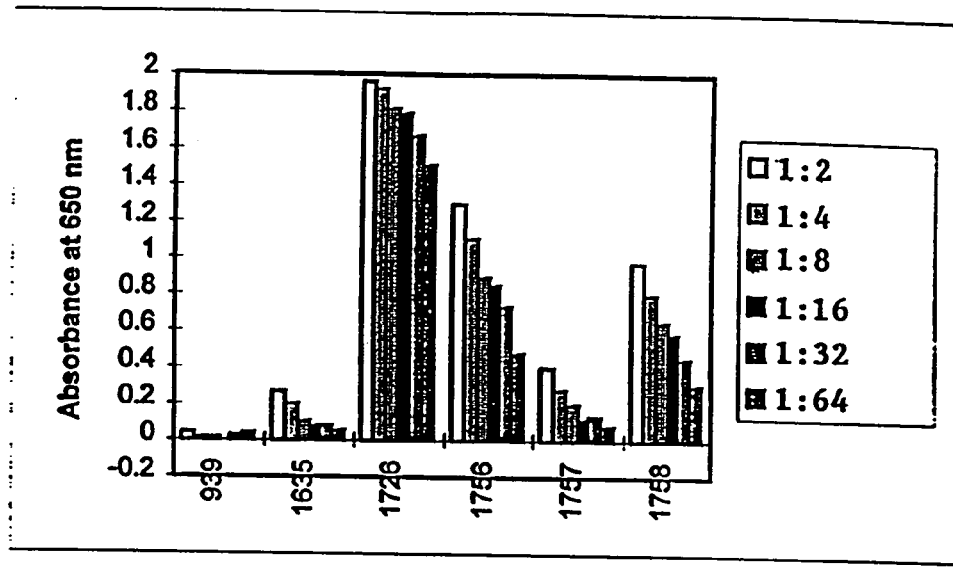
A
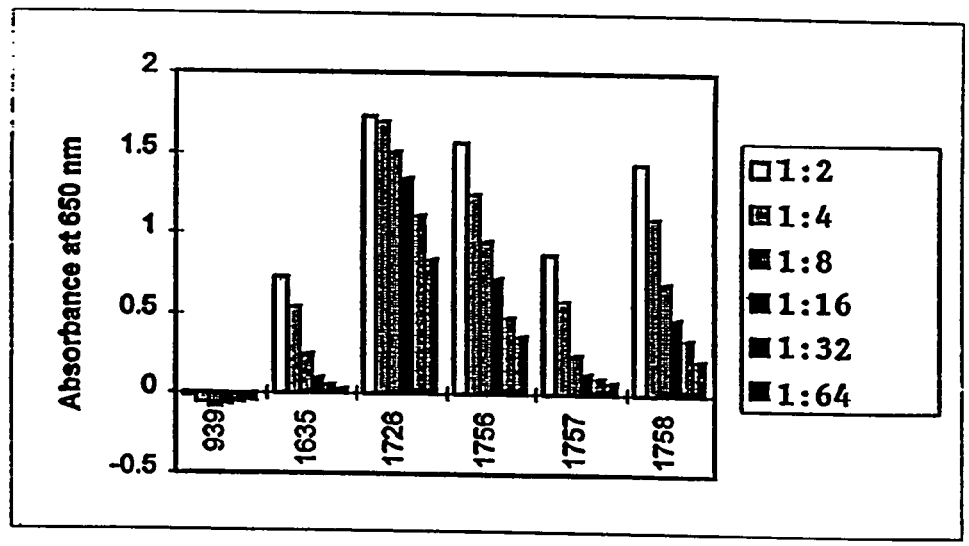
B
Fig. 15

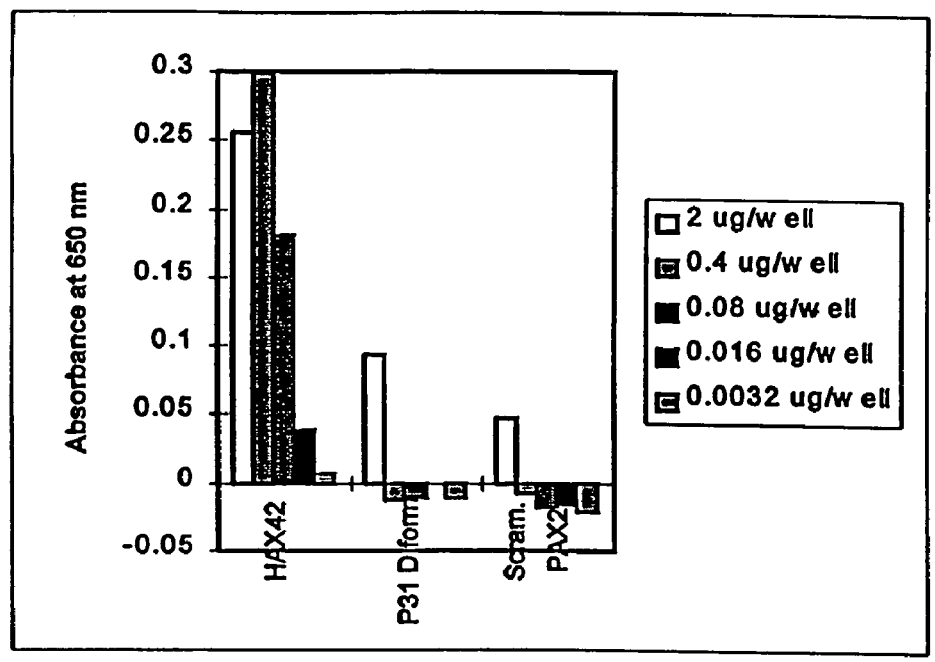
A
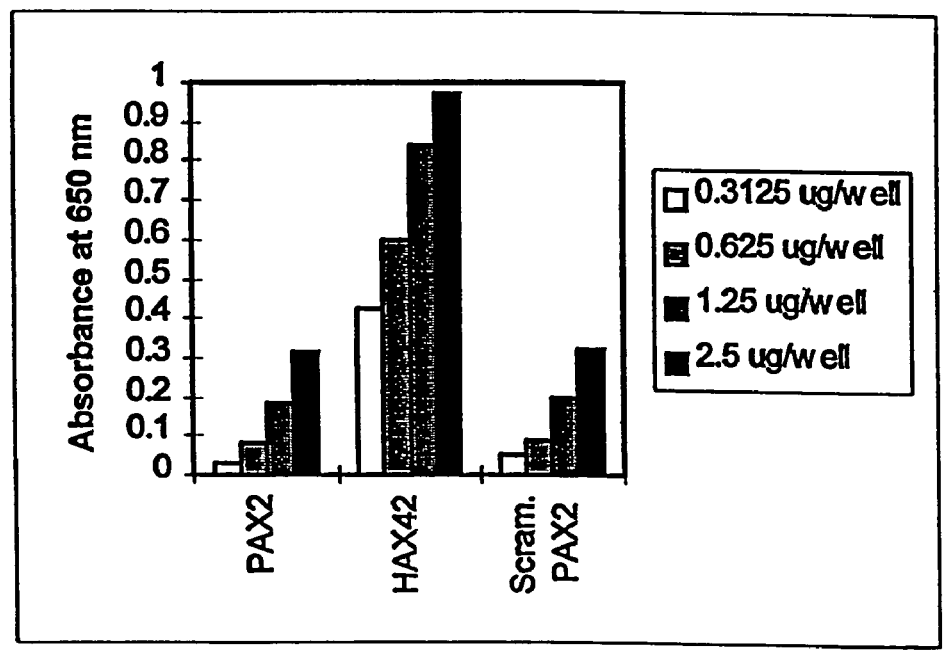
B
Fig. 16

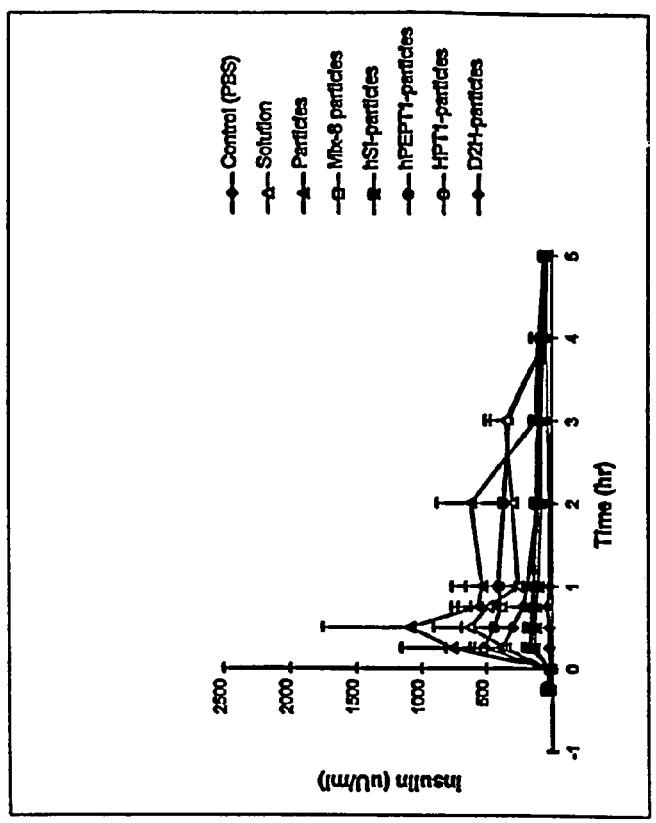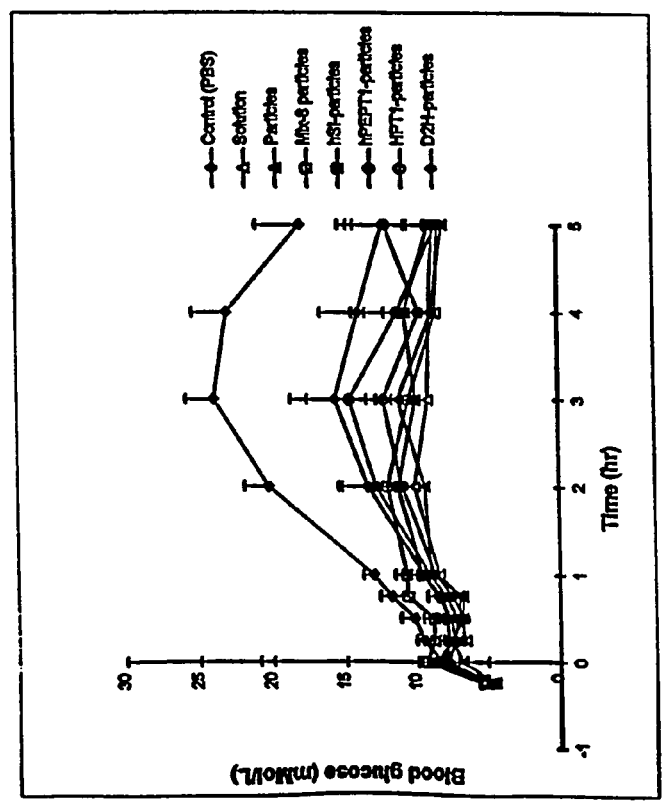
Fig. 17

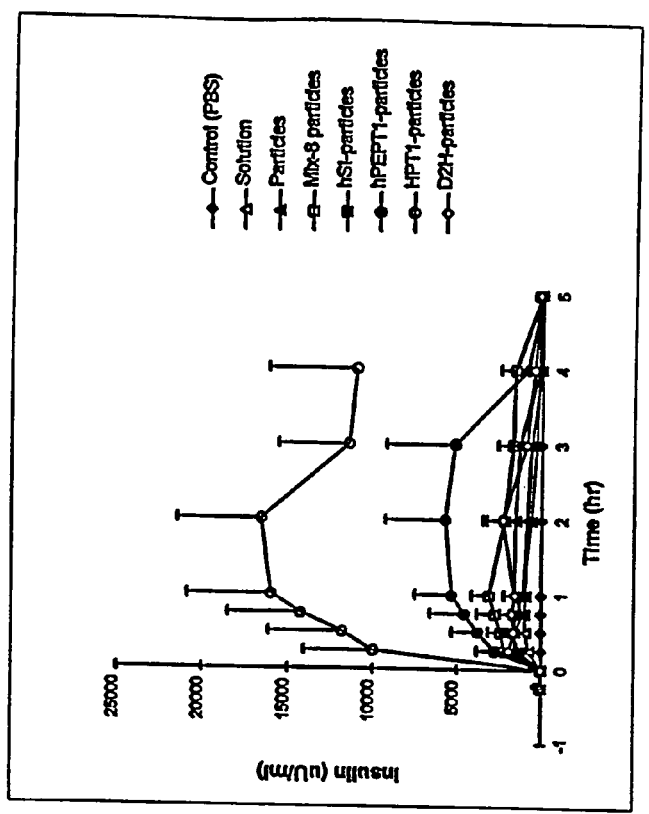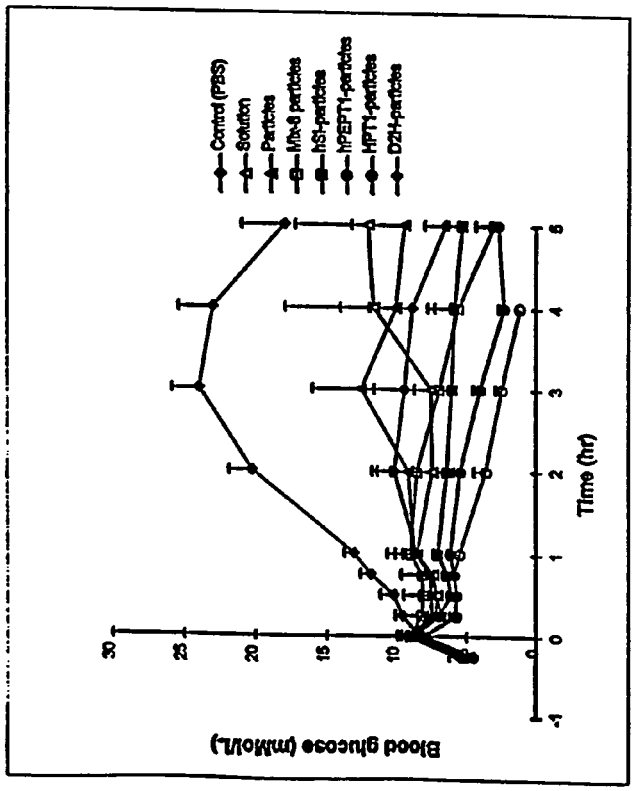
Fig. 18

| P31 AA Seq. Position | Known Protein | Homologous Seq. Position |
|---|---|---|
| 12-34 | Fasciculin 2 | 10-32 |
| 4-12 | Mesentericopeptidase | 54-62 |
| 15-31 | | 175-191 |
| 26-39 | Core protein (Hepatitis C virus) | 5-18 |
| 26-39 | | 11-24 |
| 26-39 | | 21-34 |
| 26-39 | | 38-51 |
| 23-30 | | 39-55 |
| 25-39 | | 41-55 |
| 26-39 | | 51-64 |
| 16-39 | PT-NANBH Polyprotein N-terminus | 51-64 |
| 28-40 | AL2 protein (Caenorhabditiselegans) | 70-82 |
| 26-38 | Capsid protein (Hepatitis C virus Type 3g) | 48-60 |
| 26-39 | Genome polyprotein (Hepatitis C virus) | 57-70 |

Fig. 20

| DCX8AA Seq. Position | Known Protein | Homologous Seq. Position |
|---|---|---|
| 20-27 | Endo-1,4-Beta-D-Glucanase | 78-85 |
| 30-37 | | 221-228 |
| 21-34 | P-Hydroxybenzoate Hydroxylase | 285-298 |
| 5-15 | | 54-64 |
| 7-21 | Cytochrome | 50-64 |
| 7-21 | Cytochrome C3 | 50-64 |
| | Trimethylamine Dehydrogenase | 208-219 |
| 32-43 | | 396-407 |
| 30-37 | Gag-JunD fusion protein | 24-31 |
| 26-30 | | 16-20 |
| 23-44 | Secretin precursor, N-prosecretin, secretin ainide | 18-39 |
| 33-44 | T-cell receptor V beta chain | 15-26 |
| 27-33 | | 3-9 |
| 23-44 | Secretin precursor pir | 18-39 |
| 31-44 | Hypothetical protein V (Synechocystis) | 275-288 |
| 24-30 | | 251-257 |
| 23-43 | Putative RNA binding protein | 230-250 |
| 28-40 | Mu son of sevenless 1 | 1-13 |
| 24-35 | Neuropeptide precursor | 80-91 |
| 29-43 | | 5-19 |
| 23-43 | RNA-binding protein (Macacafascicularis) | 230-250 |
| 23-43 | RNA-binding protein (Homosapiens) | 230-250 |
| 23-43 | Autosomal gene – azoospermia factor | 230-250 |
| 25-38 | Collagen | 25-28 |
| 24-35 | | 4-15 |
| 29-41 | Probable cell growth regulator | 306-318 |
| 24-35 | Ribosomal protein S2 | 24-35 |
| T6-39 | | 182-185 |
| 24-44 | Caenorhabditis elegans | 296-316 |
| 23-34 | pid:e208155 (Homo sapiens) | 61-72 |
| 36-43 | | 116-123 |

Fig. 21A

| DCX8A Seq. Position | Known Protein | Homologous Seq. Position |
|---|---|---|
| 24-38 | Xylulose Kinase | 16-30 |
| 24-39 | Caenorhabditis elegans | 57-72 |
| 26-42 |  | 65-81 |
| 27-33 | Hypothetical protein – phage BZ13 | 22-28 |
| 35-39 |  | 31-35 |
| 30-42 | Cerebelllin-like glycoprotein | 2-14 |
| 8-22 | DNA Primase | 170-184 |
| 2-7 |  | 76-81 |
| 5-21 | Coat Protein (Bean common mosaic virus) | 12-28 |
| 5-21 | Coat protein (Bean common mossaic virus) | 33-49 |
| 5-21 |  | 19-35 |
| 5-21 | Polyprotein (Bean common mossaic virus) | 215-231 |
| 5-21 |  | 39-55 |
| 5-21 | Nib proteinlcoat protein (Cowpea aphid-borne mosaic virus) | 92-108 |
| 2-13 | MHC class 1 Pipi (Pithecia) | 111-122 |
| 14-22 |  | 326-334 |
| 3-19 | Talin (Caenorhabditis elegans) | 1538-1554 |
| 2-9 | Acetamidase pir | 359-366 |
| 9-20 |  | 483-494 |
| 10-16 | Rhizobions etli strain | 134-140 |
| 17-30 |  | 173-186 |
| 31-39 |  | 200-208 |
| 2-11 | Neurotoxin 1 (toxin B) A. Stokesi | 7-16 |
| 12-33 |  | 26-47 |
| 21-27 | Suid herpes virus 1 early protein | 425-432 |
| 30-43 |  | 51-64 |
| 13-42 | Rice cDNA partial sequence | 50-151 |
| 8-15 | Fusion protein | 24-31 |
| 4-8 |  | 16-20 |
| 1-22 | Secretin precursor, N-prosecretin, secretin-amide | 18-39 |
| 11-22 | T-cell receptor V beta chain | 15-26 |
| 5-11 |  | 3-9 |
| 9-22 | Hypothetical protein | 275—288 |
| 2-8 |  | 251-257 |

Fig. 21B

| DCX8A Seq. Position | Known Protein | Homologous Seq. Position |
|---|---|---|
| 1-21 | Putative RNA binding protein | 230-250 |
| 6-18 | Hypothetical protein-mouse pir | 1-13 |
| 2-13 | Neuropeptide precursor | 80-91 |
| 7-21 | orf3-human | 5-19 |
| 1-21 | RNA-binding protein | 230-250 |
| 13-16 | Collagen | 25-28 |
| 7-19 | Probable cell growth or differentiation regulator | 306-318 |
| 2-13 | Ribosoaml protein S2 | 14-25 |
| 14-17 |  | 182-185 |
| 2-22 | Caenorhabditis elegans | 296-316 |
| 1-12 | Homosapiens | 61-72 |
| 14-21 |  | 116-123 |
| 2-16 | Xylulose Kinase | 16-30 |
| 8-15 | T cell receptor delta chain | 55-62 |
| 5-8 |  | 12-15 |
| 8-17 | Seq. 43 from patent US | 12-21 |

Fig. 21C

| DAB10 AA Seq. Position | Known Protein | Homologous Seq. Position |
|---|---|---|
| 13-34 | 1,3-Beta-Gllucanase | 231-252 |
| 3-11 | Photosynthetic Reaction Center | 20-28 |
| 16-27 | | 128-139 |
| 28-35 | MYB Proto-Oncogene Protein | 131-138 |
| 5-18 | | 32-45 |
| 23-36 | Lysozyme Mutant | 130-143 |
| 28-35 | Lipase | 400-407 |
| 3-15 | | 159-171 |
| 3-37 | Trypsin | 169-203 |
| 13-34 | 1,3-1,4-Beta-Glucanase | 232-253 |
| 4-10 | Lactate Dehydrogenase | 190-196 |
| 11-7 | | 244-250 |
| 4-10 | Apo-Lactate Dehydrogenase | 190-196 |
| 11-17 | | 244-250 |
| 4-10 | Lactate Dehydrogenase | 191-197 |
| 11-17 | | 245-251 |
| 16-26 | Ovotransferrin | 240-250 |
| 23-36 | Genome Polyprotein Matrix Protein | 1022-1035 |
| 14-20 | Rous sarcoma virus | 43-49 |
| 2-12 | | 13-23 |
| 14-20 | Hypothetical protein-avian leukosis virus | 43-49 |
| 4-20 | T cell receptor delta chain variable region | 1-4 |
| 14-18 | | 12-16 |
| 2-12 | Gag Polyprotein-avian endogenous virus RAV-0 | 139-149 |
| 14-20 | | 169-175 |
| | p19 Protein-avian erythroblastosis virus | 189-199 |
| 14-20 | | 219-225 |
| 7-19 | ALI protein-potato yellow mosaic virus | 222-234 |
| 3-22 | Endo-1,4-beta glucanase | 186-205 |
| 6-18 | I a protein-brome mosaic virus | 430-442 |
| 2-12 | Gag polyprotein-Fujinami sarcoma virus | 186-196 |
| 14-22 | | 216-222 |
| 2-12 | Gag protein-Rous sarcoma virus | 190-200 |
| 14-20 | | 220-226 |
| 1-12 | Corticotropin-like intermediate lobe peptide | 7-18 |
| 1-22 | Gene product (Caenorhabditis elegans) | 4-25 |
| 31-37 | T cell receptor delta chain | 56-62 |
| 26-39 | | 12-15 |
| 26-37 | Lysozyme Mutant | 133-144 |

Fig. 22

```
ATG TCC CCT ATA CTA GGT TAT TGG AAA ATT AAG GGC CTT GTG CAA CCC      48
Met Ser Pro Il  Leu Gly Tyr Trp Lys Ile Lys Gly Leu Val Gln Pro
1               5                   10                  15

ACT CGA CTT CTT TTG GAA TAT CTT GAA GAA AAA TAT GAA GAG CAT TTG      96
Thr Arg Leu Leu Leu Glu Tyr Leu Glu Glu Lys Tyr Glu Glu His Leu
            20                  25                  30

TAT GAG CGC GAT GAA GGT GAT AAA TGG CGA AAC AAA AAG TTT GAA TTG     144
Tyr Glu Arg Asp Glu Gly Asp Lys Trp Arg Asn Lys Lys Phe Glu Leu
        35                  40                  45

GGT TTG GAG TTT CCC AAT CTT CCT TAT TAT ATT GAT GGT GAT GTT AAA     192
Gly Leu Glu Phe Pro Asn Leu Pro Tyr Tyr Ile Asp Gly Asp Val Lys
    50                  55                  60

TTA ACA CAG TCT ATG GCC ATC ATA CGT TAT ATA GCT GAC AAG CAC AAC     240
Leu Thr Gln Ser Met Ala Ile Ile Arg Tyr Ile Ala Asp Lys His Asn
65              70                  75                      80

ATG TTG GGT GGT TGT CCA AAA GAG CGT GCA GAG ATT TCA ATG CTT GAA     288
Met Leu Gly Gly Cys Pro Lys Glu Arg Ala Glu Ile Ser Met Leu Glu
                85                  90                  95

GGA GCG GTT TTG GAT ATT AGA TAC GGT GTT TCG AGA ATT GCA TAT AGT     336
Gly Ala Val Leu Asp Ile Arg Tyr Gly Val Ser Arg Ile Ala Tyr Ser
            100                 105                 110

AAA GAC TTT GAA ACT CTC AAA GTT GAT TTT CTT AGC AAG CTA CCT GAA     384
Lys Asp Phe Glu Thr Leu Lys Val Asp Phe Leu Ser Lys Leu Pro Glu
        115                 120                 125

ATG CTG AAA ATG TTC GAA GAT CGT TTA TGT CAT AAA ACA TAT TTA AAT     432
Met Leu Lys Met Phe Glu Asp Arg Leu Cys His Lys Thr Tyr Leu Asn
    130                 135                 140

GGT GAT CAT GTA ACC CAT CCT GAC TTC ATG TTG TAT GAC GCT CTT GAT     480
Gly Asp His Val Thr His Pro Asp Phe Met Leu Tyr Asp Ala Leu Asp
145                 150                 155                 160

GTT GTT TTA TAC ATG GAC CCA ATG TGC CTG GAT GCG TTC CCA AAA TTA     528
Val Val Leu Tyr Met Asp Pro Met Cys Leu Asp Ala Phe Pro Lys Leu
                165                 170                 175

GTT TGT TTT AAA AAA CGT ATT GAA GCT ATC CCA CAA ATT GAT AAG TAC     576
Val Cys Phe Lys Lys Arg Ile Glu Ala Ile Pro Gln Ile Asp Lys Tyr
            180                 185                 190

TTG AAA TCC AGC AAG TAT ATA GCA TGG CCT TTG CAG GGC TGG CAA GCC     624
Leu Lys Ser Ser Lys Tyr Ile Ala Trp Pro Leu Gln Gly Trp Gln Ala
        195                 200                 205

ACG TTT GGT GGT GGC GAC CAT CCT CCA AAA TCG GAT CTG GTT CCG CGT     672
Thr Phe Gly Gly Gly Asp His Pro Pro Lys Ser Asp Leu Val Pro Arg
    210                 215                 220

GGA TCC CCA GGA ATT CCC GGG TCG ACT CGA GCG GCC GCA TCG TGA         717
Gly Ser Pro Gly Ile Pro Gly Ser Thr Arg Ala Ala Ala Ser
225                 230                 235
```

Fig. 23

RANDOM PEPTIDES THAT BIND TO GASTRO-INTESTINAL TRACT (GIT) TRANSPORT RECEPTORS AND RELATED METHODS

This application claims priority to U.S. provisional application Ser. No. 60/046,595 filed May 15, 1997, which is incorporated by reference herein in its entirety.

1. INTRODUCTION

The present invention relates generally to random peptides capable of specific binding to gastrointestinal tract (GIT) transport receptors. In particular, this invention relates to peptide sequences and motifs, as well as derivatives thereof, which enhance drug delivery and transport through tissue, such as epithelial cells lining the lumenal side of the gastro-intestinal tract (GIT). Production of peptides, derivatives and antibodies is also provided. The invention further relates to pharmaceutical compositions, formulations and related methods.

2. BACKGROUND OF THE INVENTION

2.1. Peptide Libraries

There have been two different approaches to the construction of random peptide libraries. According to one approach, peptides have been chemically synthesized in vitro in several formats. Examples of chemically synthesized libraries can be found in Fodor, S., et al., 1991, Science 251: 767–773; Houghten, R., et al., 1991, Nature 354: 84–86; and Lam, K., et al., 1991, Nature 354: 82–84.

A second approach to the construction of random peptide libraries has been to use the M13 phage, and, in particular, protein pIII of M13. The viral capsid protein of M13, protein III (pIII), is responsible for infection of bacteria. Several investigators have determined from mutational analysis that the 406 amino acid long pIII capsid protein has two domains. The C-terminus anchors the protein to the viral coat, while portions of the N-terminus of pIII are essential for interaction with the *E. coli* pillin protein (Crissman, J. W. and Smith, G. P., 1984, Virology 132: 445–455). Although the N-terminus of the pIII protein has shown to be necessary for viral infection, the extreme N-terminus of the mature protein does tolerate alterations. In 1985, George Smith published experiments reporting the use of the pIII protein of bacteriophage M13 as an experimental system for expressing a heterologous protein on the viral coat surface (Smith, G. P., 1985, Science 228: 1315–1317). It was later recognized, independently by two groups, that the M13 phage pIII gene display system could be a useful one for mapping antibody epitopes (De la Cruz, V., et al., 1988, J. Biol. Chem. 263: 4318–4322; Parmley, S. F. and Smith, G. P., 1988, Gene 73: 305–318).

Parmley, S. F. and Smith, G. P., 1989, Adv. Exp. Med. Biol. 251: 215–218 suggested that short, synthetic DNA segments cloned into the pIII gene might represent a library of epitopes. These authors reasoned that since linear epitopes were often ⁻6 amino acids in length, it should be possible to use a random recombinant DNA library to express all possible hexapeptides to isolate epitopes that bind to antibodies. Scott, J. K. and Smith, G. P., 1990, Science 249: 386–390 describe construction and expression of an "epitope library" of hexapeptides on the surface of M13. Cwirla, S. E., et al., 1990, Proc. Natl. Acad. Sci. USA 87: 6378–6382 also described a somewhat similar library of hexapeptides expressed as gene pIII fusions of M13 fd phage. PCT Application WO 91/19818 published Dec. 26, 1991 by Dower and Cwirla describes a similar library of pentameric to octameric random amino acid sequences. Devlin et al., 1990, Science, 249: 404–406, describes a peptide library of about 15 residues generated using an (NNS) coding scheme for oligonucleotide synthesis in which S is G or C. Christian and colleagues have described a phage display library, expressing decapeptides (Christian, R. B., et al., 1992, J. Mol. Biol. 227: 711–718).

Other investigators have used other viral capsid proteins for expression of non-viral DNA on the surface of phage particles. For example, the major capsid protein pVIII was so used by Cesareni, G., 1992, FEBS Lett. 307: 66–70. Other bacteriophage than M13 have been used to construct peptide libraries. Four and six amino acid sequences corresponding to different segments of the *Plasmodium falciparum* major surface antigen have been cloned and expressed in the filamentous bacteriophage fd (Greenwood, J., et al., 1991, J. Mol. Biol. 220: 821–827).

Kay et al., 1993, Gene 128: 59–65 (Kay) discloses a method of constructing peptide libraries that encode peptides of totally random sequence that are longer than those of any prior conventional libraries. The libraries disclosed in Kay encode totally synthetic random peptides of greater than about 20 amino acids in length. Such libraries can be advantageously screened to identify peptides, polypeptides and/or other proteins having binding specificity for a variety of ligands. (See also U.S. Pat. No. 5,498,538 dated Mar. 12, 1996; and PCT Publication No. WO 94/18318 dated Aug. 18, 1994.)

A comprehensive review of various types of peptide libraries can be found in Gallop et al., 1994, J. Med. Chem. 37:1233–1251.

Screening of peptide libraries has often been done using an antibody as ligand (Parmley and Smith, 1989, Adv. Exp. Med. Biol. 251:215–218; Scott and Smith, 1990, Science 249:386–390). In many cases, the aim of the screening is to identify peptides from the library that mimic the epitopes to which the antibodies are directed. Thus, given an available antibody, peptide libraries are excellent sources for identifying epitopes or epitope-like molecules of that antibody (Yayon et al., 1993, Proc. Natl. Acad. Sci. USA 90:10643–10647).

McCafferty et al., 1990, Nature 348:552–554 used PCR to amplify immunoglobulin variable (V) region genes and cloned those genes into phage expression vectors. The authors suggested that phage libraries of V, diversity (D), and joining (J) regions could be screened with antigen. The phage that bound to antigen could then be mutated in the antigen-binding loops of the antibody genes and rescreened. The process could be repeated several times, ultimately giving rise to phage which bind the antigen strongly.

Marks et al., 1991, J. Mol. Biol. 222:581–597 also used PCR to amplify immunoglobulin variable (V) region genes and cloned those genes into phage expression vectors.

Kang et al., 1991, Proc. Natl. Acad. Sci. USA 88:4363–4366 created a phagemid vector that could be used to express the V and constant (C) regions of the heavy and light chains of an antibody specific for an antigen. The heavy and light chain V-C regions were engineered to combine in the periplasm to produce an antibody-like molecule with a functional antigen binding site. Infection of cells harboring this phagemid with helper phage resulted in the incorporation of the antibody-like molecule on the surface of phage that carried the phagemid DNA. This allowed for identification and enrichment of these phage by screening with the antigen. It was suggested that the enriched phage could be subject to mutation and further rounds of screening, leading to the isolation of antibody-like molecules that were capable of even stronger binding to the antigen.

Hoogenboom et al., 1991, Nucleic Acids Res. 19:4133–4137 suggested that naive antibody genes might be cloned into phage display libraries. This would be followed by random mutation of the cloned antibody genes to generate high affinity variants.

Bass et al., 1990, Proteins: Struct. Func. Genet. 8:309–314 fused human growth hormone (hGH) to the carboxy terminus of the gene III protein of phage fd. This fusion protein was built into a phagemid vector. When cells carrying the phagemid were infected with a helper phage, about 10% of the phage particles produced displayed the fusion protein on their surfaces. These phage particles were enriched by screening with hGH receptor-coated beads. It was suggested that this system could be used to develop mutants of hGH with altered receptor binding characteristics.

Lowman et al., 1991, Biochemistry 30:10832–10838 used an improved version of the system of Bass et al. described above to select for mutant hGH proteins with exceptionally high affinity for the hGH receptor. The authors randomly mutagenized the hGH-pIII fusion proteins at sites near the vicinity of 12 amino acids of hGH that had previously been identified as being important in receptor binding.

Balass et al., 1993, Proc. Natl. Acad. Sci. USA 90:10638–10642 used a phage display library to isolate linear peptides that mimicked a conformationally dependent epitope of the nicotinic acetylcholine receptor. This was done by screening the library with a monoclonal antibody specific for the conformationally dependent epitope. The monoclonal antibody used was thought to be specific to the acetylcholine receptor's binding site for its natural ligand, acetylcholine.

2.2. Drug Delivery Systems

The common routes of therapeutic drug administration are oral ingestion or parenteral (intravenous, subcutaneous and intramuscular) routes of administration. Intravenous drug administration suffers from numerous limitations, including (i) the risk of adverse effects resulting from rapid accumulation of high concentrations of drug, (ii) repeated injections which can cause patient discomfort; and (iii) the risk of infection at the site of repeated injections. Subcutaneous injection is not generally suitable for delivering large volumes or for irritating substances. Whereas oral administration is generally more convenient, it is limited where the therapeutic agent is not efficiently absorbed by the gastrointestinal tract. To date, the development of oral formulations for the effective delivery of peptides, proteins and macromolecules has been an elusive target. Poor membrane permeability, enzymatic instability, large molecular size, and hydrophilic properties are four factors that have remained major hurdles for peptide and protein formulations (reviewed by Fix, J. A., 1996, J. Pharmac. Sci. 85:1282–1285). In order to develop an efficacious oral formulation, the peptide must be protected from the enzymatic environment of the gastrointestinal tract (GIT), presented to the absorptive epithelial barrier in a sufficient concentration to effect transcellular flux (Fix, J. A., 1996, J. Pharmac. Sci. 85:1282–1285), and if possible "smuggled" across the epithelial barrier in an apical to basolateral direction.

Site specific drug delivery or drug targeting can be achieved at different levels, including (i) primary targeting to a specific organ, (ii) secondary targeting to a specific cell type within that organ and (iii) tertiary targeting where the drug is delivered to specific intracellular structures (e.g., the nucleus for genes) (reviewed in Davis and Jllum, 1994, In: Targeting of Drugs 4, (Eds), Gregoriadis, McCormack and Poste, 183–194). At present there is a considerable amount of ongoing research work in the Drug Delivery Systems (DDS) area, and much of it addresses (i) targeting delivery and (ii) the development of non-invasive ways of getting macromolecules, peptides, proteins, products of the biotechnology industry, etc. into the body (Evers, P., 1995, Developments in Drug Delivery: Technology and Markets, Financial Times Management Report). It is generally accepted that targeted drug delivery is crucial to the improved treatment of certain diseases, especially cancer, and not surprisingly many of the approaches to targeted drug delivery are focused in the cancer area. Many anticancer drugs are toxic to the body as well as to malignant cells. If a drug, or a delivery system, can be modified so that it "homes in" on the tumor, then by maximizing the drug concentration at the disease site, the anti-cancer effect can be exploited to the full, while toxicity is greatly reduced. Tumors contain antigens which provoke the body to respond by producing antibodies designed to attach to the antigens and destroy them. Monoclonal antibodies are being used as both delivery vehicles targeted to tumor cells (reviewed by Pietersz, G. A., 1990, Bioconjugate Chem. 1:89–95) and as imaging agents to carry molecules of drug or imaging agent to the tumor surface.

2.3. Transport Pathways

The epithelial cells lining the lumenal side of the GIT are a major barrier to drug delivery following oral administration. However, there are four recognized transport pathways which can be exploited to facilitate drug delivery and transport: the transcellular, paracellular, carrier-mediated, and transcytotic pathways. The ability of a conventional drug, peptide, protein, macromolecule or nano- or microparticulate system to "interact" with one of these transport pathways may result in increased delivery of that drug or particle from the GIT to the underlying circulation.

In the case of the receptor-mediated, carrier-mediated or transcytotic transport pathways, some of the uptake signals have been identified. These signals include, inter alia, folic acid, which interacts with the folate receptor, and cobalamin, which interacts with Intrinsic Factor. In addition, leucine- and tyrosine-based peptide sorting motifs or internalization sequences exist, such as YSKV, FPHL, YRGV, YQTI, TEQF, TEVM, TSAF, and YTRF (SEQ ID NOS:203, 204, 205, 206, 207, 208, 209, and 210, respectively), which facilitate uptake or targeting of proteins using specific membrane receptors or binding sites to identify peptides that bind specifically to the receptor or binding site.

Non-receptor based assays to discover particular ligands have also been used. For instance, a strategy for identifying peptides that alter cellular function by scanning whole cells with phage display libraries is disclosed in Fong et al., Drug Development Research 33:64–70 (1994). However, because whole cells, rather than intact tissue or polarized cell cultures, are used for screening phage display libraries, this procedure does not provide information regarding sequences whose primary function includes affecting transport across polarized cell layers.

Additionally, Stevenson et al., Pharmaceutical Res. 12(9), S94 (1995) discloses the use of Caco-2 monolayers to screen a synthetic tripeptide combinatorial library for information relating to the permeability of di- and tri-peptides.

A method of identifying a peptide which permits or facilitates the transport of an active agent through human or animal tissues has been developed (see U.S. patent application Ser. No. 08/746,411 filed Nov. 8, 1996, which is incorporated by reference herein in its entirety). Phage from a random phage library is plated onto or brought into contact with a first side, preferably the apical side, of a tissue sample, either in vitro, in vivo or in situ, or polarized tissue cell culture. The phage which is transported to a second side of the tissue opposite the first side, preferably the basolateral side, is harvested to select transported phages. The transported phages are amplified in a host and this cycle is repeated (using the transported phage from the most recent cycle) to obtain a selected phage library containing phage which can be transported from the first side to the second side.

Discussion or citation of a reference hereinabove shall not be construed as meaning that such reference is prior art to the present invention.

3. SUMMARY OF THE INVENTION

The present invention relates generally to random peptides and peptide motifs capable of specific binding to GIT transport receptors. Such proteins can be identified using any random peptide library, e.g., a chemically synthesized peptide library or a biologically expressed peptide library. If a biological peptide expression library is used, the nucleic acid which encodes the peptide which binds to the ligand of choice can be recovered, and then sequenced to determine its nucleotide sequence and hence deduce the amino acid sequence that mediates binding. Alternatively, the amino acid sequence of an appropriate binding domain can be determined by direct determination of the amino acid sequence of a peptide selected from a peptide library containing chemically synthesized peptides. In a less preferred aspect, direct amino acid sequencing of a binding peptide selected from a biological peptide expression library can also be performed.

In particular, this invention relates to proteins (e.g., peptides) that are capable of facilitating transport of an active agent through a human or animal gastro-intestinal tissue, and derivatives (e.g., fragments) and analogs thereof, and nucleotide sequences coding for said proteins and derivatives.

Preferably, the tissue through which transport is facilitated is of the duodenum, jejunum, ileum, ascending colon, transverse colon, descending colon, or pelvic colon. The tissue is most preferably epithelial cells lining the lumenal side of the GIT.

The proteins of the invention have use in facilitating transport of active agents from the lumenal side of the GIT into the systemic blood system, and/or in targeting active agents to the GIT. Thus, for example, by binding (covalently or noncovalently) a protein of the invention to an orally administered drug, the drug can be targeted to specific receptor sites or transport pathways which are known to operate in the human gastrointestinal tract, thus facilitating its absorption into the systemic system.

The invention also relates to derivatives and analogs of the invention which are functionally active, i.e., they are capable of displaying one or more known functional activities associated with a full-length peptide. Such functional activities include but are not limited to antigenicity (ability to bind or to compete with GIT transport receptor-binding peptides for binding to an anti-GIT transport receptor antibody) and ability to bind or compete with full-length peptide for binding to a GIT transport receptor.

The invention further relates to fragments of (and derivatives and analogs thereof) GIT transport receptor-binding peptides which comprise one or more motifs of a GIT transport receptor-binding peptide.

Antibodies to GIT transport receptor-binding peptides and GIT transport receptor-binding peptide derivatives and analogs are additionally provided.

Methods of production of the GIT transport receptor-binding peptides, derivatives, fragments and analogs, e.g., by recombinant means, are also provided.

The present invention also relates to therapeutic methods, pharmaceutical compositions and formulations based on GIT transport receptor-binding peptides. Formulations of the invention include but are not limited to GIT transport receptor-binding peptides or motifs and derivatives (including fragments) thereof; antibodies thereto; and nucleic acids encoding the GIT transport receptor-binding peptides or derivatives associated with an active agent. Preferably, the active agent is a drug or drug-containing nano- or microparticle.

The GIT transport-receptor binding proteins of the invention can also be used to determine levels of the GIT transport receptors in a sample by binding thereto.

The GIT transport-receptor binding proteins can also be used to identify molecules that bind thereto, by contacting candidate test molecules under conditions conducive to binding, and detecting any binding that occurs.

4. DESCRIPTION OF THE FIGURES

FIG. 1. FIG. 1 shows the human PEPT1 predicted amino acid sequence determined from the sequence of the cDNA clone coding for human PEPT1 (SEQ ID NO:176) (Liang R. et al. J. Biol. Chem. 270(12):6456–6463 (1995)), including the extracellular domain from amino acid 391 to 573 (Fei et al., Nature 368:563 (1994)).

FIGS. 2A–2C. FIGS. 2A–2C show the DNA sequence of the cDNA coding for the human intestinal peptide-associated transporter HPT1 and the corresponding putative amino acid sequence (bases 1 to 3345; Medline:94204643) (SEQ ID NOS: 177 and 178, respectively).

FIGS. 3A–3B. FIGS. 3A–3B show the putative Human Sucrase-isomaltase complex(hSI) amino acid sequence determined from the sequence of the cDNA clone coding for human sucrase-isomaltase complex (SEQ ID NO:179) (Chantret I., et al., Biochem. J. 285(Pt 3):915–923 (1992).

FIGS. 4A–4B. FIGS. 4A–4B show the D2H nucleotide and deduced amino acid sequence for the human D2H transporter (SEQ ID NOS:180 and 181, respectively) (Wells, R. G. et al., J. Clin. Invest. 90:1959–1963 (1993).

FIGS. 5A–5C. FIG. 5A is a schematic summary of the cloning of the DNA insert present in gene III of the phages selected from the phage display libraries into the expression vector pGex-4T-2. The gene insert in gene III of the phages was amplified by PCR using DNA primers which flank the gene insert and which contained recognition sequences for specific restriction endonucleases at their extreme 5' sides. Alternatively, specific primers which amplify specific regions of the DNA inserts in gene III of the phages, and which contained recognition sequences for specific restriction endonucleases at their extreme 5' sides, were used in PCR amplification experiments. Following amplification of the gene inserts, the amplified PCR fragments were digested with the restriction endonucleases Xho1 and Not1. Similarly the plasmid pGex-4T-2, which codes for the reporter protein glutathione S-transferase (GST), was digested with the restriction endonucleases Sal1 and Not1. The digested PCR fragments were ligated into the digested plasmid pGex-4T-2 using T4 DNA Ligase and the ligated products were transformed into competent *Escherichia coli*, with selection of transformants on agar plates containing selection antibiotic. The selected clones were cultured, the plasmids were recovered and the in-frame sequence of the DNA insert in the plasmids was confirmed by DNA sequencing. The correct clones were subsequently used for expression of the GST-fusion proteins (SEQ ID NO:182); FIG. 5B shows the series of full-length P31 (designated P31) (SEQ ID NO:43) and truncated peptides derived from P31 (clones # 101, 102, 103 and 119), (SEQ ID NOS:183, 184, 185, and 186, respectively) full-length PAX2 (designated PAX2) (SEQ ID NO:55) and truncated peptides derived from PAX2 (clones # 104, 105, 106) (SEQ ID NOS:170, 187, and 188, respectively) and full-length DCX8 (DCX8) (SEQ ID NO:23) and series of truncated peptides derived from DCX8 (clones # 107, 108, 109) (SEQ ID NOS:189, 190, and 191, respectively) that were expressed as fusion proteins to GST. The construction of these GST-fusion proteins is shown in FIG. 5A. FIG. 5C shows the series of full-length P31 (designated P31) (SEQ ID NO:43) and truncated peptides derived from P31 (clones # 103, 110, 119, 111, and 112) (SEQ ID NOS:185, 192, 186, 194, and 195, respectively), full-length PAX2 (designated PAX2) (SEQ ID NO:55) and truncated peptides derived from PAX2 (clones # 106, 113, 114, 115) (SEQ ID NOS:188, 196, 197, and 198, respectively) and full-length SNi10 (designated SNi10) (SEQ ID NO:4) and series of truncated peptides derived from SNi10 (clones # 116, 117, 118) (SEQ ID NOS:199, 200, and 405, respectively) that were expressed as fusion proteins to GST. The construction of these GST-fusion proteins is shown in FIG. 5A. (Underlining and bold in FIGS. 5A–5C are for orientation of the sequences.)

FIGS. 6A–6B. FIGS. 6A–6B show the binding of GST and GST-fusion proteins to recombinant hSI and to fixed C2BBe1 fixed cells as detected by ELISA assays. FIG. 6A shows the binding of the control protein GST, which does not contain a fusion peptide, and the GST-fusion proteins from SNi10 (designated GST-SNi10) and SNi34 (designated GST-SNi34) to recombinant hSI. FIG. 6B shows the binding of the control protein GST, which does not contain a fusion peptide, and the GST-fusion proteins from SNi10 (designated GST-SNi10) and SNi34 (designated GST-SNi34) to fixed C2BBe1 cells.

FIGS. 7A–7M. FIGS. 7A–7M show the binding of GST peptide and truncated fusion proteins to fixed Caco-2 cells, fixed C2BBe1 cells, and fixed A431 cells or to recombinant GIT transport receptors D2H, HPT1, hPEPT1 or to BSA using increasing concentrations (expressed as µg/ml on the X-axis) of the control GST protein and the GST-fusion proteins, as detected by ELISA assays. FIG. 7A shows the binding of the control protein GST, which does not contain a fusion peptide, and the series of GST-fusion proteins from P31 including the fusion to full-length P31 peptide (designated P31) (SEQ ID NO:43) and clone # 101 (designated P31,101, SEQ ID NO: 183), clone # 102 (designated P31, 102 SEQ ID NO: 184) and clone # 103 (designated P31,103 SEQ ID NO: 185). FIG. 7B shows the binding of the control protein GST, which does not contain a fusion peptide, and the series of GST-fusion proteins from PAX2 including the fusion to full-length PAX2 peptide (designated PAX2) and clone # 104 (designated PAX2,104), clone # 105 (designated PAX2, 105) and clone # 106 (designated PAX2,106) (SEQ ID NOS:55, 170, 187, and 188, respectively). FIG. 7C shows the binding of the control protein GST, which does not contain a fusion peptide, and the series of GST-fusion proteins from DCX8 including the fusion to full-length DCX8 peptide (designated DCX8) and clone # 107 (designated DCX8,107), clone # 108 (designated DCX8, 108) and clone # 109 (designated DCX8,109) (SEQ ID NOS:23, 189, 190, and 191, respectively). FIG. 7D shows the binding of the control protein GST, which does not contain a fusion peptide, and the GST-fusion proteins from DCX8 (designated GST-DCX8) and DCX11 (designated GST-DCX11) to recombinant D2H. FIG. 7E shows the binding of the control protein GST, which does not contain a fusion peptide, and the GST-fusion proteins from DCX8 (designated GST-DCX8) and DCX11 (designated GST-DCX11) to fixed C2BBe1 cells. FIG. 7F shows the binding of the control protein GST, which does not contain a fusion peptide, and the GST-fusion proteins from P31 (designated GST-P31) and 5PAX5 (designated GST-5PAX5) to recombinant hPEPT1. FIG. 7G shows the binding of the control protein GST, which does not contain a fusion peptide, and the GST-fusion proteins from P31 (designated GST-P31) and 5PAX5 (designated GST-5PAX5) to fixed C2BBe1 cells. FIG. 7H shows the binding of the control protein GST, which does not contain a fusion peptide, and the GST-fusion proteins from HAX42 (designated GST-HAX42) and PAX2 (designated GST-PAX2) to recombinant HPT1. FIG. 7I shows the binding of the control protein GST, which does not contain a fusion peptide, and the GST-fusion proteins from HAX42 (designated GST-HAX42) and PAX2 (designated GST-PAX2) to fixed C2BBe1 cells. FIG. 7J shows the binding of the control protein GST, which does not contain a fusion peptide, and the GST-fusion proteins from P31 (designated GST-P31) and truncated derivatives clone # 101 (designated GST-P31-101, SEQ ID NO: 183), clone # 102 (designated GST-P31-102, SEQ ID NO: 184), clone # 103 (designated GST-P31-103, SEQ ID NO: 185) to either recombinant hPEPT1 or to BSA. FIG. 7K shows the binding of the control protein GST, which does not contain a fusion peptide, and the GST-fusion proteins from P31 (designated GST-P31) and truncated derivatives clone # 101 (designated GST-P31-101, SEQ ID NO: 183), clone # 102 (designated GST-P 31-102, SEQ ID NO: 184), clone # 103 (designated GST-P31-103, SEQ ID NO: 185) to either fixed C2BBe1 cells or to fixed A431 cells. FIG. 7L shows the binding of the control protein GST, which does not contain a fusion peptide, and the GST-fusion proteins from PAX2 (designated GST-PAX2) and truncated derivatives clone # 104 (designated GST-PAX2-104, SEQ ID NO: 170), clone # 105 (designated GST-PAX2-105, SEQ ID NO: 187), clone # 106 (designated GST-PAX2-106, SEQ ID NO: 188) to either recombinant hPEPT1 or to BSA. FIG. 7M shows the binding of the control protein GST, which does not contain a fusion peptide, and the GST-fusion proteins from PAX2 (designated GST-PAX2) and truncated derivatives clone # 106 (designated GST-PAX2-106, SEQ ID NO: 188)to either fixed Caco-2 cells or to fixed A431 cells.

FIGS. 8A–8D. FIG. 8 shows the transport of GST or GST-peptide fusion derivatives across polarized Caco-2 cells in an apical to basolateral direction as a function of time (1–4 hours) as detected by ELISA assays. FIG. 8A shows the transport of either GST, the GST fusion to full-length P31 peptide (designated P31) (SEQ ID NO:43) and the GST clone derivative clone # 103 (designated P31.103, SEQ ID NO: 185) across polarized Caco-2 cells in an apical to basolateral as a function of time (in hours) following initial administration of the proteins to the apical medium of polarized Caco-2 cells. The line designated No Protein corresponds to control assays in which buffer control was applied to the apical medium of polarized Caco-2 cells followed by sampling of the basolateral medium as a function of time (hours) and assay for GST by the ELISA assay.

FIG. 8B shows the transport of either GST, the GST fusion to full-length PAX2 peptide (designated PAX2) and the GST clone derivative clone # 106 (designated PAX2.106, SEQ ID NO: 188) across polarized Caco-2 cells in an apical to basolateral as a function of time (in hours) following initial administration of the proteins to the apical medium of polarized Caco-2 cells. The line designated No Protein corresponds to control assays in which buffer control was applied to the apical medium of polarized Caco-2 cells followed by sampling of the basolateral medium as a function of time (hours) and assay for GST by the ELISA assay. FIG. 8C shows the transport of either GST, the GST fusion to full-length DCX8 peptide (designated DCX8), and the GST clone derivatives clone # 107 (designated DCX8.107) and clone # 109 (designated DCX8.109) across polarized Caco-2 cells in an apical to basolateral as a function of time (in hours) following initial administration of the proteins to the apical medium of polarized Caco-2 cells. The line designated No Protein corresponds to control assays in which buffer control was applied to the apical medium of polarized Caco-2 cells followed by sampling of the basolateral medium as a function of time (hours) and assay for GST by the ELISA assay. FIG. 8D shows the amount of the GST and GST-fusion proteins (GST fusions to P31, P31-103 (SEQ ID NO: 183), PAX2, PAX2.106 (SEQ ID NO: 188), DCX8, DCX8-107, DCX8-109), used in the experiments shown in panels A–C above, in the apical medium of the polarized Caco-2 cells as detected by ELISA assay.

FIGS. 9A–9B. FIGS. 9A–9B show the inhibition of GST-P31 binding to C2BBe1 fixed cells with varying concentration of competitors while holding the concentration of GST-P31 constant at 0.015 µM; the peptide competitors are ZElan024 (SEQ ID NO:288) which is the dansylated peptide version of P31 (SEQ ID NO:43) and ZElan044 (SEQ ID NO:310), ZElan049 (SEQ ID NO:315) and ZElan050 (SEQ ID NO:316) which are truncated, dansylated pieces of P31 (SEQ ID NO:43). Data is presented as O.D. versus peptide concentration (FIG. 9A) and as percent inhibition of GST-P31 binding versus peptide concentration (FIG. 9B).

FIGS. 10A–10C. FIGS. 10A–10C present a compilation of the results of competition ELISA studies of GST-P31, GST-PAX2, GST-SNi10 and GST-HAX42 versus listed dansylated peptides on fixed C2BBe1 cells ("Z" denotes ϵ-amino dansyl lysine). The pI of the dansylated peptides is also included. Estimated $IC_{50}$ values are in µM and where present, $IC_{50}$ ranges refer to results from multiple assays. If the $IC_{50}$ value could not be determined, a ">" or "<" symbol is used. The GST/C2BBe1 column shows GST protein binding to fixed C2BBe1 cells.

FIGS. 11A–11B. FIG. 11A shows the transport of GST or GST-peptide fusion derivatives across polarized Caco-2 cells in an apical to basolateral direction at 0, 0.5, 2 and 4 hours as detected by ELISA assays and described elsewhere in the text in full detail. The proteins used in the assay included GST, GST-P31 fusion, GST-5PAX5 fusion, GST-DCX8 fusion, GST-DCX11 fusion, GST-PAX2 fusion, GST-HAX42 fusion, GST-SNi34 fusion and GST-SNi10 fusion. The column designated No protein refers to control experiments in which buffer was applied to the apical medium of the cells and ELISA assay was performed on the corresponding basolateral medium of these cells at 0, 0.5, 2 and 4 hours post buffer addition. FIG. 11B shows the internalization of GST or GST-peptide fusion derivatives within polarized Caco-2 cells following administration of the GST or GST-fusion protein derivatives to the apical medium of polarized Caco-2 cells and subsequent recovery of the cells from the transwells and detection of the GST or GST fusions within the recovered cell lysates as detected by ELISA assays and as described elsewhere in the text in full detail. The proteins used in the assay included GST, GST-P31 fusion, GST-5PAX5 fusion, GST-DCX8 fusion, GST-DCX11 fusion, GST-PAX2 fusion, GST-HAX42 fusion, GST-SNi34 fusion and GST-SNi10 fusion. The column designated No protein refers to control experiments in which buffer was applied to the apical medium of the cells and ELISA assay was performed on the corresponding cell lysates of these cells at the end of the experiment.

Figure 12:
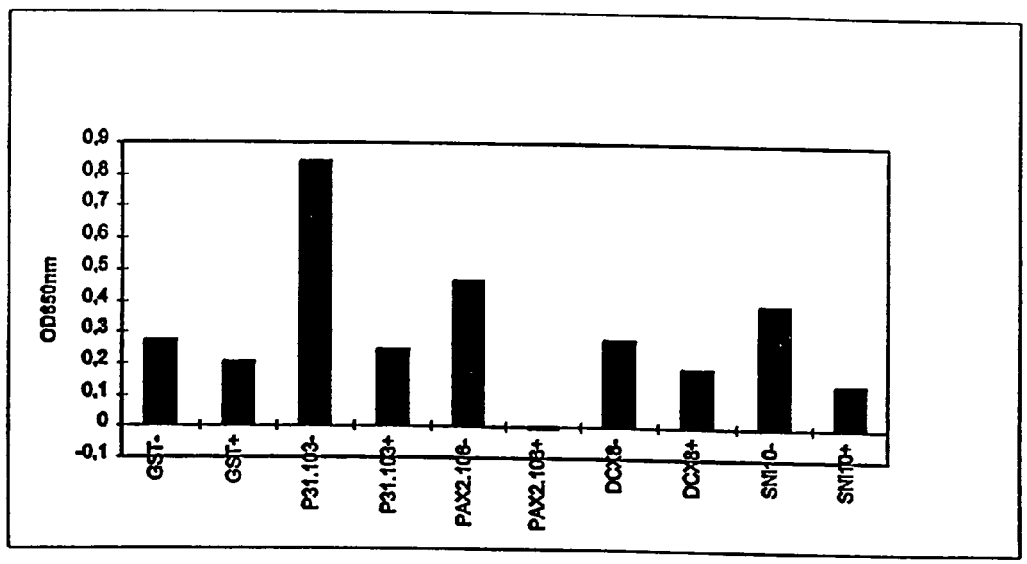

FIG. 12. FIG. 12 shows the binding of GST and GST-fusion proteins to fixed Caco-2 cells, and the corresponding proteins following digestion with the protease Thrombin which lysine). The pI of the dansylated peptides is also included. Estimated $IC_{50}$ values are in µM and where present, $IC_{50}$ ranges refer to results from multiple assays. If the $IC_{50}$ value could not be determined, a ">" or "<" symbol is used. The GST/C2BBe1 column shows GST protein binding to fixed C2BBe1 cells.

FIGS. 11A–11B. FIG. 11A shows the transport of GST or GST-peptide fusion derivatives across polarized Caco-2 cells in an apical to basolateral direction at 0, 0.5, 2 and 4 hours as detected by ELISA assays and described elsewhere in the text in full detail. The proteins used in the assay included GST, GST-P31 fusion, GST-5PAX5 fusion, GST-DCX8 fusion, GST-DCX11 fusion, GST-PAX2 fusion, GST-HAX42 fusion, GST-SNi34 fusion and GST-SNi10 fusion. The column designated No protein refers to control experiments in which buffer was applied to the apical medium of the cells and ELISA assay was performed on the corresponding basolateral medium of these cells at 0, 0.5, 2 and 4 hours post buffer addition. FIG. 11B shows the internalization of GST or GST-peptide fusion derivatives within polarized Caco-2 cells following administration of the GST or GST-fusion protein derivatives to the apical medium of polarized Caco-2 cells and subsequent recovery of the cells from the transwells and detection of the GST or GST fusions within the recovered cell lysates as detected by ELISA assays and as described elsewhere in the text in full detail. The proteins used in the assay included GST, GST-P31 fusion, GST-5PAX5 fusion, GST-DCX8 fusion, GST-DCX11 fusion, GST-PAX2 fusion, GST-HAX42 fusion, GST-SNi34 fusion and GST-SNi10 fusion. The column designated No protein refers to control experiments in which buffer was applied to the apical medium of the cells and ELISA assay was performed on the corresponding cell lysates of these cells at the end of the experiment.

FIG. 12. FIG. 12 shows the binding of GST and GST-fusion proteins to fixed Caco-2 cells, and the corresponding proteins following digestion with the protease Thrombin which cleaves at a recognition site between the GST portion and the fused peptide portion of the GST-fusion protein. The symbol "−" refers to proteins which were not digested with thrombin and the symbol "+" refers to proteins which were digested with thrombin prior to use in the binding assay. The binding of the proteins to the fixed Caco-2 cells was detected by ELISA assays.

FIGS. 13A–13B. FIGS. 13A–13B show binding of peptide-coated nanoparticles to fixed Caco-2 cells.

FIGS. 14A–14B. FIGS. 14A–14B show the binding of (A) dansylated peptide SNi10 to the purified hSI receptor and BSA and (B) dansylated peptides and peptide-loaded insulin-containing PLGA particles to fixed C2BBe1 cells. FIG. 14B depicts binding of dansylated peptides corresponding to P31 (SEQ ID NO:43), PAX2, HAX42, and SNi10 to fixed C2BBe1 cells, as well as the insulin-containing PLGA particles adsorbed with each of these peptides. Data is presented with background subtracted.

FIGS. 15A–15B. FIG. 15 shows the binding of peptide-coated particles to A) S100 and B) P100 fractions harvested from Caco-2 cells. The dilution series 1:2–1:64 represents particle concentrations in the range 0.0325–0.5 µg/well. Data is presented with background subtracted. The particles are identified as follows: 939, no peptide; 1635, scrambled PAX2; 1726, P31 D-Arg 16-mer (ZElan053, SEQ ID NO:319); 1756, HAX42; 1757, PAX2; 1758, HAX42/PAX2.

FIGS. 16A–16B. FIG. 16 shows the binding of dansylated peptides to P100 fractions harvested from Caco-2 cells. Peptides were assayed in the range 0.0032–2.5 µg/well. Data is presented with background subtracted. A) HAX42, P31 D-form (ZElan 053, (SEQ ID NO:319) and scrambled PAX2; B) PAX2, HAX42 and scrambled PAX2.

FIGS. 17A–17B. FIGS. 17A and 17B show (A) the systemic blood glucose and (B)insulin levels following intestinal administration of control (PBS); insulin solution; insulin particles; all 8 peptides mix particles and study group peptide-particles according to this invention (100 iu insulin loading).

FIGS. 18A–18B. FIGS. 18A and 18B show the (A) systemic blood glucose and (B)insulin levels following intestinal administration of control (PBS); insulin solution; insulin particles and study group peptide-particles according to this invention (300 iu insulin loading).

Figure 19:
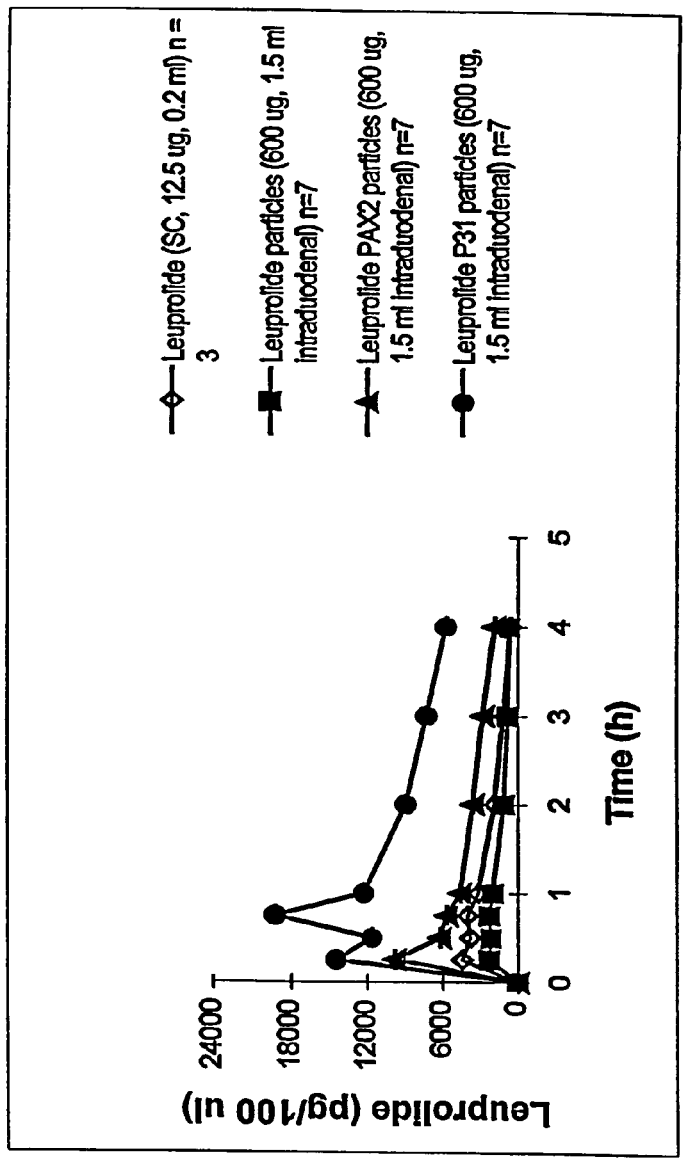

FIG. 19. FIG. 19 shows the enhanced plasma levels of leuprolide upon administration of P31 (SEQ ID NO:43) and PAX2 coated nanoparticles loaded with leuprolide relative to subcutaneous injection. Group 1 was administered leuprolide acetate (12.5 µg) subcutaneously. Group 2 was administered intraduodenally uncoated leuprolide acetate particles (600 µg, 1.5 ml). Group 3 was intraduodenally administered leuprolide acetate particles coated with PAX2 (600 µg; 1.5 ml). Group 4 was administered intraduodenally leuprolide acetate particles coated with P31 (SEQ ID NO:43) (600 µg, 1.5 ml).

FIG. 20. FIG. 20 lists P31 (SEQ ID NO:43) known protein homologies.

FIGS. 21A–21C. FIGS. 21A–21C list DCX8 known protein homologies.

FIG. 22. FIG. 22 lists DAB10 known protein homologies.

FIG. 23. FIG. 23 shows the DNA sequence (SEQ ID NO:211) and the corresponding amino acid sequence (SEQ ID NO:212) for glutathione S-transferase (Smith and Johnson, 1988, Gene 7:31–40).

5. DETAILED DESCRIPTION OF THE INVENTION

The present invention relates to proteins (e.g., peptides) that bind to GIT transport receptors and nucleic acids that encode such proteins. The invention further relates to fragments and other derivatives of such proteins. Nucleic acids encoding such fragments or derivatives are also within the scope of the invention. The invention further relates to fragments (and derivatives and analogs thereof) of GIT transport receptor-binding peptides which comprise one or more domains of the GIT transport receptor-binding peptides.

The invention also relates to derivatives of GIT transport receptor-binding proteins and analogs of the invention which are functionally active, i.e., they are capable of displaying one or more known functional activities associated with a full-length GIT transport receptor-binding peptide. Such functional activities include but are not limited to ability to bind to a GIT transport receptor, antigenicity [ability to bind (or compete with peptides for binding) to an anti-GIT transport receptor-binding peptide antibody], immunogenicity (ability to generate antibody which binds to GIT transport receptor-binding peptide), etc.

Production of the foregoing proteins and derivatives, by, e.g., recombinant methods, is also provided.

Antibodies to GIT transport receptor-binding proteins, derivatives and analogs, are additionally provided.

The present invention also relates to therapeutic and diagnostic methods and compositions based on GIT transport receptor-binding proteins and nucleic acids.

The invention is illustrated by way of examples infra.

For clarity of disclosure, and not by way of limitation, the detailed description of the invention is divided into the subsections which follow.

5.1. GIT Transport Receptor-Binding Peptides, Derivatives and Analogs

The invention relates to peptides that bind GIT transport receptors and derivatives (including but not limited to fragments) and analogs thereof. In specific embodiments, of the present invention, such peptides that bind to GIT transport receptor include but are not limited to those containing as primary amino acid sequences, all or part of the amino acid sequences substantially as depicted in Table 7 (SEQ ID NOS:1–55). Nucleic acids encoding such peptides, derivatives and peptide analogs are also provided. In one embodiment, the GIT transport receptor-binding peptides are encoded by the nucleic acids having the nucleotide sequences set forth in Table 8 infra (SEQ ID NOS:56–109). Proteins whose amino acid sequence comprise, or alternatively, consist of SEQ ID NOS:1–55 or a portion thereof that mediates binding to a GIT transport receptor are provided.

The production and use of derivatives and analogs related to GIT transport receptor-binding peptides are within the scope of the present invention. In a specific embodiment, the derivative or analog is functionally active, i.e., capable of exhibiting one or more functional activities associated with a full-length GIT transport receptor-binding peptide. For example, such derivatives or analogs which have the desired immunogenicity or antigenicity can be used, in immunoassays, for immunization, etc. A specific embodiment relates to a GIT transport receptor-binding peptide fragment that can be bound by an anti-GIT transport receptor-binding peptide antibody. In a preferred aspect, the derivatives or analogs have the ability to bind to a GIT transport receptor. Derivatives or analogs of GIT transport receptor-binding peptides can be tested for the desired activity by procedures known in the art, including binding to a GIT transport receptor domain or to Caco-2 cells, in vitro, or to intestinal tissue, in vivo. (See the Examples infra.)

In particular, derivatives can be made by altering GIT transport receptor-binding peptide sequences by substitutions, additions or deletions that provide for functionally equivalent molecules. Due to the degeneracy of nucleotide coding sequences, other nucleotide sequences which encode substantially the same amino acid sequence may be used in the practice of the present invention. These include but are not limited to nucleotide sequences which are altered by the substitution of different codons that encode a functionally equivalent amino acid residue within the sequence, thus producing a silent change. Likewise, the GIT transport receptor-binding peptide derivatives of the invention include, but are not limited to, those containing, as a primary amino acid sequence, all or part of the amino acid sequence of a GIT transport receptor-binding peptide including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or, alternatively, comprising all or a fragment of a GIT transport receptor-binding peptide consisting of at least 5, 10, 15, 20, 25, 30 or 35 (contiguous) amino acids of the full-length GIT transport receptor-binding peptide are provided. In a specific embodiment, such proteins are not more than 20, 30, 40, 50, or 75 amino acids in length. Derivatives or analogs of GIT transport receptor-binding peptides include but are not limited to those molecules comprising regions that are substantially homologous to GIT transport receptor-binding peptides or fragments thereof (e.g., at least 50%, 60%, 70%, 80% or 90% identity) (e.g., over an identical size sequence or when compared to an aligned sequence in which the alignment is done by a computer homology program known in the art) or whose encoding nucleic acid is capable of hybridizing to a coding GIT transport receptor-binding peptide sequence, under stringent, moderately stringent, or nonstringent conditions.

In a specific embodiment, the GIT transport receptor-binding derivatives of the invention are not known proteins with homology to the GIT transport receptor-binding peptides of the invention or portions thereof.

The GIT transport receptor-binding peptide derivatives and analogs of the invention can be produced by various methods known in the art. The manipulations which result in their production can occur at the gene or protein level. For example, the cloned GIT transport receptor-binding peptide gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of GIT transport receptor-binding peptides, care should be taken to ensure that the modified gene remains within the same translational reading frame uninterrupted by translational stop signals, in the gene region where the desired GIT transport receptor-binding peptides activity is encoded.

Additionally, nucleic acid sequences encoding the GIT transport receptor-binding peptides can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), use of PCR primers containing mutation(s) for use in amplification, etc.

Manipulations of GIT transport receptor-binding peptide sequences may also be made at the protein level. Included within the scope of the invention are GIT transport receptor-binding peptide fragments or other derivatives or analogs which are differentially modified during or after translation or chemical synthesis, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc. In a specific embodiment, the amino- and/or carboxy-termini are modified.

In addition, GIT transport receptor-binding peptides and analogs and derivatives thereof can be chemically synthesized. For example, a peptide corresponding to all or a portion of a GIT transport receptor-binding peptide which comprises the desired domain or which mediates the desired activity in vitro, can be synthesized by use of a peptide synthesizer. Furthermore, if desired, nonclassical amino acids or chemical amino acid analogs can be introduced as a substitution or addition into the GIT transport receptor-binding peptide sequence. Non-classical amino acids include but are not limited to the D-isomers of the common amino acids, $\alpha$-amino isobutyric acid, 4-aminobutyric acid, Abu, 2-amino butyric acid, $\gamma$-Abu, $\epsilon$-Ahx, 6-amino hexanoic acid, Aib, 2-amino isobutyric acid, 3-amino propionic acid, ornithine, norleucine, norvaline, hydroxyproline, sarcosine, 30 citrulline, cysteic acid, t-butylglycine, t-butylalanine, phenylglycine, cyclohexylalanine, $\beta$-alanine, fluoro-amino acids, designer amino acids such as $\beta$-methyl amino acids, C$\alpha$-methyl amino acids, N$\alpha$-methyl amino acids, and amino acid analogs in general. Furthermore, the amino acid can be D (dextrorotary) or L (levorotary).

In a specific embodiment, the GIT transport receptor-binding peptide derivative is a chimeric, or fusion, peptide comprising a GIT transport receptor-binding peptide or fragment thereof (preferably consisting of at least a domain or motif of the GIT transport receptor-binding peptide, or at least 6, 10, 15, 20, 25, 30 or all amino acids of the GIT transport receptor-binding peptides or a binding portion thereof) joined at its amino- or carboxy-terminus via a peptide bond to an amino acid sequence of a different peptide. In one embodiment, such a chimeric peptide is produced by recombinant expression of a nucleic acid encoding the protein (comprising a transport receptor-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of GIT transport receptor fused to any heterologous protein-encoding sequences may be constructed. A specific embodiment relates to a chimeric protein comprising a fragment of GIT transport receptor-binding peptides of at least six amino acids.

In another specific embodiment, the GIT transport receptor-binding peptide derivative is a molecule comprising a region of homology with a GIT transport receptor-binding peptide. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a GIT transport receptor-binding peptide domain (see infra) or a portion thereof.

The GIT transport receptor-binding proteins and derivatives thereof of the invention can be assayed for binding activity by suitable in vivo or in vitro assays, e.g., as described in the examples infra and/or as will be known to the skilled artisan.

Other specific embodiments of derivatives and analogs are described in the subsection below and examples sections infra.

5.2. Motifs/Derivatives of GIT Transport Receptor-Binding Peptides Containing One or More Domains of the Protein In a specific embodiment, the invention relates to GIT transport receptor-binding peptide derivatives and analogs, in particular GIT transport receptor-binding peptide fragments and derivatives of such fragments, that comprise, or alternatively consist of, one or more domains of a GIT transport receptor-binding peptide. In particular, examples of such domains are identified in the examples infra.

5.3. Synthesis of Peptides

The peptides and derivatives of the present invention may be chemically synthesized or synthesized using recombinant DNA techniques.

5.3.1. Procedure For Solid Phase Synthesis

Peptides may be prepared chemically by methods that are known in the art. For example, in brief, solid phase peptide synthesis consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, J. Am. Chem. Soc. 85:2149; Vale et al., 1981, Science 213:1394–1397; Marki et al., 1981, J. Am. Chem. Soc. 103:3178 and in U.S. Pat. Nos. 4,305,872 and 4,316,891. In a preferred aspect, an automated peptide synthesizer is employed.

By way of example but not limitation, peptides can be synthesized on an Applied Biosystems Inc. ("ABI") model 431A automated peptide synthesizer using the "Fastmoc" synthesis protocol supplied by ABI, which uses 2-(1H-Benzotriazol-1-yl)-1,1,3,3-tetramethyluronium hexafluorophosphate ("HBTU") (R. Knorr et al., 1989, Tet. Lett., 30:1927) as coupling agent. Syntheses can be carried out on 0.25 mmol of commercially available 4-(2',4'-dimethoxyphenyl-(9-fluorenyl-methoxycarbonyl)-aminomethyl)-phenoxy polystyrene resin ("Rink resin" from Advanced ChemTech) (H. Rink, 1987, Tet. Lett. 28:3787). Fmoc amino acids (1 mmol) are coupled according to the Fastmoc protocol. The following side chain protected Fmoc amino acid derivatives are used: FmocArg(Pmc)OH; FmocAsn(Mbh)OH; FmocAsp($^t$Bu)OH; FmocCys(Acm)OH; Fmoc-Glu($^t$Bu)OH; FmocGln(Mbh)OH; FmocHis(Tr)OH; FmocLys(Boc)OH; FmocSer($^t$Bu)OH; FmocThr($^t$Bu)OH; FmocTyr($^t$Bu)OH. [Abbreviations: Acm, acetamidomethyl; Boc, tert-butoxycarbonyl; $^t$Bu, tert-butyl; Fmoc, 9-fluorenylmethoxycarbonyl; Mbh, 4,4'-dimethoxybenzhydryl; Pmc, 2,2,5,7,8-pentamethylchroman-6-sulfonyl; Tr, trityl].

Synthesis is carried out using N-methylpyrrolidone (NMP) as solvent, with HBTU dissolved in N,N-dimethylformamide (DMF). Deprotection of the Fmoc group is effected using approximately 20% piperidine in NMP. At the end of each synthesis the amount of peptide present is assayed by ultraviolet spectroscopy. A sample of dry peptide resin (about 3–10 mg) is weighed, then 20% piperidine in DMA (10 ml) is added. After 30 min sonication, the UV (ultraviolet) absorbance of the dibenzofulvene-piperidine adduct (formed by cleavage of the N-terminal Fmoc group) is recorded at 301 nm. Peptide substitution (in mmol g$^{-1}$) can be calculated according to the equation:

$$\text{substitution} = \frac{A \times v}{7800 \times w} \times 1000$$

where A is the absorbance at 301 nm, v is the volume of 20% piperidine in DMA (in ml), 7800 is the extinction coefficient (in mol$^{-1}$dm$^3$ cm$^{-1}$) of the dibenzofulvene-piperidine adduct, and w is the weight of the peptide-resin sample (in mg).

Finally, the N-terminal Fmoc group is cleaved using 20% piperidine in DMA, then acetylated using acetic anhydride and pyridine in DMA. The peptide resin is thoroughly washed with DMA, CH$_2$Cl$_2$ and finally diethyl ether.

5.3.2. Cleavage and Deprotection

By way of example but not limitation, cleavage and deprotection can be carried out as follows: The air-dried peptide resin is treated with ethylmethyl-sulfide (EtSMe), ethanedithiol (EDT), and thioanisole (PhSMe) for approximately 20 min. prior to addition of 95% aqueous trifluoroacetic acid (TFA). A total volume of approximately 50 ml of these reagents per gram of peptide-resin is used. The following ratio is used: TFA:EtSMe:EDT:PhSMe (10:0.5:0.5: 0.5). The mixture is stirred for 3 h at room temperature under an atmosphere of N$_2$. The mixture is 30 filtered and the resin washed with TFA (2×3 ml). The combined filtrate is evaporated in vacuo, and anhydrous diethyl ether added to the yellow/orange residue. The resulting white precipitate is isolated by filtration. See King et al., 1990, Int. J. Peptide Protein Res. 36:255–266 regarding various cleavage methods.

5.3.3. Purification of the Peptides

Purification of the synthesized peptides can be carried out by standard methods including chromatography (e.g., ion exchange, affinity, and sizing column chromatography, high performance liquid chromatography (HPLC)), centrifugation, differential solubility, or by any other standard technique.

5.3.4. Biological Peptide Libraries

Biological peptide libraries can be used to express and identify peptides that bind to GIT transport receptors. According to this second approach, involving recombinant DNA techniques, peptides can, by way of example, be expressed in biological systems as either soluble fusion proteins or viral capsid proteins.

5.3.4.1. Methods to Identify Binders: Construction of Libraries

In a specific embodiment, the peptides of the invention that specifically bind to GIT transport receptors are identified by screening a random peptide library by contacting the library with a ligand selected from among HPT1, hPEPT1, D2H, or hSI (or a molecule consisting essentially of an extracellular domain thereof or fragment of the domain) to identify members of the library that specifically bind to the ligand.

In a particular embodiment, a process to identify the peptides of the present method utilizes a library of recombinant vectors constructed by methods well known in the art and comprises screening a library of recombinant vectors expressing inserted synthetic oligonucleotide sequences encoding extracellular GIT transport receptor domains, for example, attached to an accessible surface structural protein of a vector to isolate those members producing peptides that bind to HPT1, hPEPT1, D2H, or hSI. The nucleic acid sequence of the inserted synthetic oligonucleotides of the isolated vector is determined and the amino acid sequence encoded can be deduced to identify a binding domain that binds the ligand of choice (e.g., HPT1, hPEPT1, D2H, or hSI).

The present invention encompasses a method for identifying a peptide which binds to a ligand selected from among HPT1, hPEPT1, D2H, or hSI comprising: screening a library of random peptides with the ligand (or an extracellular domain or fragment thereof) under conditions conducive to ligand binding and isolating the peptide which binds to the ligand. Additionally, the methods of the invention further comprise determining the nucleotide sequence encoding the binding domain of the peptide identified to deduce the amino acid sequence of the binding domain.

5.3.4.2. Preparation of Extracellular Domain Ligand

In a specific embodiment, molecules consisting essentially of an extracellular domain of the desired GIT transport receptor or a fragment of an extracellular domain are used to screen a random peptide library for binding thereto. Preferably, a nucleic acid encoding the extracellular domain is cloned and recombinantly expressed, and the domain is then purified for use. The GIT transport receptor is preferably selected from among HPT1, hPEPT1, D2H, or hSI.

5.3.4.3. Methods to Identify Binders: Screening Libraries

Once a suitable random peptide library has been constructed (or otherwise obtained), the library is screened to identify peptides having binding affinity for the GIT transport receptor, e.g., HPT1, hPEPT1, D2H, or hSI. In a preferred aspect, the library is a TSAR library (see U.S. Pat. No. 5,498,538 dated Mar. 12, 1996 and PCT Publication WO 94/18318 dated Aug. 18, 1994, both of which are incorporated by reference herein in their entireties). Screening the libraries can be accomplished by any of a variety of methods known to those of skill in the art. See, e.g., the following references, which disclose screening of peptide libraries: Parmley and Smith, 1989, Adv. Exp. Med. Biol. 251: 215–218; Scott and Smith, 1990, Science 249: 386–390; Fowlkes et al., 1992; BioTechniques 13: 422–427; Oldenburg et al., 1992, Proc. Natl. Acad. Sci. USA 89: 5393–5397; Yu et al., 1994, Cell 76: 933–945; Staudt et al., 1988, Science 241: 577–580; Bock et al., 1992, Nature 355: 564–566; Tuerk et al., 1992, Proc. Natl. Acad. Sci. USA 89: 6988–6992; Ellington et al., 1992, Nature 355: 850–852; U.S. Pat. No. 5,096,815, U.S. Pat. No. 5,223,409, and U.S. Pat. No. 5,198,346, all to Ladner et al.; and Rebar and Pabo, 1993, Science 263: 671–673. See also PCT publication WO 94/18318, dated Aug. 18, 1994.

One of ordinary skill in the art will recognize that, with suitable modifications, the screening methods described below would be suitable for a wide variety of biological expression libraries.

Once a library has been constructed or otherwise obtained, the library is screened to identify binding molecules having specific binding affinity for a ligand for a GIT transport receptor preferably selected from among HPT1, hPEPT1, D2H, or hSI.

Screening the libraries can be accomplished by any of a variety of methods known to those of skill in the art. Exemplary screening methods are described in Fowlkes et al., 1992, BioTechniques, 13:422–427 and include contacting the vectors with an immobilized target ligand and harvesting those vectors that bind to said ligand. Such useful screening methods, are designated "panning" methods. In panning methods useful to screen the present libraries, the target ligand can be immobilized on plates, beads (such as magnetic beads), sepharose, beads used in columns, etc. If desired, the immobilized target ligand can be "tagged", e.g., using labels such as biotin, fluoroscein isothiocyanate, rhodamine, etc. e.g. for FACS sorting. Panning is also disclosed in Parmley, S. F. and Smith, G. P., 1988, Gene 73: 305–318.

In a particular embodiment of the invention, the library can be screened with a recombinant receptor domain. In another embodiment, the library can be screened successively with receptor domains and then on CaCO-2 cells.

For screening of the peptide libraries in vitro, the solvent requirements involved in screening are not limited to aqueous solvents; thus, nonphysiological binding interactions and conditions different from those found in vivo can be exploited.

Screening a library can be achieved using a method comprising a first "enrichment" step and a second filter lift as follows. The following description is given by way of example, not limitation.

Binders from an expressed library (e.g., in phage) capable of binding to a given ligand ("positives") are initially enriched by one or two cycles of panning or affinity chromatography. A microtiter well is passively coated with the ligand (e.g., about 10 μg in 100 μl). The well is then blocked with a solution of BSA to prevent non-specific adherence of the phage of the library to the plastic surface. For example, about $10^{11}$ phage particles expressing peptides are then added to the well and incubated for several hours. Unbound phage are removed by repeated washing of the plate, and specifically bound phage are eluted using an acidic glycine-HCl solution or other elution buffer. The eluted phage solution is neutralized with alkali, and amplified, e.g., by infection of E. coli and plating on large petri dishes containing Luria broth (LB) in agar. Amplified cultures expressing the binding peptides are then titered and the process repeated. Alternatively, the ligand can be covalently coupled to agarose or acrylamide beads using commercially available activated bead reagents. The phage solution is then simply passed over a small column containing the coupled bead matrix which is then washed extensively and eluted with acid or other eluant. In either case, the goal is to enrich the positives to a frequency of about $>1/10^5$.

Following enrichment, a filter lift assay is conducted. For example, when specific binders are expressed in phage, approximately $1-2 \times 10^5$ phage are added to 500 μl of log phase E. coli and plated on a large Luria Broth-agarose plate with 0.7% agarose in broth. The agarose is allowed to solidify, and a nitrocellulose filter (e.g., 0.45μ) is placed on the agarose surface. A series of registration marks is made with a sterile needle to allow re-alignment of the filter and plate following development as described below. Phage plaques are allowed to develop by overnight incubation at 37° C. (the presence of the filter does not inhibit this process). The filter is then removed from the plate with phage from each individual plaque adhered in situ. The filter is then exposed to a solution of BSA or other blocking agent for 1–2 hours to prevent non-specific binding of the ligand (or "probe").

The probe itself is labeled, for example, either by biotinylation (using commercial NHS-biotin) or direct enzyme labeling, e.g., with horse radish peroxidase or alkaline phosphatase. Probes labeled in this manner are indefinitely stable and can be re-used several times. The blocked filter is exposed to a solution of probe for several hours to allow the probe to bind in situ to any phage on the filter displaying a peptide with significant affinity to the probe. The filter is then washed to remove unbound probe, and then developed by exposure to enzyme substrate solution (in the case of directly labeled probe) or further exposed to a solution of enzyme-labeled avidin (in the case of biotinylated probe). Positive phage plaques are identified by localized deposition of colored enzymatic cleavage product on the filter which corresponds to plaques on the original plate. The developed filter is simply realigned with the plate using the registration marks, and the "positive" plaques are cored from the agarose to recover the phage. Because of the high density of plaques on the original plate, it may be difficult to isolate a single plaque from the plate on the first pass. Accordingly, phage recovered from the initial core can be re-plated at low density and the process can be repeated to allow isolation of individual plaques and hence single clones of phage.

Successful screening experiments are optimally conducted using 3 rounds of serial screening. The recovered cells are then plated at a low density to yield isolated colonies for individual analysis. The individual colonies are selected and used to inoculate LB culture medium containing ampicillin. After overnight culture at 37° C., the cultures are then spun down by centrifugation. Individual cell aliquots are then retested for binding to the target ligand attached to the beads. Binding to other beads having attached thereto a non-relevant ligand, can be used as a negative control.

One aspect of screening the libraries is that of elution. The following discussion is applicable to any system where the random peptide is expressed on a surface fusion molecule. It is conceivable that the conditions that disrupt the peptide-target interactions during recovery of the phage are specific for every given peptide sequence from a plurality of proteins expressed on phage. For example, certain interactions may be disrupted by acid pH but not by basic pH, and vice versa. Thus, it may be desirable to test a variety of elution conditions (including but not limited to pH 2–3, pH 12–13, excess target in competition, detergents, mild protein denaturants, urea, varying temperature, light, presence or absence of metal ions, chelators, etc.) and compare the primary structures of the binding proteins expressed on the phage recovered for each set of conditions to determine the appropriate elution conditions for each ligand/binding protein combination. Some of these elution conditions may be incompatible with phage infection because they are bactericidal and will need to be removed by dialysis (i.e., dialysis bag, Centricon/Amicon microconcentrators).

In a preferred embodiment, a phage display library of random peptides is screened to select phage expressing peptides that bind to a GIT transport receptor. Preferably, a first step is to isolate a preselected phage library. The "preselected phage library" is a library consisting of a subpopulation of a phage display library. This subpopulation can be formed by initially screening against either a target GIT transport receptor (or domain thereof) so as to permit the selection of a subpopulation of phages which specifically bind to the receptor. Alternatively, the subpopulation can be formed by screening against a target cell or cell type or tissue type or tissue barrier of the gastro-intestinal tract, so as to permit the selection of a subpopulation of phages which either bind specifically to the target cell or target cell type or target tissue or target tissue barrier, or which binds to and/or is transported across (or between) the target cell or target cell type or target tissue or target tissue barrier either in situ or in vivo. This preselected phage library or subpopulation of selected phages can also be rescreened against the target GIT transport receptor, permitting the further selection of a subpopulation of phages which bind to the GIT transport receptor or target cell or target cell type or target tissue or target tissue barrier or which bind to and/or is transported across the target cell, target tissue or target tissue barrier either in situ or in vivo. Such rescreening can be repeated from zero to 30 times with each successive "pre-selected phage library" generating additional pre-selected phage libraries.

In a preferred embodiment, a preselected phage library binding a ligand that is a GIT transport receptor preferably selected from among HPT1, hPEPT1, D2H, or hSI is obtained by an in vitro screening step as described above, and then the phage are optionally further characterized using in vitro assays consisting of binding phage directly to the receptor domain of interest or, alternatively, to Caco-2 cells or using in vivo assays. In another preferred embodiment, in vivo assays are used that measure uptake of phage by intestinal tissue or, alternatively, through the GIT. In alternative embodiments, such further in vitro or in vivo assays can be used as the initial screening step.

In vivo assays that may be used are described in the examples infra.

5.4. Generation of Antibodies to GIT Transport Receptor-Binding Peptides and Derivatives Thereof According to the invention, a GIT transport receptor-binding peptide, fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library.

Various procedures known in the art may be used for the production of polyclonal antibodies to a GIT transport receptor-binding peptide or derivative or analog. For the production of antibody, various host animals can be immunized by injection with the native GIT transport receptor-binding peptides, or a synthetic version, or derivative (e.g., fragment) thereof, including but not limited to rabbits, mice, rats, fowl, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed toward a GIT transport receptor-binding peptide or analog thereof, any technique which provides for the production of antibody molecules by continuous cell lines in culture may be used.

For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). According to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for GIT transport receptor-binding peptides together with genes from a human antibody molecule of appropriate biological activity can be used.

According to the invention, techniques described for the production of single chain antibodies (U.S. Pat. No. 4,946,778) can be adapted to produce GIT transport receptor-binding peptide-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for GIT transport receptor-binding peptides, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a GIT transport receptor-binding peptide, one may assay generated hybridomas for a product which binds to a GIT transport receptor-binding peptide fragment containing such a domain.

Antibodies specific to a domain of a GIT transport receptor-binding peptide are also provided.

The foregoing antibodies can be used in methods known in the art relating to the localization and activity of the GIT transport receptor-binding peptide sequences of the invention, e.g., for imaging these peptides after in vivo administration (e.g., to monitor treatment efficacy), measuring levels thereof in appropriate physiological samples, in diagnostic methods, etc. For instance, antibodies or antibody fragments specific to a domain of a GIT transport receptor-binding peptide or to a derivative of a peptide, such as a dansyl group or some other epitope introduced into the peptide, can be used to 1) identify the presence of the peptide on a nanoparticle or other substrate; 2) quantify the amount of peptide on the nanoparticle; 3) measure the level of the peptide in appropriate physiological samples; 4) perform immunohistology on tissue samples; 5) image the peptide after in vivo administration; 6) purify the peptide from a mixture using an immunoaffinity column or 7) bind or fix the peptide to the surface of nanoparticle. This last use envisions attaching the antibody (or fragment of the antibody) to the surface of drug-loaded nanoparticles or other substrate and then incubating this conjugate with the peptide. This procedure results in binding of the peptide in a certain fixed orientation, resulting in a particle that contains the peptide bound to the antibody in such a way that the peptide is fully active.

Abtides (or Antigen binding peptides) specific to a domain of a GIT transport receptor-binding peptide or to a derivative of a peptide, such as a dansyl group or some other epitope introduced into the peptide, can be used for the same seven purposes identified above for antibodies.

5.5. Assays of GIT Transport Receptor-Binding Peptides, Derivatives and Analogs

The functional activity of GIT transport receptor-binding peptides, derivatives and analogs can be assayed by various methods.

In a preferred embodiment, in which binding to a GIT transport receptor is being assayed, the binding can be assayed by in vivo or in vitro assays such as described in the examples infra, or by other means that are known in the art.

In another embodiment, where one is assaying for the ability to bind or compete with full-length GIT transport receptor-binding peptide for binding to anti-GIT transport receptor-binding peptide antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

Other methods will be known to the skilled artisan and are within the scope of the invention.

5.6. Uses

The invention provides compositions comprising the GIT transport receptor-binding proteins of the invention bound to a material comprising an active agent. Such compositions have use in targeting the active agent to the GIT and/or in facilitating transfer through the lumen of the GIT into the systemic circulation. Where the active agent is an imaging agent, such compositions can be administered in vivo to image the GIT (or particular transport receptors thereof). Other active agents include but are not limited to: any drug or antigen or any drug- or antigen-loaded or drug- or antigen-encapsulated nanoparticle, microparticle, liposome, or micellar formulation capable of eliciting a biological response in a human or animal. Examples of drug- or antigen-loaded or drug- or antigen-encapsulated formulations include those in which the active agent is encapsulated or loaded into nano- or microparticles, such as biodegradable nano- or microparticles, and which have the GIT transport receptor-binding protein or derivative or analog adsorbed, coated or covalently bound, such as directly linked or linked via a linking moiety, onto the surface of the nano- or microparticle. Additionally, the protein, derivative or analog can form the nano- or microparticle itself or the protein, derivative or analog can be covalently attached to the polymer or polymers used in the production of the biodegradable nano- or microparticles or drug-loaded or drug-encapsulated nano- or microparticles or the peptide can be directly conjugated to the active agent. Such conjugations to active agents include fusion proteins in which a DNA sequence coding for the peptide is fused in-frame to the gene or cDNA coding for a therapeutic peptide or protein such that the modified gene codes for a recombinant fusion protein.

In a preferred embodiment, the invention provides for treatment of various diseases and disorders by administration of a therapeutic compound (termed herein "Therapeutic"). Such "Therapeutics" include but are not limited to: GIT transport receptor-binding proteins, and analogs and derivatives (including fragments) thereof (e.g., as described hereinabove) that bind to GIT transport receptors, bound to an active agent of value in the treatment or prevention of a disease or disorder (preferably a mammalian, most preferably human, disease or disorder). Therapeutics also include but are not limited to nucleic acids encoding the GIT transport receptor-binding proteins, analogs, or derivatives bound to such a therapeutic or prophylactic active agent. The active agent is preferably a drug.

Any drug known in the art may be used, depending upon the disease or disorder to be treated or prevented, and the type of subject to which it is to be administered. As used herein, the term "drug" includes, without limitation, any pharmaceutically active agent. Representative drugs include, but are not limited to, peptides or proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins, and antidiuretic agents. Typical drugs include peptides, proteins or hormones such as insulin, calcitonin, calcitonin gene regulating protein, atrial natriuretic protein, colony stimulating factor, betaseron, erythropoietin (EPO), interferons such as $\alpha$, $\beta$ or $\gamma$ interferon, somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogs thereof; analgesics such as fentanyl, sufentanil, butorphanol, buprenorphine, levorphanol, morphine, hydromorphone, hydocodone, oxymorphone, methadone, lidocaine, bupivacaine, diclofenac, naproxen, paverin, and analogs thereof; anti-migraine agents such as heparin, hirudin, and analogs thereof; anti-coagulant agents such as scopolamine, ondansetron, domperidone, etoclopramide, and analogs thereof; cardiovascular agents, anti-hypertensive agents and vasodilators such as diltiazem, clonidine, nifedipine, verapamil, isosorbide-5-mononitrate, organic nitrates, agents used in treatment of heart disorders and analogs thereof; sedatives such as benzodiazeines, phenothiozines and analogs thereof; narcotic antagonists such as naltrexone, naloxone and analogs thereof; chelating agents such as deferoxamine and analogs thereof; anti-diuretic agents such as desmopressin, vasopressin and analogs thereof; anti-anginal agents such as nitroglycerine and analogs thereof; anti-neoplastics such as 5-fluorouracil, bleomycin and analogs thereof; prostaglandins and analogs thereof; and chemotherapy agents such as vincristine and analogs thereof. Representative drugs also include but are not limited to antisense oligonucleotides, genes, gene correcting hybrid oligonucleotides, ribozymes, aptameric oligonucleotides, triple-helix forming oligonucleotides, inhibitors of signal transduction pathways, tyrosine kinase inhibitors and DNA modifying agents. Drugs that can be used also include, without limitation, systems containing gene therapeutics, including viral systems for therapeutic gene delivery such as adenovirus, adeno-associated virus, retroviruses, herpes simplex virus, sindbus virus, liposomes, cationic lipids, dendrimers, and enzymes. For instance, gene delivery viruses can be modified such that they express the targeting peptide on the surface so as to permit targeted gene delivery.

In a preferred embodiment, a Therapeutic is therapeutically or prophylactically administered to a human patient.

Additional descriptions and sources of Therapeutics that can be used according to the invention are found in various Sections herein.

5.7. Therapeutic/Prophylactic Administration, Compositions and Formulations

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably a human.

As will be clear, any disease or disorder of interest amenable to therapy or prophylaxis by providing a drug in vivo systemically or by targeting a drug in vivo to the GIT (by linkage to a GIT transport-receptor binding protein, derivative or analog of the invention) can be treated or prevented by administration of a Therapeutic of the invention. Such diseases may include but are not limited to hypertension, diabetes, osteoporosis, hemophilia, anemia, cancer, migraine, and angina pectoris, to name but a few.

Any route of administration known in the art may be used, including but not limited to oral, nasal, topical, intravenous, intraperitoneal, intradermal, mucosal, intrathecal, intramuscular, etc. Preferably, administration is oral; in such an embodiment the GIT-transport binding protein, derivative or analog of the invention acts advantageously to facilitate transport of the therapeutic active agent through the lumen of the GIT into the systemic circulation.

The present invention also provides therapeutic compositions/formulations. In a specific embodiment of the invention, a GIT transport receptor-binding peptide or motif of interest is associated with a therapeutically or prophylactically active agent, preferably a drug or drug-containing nano- or microparticle. More preferably, the active agent is a drug encapsulating or drug loaded nano- or microparticle, such as a biodegradable nano- or microparticle, in which the peptide is physically adsorbed or coated or covalently bonded, such as directly linked or linked via a linking moiety, onto the surface of the nano- or microparticle. Alternatively, the peptide can form the nano- or microparticle itself or can be directly conjugated to the active agent. Such conjugations include fusion proteins in which a DNA sequence coding for the peptide is fused in-frame to the gene or cDNA coding for a therapeutic peptide or protein, such that the modified gene codes for a recombinant fusion protein in which the "targeting" peptide is fused to the therapeutic peptide or protein and where the "targeting"

peptide increases the absorption of the fusion protein from the GIT. Preferably the particles range in size from 200–600 nm.

Thus, in a specific embodiment, a GIT transport-binding protein is bound to a slow-release (controlled release) device containing a drug. In a specific embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)).

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

6. EXAMPLES

6.1. Selection of GIT Receptor Targets

The HPT1, hPEPT1, D2H, and hSI receptors were selected for cloning as GIT receptor targets based on several criteria, including: (1) expression on surface of epithelial cells in gastro-intestinal tract (GIT); (2) expression along the length of small intestine (HPT1, hPEPT1, D2H); (3) expression locally at high concentration (hSI); (4) large putative extracellular domains facing into the lumen of the GIT; and (5) extracellular domains that permit easy access and bioadhesion by targeting particles.

The four recombinant receptor sites screened with the peptide libraries additionally have the following characteristics:

| Receptor | Characteristics |
| --- | --- |
| D2H | Transport of neutral/basic amino acids; a transport activating protein for a range of amino acid translocases |
| hSI | Metabolism of sucrose and other sugars; represents 9% of brush border membrane protein in Jejunum |
| HPT1 | di/tri peptide transporter or facilitator of peptide transport |
| hPEPT1 | di/tri peptide transporter |

FIGS. 1–4 (SEQ ID NOS:176, 178, 179, and 181, respectively) show the predicted amino acid sequences for hPEPT1, HPT1, hSI and D2H, respectively.

6.2. Cloning of Extracellular Domain of Selected Receptor Site

The following receptor domains were cloned and expressed as His-tag fusion proteins by standard techniques:

| Receptor | Domain (amino acid residues) |
| --- | --- |
| hPEPT1[a] | 391–571 |
| HPT1[b] | 29–273 |
| hSI[c] | 272–667 |
| D2H[d] | 387–685 |

[a]Liang et al., 1995, J. Biol. Chem. 270: 6456–6463
[b]Dantzig et al., 1994, Association of Intestinal Peptide Transport with a Protein Related to the Cadherin Superfamily
[c]Chantret et al., Biochem. J. 285: 915–923
[d]Bertran et al., J. Biol. Chem. 268: 14842–14949

The receptor proteins were expressed as His-tag fusion proteins and affinity purified under denaturing conditions, using urea or guanidine HCl, utilizing the pET His-tag metal chelate affinity for Ni-NTA Agarose (Hochuli, E., Purification of recombinant proteins with metal chelate adsorbent, Genetic Engineering, Principals and Methods (J. K. Setlow, ed.), Plenum Press, N.Y., Vol. 12 (1990), pp. 87–98).

6.3. Phage Libraries

Three phage DC8, D38, and DC43 libraries expressing N-terminal pIII fusions in M13 were used to identify peptides that bind to the GIT receptors. The D38 and DC43 libraries which are composed of 37 and 43 random amino acid domains, respectively, have been described previously (McConnell et al., 1995, Molecular Diversity, 1:165–176). The DC8 library is similar to the other two except that the random insert is 8 amino acids long flanked on each side by a cysteine residue (i.e., $CX_8C$).

6.4. Biopanning

Three rounds of biopanning on the GIT receptors were performed generally by standard methods (McConnell et al., 1995, Molecular Diversity, 1:165–176), using a mixture of the DC8 ($1\times10^{10}$ pfu), D38 and DC43 ($1\times10^{11}$ pfu) phage libraries. After each round of panning the percentage of phage recovered was determined. Following the first two rounds of panning, the eluted phage were amplified overnight. Phage from the third pan were plated out and 100 plaques were picked, amplified overnight and screened in an ELISA assay for binding to the relevant receptor and BSA. After data analysis, phage clones were identified which had high absorbance in the ELISA assay and/or a good ratio of binding to target compared to binding to BSA. The Insulin Degrading Enzyme (IDE) and recombinant human tissue factor (hTF) were used as irrelevant controls. Several variations of the standard panning technique, discussed below, were used. Selection or panning methods followed one of two strategies. The first strategy involved panning the mixed libraries on the specific GIT receptor adsorbed to a solid surface. The second strategy panned the libraries twice against the GIT receptor and then against Caco-2 cells (Peterson and Mooseker, 1992, J. Cell Science 102:581–600), Selection methods are reflected in the clone nomenclature as described below:

S designates the clone was identified by binding to the hS1 receptor domain.

D designates the clone was identified by binding to the D2H receptor domain.

P designates the clone was identified by binding to the PEPT1 receptor domain.

H designates the clone was identified by binding to the HPT-1 receptor domain.

Phage designated Ni are from a solid phase band GIT receptor pan that used the standard procedure with the addition of Ni-NTA Agarose (Qiagen, Chatsworth, Calif.). Receptor coated plates were blocked with 0.5% BSA/PBS containing 160 µl Ni-NTA agarose and libraries were panned in the presence of 50 µl Ni-NTA agarose. The receptor proteins were expressed as His-tag fusions. The His-tag has a high affinity for Ni-NTA Agarose. Blocking the plate and panning in the presence of Ni-NTA agarose minimized phage binding to the His-tag portion of the recombinant receptor.

Phage with the designation AX were eluted with acid and Factor Xa. Phage were first eluted by standard acid elution then Factor Xa (New England Biolabs, Beverly, Mass.: 1 µg protease in 300 µl of 20 mM Tris-HCL, 100 mM NaCl, 2 mM $CaCl_2$) was added to the panning plate and incubated 2 hours. Phage from both elution methods were pooled together then plated.

Phage with the designation AB were eluted with acid and base. Phage were eluted first by standard acid elution then 100 mM triethylamine pH 12.1 was added to the panning plate for 10 minutes. Phage from both elution methods were pooled together then plated.

C designates panning on receptor followed by Caco-2 cells. First and second round pans were performed on the receptor while the third round pan was on snapwells of Caco-2 cells. DCX11, DCX8 and DCX33 were identified by two pans on D2H receptor, third pan on Caco-2 cells. The third round Factor Xa eluate from the Caco-2 cells was screened by ELISA on D2H, BSA and fixed Caco-2 cells. For HCA3 the first two rounds of panning were performed on the HPT-1 receptor and the third pan was on monolayers cultured on snapwells of Caco-2 cells.

Phage designated 5PAX were carried through five rounds of panning after which a number of phage were sequenced prior to screening by ELISA.

6.5. Sequencing of Selected Phage

The amino acid sequence of phage inserts demonstrating a good ratio of binding to receptor domains and/or Caco-2 cells over background BSA binding were deduced from the nucleotide sequence obtained by sequencing (Sequenase®, U.S. Biochemical Corp., Cleveland, Ohio) both DNA strands of the appropriate region in the viral genome. The third round acid eluate was screened by ELISA on HPT-1, BSA and Caco-2 fixed cells. Phage designated 5PAX were carried through five rounds of panning after which a number of phages were sequenced prior to screening by ELISA.

One well of a 24 well plate was coated with 10 µg/ml of GIT receptor and the plate was incubated overnight at 4° C. The plate was blocked with 0.5 BSA-PBS for one hour. A mixture of the DC8, D38 and DC43 phage libraries was added to the plate and the plate was incubated for 2 to 3 hours at room temperature on a rotator. After washing the well 10 times with 1% BSA plus 0.05% Tween 20 in PBS, the well was eluted with 0.05m glycine, pH2. The phage was then eluted with 0.2M $NaPO_4$. The eluted phage was titered on agar plates; the remaining phage was amplified overnight. The next day the amplified phage was added to a second coated plate and the panning procedure was repeated as described above. The eluted phage from the second pan as well as the amplified phage from the first pan was titered on agar plates. Following amplification overnight of the phage from the second pan, the panning procedure was repeated as described above. The phage eluted from the third pan and the amplified phage from the second pan were then titered overnight on agar plates. Isolated phage colonies were amplified overnight prior to use in an ELISA assay.

6.6. Receptor ELISA Procedure 96 well plates were coated overnight with GIT receptor, BSA and, optionally, IDE (insulin degrading enzyme, an irrelevant His-fusion protein)or hTF. The plates were blocked for one hour with 0.5% BSA-PBS. After clarification, the amplified phage were diluted 1:100 in 1% BSA plus 0.05% Tween 20 in PBS and added to the plates. Following incubation of the plates on a rotator for 1 to 2 hours, the plates were washed 5 times with 1% BSA plus 0.05% Tween 20 in PBS. Dilute anti-M13-HRP conjugate (anti-M13 antibody linked to horse radish peroxidase (HRP)) was added to all the wells and the plate was incubated for one hour on a rotator. After the plates were washed 5 times, as described above, TMB substrate was added to the wells. The plates were read at 650 nm absorbance.

Receptor ELISA Results:

Below are the results of ELISA assays which assessed the binding of phage panned on the hSI receptor to microtiter plates coated with hSI and BSA. Table 1 shows the OD results as well as the ratio of hSI to BSA binding.

TABLE 1

| PHAGE | hSI | BSA | hSI/BSA |
| --- | --- | --- | --- |
| S15 | 0.478 | 0.053 | 9 |
| S21 | 0.845 | 0.092 | 9 |
| S22 | 0.399 | 0.061 | 7 |

TABLE 1-continued

| PHAGE | hSI | BSA | hSI/BSA |
|---|---|---|---|
| SNi10 | 0.57 | 0.051 | 11 |
| SNi28 | 0.942 | 0.113 | 8 |
| SNi34 | 0.761 | 0.115 | 7 |
| SNi38 | 0.466 | 0.076 | 6 |
| SNi45 | 0.518 | 0.056 | 9 |
| SNiAX2 | 0.383 | 0.065 | 6 |
| SNiAX6 | 0.369 | 0.056 | 7 |
| SNiAX8 | 0.342 | 0.068 | 5 |
| BLANK | 0.063 | 0.042 | 2 |

Below are the results of an ELISA which assessed the binding of phage panned on the D2H receptor to microtiter plates coated with D2H and BSA. Table 2 shows the OD results as well as the ratio of D2H to BSA binding.

TABLE 2

| PHAGE | D2H | BSA | D2H/BSA |
|---|---|---|---|
| DAB3 | 0.406 | 0.072 | 6 |
| DAB7 | 0.702 | 0.09 | 8 |
| DAB10 | 0.644 | 0.153 | 4 |
| DAB18 | 0.467 | 0.085 | 5 |
| DAB24 | 1.801 | 0.441 | 4 |
| DAB30 | 0.704 | 0.121 | 6 |
| DAX15 | 0.391 | 0.101 | 4 |
| DAX23 | 0.698 | 0.153 | 5 |
| DAX24 | 0.591 | 0.118 | 5 |
| DAX27 | 1.577 | 0.424 | 4 |
| BLANK | 0.038 | 0.037 | 1 |

Below are the results of an ELISA which assessed the binding of phage panned for two rounds on the D2H receptor followed by a third round pan on Caco-2 snapwells. Binding to fixed Caco-2 cells, D2H and BSA was examined. Table 3 shows the OD results as well as the ratio of D2H to BSA binding.

TABLE 3

| PHAGE | Caco-2 | D2H | BSA | D2H/BSA |
|---|---|---|---|---|
| DCX8 | 0.498 | 0.163 | 0.063 | 3 |
| DCX11 | 0.224 | 0.222 | 0.071 | 3 |
| DCX26 | 0.114 | 0.956 | 0.213 | 4 |
| DCX33 | 0.164 | 0.616 | 0.103 | 6 |
| DCX36 | 0.149 | 0.293 | 0.064 | 5 |
| DCX39 | 0.121 | 0.299 | 0.066 | 5 |
| DCX42 | 0.308 | 0.158 | 0.065 | 2 |
| DCX45 | 0.147 | 0.336 | 0.075 | 4 |
| Blank | 0.065 | 0.043 | 0.04 | 1 |

Below are the results of an ELISA which assessed the binding of phage panned on the hPEPT1 receptor to hPEPT1 and BSA. Table 4 shows the OD results as well as the ratio of hPEPT1 to BSA binding.

TABLE 4

| PHAGE | hPEPT1 | BSA | PEPT1/BSA |
|---|---|---|---|
| PAX9 | 0.312 | 0.079 | 4 |
| PAX14 | 1.102 | 0.139 | 8 |
| PAX15 | 0.301 | 0.079 | 4 |
| PAX16 | 0.648 | 0.171 | 4 |
| PAX17 | 0.514 | 0.095 | 5 |
| PAX18 | 0.416 | 0.087 | 5 |
| PAX35 | 0.474 | 0.065 | 7 |
| PAX38 | 0.292 | 0.064 | 5 |

TABLE 4-continued

| PHAGE | hPEPT1 | BSA | PEPT1/BSA |
|---|---|---|---|
| PAX40 | 0.461 | 0.076 | 6 |
| PAX43 | 0.345 | 0.069 | 5 |
| PAX45 | 0.419 | 0.081 | 5 |
| PAX46 | 0.429 | 0.077 | 6 |
| P31 | 0.807 | 0.075 | 11 |
| P90 | 1.117 | 0.107 | 9 |
| 5PAX3 | 0.173 | 0.04 | 4 |
| 5PAX5 | 0.15 | 0.036 | 4 |
| 5PAX7 | 0.171 | 0.037 | 5 |
| 5PAX12 | 0.227 | 0.04 | 6 |
| Blank | 0.102 | 0.039 | 3 |

Table 5 shows the results of an ELISA which assessed the binding of phage panned on the HPT-1 receptor to HPT-1 and BSA. The table shows the OD results as well as the ratio of HPT-1 to BSA binding.

TABLE 5

| PHAGE | HPT1 | BSA | HPT/BSA |
|---|---|---|---|
| HAX9 | 0.382 | 0.075 | 5 |
| HAX40 | 0.991 | 0.065 | 15 |
| HAX42 | 0.32 | 0.071 | 5 |

Table 6 shows the results of an ELISA which assessed the binding of phage panned for two rounds on the HPT-1 receptor followed by a third round pan on Caco-2 snapwells. Binding to fixed Caco-2 cells, HPT-1 and BSA was examined. The table shows the OD results as well as the ratio of HPT-1 to BSA binding.

TABLE 6

| PHAGE | Caco-2 | HPT1 | BSA | HPT1/BSA |
|---|---|---|---|---|
| HCA3 | 0.406 | 0.048 | 0.038 | 1 |

Cell ELISA Procedure

Phage ELISA was used as described above with the following changes. Diluent and wash buffer was PBS containing 1% BSA and 0.05% Tween 20 and plates were washed five times at each wash step. Supernatant of infected bacterial cultures was diluted 1:100 and incubated with protein coated plates for 2–3 hours with mild agitation. Anti-M13 Horseradish peroxidase (HRP) conjugate (Pharmacia, Piscataway, N.J.) was diluted 1:8000.

Fixed Caco-2, C2BBe1, and A431 cell plates were prepared by growing cells on tissue culture treated microtiter plates. When cells were confluent, plates were fixed with 10% formaldehyde, washed twice with PBS and stored with 0.5% BSA-PBS at −20° C. On the day of the assay, thawed plates were treated with PBS containing 0.1% phenylhydrazine for one hour at 37° C. followed by two PBS washes and blocking for One hour with 0.5% BSA-PBS. The standard ELISA procedure was followed at this point.

Phage which showed specificity to a GIT receptor was further characterized by ELISA on a variety of recombinant proteins. Phage which continued to exhibit GIT receptor specificity was sequenced.

TABLE 7

TARGET BINDING PHAGE INSERT SEQUENCES:

| | SEQ. ID. NO. | |
|---|---|---|
| hSI | | |
| S15 | 1 | RSGAYESPDGRGGRSYVGGGGGCGNIGRKHNLWGLRTASPACWD |
| S21 | 2 | SPRSFWPVVSRHESFGISNYLGCGYRTCISGTMTKSSPIYPRHS |
| S22 | 3 | SSSSDWGGVPGKVVRERFKGRGCGISITSVLTGKPNPCPEPKAA |
| SNi10 | 4 | RVGQCTDSDVRRPWARSCAHQGCGAGTRNSHGCITRPLRQASAH |
| SNi28 | 5 | SHSGGHMRAYGDVFRELRDRWNATSHHTRPTPQLPRGPN |
| SNi34 | 6 | SPCGGSWGRFMQGGLFGGRTDGCGAHRNRTSASLEPPSSDY |
| SNi38 | 7 | RGAADQRRGWSENLGLPRVGWDAIAHNSYTFTSRRPRPP |
| SNi45 | 8 | SGGEVSSWGRVNDLCARVSWTGCGTARSARTDNKGFLPKHSSLR |
| SNiAX2 | 9 | SDSDGDHYGLRGGVRCSLRDRGCGLALSTVHAGPPSFYPKLSSP |
| SNiAX4 | 10 | RSLGNYGVTGTVDVTVLPMPGHANHLGVSSASSSDPPRR |
| SNiAX6 | 11 | RTTTAKGCLLGSFGVLSGCSFTPTSPPPHLGYPPHSVN |
| SNiAX8 | 12 | SPKLSSVGVMTKVTELPTEGPNAISIPISATLGPRNPLR |
| D2H | | |
| DAB3 | 13 | RWCGAELCNSVTKKFRPGWRDHANPSTHHRTPPPSQSSP |
| DAB7 | 14 | RWCGADDPCGASRWRGGNSLFGCGLRCSAAQSTPSGRIHSTSTS |
| DAB10 | 15 | SKSGEGGDSSRGETGWARVRSHAMTAGRFRWYNQLPSDR |
| DAB18 | 16 | RSSANNCEWKSDWMRRACIARYANSSGPARAVDTKAAP |
| DAB24 | 17 | SKWSWSSRWGSPQDKVEKTRAGCGGSPSSTNCHPYTFAPPPQAG |
| DAB30 | 18 | SGFWEFSRGLWDGENRKSVRSGCGFRGSSAQGPCPVTPATIDKH |
| DAX15 | 19 | SESGRCRSVSRWMTTWQTQKGGCGSNVSRGSPLDPSHQTGHATT |
| DAX23 | 20 | REWRFAGPPLDLWAGPSLPSFNASSHPRALRTYWSQRPR |
| DAX24 | 21 | RMEDIKNSGWRDSCRWGDLRPGCGSRQWYPSNMRSSRDYPAGGH |
| DAX27 | 22 | SHPWYRHWNHGDFSGSGQSRHTPPESPHPGRPNATI |
| DCX8 | 23 | RYKHDIGCDAGVDKKSSSVRGGCGAHSSPPRAGRGPRGTMVSRL |
| DCX11 | 24 | SQGSKQCMQYRTGRLTVGSEYGCGMNPARHATPAYPARLLPRYR |
| DCX26 | 25 | SGRTTSEISGLWGWGDDRSGYGWGNTLRPNYIPYRQATNRHRYT |
| DCX33 | 26 | RWNWTVLPATGGHYWTRSTDYHAINNHRPSIPHQHPTPI |
| DCX36 | 27 | SWSSWNWSSKTTRLGDRATREGCGPSQSDGCPYNGRLTTVKPRT |
| DCX39 | 28 | SGSLNAWQPRSWVGGAFRSHANNNLNPKPTMVTRHPT |
| DCX42 | 29 | RYSGLSPRDNGPACSQEATLEGCGAQRLMSTRRKGRNSRPGWTL |
| DCX45 | 30 | SVGNDKTSRPVSFYGRVSDLWNASLMPKRTPSSKRHDDG |
| hPEPT1 | | |
| PAX9 | 31 | RWPSVGYKGNGSDTIDVHSNDASTKRSLIYNHRRPLFP |
| PAX14 | 32 | RTFENDGLGVGRSIQKKSDRWYASHNIRSHFASMSPAGK |
| PAX15 | 33 | SYCRVKGGGEGGHTDSNLARSGCGKVARTSRLQHINPRATPPSR |
| PAX16 | 34 | SWTRWGKHTHGGFVNKSPPGKNATSPYTDAQLPSDQGPP |
| PAX17 | 35 | SQVDSFRNSFRWYEPSRALCHGCGKRDTSTTRIHNSPSDSYPTR |
| PAX18 | 36 | SFLRFQSPRFEDYSRTISRLRNATNPSNVSDAHNNRALA |
| PAX35 | 37 | RSITDGGINEVDLSSVSNVLENANSHRAYRKHRPTLKRP |
| PAX38 | 38 | SSKVSSPRDPTVPRKGGNVDYGCGHRSSARMPTSALSSITKCYT |
| PAX40 | 39 | RASTQGGRGVAPEFGASVLGRGCGSATYYTNSTCKDAMGHNYS |
| PAX43 | 40 | RWCEKHKFTAARCSAGAGFERDASRPPQPAHRDNTNRNA |
| PAX45 | 41 | SFQVYPDHGLERHALDGTGPLYAMPGRWIRARPQNRDRQ |
| PAX46 | 42 | SRCTDNEQCPDTGTRSRSVSNARYFSSRLLKTHAPHRP |
| P31 | 43 | SARDSGPAEDGSRAVRLNGVENANTRKSSRSNPRGRRHP |
| P90 | 44 | SSADAEKCAGSLLWWGRQNNSGCGSPTKKHLKHRNRSQTSSSSH |
| 5PAX3 | 45 | RPKNVADAYSSQDGAAAEETSHASNAARKSPKHKPLRRP |
| 5PAX5 | 46 | RGSTGTAGGERSGVLNLHTRDNASGSGFKPWYPSNRGHK |
| 5PAX7 | 47 | RWGWERSPSDYDSDMDLGARRYATRTHRAPPRVLKAPLP |
| 5PAX12 | 48 | RGWKCEGSQAAYGDKDIGRSRGCGSITKNNTNHAHPSHGAVAKI |
| HPT-1 | | |
| HAX9 | 49 | SREEANWDGYKREMSHRSRFWDATHLSRPRRPANSGDPN |
| HAX35 | 50 | EWYSWKRSSKSTGLGDTATREGCGPSQSDGCPYNGRLTTVKPRK |
| HAX40 | 51 | REFAERRLWGCDDLSWRLDAEGCGPTPSNRAVKHRKPRPRSPAL |
| HAX42 | 52 | SDHALGTNLRSDNAKEPGDYNCCGNGNSTGRKVFNRRRPSAIPT |
| HCA3 | 53 | RHISEYSFANSHLMGGESKRKGCGINGSFSPTCPRSPTPAFRRT |
| H40 | 54 | SRESGMWGSWWRGHRLNSTGGNANMNASLPPDPPVSTP |
| PAX2 | 55 | STPPSREAYSRPYSVDSDSDTNAKHSSHNRRLRTRSRPN |

TABLE 8

DNA Sequences for Clones used in in vivo Pan

S15 (SEQ ID NO: 56)
TCTCACTCCTCGAGATCCGGCGCTTATGAGAGTCCGGATGGTCGGGGGGGTCGGAGCTATG
TGGGGGGCGGGGGTGGNTGTGGTAACATTGGTCGGAAGCATAACCTGTGGGGCTGCGTAC
CGCGTCGCCGGCCTGCTGGGACTCTAGAATCGAAGGTCGCGCTAGACCTTCGAGA
S21 (SEQ ID NO: 57)

TABLE 8-continued

DNA Sequences for Clones used in in vivo Pan

TCTCACTCCTCGAGTCCTCGCTCTTTCTGGCCCGTTGTGTCCCGGCATGAGTCGTTTGGGA
TCTCTAACTATTTGGGNTGTGGTTATCGTACATGTATCTCCGGCACGATGACTAAGTCTAG
CCCGATTTACCCTCGGCATTCGTCTAGAATCGAAGGTCGCGCTAGACCTTCGAGA

S22 (SEQ ID NO: 58)
TCTCACTCCTCGAGTAGTAGCTCCGATTGGGGTGGTGTGCCTGGGAAGGTGGTTAGGGAGC
GCTTTAAGGGGCGCGGTTGTGGTATTTCCATCACCTCCGTGCTCACTGGGAAGCCCAATCC
GTGTCCGGAGCCTAAGGCGGCCTCTAGAATCGAAGGTCGCGCTAGACCTTCGAGA

SNi 10 (SEQ ID NO: 59)
TCTCACTCCTCGAGAGTTGGCCAGTGCACGGATTCTGATGTGCGGCGTCCTTGGGCCAGGT
CTTGCGCTCATCAGGGTTGTGGTGCGGGCACTCGCAACTCGCACGGCTGCATCACCCGTCC
TCTCCGCCAGGCTAGCGCTCATTCTAGAATCGAAGGTCGCGCTAGACCTTCGAGA

SNi 28 (SEQ ID NO: 60)
TCTCACTCCTCGAGCCACTCCGGTGGTATGAATAGGGCCTACGGGGATGTGTTTAGGGAGC
TTCGTGATCGGTGGAACGCCACTTCCCACCACACTCGCCCCACCCCTCAGCTCCCCCGTGG
GCCTAATTCTAGAATCGAAGGTCGCGCTAGACCTTCGAGA

SNi 34 (SEQ ID NO: 61)
TCTCACTCCTCGAGTCCGTGCGGGGGGTCGTGGGGGCGTTTTATGCAGGGTGGCCTTTTCG
GCGGTAGGACTGATGGTTGTGGTGCCCATAGAAACCGCACTTCTGCGTCGTTAGAGCCCCC
GAGCAGCGACTACTCTAGAATCGAAGGTCGCGCTAGACCTTCGAGA

SNi 38 (SEQ ID NO: 62)
TCTCACTCCTCGAGGGGCGCCGCCGATCAGCGGCGGGGGTGGTCCGAGAACTTGGGGTTGC
CTAGGGTGGGGTGGGACGCCATCGCTCACAATAGCTATACGTTCACCTCGCGCCGCCCGCG
CCCCCCCTCTAGA

SNi 45 (SEQ ID NO: 63)
TCTCACTCCTCGAGCGGTGGGGAGGTCAGCTCCTGGGGCCGCGTGAATGACCTCTGCGCTA
GGGTGAGTTGGACTGGTTGTGGTACTGCTCGTTCCGCGCGTACCGACAACAAAGGCTTTCT
TCCTAAGCACTCGTCACTCCGCTCTAGAATCGAAGGTCGCGCTAGACCTTCGAGA

SNi AX2 (SEQ ID NO: 64)
TCTCACTCCTCGAGTGATAGTGACGGGGATCATTATGGGCTTCGGGGGGGGGTGCGTTGTT
CGCTTCGTGATAGGGGTTGTGGTCTGGCCCTGTCCACCGTCCATGCTGGTCCCCCCTCTTT
TTACCCCAAGCTCTCCAGCCCCTCTAGAATCGAAGGTCGCGCTAGACCTTCGAGA

SNi AX4 (SEQ ID NO: 65)
TCTCACTCCTCGAGGAGCTTGGGTAATTATGGCGTCACCGGGACTGTGGACGTGACGGTTT
TGCCCATGCCTGGCCACGCCAACCACCTTGGTGTCTCCTCCGCCTCTAGCTCTGATCCTCC
GCGGCGCTCTAGAATCGAAGGTCGCGCTAGACCTTCGAGA

SNi AX6 (SEQ ID NO: 66)
TCTCACTCCTCGAGAACTACGACGGCTAAGGGGTGTCTTCTCGGAAGCTTCGGCGTTCTTA
GTGGGTGCTCATTTACGCCAACCTCTCCACCGCCCCACCTAGGATACCCCCCCCACTCCGT
CAATTCTAGAATCGAAGGTCGCGCTAGACCTTCGAGA

SNi AX8 (SEQ ID NO: 67)
TCTCACTCCTCGAGCCCGAAGTTGTCCAGCGTGGGTGTTATGACTAAGGTCACGGAGCTGC
CCACGGAGGGGCCTAACGCCATTAGTATTCCGATCTCCGCGACCCTCGGCCCGCGCAACCC
GCTCCGCTCTAGAATCGAAGGTCGCGCTAGACCTTCGAGA

DAB3 (SEQ ID NO: 68)
TCTCACTCCTCGAGGTGGTGCGGCGCTGAGCTGTGCAACTCGGTGACTAAGAAGTTTCGCC
CGGGCTGGCGGGATCACGCCAATCCCTCCACCCATCATCGTACTCCCCCGCCCAGCCAGTC
CAGCCCTTCTAGAATCGAAGGTCGCGCTAGACCTTCGAGA

DAB7 (SEQ ID NO: 69)
TCTCACTCCTCGAGGTGGTGCGGCGCTGATGACCCGTGTGGTGCCAGTCGTTGGCGGGGGG
GCAACAGCTTGTTTGGTTGTGGTCTTCGTTGTAGTGCGGCGCAGAGCACCCCGAGTGGCAG
GATCCATTCCACTTCGACCAGCTCTAGAATCGAAGGTCGCTAGACCTTCGAGA

DAB10 (SEQ ID NO: 70)
TCTCACTCCTCGAGTAAGTCCGGGGAGGGGGGTGACAGTAGCAGGGGCGAGACGGGCTGGG
CGAGGGTTCGGTCTCACGCCATGACTGCTGGCCGCTTTCGGTGGTACAACCAGTTGCCCTC
TGATCGGTCTAGAATCGAAGGTCGCGCTAGACCTTCGAGA

DAB18 (SEQ ID NO: 71)
TCTCACTCCTCGAGGTCGAGCGCCAATAATTGCGAGTGGAAGTCTGATTGGATGCGCAGGG
CCTGTATTGCTCGTTACGCCAACAGTTCGGGCCCCGCCCGCGCCGTCGACACTAAGGCCGC
GCCCTCTAGAATCGAAGGTCGCGCTAGACCTTCGAGA

DAB24 (SEQ ID NO: 72)
TCTCACTCCTCGAGTAAGTGGTCGTGGAGTTCGAGGTGGGGCTCCCCGCAGGATAAGGTTG
AGAAGACCAGGGCGGGTTGTGGTGGTAGTCCCAGCAGCACCAATTGTCACCCCTACACCTT
TGCCCCCCCCCGCAAGCCGGCTCTAGAATCGAAGGTCGCGCTAGACCTTCGAGA

DAB30 (SEQ ID NO: 73)
TCTCACTCCTCGAGTGGGTTCTGGGAGTTTAGCAGGGGGCTTTGGGATGGGGAGAAACCGTA
AGAGTGTCCGGTCGGGTTGTGGTTTTCGTGGCTCCTCTGCTCAGGGCCCGTGTCCGGTCAC
GCCTGCCACCATTGACAAACACTCTAGAATCGAAGGTCGCGCTAGACCTTCGAGA

DAX15 (SEQ ID NO: 74)
TCTCACTCCTCGAGTGAGAGCGGGCGGTGCCGTAGCGTGAGCCGGTGGATGACGACGTGGC
AGACGCAGAAGGGCGGTTGTGGTTCCAATGTTTCCCGCGGTTCGCCCCTCGACCCCTCTCA
CCAGACCGGGCATGCCACTACTTCTAGAATCGAAGGTCGCGCTAGACCTTCGAGA

DAX23 (SEQ ID NO: 75)
TCTCACTCCTCGAGGGAGTGGAGGTTTGCCGGGCCGCCGTTGGACCTGTGGGCGGGTCCGA
GCTTGCCCTCTTTTAACGCCAGTTCCCACCCTCGCGCCCTGCGCACCTATTGGTCCCAGCG
GCCCCGCTCTAGAATCGAAGGTCGCGCTAGACCTTCGAGA

DAX24 (SEQ ID NO: 76)
TCTCACTCCTCGAGGATGGAGGACATCAAGAACTCGGGGTGGAGGGACTCTTGTAGGTGGG

TABLE 8-continued

DNA Sequences for Clones used in in vivo Pan

GTGACCTGAGGCCTGGTTGTGGTAGCCGCCAGTGGTACCCCTCGAATATGCGTTCTAGCAG
AGATTACCCCGCGGGGGGCCACTCTAGAATCGAAGGTCGCGCTAGACCTTCGAGA
DAX27 (SEQ ID NO: 77)
TCTCACTCCTCGAGTCATCCGTGGTACAGGCATTGGAACCATGGTGACTTCTCTGGTTCGG
GCCAGTCACGCCACACCCCGCCGGAGAGCCCCCACCCCGGCCGCCCTAATGCCACCATTTCTAGAAT
DCX8 (SEQ ID NO: 78)
TCTCACTCCTCGAGATATAAGCACGATATCGGTTGCGATGCTGGGGTTGACAAGAAGTCGT
CGTCTGTGCGTGGTGGTTGTGGTGCTCATTNGTCGCCACCCCGCGCCGGCCGTGGTCCTCG
CGGCACGATGGTTAGCAGGCTTTCTAGAATCGAAGGTCGCGCTAGACCTTCGAGA
DCX11 (SEQ ID NO: 79)
TCTCACTCCTCGAGTCAGGGCTCCAAGCAGTGTATGCAGTACCGCACCGGTCGTTTGACGG
TGGGGTCTGAGTATGGTTGTGGTATGAACCCCGCCCGCCATGCCACGCCCGCTTATCCGGC
GCGCCTGCTGCCACGCTATCGCTCTAGAATCGAAGGTCGCGCTAGACCTTCGAGA
DCX26 (SEQ ID NO: 80)
TCTCACTCCTCGAGTGGGCGGACTACTAGTGAGATTTCTGGGCTCTGGGGTTGGGGTGACG
ACCGGAGCGGTTATGGTTGGGGTAACACGCTCCGCCCCAACTACATCCCTTATAGGCAGGC
GACGAACAGGCATCGTTATACGTCTAGAATCGAAGGTCGCGCTAGACCTTCGAGA
DCX33 (SEQ ID NO: 81)
TCTCACTCCTCGAGGTGGAATTGGACTGTCTTGCCCGCCACTGGCGGCCATTACTGGACGC
GTTCGACGGACTATCACGCCATTAACAATCACAGGCCGAGCATCCCCCACCAGCATCCGAC
CCCTATCTCTAGAATCGAAGGTCGCGCTAGACCTTCGAGA
DCX36 (SEQ ID NO: 82)
TCTCACTCCTCGAGTTGGTCGTCGTGGAATTGGAGCTCTAAGACTACTCGTCTGGGCGACA
GGGCGACTCGGGAGGGTTGTGGTCCCAGCCAGTCTGATGGCTGTCCTTATAACGGCCGCCT
TACGACCGTCAAGCCTCGCACGTCTAGAATCGAAGGTCGCGCTAGACCTTCGAGA
DCX39 (SEQ ID NO: 83)
TCTCACTCCTCGAGTGGTAGTTTGAACGCATGGCAACCGCGGTCATGGGTGGGGGGCGCGT
TCCGGTCACACGCCAACAATAACTTGAACCCCAAGCCCACCATGGTTACTNGTCACCCTAC
CTCTAGAATCGAAGGTCGCGCTAGACCTTCGAGA
DCX42 (SEQ ID NO: 84)
TCTCACTCCTCGAGGTATTCGGGTTTGTCCCCGCGGGACAACGGTCCCGCTTGTAGTCAGG
AGGCTACCTTGGAGGGTTGTGGTGCGCAGAGGCTGATGTCCACCCGTCGCAAGGGCCGCAA
CTCCCGCCCCGGGTGGACGCTCTCTAGAATCGAAGGTCGCGCTAGACCCTTCGAGA
DCX45 (SEQ ID NO: 85)
TCTCACTCCTCGAGCGTGGGGAATGATAAGACTAGCAGGCCGGTTTCCTTCTACGGGCGCG
TTAGTGATCTGTGGAACGCCAGCTTGATGCCGAAGCGTACTCCCAGCTCGAAGCGCCACGA
TGATGGCTCTAGAATCGAAGGTCGCGCTAGACCTTCGAGA
PAAX2 (SEQ ID NO: 86)
TCTCACTCCTCGAGTACTCCCCCCAGTAGGGAGGCGTATAGTAGGCCCTATAGTGTCGATA
GCGATTCGGATACGAACGCCAAGCACAGCTCCCACAACCGCCGTNTGCGGACGCGCAGCCG
CCCGAACTCTAGAATCGAAGGTCGCGCTAGACCTTCGAGA
PAX9 (SEQ ID NO: 87)
TCTCACTCCTCGAGATGGCCTAGTGTGGGTTACAAGGGTAATGGCAGTGACACTATTGATG
TTCACAGCAATGACGCCAGTACTAAGAGGTCCCTCATCTATAACCACCGCCGCCCCNTCTT
TCCCTCTAGAATCGAAGGTCGCGCTAGACCTTCGAGA
PAX14 (SEQ ID NO: 88)
TCTCACTCCTCGAGAACGTTTGAGAACGACGGGCTGGGCGTCGGCCGGTCTATTCAGAAGA
AGTCGGATAGGTGGTACGCCAGCCACAACATTCGTAGCCATTTCGCGTCCATGTCTCCCGC
TGGTAAGTCTAGAATCGAAGGTCGCGCTAGACCTTCGAGA
PAX15 (SEQ ID NO: 89)
TCTCACTCCTCGAGCTATTGTCGGGTTAAGGGTGGTGGGGAGGGGGGGCATACGGATTCCA
ATCTGGCTAGGTCGGGTTGTGGTAAGGTGGCCAGGACCAGCAGGCTTCAGCATATCAACCC
GCGCGCTACCCCCCCCTCCCGGTCTAGAATCGAAGGTC
PAX16 (SEQ ID NO: 90)
TCTCACTCCTCGAGTTGGACTCGGTGGGGCAAGCACANTCATGGGGGGTTTGTGAACAAGT
CTCCCCCTGGGAAGAACGCCACGAGCCCCTACACCGACGCCCAGCTGCCCAGTGATCAGGG
TCCTCCCTCTAGAATCGAAGGTCGCGCTAGACCTTCGAGA
PAX17 (SEQ ID NO: 91)
TCTCACTCCTCGAGTCAGGTTGATTCGTTTCGTAATAGCTTTCGGTGGTATGAGCCGAGCA
GGGCTCTGTGCCATGGTTGTGGTAAGCGCGACACCTCCACCACTCGTATCCACAATAGCCC
CAGCGACTCCTATCCTACACGCTCTAGAATCGAAGGTCGCGCTAGACCTTCGAGA
PAX18 (SEQ ID NO: 92)
TCTCACTCCTCGAGCTTTTTGCGGTTCCAGAGTCCGAGGTTCGAGGATTACAGTAGGACGA
TCTNTCGGTTGCGCAACGCCACGAACCCGAGTAATGTCTCCGATGCGCACAATAACCGGGC
CTTGGCCTCTAGAATCGAAGGTCGCGCTAGACCTTCGAGA
PAX35 (SEQ ID NO: 93)
TCTCACTCCTCGAGGAGCATCACCGACGGGGGCATCAATGAGGTGGACCTGAGTAGTGTGT
CGAACGTTCTTGAGAACGCCAACTCGCATAGGGCCTACAGGAAGCATCGCCCGACCTTGAA
GCGTCCTTCTAGAATCGAAGGTCGCGCTAGACCTTCGAGA
PAX38 (SEQ ID NO: 94)
TCTCACTCCTCGAGTTCGAAGGTGAGCAGCCCGAGGGATCCGACGGTCCCGCGGAAGGGCG
GCAATGTTGATTATGGTTGTGGTCACAGGTCTTCCGCCCGGATGCCTACCTCCGCTCTGTC
GTCGATCACGAAGTGCTACACTTCTAGAATCGAAGGTCGCGCTAGACCTTCGAGA
PAX40 (SEQ ID NO: 95)
TCTCACTCCTCGAGAGCCAGTANGCAGGGCGGCCGGGGTGTTGCCCCTGAGTTTGGGGCGA
GCGTTTTGGGTNGTGGTTGTGGTAGCGCCACTTATTACACGAACTCCACCAGCTGCAAGGA
TGCTATGGGCCACAACTACTCGTCTAGAATCGAAGGTCGCGNTAGACCTTCGAGA

TABLE 8-continued

DNA Sequences for Clones used in in vivo Pan

PAX43 (SEQ ID NO: 96)
TCTCACTCCTCGAGATGGTGCGAGAAGCACAAGTTTACGGCTGCGCGTTGCAGCGCGGGGG
CGGGTTTTGAGAGGGANGCCAGCCGTCCGCCCCAGCCTGCCCACCGGGATAATACCAACCG
TAATGCNTNTAGAATCGAAGGTCGCGCTAGACCTTCGAGA

PAX45 (SEQ ID NO: 97)
TCTCACTCCTCGAGTTTTCAGGTGTACCCGGACCATGGTCTGGAGAGGCATGCTTTGGACG
GGACGGGTCCGCTTTACGCCATGCCCGGCCGCTGGATTAGGGCGCGTCCGCAGAACAGGGA
CCGCCAGTCTAGAATCGAAGGTCGCGCTAGACCTTCGAGA

PAX46 (SEQ ID NO: 98)
TCTCACTCCTCGAGCAGGTGTACGGACAACGAGCAGTGCCCCGATACCGGGANTAGGTCTC
GTTCCGTTAGTAACGCCAGGTACTTTTCGAGCAGGTTGCTCAAGACTCACGCCCCCCATCG
CCCTTCTAGAATCGAAGGTCGCGCTAGACCTTCGAGA

P31 (SEQ ID NO: 99)
TCTCACTCCTCGAGTGCCAGGGATAGCGGGCCTGCGGAGGATGGGTCCCGCGCCGTCCGGT
TGAACGGGGTTGAGAACGCCAACACTAGGAAGTCCTCCCGCAGTAACCCGCGGGGTAGGCG
CCATCCCTCTAGAATCGAAGGTCGCGCTAGACCTTCGAGA

P90 (SEQ ID NO: 100)
TCTCACTCCTCGAGTTCCGCCGATGCGGAGAAGTGTGCGGGCAGTCTGTTGTGGTGGGGTA
GGCAGAACAACTCCGGTTGTGGTTCGCCCACGAAGAAGCATCTGAAGCACCGCAATCGCAG
TCAGACCTCCTCTTCGTCCCACTCTAGAATCGAAGGTCGCGCTAGACCTTCGAGA

5PAX3 (SEQ ID NO: 101)
TCTCACTCCTCGAGACCGAAGAACGTGGCCGATGCTTATTCGTCTCAGGACGGGGCGGCGG
CCGAGGAGACGTCTCACGCCAGTAATGCCGCGCGGAAGTCCCCTAAGCACAAGCCCTTGAG
GCGGCCTTCTAGAATCGAAGGTCGCGCTAGACCTTCGAGA

5PAX5 (SEQ ID NO: 102)
TCTCACTCCTCGAGAGGCAGTACGGGGACGGCCGGCGGCGAGCGTTCCGGGGTGCTCAACC
TGCACACCAGGGATAACGCCAGCGGCAGCGGTTTCAAACCGTGGTACCCTTCGAATCGGGG
TCACAAGTCTAGAATCGAAGGTCGCGCTAGACCTTCGAGA

5PAX7 (SEQ ID NO: 103)
TCTCACTCCTCGAGGTGGGGGTGGGAGAGGAGTCCGTCCGACTACGATTCTGATATGGACT
TGGGGGCGAGGAGGTACGCCACCCGCACCCACCGCGCGCCCCCTCGCGTCTTGAAGGCTCC
CCTGCCCTCTAGAATCGAAGGTCGCGCTAGACCTTCGAGA

5PAX12 (SEQ ID NO: 104)
TCTCACTCCTCGAGGCACTGGAAGTGCGAGGGCTCTCAGGCTGCCTACGGGGACAAGGATA
TCGGGAGGTCCAGGGGTTGTGGTTCCATTACAAAGAATAACACTAATCACGCCCATCCTAG
CCACGGCGCCGTTGCTAAGATCTCTAGAATCGAAGGTCGCGCTAGACCTTCGAGA

HAX9 (SEQ ID No: 105)
TCTCACTCCTCGAGCCGCGAGGAGGCGAACTGGGACGGCTATAAGAGGGAGATGAGCCACC
GGAGTCGCTTTTGGGACGCCACCCACCTGTCCCGCCCTCGCCGCCCCGCTAACTCGGTGA
CCCTAACTCTAGAATCGAAGGTCGCGCTAGACCTTCGAGA

HAX40 (SEQ ID NO: 106)
TCTCACTCNTCGAGAGAGTTCGCGGAGAGGAGGTTGTGGGGGTGTGATGACCTGAGTTGGC
GTCTCGACGCGGAGGGTTGTGGTCCCACTCCGAGCAATCGGGCCGTCAAGCATCGCAAGCC
CCGCCCACGCTCCCCCGCACTCTCTAGAATCGAAGGTCGCGCTAGACCTTCGAGA

HAX42 (SEQ ID NO: 107)
TCTCACTCNTNGAGTGATCACGCGTTGGGGACGAATCTGAGGTCTGACAATGCCAAGGAGC
CGGGTGATTACAACTGTTGTGGTAACGGGAACTCTACCGGGCGAAAGGTTTTTAACCGTAG
GCGCCCCTCCGCCATCCCCANTTCTAGAATCGAAGGTCGCGCTAGACCTTCGAGA

HCA3 (SEQ ID NO: 108)
TCTCACTCCTCGAGGCATATTTCTGAGTATAGCTTTGCGAATTCCCACTTGATGGGTGGCG
AGTCCAAGCGGAAGGGTTGTGGTATTAACGGCTCCTTTTCTCCCACTTGTCCCCGCTCCCC
CACCCCAGCCTTCCGCCGCACCTCTAGAATCGAAGGTCGCGCTAGACCTTCGAGA

H40 (SEQ ID NO: 109)
TCTCACTCCTCGAGCCGGGAGAGCGGGATGTGGGGTAGTTGGTGGCGTGGTCACAGGTTGA
ATTCCACGGGGGGTAACGCCAACATGAATGCTAGTCTGCCCCCCGACCCCCCTGTTTCCAC
TCCGTCTAGAATCGAAGGTCGCGCTAGACCTTCGAG

By comparison of the amino acid sequences of the clones binding GIT receptors, certain sequence similarities or "motifs" were recognized. These motifs can often represent the part of the sequence that is important for binding to the target. Table 9 identifies regions of sequence similarity or sequence motifs (in boldface) that were identified among GIT binding peptides (corresponding SEQ ID NOS. are shown in Table 7).

TABLE 9

| PEPT-1 | | SEQ. ID. NO. |
| --- | --- | --- |
| HPT1 | | |
| P31 | SARDSGPAEDGSRAVRLNGVENANTRKSSRSNPRGRRHP | 43 |
| PAX9 | RWPSVGYKGNGSDTIDVHSNDASTKRSLIYNHRRPLFP | 31 |
| HAX42 | SDHALGTNLRSDNAKEPGDYNCCGNGNSTGRK-VFNRRRPSAIPT | 52 |
| PAX2 | STPPSREAYSRPYSVDSDSDTNAKHSSHNRRLRTRSRPN | 55 |
| hSI | | |

TABLE 9-continued

| PEPT-1 | | SEQ. ID. NO. |
|---|---|---|
| SNi10 | RVGQCTDSDVRRPWARSCAHQGCGAGTRNSHGCITRPLRQASAH | 4 |
| SNi38 | RGAADQRRGWSENLGLPRVGWDAIAHNSYTFTSRRPRPP | 7 |
| S15 | RSGAYESPDGRGGRSYVGGGGGCGNIGRKHNLWGLRTASPACWD | 1 |
| SNi34 D2H | SPCGGSWGRFMQGGLFGGRTDGCGAHRNRTSASLEPPSSDY | 6 |
| | | |
| DAB10 | SKSGEGGDSSRGETGWARVRSHAMTAGRFRWYNQLPSDR | 15 |
| DAB30 | SGFWEFSRGLWDGENRKSVRSGCGFRGSSAQGPCPVTPATIDKH | 18 |
| DCX8 | RYKHDIGCDAGVDKKSSSVRGGCG-AHSSPPRAGRGPRGTMVSRL | 23 |

Phage Binding to Caco-2 Cells

Phage expressing presumed GIT binding peptide inserts were also assayed by ELISA on fixed Caco-2 or C2BBe1 cells as follows. Cells were plated at 1×10⁵ cells/well on 100 μl culture media and incubated at 30° C. in 5% $CO_2$ overnight. 100 μl 25% formaldehyde was added to each well for 15 minutes. Contents of the wells were removed by inverting the plate. The plate was then washed 3 times with DPBS. 0.1% phenylhydrazine DPBS solution was added to each well and incubated for 1 hr at 37° C. The plate was inverted and washed 3 times. The plate was blocked with 0.5% BSA-DPBS for 1 hr at room temperature. The plate was inverted and washed 3 times with 1% BPT (PBS containing 1% BSA and 0.05% Tween20). Phage diluted with 1% BPT was added to wells containing fixed cells. Wells without phage added were used to determine background binding of the HRP conjugate. The plates were incubated 2–3 hours on a rotor at room temperature. Plates were washed as before. Plates were incubated with dilute anti-M13-HRP antibody in 1% BPT for 1 hour at room temperature. Following washing, TMB substrate was added and absorbance of the plates were read at 650 nm. Table 10 shows the relative binding of phage encoding peptides to fixed Caco-2 cells.

TABLE 10

Relative binding of phage encoding peptides to fixed Caco-2 cells

| Phage | Fixed Caco-2 cell binding |
|---|---|
| SNi10 | ++ |
| SNi34 | + |
| P31 | ++ |
| 5PAX5 | ++ |
| PAX2 | + |
| HAX42 | + |
| DCX8 | +++ |
| DCX11 | + |
| H1 | + |
| M13mpl18 | − |

In Vivo Phase Selection:

Further selection of phage expressing peptides capable of binding to the GIT or transporting the GIT was done as follows. The purified library was resuspended in a buffer, such as TBS or PBS, and introduced onto one side of a tissue barrier, e.g., injected into the duodenum, jejunum, ileum, colon or other in vivo animal site using, for instance, a closed loop model or open loop model. Following injection, samples of bodily fluids located across the tissue barrier, e.g., samples of the portal circulation and/or systemic circulation, were withdrawn at predetermined time points, such as 0 to 90 minutes and/or 2 to 6 hours or more. An aliquot of the withdrawn sample (e.g., blood) was used to directly infect a host, e.g., E. coli, in order to confirm the presence of phage. The remaining sample was incubated, e.g., overnight incubation with E. coli at 37° C. with shaking. The amplified phage present in the culture can be sequenced individually to determine the identity of peptides coded by the phage or, if further enrichment is desired, can be precipitated using PEG, and resuspended in PBS. The phage can then be further precipitated using PEG or used directly for administration to another animal using a closed or open GIT loop model system. Portal or systemic blood samples are collected and the phage transported into such circulation systems is subsequently amplified. In this manner, administration of the phage display library with, if desired, repeat administration of the amplified phage to the GIT of the animal, permitted the selection of phage which was transported from the GIT to the portal and/or systemic circulation of the animal.

If desired, following administration of the phage display library to the tissue barrier (e.g., GIT) of the animal model, the corresponding region of the tissue barrier can be recovered at the end of the procedures given above. This recovered tissue can be washed repeatedly in suitable buffers, e.g., PBS containing protease inhibitors and homogenized in, for example, PBS containing protease inhibitors. The homogenate can be used to infect a host, such as E. coli, thus permitting amplification of phages which bind tightly to the tissue barrier (e.g., intestinal tissue). Alternatively, the recovered tissue can be homogenized in suitable PBS buffers, washed repeatedly and the phage present in the final tissue homogenate can be amplified in E. coli. This approach permits amplification (and subsequent identification of the associated peptides) of phages which either bind tightly to the tissue barrier (e.g., intestinal tissue) or which are internalized by the cells of the tissue barrier (e.g., epithelial cells of the intestinal tissue). This selection approach of phage which bind to tissues or which are internalized by tissues can be repeated.

Treatment of Animal Tissue Barriers In Vivo with Phase Display Populations

The purified phage display library (random or preselected) was diluted to 500 μl in PBS buffer and injected into the closed (or open) intestinal loop model (e.g., rat, rabbit or other species). At time 0 and at successive time points after injection, a sample of either the portal circulation or systemic circulation was withdrawn. An aliquot of the withdrawn blood was incubated with E. coli, followed by plating for phage plaques or for transduction units or for colonies where the phage codes for resistance to antibiotics such as tetracycline. The remainder of the withdrawn blood sample (up to 150 μl) was incubated with 250 μl of E. coli and 5 ml of LB medium or other suitable growth medium. The *E. coli* cultures were incubated overnight by incubation at 37° C. on a shaking platform. Blood samples taken at other time points (such as 15 min, 30 min, 45 min, 60 min, up to 6 hours) were processed in a similar manner, permitting amplification of phages present in the portal or systemic circulation in *E. coli* at these times. Following amplification, the amplified phage was recovered by PEG precipitation and resuspended in PBS buffer or TBS buffer. The titer of the amplified phage, before and after PEG precipitation, was determined. The amplified, PEG precipitated phage was diluted to a known phage titer (generally between $10^8$ and $10^{10}$ phage or plaque forming units (p.f.u.) per ml) and was injected into the GIT of the animal closed (or open) loop model. Blood samples were collected from portal and/or systemic circulation at various time points and the phage transported into the blood samples were amplified in *E. coli* as given above for the first cycle. Subsequently, the phage was PEG-precipitated, resuspended, titered, diluted and injected into the GIT of the animal closed (or open) loop model. This procedure of phage injection followed by collection of portal and/or systemic blood samples and amplification of phage transported into these blood samples can be repeated, for example, up to 10 times, to permit the selection of phages which are preferentially transported from the GIT into the portal and/or systemic circulation.

6.7. Transport of Phage from Rat Lumen into the Portal and Systemic Circulation

Phage from random phage display libraries as well as control phage were injected into the lumen of the rat gastro-intestinal tract (in situ rat closed loop model). Blood was collected over time from either the systemic circulation or portal circulation and the number of phage which were transported to the circulation was determined by titering blood samples in *E. coli*.

The phage display libraries used in this study were D38 and DC43 in which gene III codes for random 38-mer and 43-mer peptides, respectively. As a negative control, the identical phage M13 mp18, in which gene III does not code for a "random" peptide sequence, was used. Both the library phages D38 and DC43 were prepared from *E. coli*, mixed together, dialyzed against PBS, precipitated using PEG/NaCl and were resuspended in PBS buffer. The M13mp18 control was processed in a similar manner. The titer of each phage sample was determined and the phage samples were diluted in PBS to approximately the same titers prior to injection into the rat closed loop model.

For sampling from the systemic circulation, approximately 15 cm of the duodenum of Wistar rats was tied off (closed loop model), approximately 0.5 ml of phage solution was injected into the closed loop and blood (0.4 ml) was sampled from the tail vein at various times. The time points used (in min) were: 0, 15, 30, 45, 60, 90, 120, 180, 240 and 300 minutes. For sampling from the portal circulation, the portal vein was catheterized, approximately 15 cm of the duodenum was tied off (closed loop model), 0.5 ml of phage solution was injected into the closed loop and blood was sampled from the portal vein catheter at various times. As the portal sampling is delicate, sampling times were restricted to 15, 30, 45 and 60 minutes, where possible. The volume of phage injected into each animal was as follows:

| ANIMALS (15) | VOLUME OF PHAGE INJECTED |
|---|---|
| R1–R3 | 0.50 ml |
| R4 | 0.43 ml |
| R5–R15 | 0.45 ml |

The estimated number of transported phage has been adjusted to account for differences in volume injected into each animal (using 0.5 ml as the standard volume).

To investigate transport into the systemic circulation, animals R1, R2 and R3 received the control phage M13mp18 and animals R4, R5, R6 and R7 received the test phage D38/DC43 mix. To investigate transport into the portal circulation, animals R8, R9 and R10 received the control phage M13mp18 and animals R11, R12, R13 and R14 received the test phage D38/DC43 mix. Animal R15* received the combined phage samples from animals R4–R7 (see Table 11) which were sampled from the systemic circulation on day one, followed by amplification in. *E. coli*, PEG precipitation and resuspension in PBS. On subsequent analysis, the titer of this phage was found to be 100 times greater than the other phage samples used for animals R8-R14. Thus, the data presented for animal R15* is adjusted down.

Approximately 0.4 ml of the blood was collected at each time point in each model system. 30 μl of the collected blood (systemic) was mixed with 100 μl of the prepared *E. coli* strain K91Kan, incubated at 37° C. for 30 min, and plated out for plaque formation using Top Agarose on LB plates. Various negative controls were included in the titering experiments. The following day, the number of plaque forming units was determined. Similarly, 30 μl of the collected blood (portal) and serial dilutions (1:100, 1:1000) thereof was mixed with 100 μl of the prepared *E. coli* strain K91Kan, incubated at 37° C. for 30 min, and plated out for plaque formation using Top Agarose on LB plates. The following day, the number of plaque forming units was determined.

In addition, approximately 300 μl of the collected blood from each time point (systemic and portal) was incubated with 5 ml of prepared *E. coli* strain K91Kan in modified growth media containing 5 mM $MgCl_2/MgSO4$ at 37° C. overnight with shaking (to permit phage amplification). The samples were centrifuged and the cell pellet was discarded. Samples of the phage supernatant were collected, serially diluted ($10^{-2}$, $10^{-4}$, $10^{-6}$, $10^{-8}$) in TBS buffer, and plated for plaques in order to determine the number of plaque forming units present in the amplified phage samples.

Furthermore, an aliquot of phage was removed from the "amplified" supernatants obtained from test animals R4–R7 (samples from each time point were used), combined, and precipitated using PEG for two hours. The precipitated phage was resuspended in PBS buffer and was injected into closed loop model of animal R15*, followed by portal sampling.

The number of phage transported from the closed loop model into the systemic circulation is presented in Table 11 hereafter. The number of phage transported from the closed loop model into the portal circulation is presented in Table 12 hereafter. These numbers are corrected for phage input difference and for volume input differences. Clearly, more phage are present in the portal samples than in the systemic samples, indicative of either hepatic or RES clearance and/or phage instability in the systemic circulation. In addition, the uptake of phage from the GIT into the portal circulation is quite rapid, with substantial number of phages detected within 15 minutes. The results from the portal sampling experiments would also indicate that the kinetics of uptake of phage from the D38/DC43 libraries is quicker than that of the control phage. Thus, there may be preferential uptake of phage coding for random peptide sequences from the GIT into the portal circulation. In the case of animals R13, R14 and R15*, the % of the phage transported into the titered blood sample within the limited time frame (30, 45 and 15 mins, respectively) was estimated as 0.13%, 1.1% and 0.013%, respectively.

TABLE 11

NUMBER OF PHAGE TRANSPORTED FROM THE CLOSED LOOP MODEL INTO THE SYSTEMIC CIRCULATION

| Time (min) | R1 | R2 | R3 | R4 | R5 | R6 | R7 |
|---|---|---|---|---|---|---|---|
| 0 | 0 | 0 | 0 | 0 | 0 | 0 | 0 |
| 15 | 0 | 1 | 9 | 0 | 0 | 1 | 7 |
| 30 | 2 | 1 | 0 | 0 | 46 | 1 | 11 |
| 45 | 10 | 4 | 2 | 1 | 32 | 0 | 20 |
| 60 | 63 | 19 | 21 | 1 | 114 | 0 | 21 |
| 90 | 104 | 20 | 18 | 3 | 115 | 0 | 22 |
| 120 | 94 | 24 | 27 | 0 | 64 | 0 | 6 |
| 180 | 94 | 12 | 23 | 1 | 413 | 0 | 0 |
| 240 | 14 | 1 | 20 | 0 | 36 | 0 | 0 |
| 300 | 1 | 1 | 4 | 2 | 0 | 0 | 0 |
| Total number of transported phage | 382 | 83 | 124 | 8 | 820 | 2 | 87 |

Animals R1, R2 and R3 received the control phage M13mp18.

Animals R4, R5, R6 and R7 received the test phage D38/DC43 mix.

TABLE 12

NUMBER OF PHAGE TRANSPORTED FROM THE CLOSED LOOP MODEL INTO THE PORTAL CIRCULATION

| Time (min) | R8 | R9 | R10 | R11 | R12 | R13 | R14 | R15* |
|---|---|---|---|---|---|---|---|---|
| 15 | 15 | 6 | 3 | 1 | 19 | 231,000 | 1,000,000 | 20,000 |
| 30 | 1 | 5 | 26 | — | 0 | 60,000 | 272,000 | — |
| 45 | — | 1 | 555 | — | 1 | — | 1,240,000 | — |
| 60 | — | — | — | — | 420,000 | — | — | — |

Animals R8, R9 and R10 received the control phage M13mp18.

Animals R11, R12, R13 and R14 received the test phage D38/DC43 mix.

Animal R15* received the combined phage samples from animals R4–R7 (see Table 11) which were sampled from the systemic circulation on day one, followed by PEG precipitation and resuspension in PBS. On subsequent analysis, the titer of this phage was found to be 100 times greater than the other phage samples used for animals R8–R14. Thus, the data measuring phage transport into the portal circulation for animal R15* is adjusted down.

These studies demonstrated that both the control phage and the D38/DC43 phages are transported over time from the lumen of the GIT into the portal and systemic circulation, as demonstrated by titering the phage transported to the blood in *E. coli*. More phage were transported from the test phage samples into the portal circulation than the corresponding control phage sample. In addition, the kinetics of transport of the test phage into the portal circulation appeared to exceed that of the control phage. Phage from the D38/DC43 libraries which appeared in the systemic circulation of different animals (R4–R7) were pooled, amplified in *E. coli*, precipitated, and re-applied to the lumen of the GIT, followed by collection in the portal circulation and titering in *E. coli*. These selected phage were also transported from the lumen of the GIT into the portal circulation. This in situ loop model may represent an attractive screening model in which to identify peptide sequences which facilitate transport of phage and particles from the GIT into the circulation.

Using this screening model system, a number of preselected phage libraries now exist, including a one pass systemic phage library from animals R4–R7, a one-pass portal library from animals R11–R14, and a two pass, rapid transport, systemic-portal phage library SP-2 from animal R15*.

6.8. Transport of Phage from Preselected Phage Libraries from the Rat Lumen into the Portal and Systemic Circulation Four preselected phage libraries, GI-D2H, GI-hSI, GI-HPT1 and GI-hPEPT1, were constructed by pooling phage previously selected by screening random phage display libraries D38 and DC43 using the HPT1, HPEPT1, D2H and hSI receptor or binding sites located in the GIT. The phage pools, preselected phage libraries are shown in Table 13. Note that the sequences for PAX2, HAX1, HAX5, HAX6, HAX10, H10 and HAX44 are the same. Also, the sequence for HAX40 is the same as that for H44. The corresponding SEQ ID NOS. are shown in Table 7.

TABLE 13

PRESELECTED PHAGE LIBRARIES

| D2H | HSI | HPT1 | hPEPT1 |
|---|---|---|---|
| DAB3 | S15 | HAX9 | PAX2 (H10) |
| DAB7 | S21 | HAX35 | PAX9 |
| DAB10 | S22 | HAX40 (H44) | PAX14 |
| DAB18 | SNi10 | HAX42 | PAX15 |
| DAB24 | SNi28 | HCA3 | PAX16 |
| DAB30 | SNi34 | HAX1 | PAX17 |
| DAX15 | SNi38 | HAX5 | PAX18 |
| DAX23 | SNi45 | HAX6 | PAX35 |
| DAX24 | SNiAX2 | HAX10 | PAX38 |
| DAX27 | SNiAX6 | H40 | PAX40 |
| DCX8 | SNiAX8 | M13mp18 | PAX43 |
| DCX11 | M13mp18 | | PAX45 |
| DCX26 | | | PAX46 |
| DCX33 | | | P31 |
| DCX36 | | | P90 |
| DCX39 | | | 5PAX3 |
| DCX42 | | | 5PAX5 |
| DCX45 | | | 5PAX7 |
| M13mp18 | | | 5PAX12 |
| | | | H40 |
| | | | M13mp18 |

Similar to methods described herein above, these preselected phage libraries together with the negative control phage M13mp18 were injected into the rat closed loop model (6 animals per preselected phage library), blood was collected over time from the portal circulation via the portal vein and, at the termination of the experiment, a systemic blood sample was collected from the tail vein and the intestinal tissue region from the closed loop was collected.

In particular, phages selected in vitro to each receptor or binding site located in the GIT were amplified in *E. coli*, PEG-precipitated, resuspended in TBS and the titer of each phage sample was determined by plaquing in *E. coli* as described above. Subsequently, an equal number of each phage ($8 \times 10^8$ phage) for each receptor site was pooled into a preselected phage library together with the negative control phage M13mp18 and each preselected phage library was administered to 6 Wistar rats per library (rats 1–6; G1-D2H, rats 7–12; GI-hSI, rats 13–18; GI-hPEPT1, and rats 19–24; GI-HPT1). Using the in situ loop model described above, 0.5 ml of preselected phage library solution was injected into the tied-off portion of the duodenum/jejunum. Blood was collected into heparinized tubes from the portal vein at 0, 15, 30, 45 and 60 minutes. A blood sample was taken from the systemic circulation at the end of the experiment. Similarly, the portion of the duodenum/jejunum used for phage injection was taken at the end of the experiment.

Thirty microliters of the collected portal blood (neat and $10^{-2}$, $10^{-1}$, $10^{-6}$ dilutions) was added to 30 µl E. coli K91Kan cells (overnight culture) and incubated at 37° C. for 10 min. Subsequently, 3 ml of top agarose was added and the samples were plated for plaques. One hundred microliters of the collected portal blood was added to 100 µl of E. coli K91Kan. Five milliliters of LB medium was then added and the samples were incubated at 37° C. overnight in a rotating microbial incubator. The E. coli was removed by centrifugation and the amplified phage supernatant samples were either titered directly or were PEG-precipitated, resuspended in TBS and titered. Following titration of the amplified phage, samples containing phage from each set of animals were combined, adjusting the titer of each sample to the same titer, and were plated for plaques on LB agar lates (22 cm² square plates). Either 12,000 or 24,000 phage were lated for plaques.

Thirty microliters of the collected systemic blood (neat and $10^{-2}$, $10^{-1}$, $10^{-6}$ dilutions) was added to E. coli K91Kan cells, incubated at 37° C. for 10 min. Three ml of top agarose was then added and the samples were plated for plaques. One hundred microliters of the collected systemic blood was added to 100 µl of E. coli K91Kan, incubated at 37° C. for 10 min. Five milliliters of LB medium was then added and the samples were incubated at 37° C. overnight in a rotating microbial incubator. The E. coli was removed by centrifugation and the amplified phage supernatant samples were either titered directly or were PEG-precipitated, resuspended in TBS and titered. Following titration of the amplified phage, samples containing phage from each set of animals were combined, adjusting the titer of each sample to the same titer, and were plated for plaques on LB agar plates (22 cm² square plates). Either 12,000 or 24,000 phage were plated for plaques.

The intestinal tissue portion used in each closed loop was excised. The tissue was cut into small segments, followed by 3 washings in sterile PBS containing protease inhibitors, and homogenized in an Ultra thorex homogeniser (Int-D samples). Alternatively, the tissue (in PBS supplemented with protease inhibitors) was homogenized in an Ultra Thorex homogenizer, washed 3 times in PBS containing protease inhibitors and resuspended in PBS containing protease inhibitors (Int-G samples). In each case, serial dilutions (neat and $10^{-2}$, $10^{-4}$, $10^{-6}$ dilutions) of the tissue homogenate was titered in E. coli. In addition, an aliquot (100 µl) of the tissue homogenate was added to 100 µl of E. coli K91Kan, incubated at 37° C. for 10 min, followed by addition of 5 ml of LB medium and incubation overnight at 37° C. in a rotating microbial incubator.

The phage amplified from the portal blood, systemic blood and intestinal tissue was plated for plaques. The plaques were transferred to Hybond-N Nylon filters, followed by denaturation (1.5M NaCl, 0.5M NaOH), neutralization (0.5M TRIS-HCl, pH7.4, 1.5M NaCl), and washing in 2xSSC buffer. The filters were air-dried, and the DNA was cross-linked to the filter (UV crosslinking: 2 min, high setting). The filters were incubated in pre-hybridization buffer (6xSSC, 5x Denhardt's solution, 0.1% SDS, 20 g/ml yeast tRNA) at 40° C.–45° C. for at least 60 min.

Synthetic oligonucleotides, (22-mers), complimentary to regions coding for the receptor or binding sites used to create the preselected phage library, were synthesized (see Table 14 below).

TABLE 14

OLIGONUCLEOTIDES USED IN IN VIVO SCREEN

| CLONE NAME | OLIGO | SEQ. ID. NO. |
| --- | --- | --- |
| S15 | 5'TCCGGACTCTCATAAGCGCCGG3' | 111 |
| S21 | 5'ACAACGGGCCAGAAAGAGCGAG3' | 112 |
| S22 | 5'ACACCACCCCAATCGGAGCTAC3' | 113 |
| SNi10 | 5'TCAGAATCCGTGCACTGGCCAA3' | 114 |
| SNi28 | 5'GCCCTATTCATACCACCGGAGT3' | 115 |
| SNi34 | 5'CATCAGTCCTACCGCCGAAAAG3' | 116 |
| SNi38 | 5'CGTATAGCTATTGTGAGCGATG3' | 117 |
| SNi45 | 5'ACGCGCGGAACGAGCAGTACCA3' | 118 |
| SNiAX2 | 5'CCATAATGATCCCCGTCACTAT3' | 119 |
| SNiAX6 | 5'AGACACCCCTTAGCCGTCGTAG3' | 120 |
| SNiAX8 | 5'AGCTCCGTGACCTTAGTCATAA3' | 121 |
| DAB3 | 5'TGCACAGCTCAGCGCCGCACCA 3' | 122 |
| DAB7 | 5'ACGGGTCATCAGCGCCGCACCA 3' | 123 |
| DAB10 | 5'TGTCACCCCCCTCCCCGGACTT 3' | 124 |
| DAB18 | 5'ACTCGCAATTATTGGCGCTCGA 3' | 125 |
| DAB24 | 5'GTCTTCTCAACCTTATCCTGCG 3' | 126 |
| DAB30 | 5'AAAGCCCCCTGCTAAACTCCCA 3' | 127 |
| DAX15 | 5'CTGCGTCTGCCACGTCGTCATC 3' | 128 |
| DAX23 | 5'GTTAAAAGAGGGCAAGCTCGGA 3' | 129 |
| DAX24 | 5'CCGAGTTCTTGATGTCCTCCAT 3' | 130 |
| DAX27 | 5'TCCAATGCCTGTACCACGGATG 3' | 131 |
| DCX8 | 5'TCGCAACCGATATCGTGCTTAT3' | 132 |
| DCX11 | 5'TGCATACACTGCTTGGAGCCCT3' | 133 |
| DCX26 | 5'GAAATCTCACTAGTAGTCCGCC3' | 134 |
| DCX33 | 5'GCGGGCAAGACAGTCCAATTCC3' | 135 |
| DCX36 | 5'GAGCTCCAATTCCACGACGACC3' | 136 |
| DCX39 | 5'GGTTGCCATGCGTTCAAACTAC3' | 137 |
| DCX42 | 5'TCCCGCGGGGACAAACCCGAAT3' | 138 |
| DCX45 | 5'CTGCTAGTCTTATCATTCCCCA3' | 139 |
| PAX2 | 5'CTATCGACACTATAGGGCCTAC3' | 140 |
| PAX9 | 5'TACCCTTGTAACCCACACTAGG3' | 141 |
| PAX14 | 5'TTCTTCTGAATAGACCGGCCGA3' | 142 |
| PAX15 | 5'CCACCACCCTTAACCCGACAAT3' | 143 |
| PAX16 | 5'AGGGGGAGACTTGTTCACAAAC3' | 144 |
| PAX17 | 5'CGGCTCATACCACCGAAAGCTA3' | 145 |
| PAX18 | 5'ATCGTCCTACTGTAATCCTCGA3' | 146 |
| PAX35 | 5'GACACACTACTCAGGTCCACCT3' | 147 |
| PAX38 | 5'CCATAATCAACATTGCCGCCCT3' | 148 |
| PAX40 | 5'CAAAACGCTCGCCCCAAACTCA3' | 149 |
| PAX43 | 5'GTAAACTTGTGCTTCTCGCACC3' | 150 |
| PAX45 | 5'CCATGGTCCGGGTACACCTGAA3' | 151 |
| PAX46 | 5'GTTACTAACGGAACGAGACCTA3' | 152 |
| P31 | 5'TGTTGGCGTTCTCAACCCCGTT3' | 153 |
| P90 | 5'ACAACCGGAGTTGTTCTGCCTA3' | 154 |
| 5PAX3 | 5'TAAGCATCGGCCACGTTCTTCG3' | 155 |
| 5PAX5 | 5'TTATCCCTGGTGTGCAGGTTGA3' | 156 |
| 5PAX7 | 5'TATCAGAATCGTAGTCGGACGG3' | 157 |
| 5PAX12 | 5'CTTTGTAATGGAACCACAACCC3' | 158 |
| HAX9 | 5'CGGTGGCTCATCTCCCTCTTAT3' | 159 |
| HAX35 | 5'ATCAGACTGGCTGGGACCACAA3' | 160 |
| HAX40 | 5'CACAACCTCCTCTCCGCGAACT3' | 161 |
| HAX42 | 5'AGATTCGTCCCCAACGCGTGAT3' | 162 |
| HCA3 | 5'GGGAATTCGCAAAGCTATACTC3' | 163 |
| H40 | 5'CCCCGTGGAATTCAACCTGTGA3' | 164 |
| M13 (positive) | 5'GTCGTCTTTCCAGACGT3' | 165 |
| M13 (negative) | 5'CTTGCATGCCTGCAGGTCGAC3' | 166 |

The oligonucleotides (5 pmol) were 5'end labelled with $^{32}$P-ATP and T4 polynucleotide kinase and approximately 2.5 pmol of labelled oligonucleotide was used in hybridization studies. Hybridizations were performed at 40–45° C.

overnight in buffer containing 6×SSC, 5× Denhardt's solution, 0.1% SDS, 20 μg/ml yeast tRNA and the radiolabeled synthetic oligonucleotide, followed by washings (20–30 min at 40–45° C.) in the following buffers: (i) 2×SSC/0.1% SDS, (ii) 1×SSC/0.1% SDS, (iii) 0.1×SSC/0.1% SDS. The filters were air-dried and exposed for autoradiography for 15 hours, 24 hours or 72 hours.

Hybridization data indicated that all the oligonucleotide probes bound specifically to their phage target except for the HAX9 probe which apparently was not labeled. A negative control probe that hybridized only to M13mp18 DNA showed a weak to negative signal in all samples tested (data not shown).

Hybridization data for pools from each receptor group of rats was compiled. Tables 15, 16, 17 and 18 show a representative compilation of autoradiograph signals of the HS1, D2H, HPT1 and hPEPT1 receptor groups. These Tables show the phage absorption and uptake from the closed loop GIT model to portal and systemic circulation and phage absorption/internalization to intestinal tissue. In these Tables, Int-G refers to intestinal tissue homogenized prior to washing and recovery while Int-D refers to intestinal tissue washed prior to homogenization and phage recovery. In all cases, leading phage candidates were present in more than one animal.

TABLE 15

SUMMARY OF AUTORADIOGRAPH SIGNALS OF HSI ANIMAL STUDY

| Phage | Portal | Int.-G | Int.-D |
|---|---|---|---|
| S15 | ++ | +/− | +/− |
| S21 | − | − | − |
| S22 | − | −/+ | − |
| SNi-10 | +++/+ | ++ | ++ |
| SNi-28 | − | − | − |
| SNi-34 | ++ | − | − |
| SNi-38 | ++ | − | − |
| SNi-45 | − | − | − |
| SNiAX-2 | − | − | − |
| SNiAX-6 | − | − | − |
| SNiAX-8 | − | − | − |
| M13 | ++++++ | ++++++ | ++++++ |
| M13 | nd* | + | − |

*not detected

TABLE 16

SUMMARY OF AUTORADIOGRAPH SIGNALS OF D2H ANIMAL STUDY

| Phage | Portal | Int.-G | Int.-D |
|---|---|---|---|
| DAB3 | +++ | +/− | −/+ |
| DAB7 | ++ | ++ | −/+ |
| DAB10 | ++++++ | +/− | −/+ |
| DAB18 | − | − | − |
| DAB24 | − | − | − |
| DAB30 | ++++ | ++ | +++ |
| DAX15 | − | − | − |
| DAX23 | −/+ | + | −/+ |
| DAX24 | − | − | − |
| DAX27 | − | + | − |
| DCX8 | +++++ | +/− | − |
| DCX11 | ++++++ | ++ | −/+ |
| DCX26 | − | − | − |
| DCX33 | +++ | ++ | ++ |
| DCX36 | − | − | − |
| DCX39 | − | −/+ | − |
| DCX42 | − | − | −/+ |
| DCX45 | − | ++ | − |

TABLE 16-continued

SUMMARY OF AUTORADIOGRAPH SIGNALS OF D2H ANIMAL STUDY

| Phage | Portal | Int.-G | Int.-D |
|---|---|---|---|
| M13 (+) | +++++ | +++++ | +++++ |
| M13 (−) | +/− | −/+ | − |

TABLE 17

SUMMARY OF AUTORADIOGRAPH SIGNALS OF HPT1 ANIMAL STUDY

| Phage | Int.-G | Portal | Systemic |
|---|---|---|---|
| H40 | − | − | ++++ |
| HAX9 | ND | ND | ND |
| HAX35 | − | + | − |
| HAX40 | − | − | − |
| HAX42 | − | ++ | ++ |
| HCA3 | − | − | − |
| PAX2 | − | +++ | ++++ |
| M13 (+) | ++++++ | ++++++ | ++++++ |
| M13 (−) | − | −−/+ | − |

TABLE 18

SUMMARY OF AUTORADIOGRAPH SIGNALS OF hPEPT1 ANIMAL STUDY

| Phage | Int.-G | Portal | Systemic |
|---|---|---|---|
| PAX2 | − | ++ | − |
| PAX9 | ++ | +++ | − |
| PAX14 | − | ++ | − |
| PAX15 | −/+ | − | − |
| PAX16 | − | − | − |
| PAX17 | + | ++/+ | − |
| PAX18 | − | − | − |
| PAX35 | − | − | − |
| PAX38 | −/+ | − | − |
| PAX40 | + | +++ | − |
| PAX43 | + | − | − |
| PAX45 | − | − | − |
| PAX46 | − | +++ | − |
| P31 | ++ | ++++ | ++ |
| 5PAX3 | ++/+ | ++ | − |
| 5PAX5 | − | − | ++ |
| 5PAX7 | +++ | − | − |
| 5PAX12 | ++++ | ++ | − |
| H40 | ++ | ++ | − |
| M13 (+) | ++++++ | ++++++ | ++++++ |
| M13 (−) | − | − | − |

Apart from the synthetic oligonucleotide to HAX9, all oligonucleotides were initially confirmed to be radiolabeled, as determined by hybridization to the corresponding phage target (eg., phage S15 hybridized to the oligonucleotide S15). In addition, under the experimental conditions used, the oligonucleotides essentially did not hybridize to the negative control phage template M13mp18. Two oligonucleotides were synthesized to the phage M13mp18: (1) a positive oligonucleotide which hybridizes to a conserved sequence in both M13mp18 and each of the GIT receptor or GIT binding site selected phages [designated M13 (positive)]; and (2) a negative oligonucleotide which only hybridizes to a sequence unique to the multiple cloning site of phage M13mp18 and which does not hybridize to any of the GIT receptor or GIT binding site selected phages.

In the case of the hSI pool of phages, only four phages were transported from the closed loop model into the portal circulation: phages S15, SNi-10, SNi-34 and SNi-38. The other phages, S21, S22, SNi-28, SNi-45, SNiAX-2, SNiAX-6 and SNiAX-8, were not transported from the GIT into the portal circulation. In addition, phages SNi-10 and to a lesser extent phages S15 and S22 were found in the intestine samples or fractions, whereas the other phages were not. There was a very low presence (<0.1%) of the phage M13mp18 in the Int-G samples. These results show that phages can be further selected from pre-selected libraries, permitting the identification of phages which are transported from the GIT closed loop into the portal circulation or phages which bind to or are internalized by intestinal tissue.

In the case of the D2H pool of phages, there was a rank order by which phages were transported from the GIT closed loop model into the portal circulation, with phages DCX11 and DAB10 preferably transported, followed by phages DCX8, DAB30, DAB3 and DAB7. A number of phages from this pool were not transported into the portal circulation, including phages DAB18, DAB24, DAX15, DAX24, DAX27, DCX26, DCX36, DCX39, DCX42, DCX45. There is a very low level of transport of phage DAX23 from the GIT into the portal circulation. Similarly, only some of the phages were found in the intestinal samples fractions, including phages DAB30, DCX33, DAB7, DCX11, DCX45 and to a much lesser extent phages DAB3, DAB10, DCX8, DCX39, DCX42. Some phages were not found in the intestinal samples, including phages DAB18, DAB24, DAX15, DAX24, DCX26, and DCX36. There was a very low presence (<0.1%) of the phage M13mp18 in the Int-G samples. These results showed that phages can be further selected from pre-selected libraries, permitting the identification of phages which are transported from the GIT closed loop into the portal circulation or phages which bind to or are internalized by intestinal tissue.

In the case of the HPT1 pool of phages, there was a rank order by which phages were transported from the GIT closed loop model into the portal or systemic circulation. Phage PAX2 (which was used at a 4× concentration relative to the other phages in this pool) followed by phage HAX42 was found in the portal and systemic circulation; phage H40 was found in the systemic circulation only. None of the phages in this pool were found in the intestine samples or fractions. Phage M13mp18 was not found in the intestine fractions or systemic circulation, with very low incidence (<0.001%) in the portal circulation. These results show that phages can be further selected from pre-selected libraries, permitting the identification of phages which are transported from the GIT closed loop into the portal and/or systemic circulation or phages which bind to or are internalized by intestinal tissue.

In the case of the hPEPT1 pool of phages, the phages PAX2 and H40 were also included in this pool. A number of phages from this pool were found in the portal circulation, including phages P31 (SEQ ID NO:43), PAX46, PAX9, H40, PAX17, PAX40, PAX2, PAX14, 5PAX3 and 5PAX12. A number of phages were not found in the portal blood including the negative control phage M13mp18, PAX15, PAX16, PAX18, PAX35, PAX38, PAX43, PAX45, P90, 5PAX5 and 5PAX7. The only phage found in the systemic circulation were phages 5PAX5 and P31 (SEQ ID NO:43). In addition, there was preferential binding of some phages to the intestine, including phages 5PAX12, 5PAX7, 5PAX3, H40, P31 (SEQ ID NO:43), PAX9, and to a lesser extent phages PAX38 and PAX15. Some phages were not found in the intestine samples, including the negative control phage M13mp18 and the phages PAX2, PAX14, PAX16, PAX18, PAX35, PAX45, PAX46, P90 and 5PAX5. These results show that phages can be further selected from pre-selected libraries, permitting the identification of phages which are transported from the GIT closed loop into the portal and/or systemic circulation or phages which bind to or are internalized by intestinal tissue.

Further Characterization of Select Sequences

Following initial screening of the four recombinant receptor sites (hPEPT1, HPT1, D2H, hSI) of the gastrointestinal tissue, with the phage display libraries, a series of phage were isolated which showed preferential binding to the respective target receptor sites in comparison to negative control protein BSA protein and the recombinant protein recombinant human tissue factor (hTF) (which, like the recombinant receptors of the gastrointestinal tissue, contained a poly-histidine tag at its $NH_2$-terminal end). In subsequent experiments same titers of the selected phage which bound to each target receptor site were combined into a single pool (i.e., one pool of HPT1 binding phage, one pool of hPEPT1 binding phage, one pool of D2H binding phage, and one pool of hSI binding phage). Each pool was supplemented with an equivalent titer of the negative control phage M13mp18. These phage pools were injected into a closed duodenal loop region of rat intestinal tissue and subsequently phage was harvested and recovered which was bound to and retained by the intestinal tissue and/or was absorbed from the intestinal loop into the portal and/or systemic circulation. In addition, a selection of the initial phages which bound to the target recombinant receptor site were analyzed for binding to either fixed Caco-2 cells and/or to fixed C2BBe1 cells. The selection of the final lead peptide sequences was based on the ability of the phage, coding for that peptide sequence (1) to bind to the target recombinant receptor site in vitro in preference to its binding to the negative control proteins BSA and/or hTFs, (2) to bind to rat intestinal tissue following injection into a closed duodenal loop of rat intestinal tissue in preference to the negative control phage M13mp18, (3) to be absorbed from rat intestinal tissue into either the portal and/or systemic circulation following injection into a closed duodenal loop of rat intestinal tissue in preference to the negative control phage M13mp18, and (4) to bind to either fixed Caco-2 cells or fixed C2BBe1 cells in phage binding studies in preference to the negative control phage M13mp18. Peptides were also selected with consideration to the ease of chemical synthesis.

6.9. GST Fusion Proteins of GIT Targeting Peptides

Construction of GST Fusion Proteins of GI Targeting Peptides

Glutathione S-transferase (GST) vectors encoding fusion proteins of GI targeting peptides were constructed in the vector pGEX4T-2 (source, Pharmacia Biotech, Piscataway, N.J.). Briefly, single-strand DNA from the clones of interest were amplified by the polymerase chain reaction. The amplified DNA was then cleaved with the restriction enzymes XhoI and NotI and then ligated into SalI/NotI cleaved pGEX4T-2. Following transformation, the DNA sequence for each construct was verified by sequencing.

For construction of the truncated versions of the GST fusion proteins, where the inserted sequence was less than 45 base pairs, overlapping oligonucleotides containing cohesive SaI and NotI termini, and encoding the sequence of interest, were annealed and then ligated directly into SalI/NotI cleaved pGEX4T-2. Following transformation, the DNA sequence for each construct was verified.

A diagrammatic representation of the various GST fusion protein constructs that have been synthesized is indicated in FIGS. 5A–5C.

Expression and Purification of GST Fusion Proteins

*Escherichia coli* BL21 cells containing GST fusion protein constructs were grown overnight in 2×YT media containing 100 μg/ml ampicillin (2×YT/amp). Overnight cultures were diluted 1:100 in 2×YT broth (100 ml), and cells were grown to an $A_{600}$ of 0.5 at 30° C., induced with 1 mM isopropyl-1-thio-B-D-galactopyranoside, and grown for an additional 3 h. Cells were harvested by centrifugation and resuspended in 5 ml of PBS containing a mixture of the proteinase inhibitors (Boehringer/Mannheim). Cells were sonicated on ice, and the cell lysates were centrifuged at 12,000×g for 10 minutes at 4° C. Supernatant fractions were reacted for 30 minutes at room temperature with 2 ml of a 50% slurry of glutathione-Sepharose® 4B, washed 3 times with 1.5 ml of PBS (at room temperature), and the bound GST fusion proteins were eluted by reaction for 10 minutes at room temperature with 3×1 ml of 10 mM reduced glutathionein 50 mM Tris HCl pH 8.0. Protein was quantified by the Bio-Rad protein assay followed by characterization by SDS- polyacrylamide gel electrophoresis.

ELISA of GST Fusion Peptides

The standard ELISA procedure was modified as follows. GST proteins were diluted to an appropriate concentration in PBS containing 1% BSA and 0.05% Tween20 (1% BPT), titered and incubated one hour at room temperature. Following five washes an anti-GST monoclonal antibody was added (Sigma, St. Louis Clone GST-2 diluted 1:10,000 in 1% BPT) and incubated one hour. After five more washes goat anti-mouse IgG2b-HRP was added (Southern Biotechnology Associates Inc., Birmingham, Ala., diluted 1:4000 in 1% BPT) and incubated one hour. After five washes plates were developed with TMB peroxidase substrate (Kirkegard and Perry, Gaithersburg, Md.). All data is presented with background binding subtracted.

FIG. 6 shows the binding of GST-SNi10, GST-SNi34 and GST alone to the hSI receptor and to fixed C2BBe1 cells.

GST Fusion Proteins of Selected GIT Targeting Peptides

Results show that GST-DXB8, GST-PAX2, GST-P31, GST-SNi10 and GST-SNi34 bound fixed Caco-2 or C2BBe1 cells (FIGS. 7 and 8) relative to GST control binding. GST-HAX42, GST-5PAX5, all showed weak to moderate binding relative to GST control.

Interestingly, P31 truncation 103-GST (SEQ ID NO: 185) fusion protein bound almost as well as full-length P31 (SEQ ID NO:43) to fixed Caco-2 cells (A). This suggests the portion of the P31 sequence (SEQ ID NO:43) responsible for binding resides in this portion. PAX2.107 bound similarly to full-length PAX2; therefore, this portion most likely contains the amino acid sequence responsible for binding (B). In preliminary assays, none of the DCX8 truncations bound similarly to full-length DCX8 to Caco-2 cells suggesting the binding region spans more than one of these pieces.

Inhibition of Binding by Synthetic Peptides Binding of GST-P31 to Fixed C2BBe1 Cells The standard ELISA procedure was modified as follows. GST fusion proteins and peptides were diluted to an appropriate concentration in PBS containing 1% BSA and 0.05% Tween 20. Peptides were titered, a constant concentration of diluted GST protein was added to titered peptides and the mixture was incubated one hour at room temperature. Following five washes, an anti-GST monoclonal antibody was added (Sigma, St. Louis Clone GST-2 diluted 1:10,000 in 1% BPT) and incubated one hour. After five more washes goat anti-mouse IgG2b-HRP was added (Southern Biotechnology Associates Inc., Birmingham, Ala., diluted 1:4000 in 1% BPT) and incubated one hour. After five washes plates were developed with TMB peroxidase substrate (Kirkegard and Perry, Gaithersburg, Md.). All data is presented with background binding subtracted.

FIGS. 9A and 9B show the inhibition of GST-P31 binding to C2BBe1 fixed cells. The peptide competitors are ZElan024 (SEQ ID NO:288) which is the dansylated peptide version of P31 (SEQ ID NO:43) and ZElan044 (SEQ ID NO:310), ZElan049 (SEQ ID NO:315) and ZElan050 (SEQ ID NO:316) which are truncated, dansylated pieces of P31 (SEQ ID NO:43). Data is presented as O.D. vs. peptide concentration and as percent inhibition of GST-P31 binding vs. peptide concentration. Uncompeted GST-P31 binding was considered as 100% binding. $IC_{50}$ values are estimates using the 50% line on the percent inhibition graph.

GST-P31 and GST-PAX2 exhibited no crossreactive binding to ZElan024 (P31) (SEQ ID NO:286) and ZElan018 (PAX2) (SEQ ID NO:281) at the 0.5 μg/ml concentration used in competition assays. GST-HAX42 exhibited crossreactivity to ZElan018 (PAX2) (SEQ ID NO:281) and ZElan021 (HAX42) (SEQ ID NO:281) at the 5 μg/ml concentration used in competition assays.

FIGS. 10A–10C present a compilation of data generated by competition ELISA of GST-P31, GST-PAX2, GST-SNi10 and GST-HAX42 versus various dansylated peptides on fixed C2BBe1 cells. $IC_{50}$ values are in μM and include ranges determined from multiple assays. The GST/C2BBe1 column is a summary of GST protein binding to fixed C2BBe1 cells.

Binding to Fixed Caco-2 Cells

Caco-2 cells were fixed, treated with phenylhydrazin and blocked as described above. Synthetic peptides (100 μg/ml) were applied in duplicate to Caco-2 cells and serially diluted down the 96-well plate. The corresponding GST-peptide fusion protein (10 μg) was added to each well and the plates were incubated for 2h at room temperature with agitation. Binding of the GST-peptide fusion proteins to the cells was assayed using the ELISA technique described above. GST-P31 binding was inhibited by ZElan024 (SEQ ID NO:288), ZElan028 (SEQ ID NO:294) and ZElan031 (SEQ ID NO:297) as well as the two D forms ZElan053 (SEQ ID NO:319) and ZElan054 (SEQ ID NO:320). GST-PAX2 binding was inhibited by ZElan032 (SEQ ID NO:298), ZElan033 (SEQ ID NO:299), and ZElan035 (SEQ ID NO:301). GST-HAX42 binding was not inhibited by ZElan021 (SEQ ID NO:285) (full length HAX42) but it was inhibited by ZElan018 (SEQ ID NO:281) (PAX2) and ZElan026 (SEQ ID NO:290) and ZElan038 (SEQ ID NO:304) (scrambled PAX2 peptides).

Transport and Uptake of GST-Peptide Fusions into Live Caco-2 Cells

Transport and uptake of GST-peptide fusions and deletion derivatives across cultured polarized Caco-2 monolayers over 4 hours in HBSS buffer was examined using an anti-GST ELISA assay. In another experiment, transport and uptake of GST-peptide fusions and deletion derivatives across cultured polarized Caco-2 monolayers over 24 hours in serum-free medium (SFM) was examined using an anti-GST ELISA assay.

Materials

Buffered Hank's balanced salt solution (bHBSS)=1× HBSS (Gibco CN.14065-031) supplemented with 0.011M glucose (1 g/l), 25 mM Hepes (15 mM acid (3.575 g/l; Sigma CN.H3375); 10 mM base (2.603 g/l; Sigma CN.H1016)].

Chloroquine: Made up as 10 mM solution in water [Sigma CN C6628]

Lysate buffer: 30 mM Tris-HCl pH8.0; 1 mM EDTA

Serum-free medium (SFM) is normal medium without serum.

Method a) 4h HBSS study: Transepithelial electrical flux (TER) across the Caco-2 monolayers grown on snapwells (passage 33; 23 days old) was measured to confirm monolayer integrity before beginning the experiment. The medium was removed and the cells were washed once with bHBSS. bHBSS containing 100 µM chloroquine was added and the cells were incubated for 2h at 37° C. The bHBSS+chloroquine was replaced with 0.5 ml bHBSS containing GST-peptide fusions (100 µg/ml) and the cells were incubated as before. Basolateral samples were removed at the following times: 0, 0.5h, 2h, and 4h. At 4h, TER was measured, the apical medium was sampled and the apical reservoir was washed 6 times with HBSS. The cells were allowed to lyse for 1 h on ice in lysate buffer, after which, lysate sample was collected. All samples were stored at −70° C. until assay by anti-GST ELISA. Before analysis, samples were normalized for protein content relative to each other using a BioRad protein assay.

b) 24h SFM study: Transepithelial electrical flux (TER) across the Caco-2 monolayers grown on snapwells (passage 33; 23 days old) was measured to confirm monolayer integrity before beginning the experiment. The medium was removed and the cells were washed once with SFM. SFM containing GST-peptide fusions (100 µg/ml) was added to the cells which were incubated at 37° C. for 24h at 5% CO2. After 24 hours, TER readings were taken, and samples from the basolateral and apical reservoirs were removed. The apical reservoir was washed 6 times with PBS. The cells were allowed to lyse for 1 h on ice in lysate buffer, after which lysate sample was collected. All samples were stored at −70° until assay by anti-GST ELISA. Before analysis, samples were normalized for protein content relative to each other using a BioRad protein assay.

Results

All of the GST-peptide fusions and controls examined were transported across live Caco-2 monolayers. Full-length GST-P31 and GST-DCX8, but not truncations of these molecules had a higher flux than GST alone.

Internalization of GST-peptide fusions into polarized Caco-2 cells was investigated in two experiments. In experiment 1, 15 µg of GST-peptide fusion was applied in bHBSS and internalized GST-peptide was recovered by lysing the cells after 4h. In experiment 2, 10 µg of GST-peptide was applied in either a) bHBSS (lysate recovered after 4h), or b) serum-free medium (lysate recovered after 24h).

FIG. 11A describes complete transport of GST-peptide across a polarized Caco-2 monolayer and does not necessarily refer to internalization, i.e., the GST-peptide was recovered from the basolateral reservoir of a snapwell but the proteins could have crossed the barrier by the paracellular route.

Effect of Thrombin Cleavage on Binding of GST-Peptide Fusions to Fixed Caco-2 Cells Binding of intact and thrombin-cleaved GST-peptide fusions to fixed Caco-2 cells was compared. Reduced binding of the thrombin-cleaved GST-peptide fusions relative to intact fusions indicates that the peptide component of the fusion, and not the GST domain, mediates binding.

Method

Confluent Caco-2 monolayers grown in 96-well plates (p38) were fixed and treated with 0.1% phenylhydrazine before blocking with 0.1% BSA in PBS. Thirty micrograms of each GST-peptide was treated with bovine thrombin (1 µ/ml; 0.4 NIH units; Sigma CN.T9681) for 18h at room temperature in 20 mM Tris-HCl pH8.0, 150 mM NaCl, 2.5 mM $CaCl_2$. Controls were similarly treated without addition of thrombin. Ten micrograms of each GST-peptide fusion was removed for PAGE analysis, and 10 µg of fusions were added in duplicate to the fixed Caco-2 cells before 5-fold serial dilutions (1% BPT diluent). The fusions were allowed to bind for 1h at room temperature. Following 6 washes with 1% BPT, binding was assayed by ELISA.

Results

Results are shown in FIG. 12.

Conclusions:

PAGE analysis confirmed that the GST-peptide fusions were effectively cleaved with thrombin. Cleavage with thrombin significantly reduced detection of binding of GST-P31.103 (SEQ ID NO: 183), GST-PAX2.106 (SEQ ID NO: 188), GST-DCX8, GST-SNi10 to fixed Caco-2 cells, indicating that the peptide component, and not the GST domain, mediates binding.

6.10. Synthesis of Peptides 6.10.1. Procedure for Solid Phase Synthesis

Peptides may be prepared by methods that are known in the art. For example, in brief, solid phase peptide synthesis consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, J. Am. Chem. Soc. 85:2149; Vale et al., 1981, Science 213:1394–1397; Marki et al., 1981, J. Am. Chem. Soc. 103:3178 and in U.S. Pat. Nos. 4,305,872 and 4,316,891. In a preferred aspect, an automated peptide synthesizer is employed.

By way of example but not limitation, peptides can be synthesized on an Applied Biosystems Inc. ("ABI") model 431A automated peptide synthesizer using the "Fastmoc" synthesis protocol supplied by ABI, which uses 2-(1H-Benzotriazol-1-yl)-1,1,3,3-tetramethyluronium hexafluorophosphate ("HBTU") (R. Knorr et al., 1989, Tet. Lett., 30:1927) as coupling agent. Syntheses can be carried out on 0.25 mmol of commercially available 4-(2',4'-dimethoxyphenyl-(9-fluorenyl-methoxycarbonyl)-aminomethyl)-phenoxy polystyrene resin ("Rink resin" from Advanced ChemTech) (H. Rink, 1987, Tet. Lett. 28:3787). Fmoc amino acids (1 mmol) are coupled according to the Fastmoc protocol. The following side chain protected Fmoc amino acid derivatives are used: FmocArg(Pmc)OH; FmocAsn(Mbh)OH; FmocAsp($^t$Bu)OH; FmocCys(Acm)OH; FmocGlu($^t$Bu)OH; FmocGln(Mbh)OH; FmocHis(Tr)OH; FmocLys(Boc)OH; FmocSer($^t$Bu)OH; FmocThr($^t$Bu)OH; FmocTyr($^t$Bu)OH. [Abbreviations: Acm, acetamidomethyl; Boc, tert-butoxycarbonyl; $^t$Bu, tert-butyl; Fmoc, 9-fluorenylmethoxycarbonyl; Mbh, 4,4'-dimethoxybenzhydryl; Pmc, 2,2,5,7,8-pentamethylchroman-6-sulfonyl; Tr, trityl].

Synthesis is carried out using N-methylpyrrolidone (NMP) as solvent, with HBTU dissolved in N,N-dimethylformamide (DMF). Deprotection of the Fmoc group is effected using approximately 20% piperidine in NMP. At the end of each synthesis the amount of peptide present is assayed by ultraviolet spectroscopy. A sample of dry peptide resin (about 3–10 mg) is weighed, then 20% piperidine in DMA (10 ml) is added. After 30 min sonication, the UV (ultraviolet) absorbance of the dibenzofulvene-piperidine adduct (formed by cleavage of the N-terminal Fmoc group) is recorded at 301 nm. Peptide substitution (in mmol g$^{-1}$) can be calculated according to the equation:

$$\text{substitution} = \frac{A \times v}{7800 \times w} \times 1000$$

where A is the absorbance at 301 nm, v is the volume of 20% piperidine in DMA (in ml), 7800 is the extinction coefficient (in mol$^{-1}$dm$^3$ cm$^{-1}$) of the dibenzofulvene-piperidine adduct, and w is the weight of the peptide-resin sample (in mg).

Finally, the N-terminal Fmoc group is cleaved using 20% piperidine in DMA, then acetylated using acetic anhydride and pyridine in DMA. The peptide resin is thoroughly washed with DMA, CH$_2$Cl$_2$ and finally diethyl ether.

6.10.2°. Cleavage and Deprotection

By way of example but not limitation, cleavage and deprotection can be carried out as follows: The air-dried peptide resin is treated with ethylmethyl-sulfide (EtSMe), ethanedithiol (EDT), and thioanisole (PhSMe) for approximately 20 min. prior to addition of 95% aqueous trifluoracetic acid (TFA). A total volume of approximately 50 ml of these reagents are used per gram of peptide-resin. The following ratio is used: TFA:EtSMe:EDT:PhSme (10:0.5:0.5:0.5). The mixture is stirred for 3 h at room temperature under an atmosphere of N$_2$. The mixture is filtered and the resin washed with TFA (2×3 ml). The combined filtrate is evaporated in vacuo, and anhydrous diethyl ether added to the yellow/orange residue. The resulting white precipitate is isolated by filtration. See King et al., 1990, Int. J. Peptide Protein Res. 36:255–266 regarding various cleavage methods.

6.10.3. Purification of the Peptides

Purification of the synthesized peptides can be carried out by standard methods including chromatography (e.g., ion exchange, affinity, and sizing column chromatography, high performance liquid chromatography (HPLC)), centrifugation, differential solubility, or by any other standard technique.

6.10.4. Conjugation of Peptides to Other Molecules

The peptides of the present invention may be linked to other molecules (e.g., a detectable label, a molecule facilitating adsorption to a solid substratum, or a toxin, according to various embodiments of the invention) by methods that are well known in the art. Such methods include the use of homobifunctional and heterobifunctional cross-linking molecules.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a cross-linking agent was disclosed by Poznansky et al., 1984, Science 223:1304–1306.

Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. Some examples of heterobifunctional reagents containing reactive disulfide bonds include N-succinimidyl 3-(2-pyridyl-dithio)propionate (Carlsson et al., 1978, Biochem J. 173:723–737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce.

Additional information regarding how to make and use these as well as other polyfunctional reagents may be obtained from the following publications or others available in the art: Carlsson et al., 1978, Biochem. J. 173:723–737; Cumber et al., 1985, Methods in Enzymology 112:207–224; Jue et al., 1978, Biochem 17:5399–5405; Sun et al., 1974, Biochem. 13:2334–2340; Blattler et al., 1985, Biochem. 24:1517–152; Liu et al., 1979, Biochem. 18:690–697; Youle and Neville, 1980, Proc. Natl. Acad. Sci. USA 77:5483–5486; Lerner et al., 1981, Proc. Natl. Acad. Sci. USA 78:3403–3407; Jung and Moroi, 1983, Biochem. Biophys. Acta 761:162; Caulfield et al., 1984, Biochem. 81:7772–7776; Staros, 1982, Biochem. 21:3950–3955; Yoshitake et al., 1979, Eur. J. Biochem. 101:395–399; Yoshitake et al., 1982, J. Biochem. 92:1413–1424; Pilch and Czech, 1979, J. Biol. Chem. 254:3375–3381; Novick et al., 1987, J. Biol. Chem. 262:8483–8487; Lomant and Fairbanks, 1976, J. Mol. Biol. 104:243–261; Hamada and Tsuruo, 1987, Anal. Biochem. 160:483–488; Hashida et al., 1984, J. Applied Biochem. 6:56–63.

Additionally, methods of cross-linking are reviewed by Means and Feeney, 1990, Bioconjugate Chem. 1:2–12.

6.10.4.1. Biotinylation of Peptides

Methods of biotinylating peptides are well known in the art. Any convenient method may be employed in the practice of the invention. For example, the following procedure was used. Ten micrograms of peptide was dissolved in 100 μl of 0.1% acetic acid. PBS (900 μl) and 3.3 mg of biotin-LC-NHS (Pierce, Rockford, Ill.) was added. Following incubation for 30 minutes at room temperature the biotinylated peptides were purified over a Superose 12 column (Pharmacia, Piscataway, N.J.).

6.10.5. Synthetic Peptides

Tables 19, 20 and 21 provide the primary structure for various synthetic peptides manufactured in the practice of the present invention.

TABLE 19

| SEQ ID NO. | Peptide name | Sequence |
|---|---|---|
| 266 | ELAN005 | $H_2N$-C-K(dns)-FITKALGISYGRKKRRQRRRPPQGSQTHQVSLSKQ-$CONH_2$ |
| 267 | ELAN006 | Ac-CLNGGVKMYVESVDRYVC-$CONH_2$ |
| 268 | FITC-ELAN006 | Ac-CLNGGVK(FITC)MYVESVDRYVC-$CONH_2$ |
| 269 | ELAN006ii | $H_2N$-C-K(dns)-RLNGGVSMYVESVDRYVCR-$CONH_2$ |
| 167 | ELAN007 | $H_2N$-RIAGLPWYRCRTVAFETGMQNTQLCSTIVQLSFTPEE-COOH |
| 193 | ELAN007ii | $H_2N$-KKRIAGLPWYRCRTVAFETGMQNTQLCSTIVQLSFTPEE-$CONH_2$ |
| 270 | bZElan008 (P31) | biotin-K(dns)SARDSGPAEDGSRAVRLNGVENANTRKSSRSNPRGRRHP-COOH |
| 271 | bZElan009 | biotin-K(dns)SSADAEKCAGSLLWWGRQNNSGCGSPTKKHLKHRNRSQTSSSSHG-COOH |
| 168 | ELAN010 | $H_2N$-REFAERRLWGCDDLSWRLDAEGCGPTPSNRAVKHRKPRPRSPAL-COOH |
| 272 | bZElan010 | biotin-K(dns)REFAERRLWGCDDLSWRLDAEGCGPTPSNRAVKHRKPRPRSPAL-COOH |
| 169 | ELAN012 | $H_2N$-SGSHSGGMNRAYGDVFRELRDRWYATSHHTRPTPQLPRGPN-COOH |
| 273 | bELAN012 | biotin-SGSHSGGMNRAYGDVFRELRDRWYATSHHTRPTPQLPRGPN-COOH |
| 274 | ZElan012 | $H_2N$-K(dns) SGSHSGGI4NRAYGDVFRELRDRWYATSHHTRPTPQLPRGPN-COOH |
| 249 | ELAN013 | $H_2N$-SGSPPCGGSWGRFMQGGLFGGRTDGCGAHRNRTSASLEPPSSDY-$CONH_2$ |
| 250 | ELAN014 | $H_2N$-SHSGGMNRAYGDVFRELRDRWNATSHHTRPTPQLPRGPNS-$CONH_2$ |
| 275 | bZElan014 | biotin-K(dns)SHSGGMNRAYGDVFRELRDRWNATSHHTRPTPQLPRGPNS-$CONH_2$ |
| 276 | ZElan014 | $H_2N$-K(dns)SHSGGMNRAYGDVFRELRDRWNATSHHTRPTPQLPRGPNS-$CONH_2$ |
| 277 | ZElan015 (DCX11) | $H_2N$-K(dns)SQGSKQCMQYRTGRLTVGSEYGCGMNPARHATPAYPARLLPRYR-$CONH_2$ |
| 278 | ZElan016 (SNi10) | $H_2N$-K(dns)RVGQCTDSDVRRPWARSCAHQGCGAGTRNSHGCITRPLRQASAH-$CONH_2$ |
| 279 | bZElan017 | biotin-K(dns)SGSGRVGQCTDSDVRRPWARSCA-$CONH_2$ |
| 280 | ZElan017 | $H_2N$-K(dns)RVGQCTDSDVRRPWARSCA-$CONH_2$ |
| 281 | ZElan018 (PAX2) | $H_2N$-K(dns)STPPSREAYSRPYSVDSDSDTNAKHSSHNRRLRTRSRPNG-$CONH_2$ |
| 282 | ZElan019 (5PAX5) | $H_2N$-K(dns)RGSTGTAGGERSGVLNLHTRDNASGSGFKPWYPSNRGHK-$CONH_2$ |
| 283 | ZElan020 (CY09) | $H_2N$-K(dns)SGSGLYANPGMYSRLHSPA-$CONH_2$ |
| 284 | bZElan020 (CY09) | biotin-K(dns)SGSGLYANPGMYSRLHSPA-$CONH_2$ |
| 285 | ZElan021 (HAX42) | $H_2N$-K(dns)SDHALGTNLRSDNAKEPGDYNCCGNGNSTGRKVFNRRRPSAIPT-$CONH_2$ |
| 286 | ZElan022 (SNi34) | $H_2N$-K (dns) SPCGGSWGRFMQGGLFGGRTDGCGAHRNRTSASLEPPSSDY-$CONH_2$ |
| 287 | ZElan023 (DCX8) | $H_2N$-K(dns)RYKHDIGCDAGVDKKSSSVRGGCGAHSSPPRAGRGPRGTMVSRL-$CONH_2$ |
| 288 | ZElan024 (P31) | $H_2N$-K(dns)SARDSGPAEDGSRAVRLNGVENANTRKSSRSNPRGRRHPGG-$CONH_2$ |

TABLE 19-continued

| SEQ ID NO. | Peptide name | Sequence |
|---|---|---|
| 289 | ZElan025 (DAB10) | H₂N-K(dns)SKSGEGGDSSRGETGWARVRSHAMTAGRFRWYNQLPSDR-CONH₂ |
| 290 | ZElan026 (PAX2/ control) | H₂N-K(dns)SEANLDGRKSRYSSPRRNSSTRPRTSPNSVHARYPSTDHD-CONH₂ |
| 291 | bELANO27 (PAX2) | biotin-SGSGSTPPSREAYSRPYSVDSDSDTNAKHSSHNRRLRTRSRPNG-CONH₂ |
| 251 | 18C21 | H₂N-DTNAKHSSHNRRLRTRSRPNG-CONH₂ |
| 292 | Fmoc-Z16N23 | Fmoc-K(dns)RVGQCTDSDVRRPWARSCAHQG-COOH |
| 252 | 16C23 | H₂N-CGAGTRNSHGCITRPLRQASAHG-CONH₂ |
| 293 | Z16C23 | H₂N-K(dns)CGAGTRNSHGCITRPLRQASAHG-CONH₂ |
| 294 | ZElan028 (P31 fragment) | H₂N-K(dns)ENANTRKSSRSNPRGRRHPG-CONH₂ |
| 295 | ZElan029 (P31 fragment) | H₂N-K(dns)TRKSSRSNPRG-CONH₂ |
| 296 | ZElan030 (P31 fragment) | H₂N-K(dns)ENANTRKSSRSNPRG-CONH₂ |
| 297 | ZElan031 (P31 fragment) | H₂N-K(dns)TRKSSRSNPRGRRHPG-CONH₂ |
| 298 | ZElan032 (PAX2 fragment) | H₂N-K(dns)TNAKHSSHNRRLRTRSRPN-CONH₂ |
| 299 | ZElan033 (PAX2 fragment) | H₂N-K(dns)TNAKHSSHNRRLRTR-CONH₂ |
| 300 | ZElan034 (PAX2 fragment) | H₂N-K(dns)SSHNRRLRTRSRPN-CONH₂ |
| 301 | ZElan035 (PAX2 fragment) | H₂N-K(dns)SSHNRRLRTR-CONH₂ |
| 302 | ZElan036 (SNi10 fragment) | H₂N-K(dns)VRRPWARSCAHQGCGAGTRNS-CONH₂ |
| 303 | ZElan037 (SNi10 fragment) | H₂N-K(dns)CTDSDVRRPWARSC-CONH₂ |
| 304 | ZElan038 (PAX2/ control) | H₂N-K(dns)SRANTDGRKSRYSSPRRNSSTEPRLSPNSVHARYPSTDHD-CONH₂ |
| 192305 | ZElan039 (P31 fragment) | H₂N-K(dns)ENANTRKSSR-CONH₂ |
| 306 | ZElan040 (P31 fragment) | H₂N-K(dns)SNPRGRRHPG-CONH₂ |
| 307 | ZElan041 (P31 fragment) | H₂N-K(dns)ENANT-CONH₂ |
| 308 | ZElan042 (P31 fragment) | H₂N-K(dns)ANTRKS-CONH₂ |
| 309 | ZElan043 (P31 fragment) | H₂N-K(dns)TRKSS-CONH₂ |
| 310 | ZElan044 (P31 fragment) | H₂N-K(dns)RKSSR-CONH₂ |
| 311 | ZElan045 (P31 fragment) | H₂N-K(dns)KSSRSN-CONH₂ |
| 312 | ZElan046 (P31 fragment) | H₂N-K(dns)SSRSNPG-CONH₂ |
| 313 | ZElan047 (P31 fragment) | H₂N-K(dns)RSNPRG-CONH₂ |

TABLE 19-continued

| SEQ ID NO. | Peptide name | Sequence |
|---|---|---|
| 314 | ZElan048 (P31 fragment) | H₂N-K(dns)SNPRG-CONH₂ |
| 315 | ZElan049 (P31 fragment) | H₂N-K(dns)PRGRRH-CONH₂ |
| 316 | ZElan050 (P31 fragment) | H₂N-K(dns)RRHPG-CONH₂ |
| 317 | ZElan051 (HepC) | H₂N-K(dns)KSSRGN-CONH₂ |
| 318 | ZElan052 (HepC) | H₂N-K(dns)KTSERSQPRGRRQPG-CONH₂ |
| 319 | ZElan053 (P31 analog) | H₂N-K(dns)TrKSSrSNPrGrrHPG-CONH₂ |
| 320 | ZElan054 (P31 analog) | H₂N-K(dns)TRKSSrSNPRGrRHPG-CONH₂ |
| 321 | ZElan055 (PAX2 fragment) | H₂N-K(dns)TNAKHSSHN-CONH₂ |
| 322 | ZElan056 (PAX2 fragment) | H₂N-K(dns)RRLRTRSRPN-CONH₂ |
| 323 | ZElan057 (PAX2 fragment) | H₂N-K(dns)RRLRTRSR-CONH₂ |
| 324 | ZElan058 (PAX2 fragment) | H₂N-K(dns)RRLRTR-CONH₂ |
| 325 | ZElan059 (PAX2 analog) | H₂N-K(dns)rrLrTrSrPN-CONH₂ |
| 326 | ZElan06O (HAX42 fragment) | H₂N-K(dns)SDHALGTNLRSDNAKEPGDYNCCGNG-CONH₂ |
| 327 | ZElan061 (HAX42 fragment) | H₂N-K(dns)GDYNCCGNGNSTGRKVFNRRRPSAIPT-CONH₂ |
| 328 | ZElan062 (HAX42 fragment) | H₂N-K(dns)SDHALGTNLRSDNAKEPG-CONH₂ |
| 329 | ZElan063 (HAX42 fragment) | H₂N-K(dns)GDYNCCGNGNSTG-CONH₂ |
| 330 | ZElan064 (HAX42 fragment) | H₂N-K(dns)RKVFNRRRPSAIPT-CONH₂ |
| 331 | ZElan065 (HAX42 fragment) | H₂N-K(dns)RKVFNRRRPS-CONH₂ |
| 332 | ZElan066 (HAX42 fragment) | H₂N-K(dns)NRRRPSAIPT-CONH₂ |
| 333 | ZElan067 (HAX42 fragment) | H₂N-K(dns)NRRRPS-CONH₂ |
| 334 | Elan018 (PAX2 no dns) | H₂N-STPPSREAYSRPYSVDSDSDTNAKMSSHNRRLRTRSRPNG-CONH₂ |
| 335 | Elan021 (HAX42 no due) | H₂N-SDHALGTNLRSDNAKEPGDYNCCGNGNSTGRKVFNRRRPSAIPT-CONH₂ |
| 336 | ZElan070 (HAX42 fragment) | H₂N-K(dns)SDHALGTNLRSDNAKEPGDYNCCGNGNST-CONH₂ |
| 337 | ZElan071 (HAX42 fragment) | H₂N-K(dns)NLRSDNAKEPGDYNCCGNGNSTGRKVFNR-CONH₂ |
| 338 | ZElan072 (HAX42 fragment) | H₂N-K(dns)PGDYNCCGNGNSTGRKVFNRRRPSAIPT-CONH₂ |

TABLE 19-continued

| SEQ ID NO. | Peptide name | Sequence |
|---|---|---|
| 339 | ZElan073 (PAX2 fragment) | H$_2$N-K(dns)ASHNRRLRTR-CONH$_2$ |
| 340 | ZElan074 (PAX2 fragment) | H$_2$N-K(dns)SAHNRRLRTR-CONH$_2$ |
| 341 | ZElan075 (PAX2 fragment) | H$_2$N-K(dns)SSANRRLRTR-CONH$_2$ |
| 342 | ZElan076 (PAX2 fragment) | H$_2$N-K(dns)SSHARRLRTR-CONH$_2$ |
| 343 | ZElan077 (PAX2 fragment) | H$_2$N-K(dns)SSHNARLRTR-CONH$_2$ |
| 344 | ZElan078 (PAX2 fragment) | H$_2$N-K(dns)SSHNRALRTR-CONH$_2$ |
| 345 | ZElan079 (PAX2 fragment) | H$_2$N-K(dns)SSHNRRARTR-CONH$_2$ |
| 346 | ZElan080 (PAX2 fragment) | H$_2$N-K(dns)SSHNRRLATR-CONH$_2$ |
| 347 | ZElan081 (PAX2 fragment) | H$_2$N-K(dns)SSHNRRLRAR-CONH$_2$ |
| 348 | ZElan082 (PAX2 fragment) | H$_2$N-K(dns)SSHNRRLRTA-CONH$_2$ |
| 349 | Elan035 | H$_2$N-SSHNRRLRTR-CONH$_2$ |
| 350 | ZElan083 (PAX2/control) | H$_2$N-K (dns) GRNHDVVSSNTHKSYRSPRSASYPRLSNDRTDRTEPAPSS-CONH$_2$ |
| 351 | ZElan084 (PAX2/control) | H$_2$N-K(dns)RNTRNKTSRLSANPHRSHR-CONH$_2$ |
| 352 | Elan032Z (PAX2 fragment) | H$_2$N-TNAKHSSHNRRLRTRSRPN K(dns)-CONH$_2$ |
| 353 | Elan057Z (PAX2 fragment) | H$_2$N-RRLRTRSRK(dns)-CONH$_2$ |

TABLE 20

| Name | Description | Sequence | SEQ. ID. No. |
|---|---|---|---|
| ZElan087 | HAX42-1 (20 mer) | H$_2$N—K(dns)SDHALGTNLRSDNAKEPGDY | 354 |
| ZElan088 | HAX42-2 (20 mer) | H$_2$N—K(dns)SDNAKEPGDYNCCGNGNSTG | 355 |
| ZElan089 | HAX42-3 (15 mer) | H$_2$N—K(dns)SDHALGTNLRSDNAK | 356 |
| ZElan090 | HAX42-4 (15 mer) | H$_2$N—K(dns)EPGDYNCCGNGNSTG | 357 |
| ZElan091 | HAX42-5 (14 mer) | H$_2$N—K(dns)PGDYNCCGNGNSTG | 358 |
| ZElan092 | HAX42-6 (10 mer) | H$_2$N—K(dns)PGDYNCCGNG | 359 |
| ZElan093 | HAX42-7 (10 mer) | H$_2$N—K(dns)NCCGNGNSTG | 360 |
| ZElan100 | P31 16 mer cyclic | H$_2$N—K(dns)Lys-TRKSSRSNPRGRRHPG (cyclic) | 361 |
| ZElan101 | P31 16 mer cyclic D form | H$_2$N—K(dns)Lys-TrKSSrSNPrGrrHPG (cyclic) | 362 |

TABLE 20-continued

| Name | Description | Sequence | SEQ. ID. No. |
|---|---|---|---|
| ZElan103 | PAX2 15 mer cyclic | H₂N—K(dns)Lys-TNAKHSSHNRRLRTR | 363 |
| ZElan103 A | PAX2 15 mer cyclic (internal) | H₂N—K(dns)TNAKHSSCNRRCRTR | 364 |
| ZElan104 | PAX2 15 mer cyclic (internal) | H₂N—K(dns)TNAKHSSCNRRLRCR | 365 |
| ZElan105 | PAX2 Ala Scan 1 | H₂N—K(dns)ANAKHSSHNRRLRTR | 366 |
| ZElan106 | PAX2 Ala Scan 2 | H₂N—K(dns)TAAKNSSHNRRLRTR | 367 |
| ZElan107 | PAX2 Ala Scan 3 | H₂N—K(dns)TNGKNSSHNRRLRTR | 368 |
| ZElan108 | PAX2 Ala Scan 4 | H₂N—K(dns)TNAAHSSHNRRLRTR | 369 |
| ZElan109 | PAX2 Ala Scan 5 | H₂N—K(dns)TNAKASSHNRRLRTR | 370 |
| ZElan110 | PAX2 Ala Scan 6 | H₂N—K(dns)TNAKHASHNRRLRTR | 371 |
| ZElan111 | PAX2 Ala Scan 7 | H₂N—K(dns)TNAKHSAHNRRLRTR | 372 |
| ZElan112 | PAX2 Ala Scan 8 | H₂N—K(dns)TNAKHSSANRRLRTR | 373 |
| ZElan113 | PAX2 Ala Scan 9 | H₂N—K(dns)TNAKHSSHARRLRTR | 374 |
| ZElan114 | PAX2 Ala Scan 10 | H₂N—K(dns)TNAKHSSHNARLRTR | 375 |
| ZElan115 | PAX2 Ala Scan 11 | H₂N—K(dns)TNAKHSSHNRALRTR | 376 |
| ZElan116 | PAX2 Ala Scan 12 | H₂N—K(dns)TNAKHSSHNRRARTR | 377 |
| ZElan117 | PAX2 Ala Scan 13 | H₂N—K(dns)TNAKHSSHNRRLATR | 378 |
| ZElan118 | PAX2 Ala Scan 14 | H₂N—K(dns)TNAKHSSHNRRLRAR | 379 |
| ZElan119 | PAX2 Ala Scan 15 | H₂N—K(dns)TNAKHSSHNRRLRTA | 380 |
| ZElan123 | PAX2 15 mer cyclic D form | H₂N—K(dns)Lys-TNAKHSSHNrrLrTr | 381 |
| ZElan124 | PAX2 15 mer D form | H₂N—K(dns)TNAKHSSHNrrLrTr | 382 |
| ZElan125 | PAX2 10 mer cyclic | H₂N—K(dns)Lys-SSHNRRLRTR | 383 |
| ZElan126 | PAX2 10 mer cyclic D form | H₂N—K(dns)Lys-SSHNrrLrTr | 384 |
| ZElan127 | PAX2 10 mer cyclic | H₂N—K(dns)Lys-TNAKHSSHNR | 385 |
| ZElan128 | PAX2 10 mer cyclic D form | H₂N—K(dns)Lys-TNAKHSSHNr | 386 |
| ZElan129 | PAX2 15 mer | H₂N—K(dns)TNAKHSSHNRRLRTR | 387 |
| ZElan130 | HAX42 14 mer Ala Scan 1 | H₂N—K(dns)AGDYNCCGNGNSTG | 388 |
| ZElan131 | HAX42 14 mer Ala Scan 2 | H₂N—K(dns)PADYNCCGNGNSTG | 389 |
| ZElan132 | HAX42 14 mer Ala Scan 3 | H₂N—K(dns)PGAYNCCGNGNSTG | 390 |
| ZElan133 | HAX42 14 mer Ala Scan 4 | H₂N—K(dns)PGDANCCGNGNSTG | 391 |
| ZElan134 | HAX42 14 mer Ala Scan 5 | H₂N—K(dns)PGDYACCGNGNSTG | 392 |
| ZElan135 | HAX42 14 mer Ala Scan 6 | H₂N—K(dns)PGDYNACGNGNSTG | 393 |
| ZElan136 | HAX42 14 mer Ala Scan 7 | H₂N—K(dns)PGDYNCAGNGNSTG | 394 |
| ZElan137 | HAX42 14 mer Ala Scan 8 | H₂N—K(dns)PGDYNCCANGNSTG | 395 |
| ZElan138 | HAX42 14 mer Ala Scan 9 | H₂N—K(dns)PGDYNCCGAGNSTG | 396 |
| ZElan139 | HAX42 14 mer Ala Scan 10 | H₂N—K(dns)PGDYNCCGNANSTG | 397 |
| ZElan140 | HAX42 14 mer Ala Scan 11 | H₂N—K(dns)PGDYNCCGNGASTG | 398 |
| ZElan141 | HAX42 14 mer Ala Scan 12 | H₂N—K(dns)PGDYNCCGNGNATG | 399 |

TABLE 20-continued

| Name | Description | Sequence | SEQ. ID. No. |
|---|---|---|---|
| ZElan142 | HAX42 14 mer Ala Scan 13 | H₂N—K(dns)PGDYNCCGNGNSAG | 400 |
| ZElan143 | HAX42 14 mer Ala Scan 14 | H₂N—K(dns)PGDYNCCGNGNSTA | 401 |

GST fusion proteins of GIT peptides are shown in Table 21.

TABLE 21

| Source | Clone # | GST Fusion Sequence | SEQ ID NO. |
|---|---|---|---|
| DCX11 | 98 | gst-SQGSKQCMQYRTGRLTVGSEYGCGMNPARHATPAYPARLLPRYR | 213 |
| HAX42 | 99 | gst-SDHALGTNLRSDNAKEPGDYNCCGNGNSTGRKVFNRRRPSAIPT | 214 |
| SNi34 | 100 | gst-SPCGGGSWGRFMQGGLFGGRTDGCGAHRNRTSASLEPPSSDY | 215 |
| 5PAX5 | 97 | gst-RGSTGTAGGERSGVLNLHTRDNASGSGFKPWYPSNRGHK | 216 |
| SNi28 | 84 | gst-SHSGGMNRAYGDVFRELRDRWNATSHHTRPTPQLPRGPN | 217 |
| SNi28 | 85 | gst-SHSGGNNRAY | 218 |
| SNi28 | 86 | gst-GDVFRELRDR | 219 |
| SNi28 | 87 | gst-WNATSHHTRP | 220 |
| SNi28 | 88 | gst-TPQLPRGPN | 221 |
| SNi28 | 89 | gst-GDVFRELRDRWNATSHHTRP | 222 |
| SNi28 | 90 | gst-WNATSHHTRPTPQLPRGPN | 223 |
| SNi28 | 91 | gst-GDVFRELRDRWNATSHHTRPTPQLPRGPN | 224 |
| SNi28 | 92 | gst-SHSGGMNRAYGDVFRELRDRWNATSAATRPTPQLPRGPN | 225 |
| P31 | 93 | gst-SARDSGPAEDGSRAVRLNGVENANTRKSSRSNPRGRRHP | 226 |
| P31 | 101 | gst-SARDSGPAEDGSRAVRLNG | 227 |
| P31 | 102 | gst-DGSRAVRLNGVENANTRKSSR | 228 |
| P31 | 103 | gst-ENANTRKSSRSNPRGRRHP | 229 |
| P31 | 110 | gst-ENANTRKSSR | 230 |
| P31 | 111 | gst-RKSSRSNPRG | 231 |
| P31 | 112 | gst-SNPRGRRHP | 232 |
| P31 | 119 | gst-TRKSSRSNPRG | 233 |
| PAX2 | 94 | gst-STPPSREAYSRPYSVDSDSDTNAKHSSHNRRLRTRSRPN | 234 |
| PAX2 | 104 | gst-STPPSREAYSRPYSVDSDSD | 235 |
| PAX2 | 105 | gst-SRPYSVDSDSDTNAKHSSHNR | 236 |
| PAX2 | 106 | gst-TNAKHSSHNRRLRTRSRPN | 237 |
| PAX2 | 113 | gst-TNAKHSSHN | 238 |
| PAX2 | 114 | gst-SSHNRRLRTR | 239 |
| PAX2 | 115 | gst-RRLRTRSRPN | 240 |
| SNi10 | 96 | gst-RVGQCTDSDVRRPWARSCAHQGCGAGTRNSHGCITRPLRQASAH | 241 |
| SNi10 | 116 | gst-RVGQCTDSDVRRPWARSCA | 242 |
| SNi10 | 117 | gSt-VRRPWARSCAHQGCGAGTRNS | 243 |
| SNi10 | 118 | gst-GTRNSHGCITRPLRQASAH | 244 |
| DCX8 | 95 | gst-RYKHDIGCDAGVDKKSSSVRGGCGAHSSPPRAGRGPRGTMVSRL | 245 |
| DCX8 | 107 | gst-RYKHDIGCDAGVDKKSSSVRGGCG | 246 |
| DCX8 | 108 | gst-GCDAGVDKKSSSVRGGCGAHSSPPRA | 247 |
| DCX8 | 109 | gst-GAHSSPPRAGRGPRGTMVSRL | 248 |

6.10.6. Peptide Stability

The relative stability for ZElan031 (SEQ ID NO:297), ZElan053 (SEQ ID NO:319) and ZElan054 (SEQ ID NO:320) was determined in simulated intestinal fluid (SIF) SIF was made by dissolving 100 mg of pancreatin (Sigma cat#P-1625, lot# 122H0812)in 8.4 ml of phosphate stock solution, adjusting the pH to 7.5 with 0.2N NaOH and adjusting the volume to 10 ml with water.

Peptide (3.25 mg) was dissolved in 3.25 ml of 10,000 fold diluted SIF solution at 37° C. Aliquots (0.7 ml) of the digestion solution were then withdrawn at <1 min, 1h, 3h, and 21h or 24h. The samples were quickly passed through a syringe filter (Millipore Millex-GV 0.22 μm, part# SLGV025LS, lot# H2BM95250) and 300 μL of the filtered solution was immediately injected onto a Hewlett-Packard HPLC system equipped with a C-8 column (Applied Biosystems column and guard column: column-p/n 0711-0023 Spheri-5 ODS 5 μm, 220×4.6 mm). The products were eluted at 1.5 ml/min using an acetonitrile-water gradient. The major fluorescent peaks were collected, lyopholized and identified by MS analysis.

The HPLC gradient used was:

| Time (min) | Solvent Mixture |
|---|---|
| 0 | 95% H₂0–5% acetonitrile (0.1% TFA) |
| 5 | 95% H₂0–5% acetonitrile (0.1% TFA) |
| 35 | 85% H₂0–15% acetonitrile (0.1% TFA) linear solvent change |
| 40 | 0% H₂0–100% acetonitrile (0.1% TFA) linear solvent change |
| 45 | 95% H₂0–5% acetonitrile (0.1% TFA) linear solvent change |
| 52 | 95% H₂0–5% acetonitrile (0.1% TFA) linear solvent change |

As shown in Table 22, the relative stability (to SIF) for the three peptides was found to be ZElan053>ZElan054>ZElan031 (SEQ ID NOs:319,320, 297, respectively). Enzymatic cleavage of the peptide was found to occur at arginine and/or lysine as expected. The replacement of 1-amino acids with their D-amino acid analogs significantly reduced the rate of proteolysis at these residues.

TABLE 22

| Peptide | Percent Remaining at: | | | | Rel. Stab. | SEQ ID NO |
|---|---|---|---|---|---|---|
| | 1 m | 1 h | 3 h | 24 h | | |
| ZElan031 | 100 | 38.7 | 0 | 0 | 3 | 297 |
| ZElan054 | 97.4 | 58.2 | 11.6 | 2.7 | 2 | 320 |
| ZElan053 | 100 | 98.3 | 98.1 | 94.0 | 1 | 321 |

7. Characterization of Peptide-Coated Particles

Binding of Peptide-Coated PLGA Nanoparticles to Fixed Caco-2 Cells

Binding of nanoparticles coated with targeting peptides to fixed Caco-2 cells was investigated using an ELISA assay based on reaction of antibody with the dansyl moiety present on the peptides. Isoelectric points of selected synthetic peptides are shown in Table 23 (corresponding SEQ ID NOS. are shown in Table 7). Corresponding dansylated synthetic GIT binding peptides are given in Table 24.

TABLE 23

| Peptide | Sequence | pI | SEQ ID NO. |
|---|---|---|---|
| P31 | SARDSGPAEDGSRAVRLNGVENANTRKSSRSNPRGRRHP | 12.26 | 43 |
| 5PAX5 | RGSTGTAGGERSGVLNLHTRDNASGSGFKPWYPSNRGHK | 11.49 | 46 |
| SNi10 | RVGQCTDSDVRRPWARSCAHQGCGAGTRNSHGCITRPLRQASAH | 10.45 | 4 |
| SNi34 | SPCGGSWGRFMQGGLFGGRTDGCGAHRNRTSASLEPPSSDY | 8.25 | 6 |
| DCX11 | SQGSKQCMQYRTGRLTVGSEYGCGMNPARHATPAYPARLLPRYR | 10.44 | 24 |
| DCX8 | RYKHDIGCDAGVDKKSSSVRGGCGAHSSPPRAGRGPRGTMVSRL | 11.03 | 23 |
| HAX42 | SDHALGTNLRSDNAKEPGDYNCCGNGNSTGRKVFNRRRPSAIPT | 9.62 | 52 |
| PAX2 | STPPSREAYSRPYSVDSDSDTNAKHSSHNRRLRTRSRPN | 11.26 | 55 |

TABLE 24

| Peptide | Sequence | SEQ ID NO. |
|---|---|---|
| P31 | H$_2$N-K(dns)SARDSGPAEDGSRAVRLNGVENANTRKSSRSNPRGRRHPGG-CONH$_2$ | 288 |
| 5PAX5 | H$_2$N-K(dns)RGSTGTAGGERSGVLNLHTRDNASGSGFKPWYPSNRGHK-CONH$_2$ | 282 |
| SNi10 | H$_2$N-K(dns)RVGQCTDSDVRRPWARSCAHQGCGAGTRNSHGCITRPLRQASAH-CONH$_2$ | 278 |
| SNi34 | H$_2$N-K(dns)SPCGGSWGRFMQGGLFGGRTDGCGAHRNRTSASLEPPSSDY-CONH$_2$ | 286 |
| DCX11 | H$_2$N-K(dns)SQGSKQCMQYRTGRLTVGSEYGCGMNPARHATPAYPARLLPRYR-CONH$_2$ | 277 |
| DCX8 | H$_2$N-K(dns)RYKHDIGCDAGVDKKSSSVRGGCGAHSSPPRAGRGPRGTMVSRL-CONH$_2$ | 287 |
| HAX42 | H$_2$N-K(dns)SDHALGTNLRSDNAKEPGDYNCCGNGNSTGRKVFNRRRPSAIPT-CONH$_2$ | 285 |
| PAX2 | H$_2$N-K(dns)STPPSREAYSRPYSVDSDSDTNAKHSSHNRRLRTRSRPNG-CONH$_2$ | 281 |
| DAB10 | H$_2$N-K(dns)SKSGEGGDSSRGETGWARVRSHAMTAGRFRWYNQLPSDR-CONH$_2$ | 289 |

Method:

Confluent Caco-2 monolayers grown in 96-well plates (p38) were fixed and treated with 0.1% phenylhydrazine before blocking with 0.1% BSA in PBS. Control and dansyl peptide-coated nanoparticles were resuspended in sterile water at 10 mg/ml and stirred with a magnet for 1 h at room temperature. Samples consisted of: (1) blank nanoparticle control, (2) scrambled PAX2-coated nanoparticles, (3) PAX2-coated nanoparticles, (4) HAX42-coated nanoparticles, (5) PAX2/HAX42-coated nanoparticles, and (6) 8 peptide-coated nanoparticles.

Nanoparticles were added to the cells at 10 mg/ml in 100 µl 1% BSA-PBS (no Tween80 is used in this assay) and 2-fold serially-diluted. The 96-well plates were incubated for 1 h at room temperature. The plates were washed 5 times with 1% BSA-PBS and 100 µl of anti-dansyl antibody (Cytogen DB3-226.3; 0.5 µg/ml; batch May 1997) was added per well and the plates incubated 1 h at room temperature. The wells were washed 5 times with 1% BSA-PBS; 100l of goat anti-mouse λ:HRP antibody (Southern Biotechnology CN. 1060-05; 1:10,000) was added per well, and the plates incubated 1 h at room temperature. After washing 5 times with 1% BSA-PBS, 100 µl of MB peroxidase substrate (KPL CN. 50-76-00) was added to the wells and the optical density at 650 nm was measured after 15 minutes.

As shown in FIGS. 13A–B, a decreasing anti-dansyl ELISA response was observed for nanoparticles coated with PAX2, HAX2, PAX2+HAX2, and a mixture of 8 targeting peptides, when decreasing amounts of the nanoparticles were applied to fixed Caco-2 cells. No concentration effect was observed for blank nanoparticles or nanoparticles coated with a scrambled version of PAX2 peptide. Nanoparticles coated with PAX2, HAX2, PAX2+HAX2, and the 8 peptide mix, showed increased response relative to blank nanoparticles or nanoparticles coated with a scrambled version of PAX2 peptide. The OD values were low relative to those normally observed for GST-peptide fusion binding to fixed Caco-2 cells.

Table 25 below shows the insulin potency and level of peptides coated onto the particles (measured by fluorescense) for formulation 1 particles (formulation by the coacervation method given below).

TABLE 25

ELISA of dansylated peptides and insulin coated PLGA particles

| Peptide | Blend | |
|---|---|---|
| | Insulin mg/g | Peptide μl/mg |
| PAX2 | 60.7 | 3.51 |
| HAX42 | 55.9 | 2.93 |
| PAX2 SCRAMBLED | 57.7 | 1.26 |
| P31 | 67.0 | 1.22 |
| 5PAX5 | 52.7 | 2.83 |
| SNi10 | 59.5 | 1.75 |
| SNi34 | 61.5 | 4.03 |
| DCX8 | 59.1 | 1.87 |
| DAB10 | 55.9 | 1.99 |

The standard ELISA procedure was modified as follows. Peptides and particles were diluted to an appropriate concentration in PBS containing 1% BSA (particles were sonicated to achieve a homogeneous solution), titered and incubated one hour at room temperature. Following five washes with PBS containing 1% BSA, an in-house IgG1λ anti-dansyl monoclonal antibody was added (diluted to 1 μg/ml in 1% BSA-PBS) and the plates were incubated for one hour. After five more washes goat anti-mouse λ-HRP was added (Southern Biotechnology Associates Inc., Birmingham, Ala., diluted 1:10,000 in 1% BSA-PBS) and the plates were incubated one hour. After five washes, plates were developed with TMB peroxidase substrate (Kirkegard and Perry, Gaithersburg, Md.). All data is presented with background binding subtracted. Tween 20 was not added to the diluent or the washes when insulin coated PLGA particles were included in the assay.

FIGS. 14A–14B show the binding of the dansylated peptide SNi10 to hSI and BSA.

8. Binding of Synthetic Peptides and Peptide-Coated Particles to S100 and P100 Fractions Derived from Caco-2 Cells 8.1. Detection of Binding to Membrane (P100) and Cytosolic (S100) Fractions Caco-2 cell membrane (P100) and cytosolic (S100) fractions were prepared using a modification of the method described in Kinsella, B. T., O'Mahony, D. J. and G. A. FitzGerald, 1994, J. Biol. Chem. 269(47): 29914–29919. Confluent Caco-2 cell monolayers (grown in 75 cm² flasks for up to 1 week at 37° C. and 5% $CO_2$) were washed twice in Dulbecco's PBS (DPBS) and the cells were harvested by centrifugation at 1000 rpm after treatment with 10 mM EDTA-DPBS. The cells were washed 3 times in DPBS and the final cell pellet was resuspended in 3 volumes of ice cold HED buffer (20 mM HEPES (pH 7.67), 1 mM EGTA, 0.5 mM dithiothreitol, 1 mM phenylmethylsulphonyl fluoride (PMSF)). The cells were allowed to swell for 5 min on ice prior to homogenization for 30 sec. The homogenates were centrifuged at 40,000 rpm for 45 min at 4° C. The supernatant (S100) was removed and the pellet (P100) was resuspended in HEDG buffer (20 mM HEPES (pH 7.67), 1 mM EGTA, 0.5 mM dithiothreitol, 100 mM NaCl, 10% glycerol, 1 mM PMSF). Protein concentrations were determined using the Bradford assay (Bradford, M. M., 1976, Anal. Biochem. 72: 248–254).

Binding of peptide and/or peptide-coated PLGA particles to membrane (P100) and cytosolic (S100) fractions was assessed by detection of the dansyl moiety incorporated in the peptide. Costar ninety six well ELISA plates were coated with S100 and P100 fractions (100 μg/ml in 0.05 M $NaHCO_3$) overnight at 4° C. The plates were blocked with 0.5% bovine serum albumin in DPBS for 1 h at room temperature and washed 3 times in 1% BSA-DPBS. Peptide-coated particles or peptides were dispersed in the same buffer and added to the plates at concentrations in the range 0.0325–0.5 mg/well. After 1 h at room temperature the plates were washed 5 times in 1% BSA-DPBS and 100 μl of anti-dansyl antibody (Cytogen DB3-226.3; 0.5 μg/ml) was added per well. The plates were incubated for 1 h at room temperature. The wells were washed 3 times in 1% BSA-DPBS and 100 μl of goat anti-mouse IgGλ:HRP antibody (Southern Biotechnology 1060-05; 1:10,000) was added per well. The plates were incubated for 1 h at room temperature. After washing 3 times in 1% BSA-DPBS 100 μl of TMB substrate (3,3',5',5-tetramethylbenzidine; Microwell Peroxidase Substrate System (Kirkegaard and Perry Laboratories 50-76-00)) was added and the optical density was measured at 650 nm at various time intervals.

8.2. Binding of Peptide-Coated PLGA Particles

A novel assay system is provided by the instant invention for detection of binding of peptide-coated PLGA particles to membrane (P100) and cytosolic (S100) fractions derived from live Caco-2 cells. The absorbance readings obtained using this assay system were substantially higher than those obtained using similar peptide-coated PLGA particle concentrations on fixed Caco-2 cells. This greater sensitivity together with the derivation of the S100 and P100 fractions from live Caco-2 cells suggests that this assay may be the assay system of choice for detection of peptide-coated PLGA particle binding. The assay was concentration dependent and peptide/particle correlation permitted differentiation between specific and non-specific binding interactions.

Binding of peptide-coated PLGA particles was assessed using S100 and P100 fractions derived from live Caco-2 cells as described above. The fractions were coated onto 96-well plates at 10 μg/well in 0.05 M $NaHCO_3$ and peptide-coated PLGA particles were assayed by ELISA at concentrations in the range 0.0325–0.5 mg/well.

FIGS. 15A and 15B illustrate the data obtained on S100 and P100 fractions respectively for particles coated with no peptide, scrambled PAX2 (control), P31 D-Arg 16-mer (ZElan053, SEQ ID NO: 319), HAX42, PAX2 and HAX42/PAX2. Using particle concentrations of 0.0325–0.5 mg/well all test peptide-coated PLGA particles exhibited greater binding to both the S100 and P100 fractions than the scrambled PAX2 coated control particles. All particles except P31 D-Arg 16-mer (ZElan053, SEQ ID NO: 319) exhibited greater binding to the P100 fraction than the S100 fraction. Greater binding of the P31 D-Arg 16-mer (ZElan053, SEQ ID NO: 319) coated particles to the S100 fraction may be indicative of non-specific binding due to the D-Arg modification of the P31 peptide (SEQ ID NO:270).

Binding of PLGA particles coated with varying concentrations of PAX2 peptide ranging from 0.05–5.0 mg/g was assessed using a) fixed Caco-2 cells (P35) and b) S100 and P100 fractions (Caco-2 P33). The particles were assayed at concentrations in the range 0.03125–0.0625 mg/well.

Using a particle concentration of 0.0625 mg/well, all PAX2 coated particles except those coated at 0.05 mg/g exhibited greater binding to fixed Caco-2 cells than the scrambled PAX2 coated control particles. There appeared to be a concentration effect with increasing PAX2 peptide concentration resulting in improved Caco-2 cell binding (in the range 0.05–1.0 mg/g). However all absorbance readings were low and binding of the PAX2 (5 mg/g) was not consistent with this pattern.

Using particle concentrations of 0.03125–0.0625 mg/well all test peptide coated particles except PAX2 (0.05 mg/g) exhibited comparable or greater binding to both the S100 and P100 fractions than the scrambled PAX2 coated control particles. All particles exhibited greater binding to the P100 fraction than the S100 fraction. Binding to both the S100 and P100 fractions was directly proportional to the concentration of the PAX2 peptide on the particle. The absorbance readings obtained using this assay system were substantially higher than those obtained on the fixed Caco-2 cells.

The effect of blocking solution on binding of peptide-coated PLGA particles to P100 fractions (Caco-2 P35) was assessed using 1% bovine serum albumin (BSA) and 1% milk powder blocking solutions to assess background binding. The following particles were assayed at concentrations in the range 0.03125–0.0625 mg/well: no peptide; scrambled PAX2; and a range of PAX2 coated particles having peptide concentrations from 5–0.05 mg/g. As previously observed using 1% BSA, all test peptide coated particles except PAX2 coated at 0.05 mg/g exhibited comparable or greater binding to the P100 fractions than the scrambled PAX2 coated control particles. Binding to P100 fractions was directly proportional to the concentration of the PAX2 peptide on the particle (although in this instance PAX2 (5 mg/g) exhibited slightly lower binding than PAX2 (1 mg/g)). A similar trend was observed using 1% milk powder and a particle concentration of 0.0625 mg/well. However all absorbance readings were low when 1% milk powder was used and the binding pattern was not detectable using particles at a concentration of 0.0625 mg/well.

Non-specific binding of peptide-coated PLGA particles to plastic was also assessed using 1% BSA and 1% milk powder blocking solutions. The binding pattern observed above could be detected when BSA was used; however, absorbance readings were substantially lower and binding of particles PAX2 (0.1 and 0.05 mg/g respectively) was not detectable. When 1% milk powder was used, all absorbance readings were low and no binding pattern was detectable. BSA was chosen for blocking in subsequent assays.

8.3. Comparison of Peptide-Coated Particle and Synthetic Peptide Binding to P100 Fractions Binding of dansylated peptides to P100 fractions was assessed to determine if peptide binding was predictive of peptide-coated particle binding. FIG. 16 illustrates the data obtained for the dansylated peptides A) HAX42, P31 D-form and scrambled PAX2 and B) PAX2, HAX42 and scrambled PAX2.

Two consecutive assays produced substantial variations in absorbance readings. Initially, the HAX42 peptide exhibited strong binding when compared to the scrambled PAX2 control. The P31 D-form peptide (ZElan053, SEQ ID NO: 319) exhibited binding at the highest dilution only. In the repeat assay, HAX42 also exhibited significant binding compared to the scrambled PAX2 control. However, the scrambled PAX2 control and HAX42 produced relatively high absorbance values compared to those obtained in the previous assay. The PAX2 peptide was indistinguishable from the scrambled PAX2 control. Peptide/particle binding correlation is summarized as follows in Table 26:

TABLE 26

Peptide/particle assay correlation

| Peptide | Assay correlation |
|---|---|
| HAX42 | + |
| PAX2 | +/− |
| P31 D-form | − |
| Scrambled PAX2 | +/− |

+ positive; +/− equivocal; − negative

Peptide/particle binding correlated well for the HAX42 peptide. In contrast, no correlation could be detected for the P31 D-form (ZElan053, SEQ ID NO: 319) peptide. Since the P31 D-form peptide-coated particles exhibited greater binding to the S100 fraction than the P100 fraction (unlike the other test peptides) it appears that the particle binding interaction was non-specific or that some other molecule was competing for binding to the P100 fraction but not to the S100 fraction. Thus the peptide/particle assay correlation may be useful for distinguishing between specific and non-specific binding interactions. The scrambled PAX2 control produced variable results so that it was difficult to assess the PAX2 binding correlation.

8.4. Determination of HAX42 and PAX2 Binding Motif Sequences

Peptides and GST fusion proteins of HAX42, PAX2 and various derivatives were assayed using peptide ELISA to P100 membrane fractions derived from Caco-2 cells. The GST-PAX2 protein and PAX2 peptide data indicate that a core binding motif lies in the amino acid sequence TNAKHSSHNRRLRTR (SEQ ID NO: 402) otherwise named GST-106 and ZElan033 (SEQ ID NO: 299). Similarly, the HAX42 peptide data suggest that a core binding motif for HAX42 lies in the amino acid sequence PGDYNCCGNCNSTG (SEQ ID NO: 403), otherwise named ZElan091 (SEQ ID NO: 358).

The peptides and proteins were analyzed by a dansylated peptide ELISA method in which 96 well plates were coated overnight at 4° C. with 100 μl/well coating protein (normally 100 μg/ml P100 membrane fraction) in 0.05M carbonate buffer pH9.6. Nonspecific binding was blocked using 200 μl/well, 2% Marvel/PBS for 2 hours at 37° C. prior to incubation with dansylated peptides. The plates were washed three times with PBS/0.05% Tween 20 and after each subsequent incubation step. The peptides were diluted in blocking solution at a starting concentration of 100 μg/ml and diluted 1:2 downwards, 100 μl/well, followed by incubation at room temperature for 1 hour, exactly. A buffer blank control was included to ensure that background binding to plastic was not due to the antibodies used in the assay system. To detect the dansylated peptides, a mouse anti-dansyl antibody (DB3, Cytogen Corp.) at 1:1340 dilution in blocking buffer and 100 μl/well was added followed by incubation at room temperature for 1 hour. The plates were then incubated with an anti-mouse λ-HRP conjugated antibody (Southern Biotech 1060-05) at a 1:10,000 dilution in blocking solution, 100 μl/well for 1 hour at room temperature. Plates were developed using 75 μl/well Bionostics TMB substrate and incubated for approximately 10 minutes. The developing reaction was stopped using Bionostics Red Stop solution (25 μl/well), and the optical density of the plates was read at 650 nm.

GST-PAX2 Peptides—Relative Binding to P100 Fractions

After subtraction of the GST-peptide binding to plastic from P100 binding values, the binding of GST-PAX2 peptides were represented as a ratio of GST-HAX42 binding to P100, which was given the arbitrary value of 1.00. The following ratios were determined from binding to P100 of GST-peptides at a peptide concentration of 20 μg/ml. Bold denotes positive binding to the P100 membrane fraction.

TABLE 27

| GST-peptide | Value |
|---|---|
| GST-HAX42 | 1.00 |
| GST-PAX2 | 1.79 |
| GST-104 | 0.01 |
| GST-105 | −0.08 |
| GST-106 | 2.71 |
| GST-113 | 0.26 |
| GST-114 | 0.17 |
| GST-115 | 0.36 |
| GST | 0.48 |

PAX2 Peptides—Relative Binding to P100 Fractions

ZElan021 (SEQ ID NO: 285), full length HAX42, was given the arbitrary value of 1.00 for binding to P100 at a given peptide concentration determined from the signal-to-noise ratio data. PAX2 and its derivatives are given as a ratio of HAX42 value to reflect their binding abilities to P100 membrane fractions derived from a Caco-2 cell line as shown in Table 329. Table 30 provides a line-up of the PAX2 peptides showing the positive binding peptides in boldface. The GST-PAX2 peptide and PAX2 peptide data agree, demonstrating that a binding motif is in the amino acid sequence TNAKHSSHNRRLRTR (SEQ ID NO: 402)(GST-106 and ZElan033, SEQ ID NO: 299).

TABLE 28

| | GST-peptide Amino Acid Sequence | SEQ. ID. No. |
|---|---|---|
| GST-PAX2 | STPPSREAYSRPYSVDSDSDTNAKHSSHNRRLRTRSRPN | 55 |
| GST-104 | STPPSREAYSRPYSVDSDSD | 170 |
| GST-105 | STPPSREAYSRPYSVDSDSDTNAKHSSHN | 171 |
| GST-106 | TNAKHSSHNRRLRTRSRPN | 172 |
| GST-113 | TNAKHSSHN | 173 |
| GST-114 | SSHNRRLRTRSRPN | 174 |
| GST-115 | RRLRTRSRPN | 175 |

TABLE 29

| SEQ ID NO. | PAX2 peptide | Binding value at 20 μg/ml | Binding value at 20 μg/ml | Binding value at 50 μg/ml | Binding value at 50 μg/ml | Binding value at 50 μg/ml (Jackson Ab) | Binding value at 50 μg/ml (Southern Ab) |
|---|---|---|---|---|---|---|---|
| 281 | ZElan018 | −0.33 | 1.07 | 0.95 | 1.01 | | |
| 298 | ZElan032 | 1.43 | 2.87 | 0.95 | 1.06 | | |
| 299 | ZElan033 | 0.35 | 1.57 | 0.80 | 0.66 | | |
| 301 | ZElan035 | 0.12 | 0.43 | 0.81 | 0.77 | | |
| 321 | ZElan055 | 0.99 | 0.73 | 1.10 | 0.59 | | |
| 322 | ZElan056 | 0.00 | 0.16 | 0.21 | 0.21 | | |
| 323 | ZElan057 | 0.08 | | 0.56 | 0.25 | | |
| 324 | ZElan058 | 0.05 | | 0.47 | 0.16 | | |
| 339 | ZElan073 | 0.07 | | −0.11 | 0.49 | 0.66 | 0.49 |
| 340 | ZElan074 | 0.06 | | 0.82 | 0.52 | 0.71 | 0.48 |
| 341 | ZElan075 | 0.13 | | 0.52 | 0.38 | 0.47 | 0.32 |
| 342 | ZElan076 | 0.08 | | 1.00 | 0.41 | 0.60 | 0.42 |
| 343 | ZElan077 | 0.20 | | 0.76 | 0.54 | 0.73 | 0.52 |
| 344 | ZElan078 | 0.11 | | 0.87 | 0.69 | 0.68 | 0.47 |
| 345 | ZElan079 | 0.31 | | 0.97 | 0.68 | 0.83 | 0.53 |
| 346 | ZElan080 | 0.23 | | 0.84 | 0.45 | 0.67 | 0.38 |
| 347 | ZElan081 | 0.01 | | 0.89 | 0.47 | | |
| 348 | ZElan082 | 0.00 | | 0.92 | 0.40 | | |
| 350 | ZElan083 | 0.43 | 0.63 | 1.03 | 0.88 | | |
| 351 | ZElan084 | 1.06 | 0.93 | 1.16 | 0.77 | | |

TABLE 30

| | Amino acid sequence | SEQ ID NO: |
|---|---|---|
| PAX2 Peptide | | |
| ZElan018 | H₂N-K(dns)STPPSREAYSRPYSVDSDSDTNAKHSSHNRRLRTRSRPNG -CONH₂ | 281 |
| ZElan032 | H₂N-K(dns)TNAKHSSHNRRLRTRSRPN-CONH₂ | 298 |
| ZElan033 | H₂N-K(dns)TNAKHSSHNRRLRTR-CONH₂ | 299 |
| ZElan034 | H₂N-K(dns)SSHNRRLRTRSRPN-CONH₂ | 300 |
| ZElan035 | H₂N-K(dns)SSHNRRLRTR-CONH₂ | 301 |
| ZElan055 | H₂N-K(dns)TNAKHSSHN-CONH₂ | 321 |
| ZElan056 | H₂N-K(dns)RRLRTRSRPN-CONH₂ | 322 |
| ZElan057 | H₂N-K(dns)RRLRTRSR-CONH₂ | 323 |
| ZElan058 | H₂N-K(dns)RRLRTR-CONH₂ | 324 |
| ZElan059 | H₂N-K(dns)rrLrTrSrPN-CONH₂ | 325 |
| ZElan073 | H₂N-K(dns)ASHNRRLRTR-CONH₂ | 339 |
| ZElan074 | H₂N-K(dns)SAHNRRLRTR-CONH₂ | 340 |
| ZElan075 | H₂N-K(dns)SSANRRLRTR-CONH₂ | 341 |
| ZElan076 | H₂N-K(dns)SSHARRLRTR-CONH₂ | 342 |
| ZElan077 | H₂N-K(dns)SSHNARLRTR-CONH₂ | 343 |
| ZElan078 | H₂N-K(dns)SSHNRALRTR-CONH₂ | 344 |
| ZElan079 | H₂N-K(dns)SSHNRRARTR-CONH₂ | 345 |
| ZElan080 | H₂N-K(dns)SSHNRRLATR-CONH₂ | 346 |
| ZElan081 | H₂N-K(dns)SSHNRRLRAR-CONH₂ | 347 |
| ZElan082 | H₂N-K(dns)SSHNRRLRTA-CONH₂ | 348 |
| SCRAMBLED PAX2 PEPTIDES: | | |
| ZElan083 | H₂N-K(dns)GRNHDVVSSNTHKSYRSPRSASYPRLSNDRTDRTEPAPSS-CONH₂ | 350 |
| ZElan084 | H₂N-K(dns)RNTRNKTSRLSANPHRSHR-CONH₂ | 351 |

HAX42 Peptides—Relative Binding to P100 Fractions

ZElan021 (SEQ ID NO: 285), full length HAX42, was given the arbitrary value of 1.00 for binding to P100 at a given peptide concentration determined from the signal-to-noise ratio data. HAX42 and its derivatives are given as a ratio of HAX42 value to reflect their binding abilities to P100 membrane fractions derived from a Caco-2 cell line as shown in Table 31. Table 32 provides a line-up of the HAX42 peptides showing the positive binding peptides in boldface. A core binding motif appears to lie in the amino acid sequence PGDYNCCGNCNSTG (ZElan091, SEQ ID NO:358).

TABLE 31

| SEQ ID NO. | HAX42 peptide | Binding value at 20 µg/ml | Binding value at 50 µg/ml | Binding value at 50 µg/ml | Binding value at 25 µg/ml | Binding value at 25 µg/ml | Binding value at 25 µg/ml |
|---|---|---|---|---|---|---|---|
| 285 | ZElan021 | 1.00 | 1.00 | 1.00 | 1.00 | 1.00 | 1.00 |
| 326 | ZElan060 | 0.44 | 0.56 | 0.43 | | | |
| 327 | ZElan061 | 0.20 | 0.60 | 0.38 | | | |
| 328 | ZElan062 | 0.11 | 0.42 | 0.34 | | | |
| 331 | ZElan065 | 0.00 | 0.54 | 0.30 | | | |
| 333 | ZElan067 | 0.08 | 0.52 | 0.40 | | | |
| 336 | ZElan070 | 0.59 | 0.97 | 0.39 | | | |
| 337 | ZElan071 | 1.22 | 0.89 | 0.75 | | | |
| 338 | ZElan072 | 0.83 | 0.61 | 0.88 | | | |
| 354 | ZElan087 | | | | 0.46 | 0.44 | |

TABLE 31-continued

| SEQ ID NO. | HAX42 peptide | Binding value at 20 µg/ml | Binding value at 50 µg/ml | Binding value at 50 µg/ml | Binding value at 25 µg/ml | Binding value at 25 µg/ml | Binding value at 25 µg/ml |
|---|---|---|---|---|---|---|---|
| 355 | ZElan088 | | | | 2.21 | 1.41 | 1.63 |
| 356 | ZElan089 | | | | 0.55 | 0.44 | 0.49 |
| 357 | ZElan090 | | | | 2.06 | 1.54 | 2.16 |
| 358 | ZElan091 | | | | 2.02 | 1.37 | 1.20 |
| 359 | ZElan092 | | | | 1.41 | 1.90 | 0.91 |
| 360 | ZElan093 | | | | 1.88 | 1.37 | 1.33 |

TABLE 32

| HAX42 Peptide | Amino acid sequence | SEQ. ID. NO. |
|---|---|---|
| ZElan021 | H₂N-K(dns)SDHALGTNLRSDNAKEPGDYNCCGNGNSTGRKVFNRRRPSAIPT-CONH₂ | 285 |
| ZElan060 | H₂N-K(dns)SDHALGTNLRSDNAKEPGDYNCCGNG-CONH₂ | 326 |
| ZElan061 | H₂N-K(dns)GNGNSTGRKVFNRRRPSAIPT-CONH₂ | 327 |
| ZElan062 | H₂N-K(dns)SDHALGTNLRSDNAKEPG-CONH₂ | 328 |
| ZElan065 | H₂N-K(dns)RKVFNRRRPS-CONH₂ | 331 |
| ZElan067 | H₂N-K(dns)NRRRPS-CONH₂ | 333 |
| ZElan070 | H₂N-K(dns)SDHALGTNLRSDNAKEPGDYNCCGNGNST-CONH₂ | 336 |
| ZElan071 | H₂N-K(dns)NLRSDNAKEPGDYNCCGNGNSTGRKVFNR-CONH₂ | 337 |
| ZElan072 | H₂N-K(dns)PGDYNCCGNGNSTGRKVFNRRRPSAIPT-CONH₂ | 338 |
| ZElan087 | H₂N-K(dns)SDHALGTNLRSDNAKEPGDY-CONH₂ | 354 |
| ZElan088 | H₂N-K(dns)SDNAKEPGDYNCCGNGNSTG-CONH₂ | 355 |
| ZElan089 | H₂N-K(dns)SDHALGTNLRSDNAK-CONH₂ -CONH₂ | 356 |
| ZElan090 | H₂N-K(dns)EPGDYNCCGNGNSTG | 357 |
| ZElan091 | H₂N-K(dns)PGDYNCCGNGNSTG-CONH₂ | 358 |
| ZElan092 | H₂N-K(dns)PGDYNCCGNG-CONH₂ | 359 |
| ZElan093 | H₂N-K(dns)NCCGNGNSTG-CONH₂ | 360 |

9. Formulations

General Method for Preparation of Coacervated Particles.

Solid particles containing a Therapeutic as defined herein are prepared using a coacervation method. The are particles are formed from a polymer and have a particle size of between about 10 nm and 500 µm, most preferably 50 to 800 nm. In addition the particles contain targeting ligands which are incorporated into the particles using a number of methods.

The organic phase (B) polymer of the general method given above may be soluble, permeable, impermeable, biodegradable or gastroretentive. The polymer may consist of a mixture of polymer or copolymers and may be a natural or synthetic polymer. Representative biodegradable polymers include without limitation polyglycolides; polylactides; poly (lactide-co-glycolides), including DL, L and D forms; copolyoxalates; polycaprolactone; polyesteramides; polyorthoesters; polyanhydrides; polyalkylcyanoacrylates; polyhydroxybutyrates; polyurethanes; albumin; casein; citosan derivatives; gelatin; acacia; celluloses; polysaccharides; alginic acid; polypeptides; and the like, copolymers thereof, mixtures thereof and stereoisomers thereof. Representative synthetic polymers include alkyl celluloses; hydroxalkyl celluloses; cellulose ethers; cellulose esters; nitrocelluloses; polymers of acrylic and methacrylic acids and esters thereof; dextrans; polyamides; polycarbonates; polyalkylenes; polyalkylene glycols; polyalkylene oxides; polyalkylene terephthalates; polyvinyl alcohols; polyvinyl ethers; polyvinyl esters; polyvinyl halides; poyvinylpyrrolidone; polysiloxanes and polyurethanes and co-polymers thereof.

Typically, particles are formed using the following general method:

An aqueous solution (A) of a polymer, surface active agent, surface stabilising or modifying agent or salt, or surfactant preferably a polyvinyl alcohol (PVA) or derivative with a % hydrolysis 50–100% and a molecular weight range 500–500,000, most preferably 80–100% hydrolysis and 10,000–150,000 molecular weight, is introduced into a vessel. The mixture (A) is stirred under low shear conditions at 10–2000 rpm, preferably 100–600 rpm. The pH and/or ionic strength of this solution may be modified using salts, buffers or other modifying agents. The viscosity of this solution may be modified using polymers, salts, or other viscosity enhancing or modifying agents.

A polymer, preferably poly(lacide-co-glycolide), polylactide, polyglycolide or a combination thereof or in any enantiomeric form or a covalent conjugate of the these polymers with a targeting ligand is dissolved in water miscible organic solvents to form organic phase (B). Most preferably, a combination of acetone and ethanol is used in a range of ratios from 0:100 acetone: ethanol to 100:0 acetone: ethanol depending upon the polymer used.

Additional polymer(s), peptide(s) sugars, salts, natural/biological polymers or other agents may also be added to the organic phase (B) to modify the physical and chemical properties of the resultant particle product.

A drug or bioactive substance may be introduced into either the aqueous phase (A) or the organic phase (B). A targeting ligand may also be introduced into either the aqueous phase (A) or the organic phase (B) at this point.

The organic phase (B) is added into the stirred aqueous phase (A) at a continuous rate. The solvent is evaporated, preferably by a rise in temperature over ambient and/or the use of a vacuum pump. The particles are now present as a suspension (C). A targeting ligand may be introduced into the stirred suspension at this point.

A secondary layer of polymer(s), peptide(s) sugars, salts, natural/biological polymers or other agents may be deposited on to the pre-formed particulate core by any suitable method at this stage.

The particles (D) are then separated from the suspension (C) using standard colloidal separation techniques, preferably by centrifugation at high 'g' force, filtration, gel permeation chromatography, affinity chromatography or charge separation techniques. The supernatant is discarded and the particles (D) re-suspended in a washing solution (E) preferably water, salt solution, buffer or organic solvent(s). The particles (D) are separated from the washing liquid in a similar manner as previously described and re-washed, commonly twice. A targeting ligand may be dissolved in washing solution (E) at the final washing stage and may be used to wash the particles (D).

The particles may then be dried. Particles may then be further processed for example, tabletted, encapsulated or spray dried.

The release profile of the particles formed above may be varied from immediate to controlled or delayed release dependent upon the formulation used and/or desired.

Drug loading may be in the range 0–90% w/w. Targeting ligand loading may be in the range 0–90% w/w.

Specific examples include the following examples:

EXAMPLE 1

Peptide Added at the Final Washing Stage

Product: Bovine Insulin loaded nanoparticles
Aim: To prepare a 2 g batch of insulin loaded nanoparticles at a theoretical loading of 50 mg/g and with the peptide ZElan018 (SEQ ID NO: 281) added.

| Formulation Details | |
|---|---|
| RG504H (Lot no. 250583) | 2.0 g |
| Acetone | 45 ml |
| Ethanol: | 5 ml |
| PVA (aq. 5% w/v) | 400 ml |
| Bovine Insulin (Lot no. 86H0674) | 100 mg |
| Peptide: PAX2 (ZElan018, SEQ ID NO: 281) | 10 mg/50 ml dH$_2$O |

Experimental Details:

The 5% w/v PVA solution was prepared by heating water until near boiling point, adding PVA and stirring until cool. The organic phase was prepared by adding acetone, 45 ml, and ethanol, 5 ml, together. The polymer solution was prepared by adding RG504H, 2 g, to the organic phase and stirring until dissolved. The IKA™ reactor vessel was set up, all seals greased and the temperature was set at 25° C. The PVA solution, 400 ml, was added into the reactor vessel and stirred at 400 rpm.

Bovine insulin, 100 mg, was added into the stirring PVA solution. Using clean tubing and a green needle, the polymer solution was slowly dripped in the stirring PVA solution with the peristaltic pump set at 40. The solvent was allowed to evaporate by opening the ports and allowing the dispersion to stir overnight at 400 rpm.

The suspension was centrifuged in a Beckman Ultracentrifuge™ with swing-out rotor at 12,500 rpm, 4° C. The supernatant was decanted and discarded. The "cake" of particles was broken up and dH$_2$O (200 mls) was added to wash the particles. The centrifugation and washing steps were repeated twice.

The peptide solution, (ZElan018, SEQ ID NO: 281), 10 mg in 50 ml dH$_2$O) was prepared and added to the particles for a final washing stage. The suspended particles were centrifuged as before. The supernatant liquid was decanted, the 'cake' broken up, and the particles were dried in the vacuum oven.

The particles were ground, placed in a securitainer and sent for analysis. The weight of particles recovered was 1.45 g. A SEM showed discrete, reasonably spherical particles in the 300–500 nm size range. The potency was 49.2 mg/g (98.0% of label claim). Peptide loading was 2.42 µg/mg (48.4% of label claim).

EXAMPLE 2

Peptide Added at the Beginning of Manufacture

Product: Bovine Insulin loaded nanoparticles
Aim: To prepare a 2 g batch of insulin loaded nanoparticles at a theoretical loading of 50 mg/g and with the peptide ZElan018 (SEQ ID NO: 281) added at the beginning of manufacture.

| Formulation Details | |
|---|---|
| RG504H (Lot no. 250583) | 2.0 g |
| Acetone | 45 ml |
| Ethanol: | 5 ml |
| PVA (aq. 5% w/v) | 400 ml |
| Bovine Insulin (Lot no. 65H0640) | 100 mg |
| Peptide: PAX2 (ZElan018ii) | 10 mg |

Experimental Details:

The 5% w/v PVA solution was prepared by heating water until near boiling point, adding PVA and stirring until cool. The organic phase was prepared by adding acetone, 45 ml, and ethanol, 5 ml, together. The polymer solution was prepared by adding RG504H (polyactide-co-glycolide, Boehringer Ingelheim), 2 g, to the organic phase prepared in step above and stirring until dissolved. The IKA™ reactor vessel was set up, all seals greased and the temperature was set at 25° C. The PVA solution, 400 ml, was added into the reactor vessel and stirred at 400 rpm.

Bovine insulin, 100 mg, was added into the stirring PVA solution. PAX2 (ZElan018ii, 10 mg) was added to the stirring PVA solution. Using clean tubing and a green needle, the polymer solution was slowly dripped into the stirring PVA solution with the peristaltic pump set at 40. The solvent was allowed to evaporate by opening the ports and allowing the dispersion to stir overnight at 400 rpm. The suspension was centrifuged in a Beckman Ultracentrifuge™ with swing-out rotor at 12,500 rpm, 4° C. The supernatant was decanted and discarded.

The "cake" of particles was broken up and dH$_2$O (200 ml) was added to wash the particles. The centrifugation and washing steps were repeated twice. The 'cake' was broken up and the particles were dried in the vacuum oven.

The particles were ground, placed in a securitainer and sent for analysis. The weight of the particles recovered was 1.6 g. The potency was 47.3 mg/g (94.6% of label claim). Peptide loading was 1.689 µg/mg (33.8% of label claim).

EXAMPLE 3

Peptide Added 1 Hour Before Centrifugation

Product: Bovine Insulin loaded nanoparticles
Aim: To prepare a 1 g batch of insulin loaded nanoparticles at a theoretical loading of 50 mg/g and with the peptide ZElan018 (SEQ ID NO: 281) added 1 hour before centrifugation.

| Formulation Details | |
| --- | --- |
| RG504H (Lot no. 250583) | 1.0 g |
| Acetone | 22.5 ml |
| Ethanol: | 2.5 ml |
| PVA (aq. 5% w/v) | 200 ml |
| Bovine Insulin (Lot no. 65H0640) | 50 mg |
| Peptide: PAX2 (ZElan018, SEQ ID NO: 281) | 5 mg |

Experimental Details:

The 5% w/v PVA solution was prepared by heating water until near boiling point, adding PVA and stirring until cool. The organic phase was prepared by adding acetone, 22.5 ml, and ethanol, 2.5 ml, together. The polymer solution was prepared by adding RG504H, 1 g, to the organic phase prepared above and stirring until dissolved. The IKA™ reactor vessel was set up, all seals greased and the temperature was set at 25° C. The PVA solution, 200 ml, was added into the reactor vessel and stirred at 400 rpm.

Bovine insulin, 50 mg, was added into the stirring PVA solution. Using clean tubing and a green needle, the polymer solution was slowly dripped in the stirring PVA solution with the peristaltic pump set at 40. The solvent was allowed to evaporate by opening the ports and allowing the dispersion to stir overnight at 400 rpm.

PAX2 ((ZElan018, SEQ ID NO: 281) 5 mg) was added to the stirring particle suspension. After 1 hr, the suspension was centrifuged in a Beckman Ultracentrifuge™ with swing-out rotor at 12,500 rpm, 4° C. The supernatant was decanted and discarded. The "cake" of particles was broken up and dH$_2$O (200 ml) was added to wash the particles. The centrifugation and washing steps were repeated twice.

The 'cake' was broken up and the particles were dried in the vacuum oven. The particles were ground, placed in a securitainer and sent for analysis. Potency was 20.75 mg/g (41.5% of label claim). Peptide loading was 1.256 µg/mg (25.12% of label claim).

EXAMPLE 4

Leuprolide Acetate Loaded Nanoparticles

Aim: To prepare a 3 g batch of leuprolide-acetate loaded nanoparticles at a theoretical loading of 20 mg/g and with the peptide ZElan024 (SEQ ID NO: 288) added.

| Formulation Details | |
| --- | --- |
| RG504H (Lot no. 271077) | 3.0 g |
| Acetone | 67.5 ml |
| Ethanol: | 7.5 ml |
| PVA (aq. 5% w/v) | 600 ml |
| Leuprolide acetate (Lot no. V14094) | 60 mg |
| Peptide: P31 (ZElan024, SEQ ID NO: 288) | 15 mg/50 ml dH$_2$O |

Experimental Details:

The PVA solution was prepared and the organic phase was prepared by adding acetone, 67.5 ml, and ethanol, 7.5 ml, together. The polymer solution was prepared by adding RG504H, 3 g, to the organic phase prepared above and stirring until dissolved. The IKA™ reactor vessel was set up, all seals greased and the temperature was set at 25° C. The PVA solution, 600 ml, was added into the reactor vessel and stirred at 400 rpm.

Leuprolide acetate, 60 mg, was added into the stirring PVA solution. Using clean tubing and a green needle, the polymer solution, was slowly dripped in the stirring PVA solution with the peristaltic pump set at 40. The solvent was allowed to evaporate by opening the ports and allowing the dispersion to stir overnight at 400 rpm. The suspension was centrifuged in a Beckman Ultracentrifuge™ with swing-out rotor at 15,000 rpm, 4° C. The supernatant was decanted and retained for analysis.

The "cake" of particles was broken up and dH$_2$O 200 ml) was added to wash the particles. The centrifugation and washing steps were repeated twice.

The peptide solution (P31 (SEQ ID NO:270), 15 mg in 50 ml dH$_2$O) was prepared and added to the particles for a final washing stage. The suspended particles were centrifuged as before. The supernatant liquid was decanted, and the particles were dried in the vacuum oven.

The particles were ground, placed in a securitainer and sent for analysis. The weight of particles recovered was 1.87 g. SEM showed discrete, reasonably spherical particles in the 300–500 nm size range. The potency was 4.7 mg/g (23.4% of label claim). Peptide loading was 1.76 µg/mg.

EXAMPLE 5

Peptide Added by 'Spiking' Polymer Phase with Polymer-Peptide Conjugate

Product: Bovine Insulin loaded nanoparticles
Aim: To prepare a 3 g batch of insulin loaded nanoparticles at a theoretical loading of 50 mg/g and with the polymer-peptide conjugate PLGA-ZElan019 added.

| Formulation Details | | |
| --- | --- | --- |
| RG504H (Lot no. 271077) | 2.85 | g |
| RG504H-ZElan019 conjugate (5PAX5-conjugate) | 0.15 | g |

-continued

| Formulation Details | | |
|---|---|---|
| Acetone | 67.5 | ml |
| Ethanol: | 7.5 | ml |
| PVA (aq. 5% w/v) | 600 | ml |
| Bovine Insulin (Lot no. 86H0674) | 150 | mg |

Experimental Details:

The 5% w/v PVA solution was prepared by heating water until near boiling point, adding PVA and stirring until cool. The organic phase was prepared by adding acetone, 67.5 ml, and ethanol, 7.5 ml, together. The polymer solution was prepared by adding RG504H and the polymer-peptide conjugate to the organic phase and stirring until dissolved.

The IKA™ reactor vessel was set up, all seals greased and the temperature was set at 25° C. The PVA solution, 400 ml, was added into the reactor vessel and stirred at 400 rpm.

Bovine insulin, 100 mg, was added into the stirring PVA solution. Using clean tubing and a green needle, the polymer solution, was slowly dripped in the stirring PVA solution with the peristaltic pump set at 40. The solvent was allowed to evaporate by opening the ports and allowing the dispersion to stir overnight at 400 rpm.

The suspension was centrifuged in a Beckman Ultracentrifuge™ with swing-out rotor at 12,500 rpm, 4° C. The supernatant was decanted and discarded. The "cake" of particles was broken up and dH$_2$O (200 ml) was added to wash the particles. The centrifugation washing step was repeated twice.

The 'cake' was broken up and the particles were dried in the vacuum oven. The particles were ground, placed in a securitainer and sent for analysis. The weight of particles recovered was 2.8 g. The potency was 53.1 mg/g 106.2% of label claim). Peptide loading was 4.02 µg/mg (80.4% of label claim).

10. Animal Studies

Study 1

An open-loop study in which the test solution was injected directly into the ileum was done. Wistar rats (300–350 g) were fasted for 4 hours and anaesthetized by intramuscular administration 15 to 20 minutes prior to administration of the test solution with a solution of ketamine [0.525 ml of ketamine (100 mg/ml) and 0.875 ml of acepromazine maleate-BP ACP (2 mg/ml)]. The rats were then injected with a test solution (injection volume: 1.5 ml PBS) intra-duodenally at 2–3 cm below the pyloris. The test solution contained either PLGA particles manufactured according to the coacervation procedure given above with or without targeting peptides or by the "spiked" method given above. Insulin (fast-acting bovine; 28.1 iu/mg) was incorporated in the particles at 5% drug loading for a total of 100 iu insulin (70 mg particles) or 300 iu insulin (210 mg particles). Blood glucose values for the rats were measured using a Glucometer™ (Bayer; 0.1 to 33.3 m/mol/L); plasma insulin values were measured using a Phadeseph RIA Kit™ (Upjohn Pharmacia; 3 to 240 µU/ml-assayed in duplicate). Systemic and portal blood was sampled.

Study groups included animals receiving test solutions containing particles coated with the following peptides shown in Table 33.

TABLE 33

| Study Group | Receptor | Peptide |
|---|---|---|
| I | hSI | SNi10 |
| | | SNi34 |
| II | hPEPT1 | P31 |
| | | 5PAX5 |
| III | HPT1 | PAX2 |
| | | HAX42 |
| IV | D2H | DCX8 |
| | | DCX11 |
| V ("spiked") | hPEPT1 | P31-PLGA conjugate |
| | | 5PAX5-PLGA conjugate |

Control groups included: 1) PBS control (1.5 ml) Open-Loop; 2) Insulin solution (1 iu/0.2 ml) subcutaneous; 3) Insulin particles—no peptide (1 iu/0.2 ml) subcutaneous; 4) Insulin particles/all 8 peptides mix (1 iu/0.2 ml) subcutaneous; 5) Insulin loaded particles/peptide control (scrambled 5PAX5) (100 iu/1.5 ml) Open-Loop; 6) Insulin loaded particles/peptide control (scrambled 5PAX5) (300 iu/1.5 ml) Open-Loop; 7) Control particles (insulin-free)/all 8 peptide mix (equivalent 100 iu/1.5 ml) Open-Loop; and 8) Control particles (insulin-free)/all 8 peptide mix (equivalent 300 iu/1.5 ml) Open-Loop.

The following describes the pharmacokinetics for 300 iu-loading:

| Target Receptor | F %* | Fold-increase** | Stat. Sig.** |
|---|---|---|---|
| HPT1 | 10.37 | 17.0 | <0.001 |
| Spiked hPEPT1 | 4.94 | 7.5 | 0.005 |
| PAX2 scrambled | 3.50 | 3.6 | NS |
| Mix-8 | 2.00 | 2.0 | NS |
| hPEPT1 | 1.60 | 1.5 | NS |
| D2H | 1.57 | 1.4 | NS |
| hSI | 0.54 | 0.9 | NS |

*based on area under the curve (AUC) (1–4h), base-line adjusted, relative to subcutaneous insulin solution Iiu
**Fold increase in AUC compared to insulin particles: 300iu FIGS. 17A and 17B show the systemic blood glucose and insulin levels following intestinal administration of control (PBS); insulin solution; insulin particles; all 8 peptides mix particles and study group peptide-particles (100 iu). FIGS. 18A and 18B show the systemic blood glucose and insulin levels following intestinal administration of control (PBS); insulin solution; insulin particles and study group peptide-particles (300 iu).

HPT1 targeted peptide coated particles provided the most potent enhancement of the delivery of insulin over subcutaneous injection of insulin followed by hPEPT1 spiked>PAX2 scrambled>mix-8>hPEPT1>D2H>uncoated particles>hSI>solution. In a repeat study, the uncoated particles containing insulin gave similar profiles but the HPT1-peptide targeted particles gave a reduced profile (3-fold). The insulin-free PLGA particles and the all-8 mix particles did not show an effect on the basal insulin or glucose levels. The HPT1 targeting particles, the PEPT1 spiked, targeting particles, and the PEPT1 targeting particles also reduced blood glucose levels indicative that the insulin delivered was bioactive. The other targeting particles were also shown to reduce blood glucose levels although not to the same extent as the HPT1 and PEPT1 spiked particles. No histological differences were observed in the small intestine for any of the formulations evaluated.

Study 2

A second open-loop study, similar to study 1 above, was undertaken with the following treatment groups as shown in Table 34.

TABLE 34

| Group Number | Dose Insulin (iu) | Description |
|---|---|---|
| 1 | | PBS control |
| 2a | 1 | subcutaneous, bovine insulin |
| 2b | 2 | subcutaneous, bovine insulin |
| 2c | 3 | subcutaneous, bovine insulin |
| 2d | 4 | subcutaneous, bovine insulin |
| 2e | 10 | subcutaneous, bovine insulin |
| 2f | 20 | subcutaneous, bovine insulin |
| 2g | 4 | subcutaneous, human insulin |
| 3 | 300 | uncoated insulin particles |
| 4 | 100 | HAX42/PAX2 with 300 iu particle loading |
| 5 | 300 | HAX42/PAX2 (40mer) particles |
| 6 | 300 | HAX42 (40mer) particles |
| 7 | 300 | HAX42 particles + 10-fold excess free HAX42 (40mer) |
| 8 | 300 | PAX2 (40mer) particles |
| 9 | 300 | PAX2 freeze-dried (40mer) particles |
| 10 | 300 | PAX2 scrambled particles III (40mer) |
| 11 | 300 | PAX2 scrambled particles IV (19mer) |
| 12 | 300 | 5PAX5/P31 (40mer) particles |
| 13 | 300 | P31 (40mer) particles |
| 14 | 300 | 5PAX5 (40mer) particles |
| 15 | 300 | HAX42 (27mer) particles |
| 16 | 300 | PAX2 (20mer) particles |
| 17 | 300 | P31 (20mer) particles |
| 18 | 300 | PAX2 (15mer) particles |
| 19 | 300 | P31 (15mer) particles |
| 20 | 300 | P31 D-form I(5 D-arginine)(16mer) particles |
| 21 | 300 | P31 D-form II(2 D-arginine) (16mer) particles |
| 22 | 300 | HAX42 (10mer) |

Availability of insulin following administration was assessed relative to a 1 and 20 iu subcutaneous dose because the response to increasing subcutaneous doses of bovine insulin does not increase linearly over the range of 1 to 20 iu. Data up to three hours post-dosing was available for most animals. Therefore, availability was first assessed using individual AUC(0–3h) data estimated from baseline-subtracted data for which data up to 3 hours was available. This approach may lead to an underestimation of the availability as some animals that gave a high response often did not survive for 3 hours and, therefore, were excluded from the analyses. In an attempt to capture as much of these high responses observed at the earlier timepoints as possible, the mean baseline-subtracted plasma concentration data was used to estimate an AUC for each group. Table 35 shows the results based on this second approach (AUC(0–3h) calculated from the mean plasma concentration data).

TABLE 35

| Group | Dose iu | Mean AUC$_{(0-3h)}$ | F vs. 1 iu | F vs. 20 iu |
|---|---|---|---|---|
| 1 | 0 | 2.14 | | |
| 2a | 1 | 875.27 | 100.00 | 28.86 |
| 2b | 2 | 2439.36 | 139.35 | 40.22 |
| 2c | 3 | 3671.44 | 139.82 | 40.36 |
| 2d | 4 | 6912.18 | 197.43 | 56.98 |
| 2e | 10 | 27224.41 | 311.04 | 89.77 |
| 2f | 20 | 60651.28 | 346.47 | 100.00 |
| 2g | 4 | 14255.49 | 407.17 | 117.52 |
| 3 | 300 | 10677.78 | 4.07 | 1.17 |
| 3 -Rat43 | 300 | 4645.06 | 1.77 | 0.51 |

TABLE 35-continued

| Group | Dose iu | Mean AUC$_{(0-3h)}$ | F vs. 1 iu | F vs. 20 iu |
|---|---|---|---|---|
| 4 | 100 | 3527.18 | 4.03 | 1.16 |
| 5 | 300 | 27112.26 | 10.33 | 2.98 |
| 6 | 300 | 33091.68 | 12.60 | 3.64 |
| 7 | 300 | 9303.09 | 3.54 | 1.02 |
| 8 | 300 | 34241.83 | 13.04 | 3.76 |
| 9 | 300 | 10968.83 | 4.18 | 1.21 |
| 10 | 300 | 27692.78 | 10.55 | 3.04 |
| 11 | 300 | 3004.29 | 1.14 | 0.33 |
| 12 | 300 | 18852.61 | 7.18 | 2.07 |
| 13 | 300 | 20278.43 | 7.72 | 2.23 |
| 14 | 300 | 17400.38 | 6.63 | 1.91 |
| 15 | 300 | 16775.69 | 6.39 | 1.84 |
| 16 | 300 | 14217.47 | 5.41 | 1.56 |
| 17 | 300 | 8197.97 | 3.12 | 0.90 |
| 18 | 300 | 25050.59 | 9.54 | 2.75 |
| 19 | 300 | 7927.96 | 3.02 | 0.87 |
| 20 | 300 | 21519.57 | 8.20 | 2.37 |
| 21 | 300 | 6322.41 | 2.41 | 0.69 |
| 22 | 300 | 12553.01 | 4.78 | 1.38 |

The data for group 3 (uncoated insulin particles) are expressed with and without Rat 43. This animal had an atypically high response to these uncoated particles and, therefore, may have biased the data for this group.

This data shows that a combination of peptide-coated particles (HAX42/PAX2 or 5PAX5/P31) shows no greater availability than particles coated with the individual peptides. Further, peptide-coated particles have a greater availability than uncoated peptides. Scrambling the 40mer PAX2 peptide did not result in a loss of bioavailability. Scrambling the PAX2 peptide and reducing the size to 19mer resulted in a loss of bioavailability although this loss may be attributed in part to the reduction in peptide size. Reducing peptide size resulted in loss of bioavailability. The D-form of P31 (ZElan053, SEQ ID NO: 319) had increased bioavailability possibly due to greater resistance to peptide breakdown. A competitive excess of peptide resulted in a loss of bioavailability, and freeze drying caused a loss in bioavailability. By way of example, measurement of blood glucose levels showed that the HPT1 and hPEPT1 targeting particles incorporating HAX42, PAX2, P31 (SEQ ID NO:270), and P31 D-form (ZElan053, SEQ ID NO: 319) reduced blood glucose levels indicating that the insulin delivered was bioactive.

In further studies, insulin was recovered from the targeting particles following particle formation by dissolution and analyzed by electrophoresis in non-denaturing sodium dodecyl sulfate (SDS) polyacrylamide gel electrophoresis (PAGE). The analysis of the insulin by non-denaturing SDS-PAGE and also by western blot transferred to membranes and subsequent screening with an antibody to insulin, indicated that the insulin was intact, with no evidence of degradation, dimerization, or aggregation during the process of particle formation.

Study 3

An intraduodenal open loop model study was carried out on Wistar rats (300–350 g). Group 1 was administered leuprolide acetate (12.5 µg) subcutaneously. Group 2 was administered intraduodenally uncoated leuprolide acetate particles (600 µg, 1.5 ml). Group 3 was intraduodenally administered leuprolide acetate particles coated with PAX2 (600 µg; 1.5 ml). Group 4 was administered intraduodenally leuprolide acetate particles coated with P31 (SEQ ID NO:270) (600 µg, 1.5 ml). FIG. 19 shows the leuprolide plasma concentration following administration to these four groups. Both the P31 (SEQ ID NO:270) and the PAX2 coated leuprolide particles administered intraduodenally provided enhanced plasma levels of leuprolide relative to subcutaneous injection.

Homologies of GIT transport-binding peptides to known proteins are shown in FIGS. 20, 21A–F, and 22 A–D.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

SEQUENCE LISTING

```
<160> NUMBER OF SEQ ID NOS: 30

<210> SEQ ID NO 1
<211> LENGTH: 18
<212> TYPE: PRT
<213> ORGANISM: Artificial Sequence
<220> FEATURE:
<221> NAME/KEY: MOD_RES
<222> LOCATION: (1)
<223> OTHER INFORMATION: Asp in position 1 is attached to one or more
      modified amino acids or to a chemical group
<221> NAME/KEY: MOD_RES
<222> LOCATION: (4)
<223> OTHER INFORMATION: Xaa can be Ser or any amino acid
<221> NAME/KEY: MOD_RES
<222> LOCATION: (5)
<223> OTHER INFORMATION: Xaa can be Tyr or any amino acid
<221> NAME/KEY: MOD_RES
<222> LOCATION: (17)
<223> OTHER INFORMATION: Xaa can be Asn or any amino acid
<221> NAME/KEY: MOD_RES
<222> LOCATION: (18)
<223> OTHER INFORMATION: Xaa can be Arg or any amino acid and is
      attached to one or more modified amino acids or to a chemical
      group
<223> OTHER INFORMATION: modification of Pyrrhocoricin

<400> SEQUENCE: 1

Asp Lys Gly Xaa Xaa Leu Pro Arg Pro Thr Pro Pro Arg Pro Ile Tyr
  1               5                  10                  15

Xaa Xaa

<210> SEQ ID NO 2
<211> LENGTH: 20
<212> TYPE: PRT
<213> ORGANISM: Pyrrhocoricin
<220> FEATURE:
<221> NAME/KEY: MOD_RES
<222> LOCATION: (11)
<223> OTHER INFORMATION: Thr in position 11 is modified with Gal-GalNAc

<400> SEQUENCE: 2

Val Asp Lys Gly Ser Tyr Leu Pro Arg Pro Thr Pro Pro Arg Pro Ile
  1               5                  10                  15

Tyr Asn Arg Asn
            20

<210> SEQ ID NO 3
<211> LENGTH: 10
<212> TYPE: PRT
<213> ORGANISM: Artificial Sequence
<220> FEATURE:
<223> OTHER INFORMATION: modification of Pyrrhocoricin

<400> SEQUENCE: 3

Arg Pro Pro Thr Pro Arg Pro Leu Lys Val
  1               5                  10
```

```
<210> SEQ ID NO 4
<211> LENGTH: 18
<212> TYPE: PRT
<213> ORGANISM: Artificial Sequence
<220> FEATURE:
<221> NAME/KEY: MOD_RES
<222> LOCATION: (1)
<223> OTHER INFORMATION: Asp in position 1 is modified by a
      1-aminocyclo-hexane carboxylic acid
<221> NAME/KEY: MOD_RES
<222> LOCATION: (18)
<223> OTHER INFORMATION: Arg in position 18 is modified by an amino
      linker moiety
<223> OTHER INFORMATION: modification of Pyrrhocoricin

<400> SEQUENCE: 4

Asp Lys Gly Ser Tyr Leu Pro Arg Pro Thr Pro Pro Arg Pro Ile Tyr
 1               5                  10                  15

Asn Arg

<210> SEQ ID NO 5
<211> LENGTH: 5
<212> TYPE: PRT
<213> ORGANISM: Artificial Sequence
<220> FEATURE:
<223> OTHER INFORMATION: modification of Pyrrhocoricin

<400> SEQUENCE: 5

Lys Val Asp Lys Val
 1               5

<210> SEQ ID NO 6
<211> LENGTH: 20
<212> TYPE: PRT
<213> ORGANISM: Artificial Sequence
<220> FEATURE:
<223> OTHER INFORMATION: modification of Pyrrhocoricin

<400> SEQUENCE: 6

Val Asp Lys Gly Ser Tyr Leu Pro Arg Pro Thr Pro Pro Arg Pro Ile
 1               5                  10                  15

Tyr Asn Arg Asn
            20

<210> SEQ ID NO 7
<211> LENGTH: 24
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<223> OTHER INFORMATION: modification of Pyrrhocoricin

<400> SEQUENCE: 7

Lys Val Asp Lys Val Asp Lys Gly Ser Tyr Leu Pro Arg Pro Thr Pro
 1               5                  10                  15

Pro Arg Pro Ile Tyr Asn Arg Asn
            20

<210> SEQ ID NO 8
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
```

```
<223> OTHER INFORMATION: modification of Pyrrhocoricin

<400> SEQUENCE: 8

Arg Val Asp Lys Gly Ser Tyr Leu Pro Arg Pro Thr Pro Pro Arg Pro
 1               5                  10                  15

Ile Tyr Asn Arg Asn
            20

<210> SEQ ID NO 9
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<223> OTHER INFORMATION: modification of Pyrrhocoricin

<400> SEQUENCE: 9

Lys Val Asp Lys Gly Ser Tyr Leu Pro Arg Pro Thr Pro Pro Arg Pro
 1               5                  10                  15

Ile Tyr Asn Arg Asn
            20

<210> SEQ ID NO 10
<211> LENGTH: 19
<212> TYPE: PRT
<213> ORGANISM: Artificial Sequence
<220> FEATURE:
<221> NAME/KEY: MOD_RES
<222> LOCATION: (1)
<223> OTHER INFORMATION: Asp in position 1 is modified by a
      1-aminocyclo-hexane carboxylic acid
<223> OTHER INFORMATION: modification of Pyrrhocoricin

<400> SEQUENCE: 10

Asp Lys Gly Ser Tyr Leu Pro Arg Pro Thr Pro Pro Arg Pro Ile Tyr
 1               5                  10                  15

Asn Arg Asn

<210> SEQ ID NO 11
<211> LENGTH: 20
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (11)
<223> OTHER INFORMATION: Thr in position 11 is modified with Gal-GalNAc
<223> OTHER INFORMATION: modification of Pyrrhocoricin

<400> SEQUENCE: 11

Val Asp Lys Gly Ser Tyr Leu Pro Arg Pro Thr Pro Pro Arg Pro Ile
 1               5                  10                  15

Tyr Asn Arg Asn
            20

<210> SEQ ID NO 12
<211> LENGTH: 20
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
```

```
<221> NAME/KEY: MOD_RES
<222> LOCATION: (20)
<223> OTHER INFORMATION: Arg in position 20 is modified by an imide
      group
<223> OTHER INFORMATION: modification of Pyrrhocoricin

<400> SEQUENCE: 12

Lys Val Asp Lys Gly Ser Tyr Leu Pro Arg Pro Thr Pro Pro Arg Pro
 1               5                  10                  15

Ile Tyr Asn Arg
            20

<210> SEQ ID NO 13
<211> LENGTH: 20
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (20)
<223> OTHER INFORMATION: Arg in position 20 is modified by a
      beta-acetyl-2,3-diamino propionic acid group
<223> OTHER INFORMATION: modification of Pyrrhocoricin

<400> SEQUENCE: 13

Lys Val Asp Lys Gly Ser Tyr Leu Pro Arg Pro Thr Pro Pro Arg Pro
 1               5                  10                  15

Ile Tyr Asn Arg
            20

<210> SEQ ID NO 14
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (21)
<223> OTHER INFORMATION: Asn in position 21 is modified by a
      2-acetamido-2-deoxyglucose group
<223> OTHER INFORMATION: modification of Pyrrhocoricin

<400> SEQUENCE: 14

Lys Val Asp Lys Gly Ser Tyr Leu Pro Arg Pro Thr Pro Pro Arg Pro
 1               5                  10                  15

Ile Tyr Asn Arg Asn
            20

<210> SEQ ID NO 15
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (21)
<223> OTHER INFORMATION: Asn in position 21 is modified by a
      triacetyl-2-acetamido-2-deoxyglucose group
<223> OTHER INFORMATION: modification of Pyrrhocoricin

<400> SEQUENCE: 15

Lys Val Asp Lys Gly Ser Tyr Leu Pro Arg Pro Thr Pro Pro Arg Pro
 1               5                  10                  15
```

Ile Tyr Asn Arg Asn
            20

<210> SEQ ID NO 16
<211> LENGTH: 20
<212> TYPE: PRT
<213> ORGANISM: Artificial Sequence
<220> FEATURE:
<221> NAME/KEY: MOD_RES
<222> LOCATION: (1)
<223> OTHER INFORMATION: Val in position 1 is in the D configuration
<221> NAME/KEY: MOD_RES
<222> LOCATION: (20)
<223> OTHER INFORMATION: Asn in position 20 is in the D configuration
<223> OTHER INFORMATION: modification of Pyrrhocoricin

<400> SEQUENCE: 16

Val Asp Lys Gly Ser Tyr Leu Pro Arg Pro Thr Pro Pro Arg Pro Ile
 1               5                  10                  15

Tyr Asn Arg Asn
            20

<210> SEQ ID NO 17
<211> LENGTH: 21
<212> TYPE: PRT
<213> ORGANISM: Artificial Sequence
<220> FEATURE:
<221> NAME/KEY: PEPTIDE
<222> LOCATION: (1)..(21)
<223> OTHER INFORMATION: is a cyclic peptide
<223> OTHER INFORMATION: modification of Pyrrhocoricin

<400> SEQUENCE: 17

Lys Val Asp Lys Gly Ser Tyr Leu Pro Arg Pro Thr Pro Pro Arg Pro
 1               5                  10                  15

Ile Tyr Asn Arg Asp
            20

<210> SEQ ID NO 18
<211> LENGTH: 29
<212> TYPE: PRT
<213> ORGANISM: Artificial Sequence
<220> FEATURE:
<221> NAME/KEY: PEPTIDE
<222> LOCATION: (1)..(29)
<223> OTHER INFORMATION: is a cyclic peptide
<223> OTHER INFORMATION: modification of Pyrrhocoricin

<400> SEQUENCE: 18

Arg Pro Pro Thr Pro Arg Pro Leu Lys Val Asp Lys Gly Ser Tyr Leu
 1               5                  10                  15

Pro Arg Pro Thr Pro Pro Arg Pro Ile Tyr Asn Arg Asn
            20                  25

<210> SEQ ID NO 19
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: Lys in position 1 has a biotin attached
<223> OTHER INFORMATION: modification of Pyrrhocoricin

<400> SEQUENCE: 19

Lys Val Asp Lys Gly Ser Tyr Leu Pro Arg Pro Thr Pro Pro Arg Pro
 1               5                  10                  15

```
Ile Tyr Asn Arg Asn
            20

<210> SEQ ID NO 20
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: Lys in position 1 is modified by  a
      5(6)-carboxyfluorescein group
<223> OTHER INFORMATION: modification of Pyrrhocoricin

<400> SEQUENCE: 20

Lys Val Asp Lys Gly Ser Tyr Leu Pro Arg Pro Thr Pro Pro Arg Pro
 1               5                  10                  15

Ile Tyr Asn Arg Asn
            20

<210> SEQ ID NO 21
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<223> OTHER INFORMATION: modification of Pyrrhocoricin

<400> SEQUENCE: 21

Lys Val Asp Lys Gly Ser Tyr Leu Pro Arg Pro Thr Pro Pro Arg Pro
 1               5                  10                  15

Ile Tyr Asn Arg Asp
            20

<210> SEQ ID NO 22
<211> LENGTH: 18
<212> TYPE: PRT
<213> ORGANISM: Artificial Sequence
<220> FEATURE:
<221> NAME/KEY: MOD_RES
<222> LOCATION: (1)
<223> OTHER INFORMATION: Asp in position 1 is modified by a
      1-aminocyclo-hexane carboxylic acid group
<221> NAME/KEY: MOD_RES
<222> LOCATION: (18)
<223> OTHER INFORMATION: Arg in position 18 is modified by a
      beta-acetyl-2,3-diaminopropionic acid group
<223> OTHER INFORMATION: modification of Pyrrhocoricin

<400> SEQUENCE: 22

Asp Lys Gly Ser Tyr Leu Pro Arg Pro Thr Pro Pro Arg Pro Ile Tyr
 1               5                  10                  15

Asn Arg

<210> SEQ ID NO 23
<211> LENGTH: 20
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (20)
<223> OTHER INFORMATION: Arg in position 20 is modified by a
      beta-acetyl-2,3-diamino propionic acid group
```

<223> OTHER INFORMATION: modification of Pyrrhocoricin

<400> SEQUENCE: 23

Arg Val Asp Lys Gly Ser Tyr Leu Pro Arg Pro Thr Pro Pro Arg Pro
 1               5                  10                  15

Ile Tyr Asn Arg
            20

<210> SEQ ID NO 24
<211> LENGTH: 18
<212> TYPE: PRT
<213> ORGANISM: Artificial Sequence
<220> FEATURE:
<221> NAME/KEY: MOD_RES
<222> LOCATION: (1)
<223> OTHER INFORMATION: Asp in position 1 is modified by a
      1-aminocyclo-hexane carboxylic acid group
<221> NAME/KEY: MOD_RES
<222> LOCATION: (18)
<223> OTHER INFORMATION: Arg in position 18 is modified by a
      beta-acetyl-2,3-diamino propionic acid group
<223> OTHER INFORMATION: modification of Pyrrhocoricin

<400> SEQUENCE: 24

Asp Lys Gly Ala Phe Leu Pro Arg Pro Thr Pro Pro Arg Pro Ile Tyr
 1               5                  10                  15

Asn Arg

<210> SEQ ID NO 25
<211> LENGTH: 19
<212> TYPE: PRT
<213> ORGANISM: Artificial Sequence
<220> FEATURE:
<221> NAME/KEY: MOD_RES
<222> LOCATION: (19)
<223> OTHER INFORMATION: Arg in position 19 is modified by a
      beta-acetyl-2,3-diamino propionic acid group
<223> OTHER INFORMATION: modification of Pyrrhocoricin

<400> SEQUENCE: 25

Val Asp Lys Gly Ser Tyr Leu Pro Arg Pro Thr Pro Pro Arg Pro Ile
 1               5                  10                  15

Tyr Asn Arg

<210> SEQ ID NO 26
<211> LENGTH: 20
<212> TYPE: PRT
<213> ORGANISM: Artificial Sequence
<220> FEATURE:
<221> NAME/KEY: PEPTIDE
<222> LOCATION: (1)..(20)
<223> OTHER INFORMATION: D configuration
<223> OTHER INFORMATION: modification of Pyrrhocoricin

<400> SEQUENCE: 26

Val Asp Lys Gly Ser Tyr Leu Pro Arg Pro Thr Pro Pro Arg Pro Ile
 1               5                  10                  15

Tyr Asn Arg Asn
            20

<210> SEQ ID NO 27
<211> LENGTH: 26
<212> TYPE: PRT
<213> ORGANISM: Melittin
<220> FEATURE:
<221> NAME/KEY: MOD_RES
<222> LOCATION: (26)

-continued

```
<223> OTHER INFORMATION: AMIDATION

<400> SEQUENCE: 27

Gly Ile Gly Ala Val Leu Lys Val Leu Thr Thr Gly Leu Pro Ala Leu
 1               5                  10                  15

Ile Ser Trp Ile Lys Arg Lys Arg Gln Gln
            20                  25

<210> SEQ ID NO 28
<211> LENGTH: 15
<212> TYPE: PRT
<213> ORGANISM: T helper cell epitope
<220> FEATURE:
<221> NAME/KEY: MOD_RES
<222> LOCATION: (15)
<223> OTHER INFORMATION: AMIDATION

<400> SEQUENCE: 28

Ala Val Tyr Thr Arg Ile Met Met Asn Gly Gly Arg Leu Lys Arg
 1               5                  10                  15

<210> SEQ ID NO 29
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<223> OTHER INFORMATION: modification of Pyrrhocoricin

<400> SEQUENCE: 29

Lys Val Asp Lys Val
 1               5

<210> SEQ ID NO 30
<211> LENGTH: 23
<212> TYPE: PRT
<213> ORGANISM: Artificial Sequence
<220> FEATURE:
<223> OTHER INFORMATION: modification of Pyrrhocoricin

<400> SEQUENCE: 30

Val Asp Lys Val Asp Lys Gly Ser Tyr Leu Pro Arg Pro Thr Pro Pro
 1               5                  10                  15

Arg Pro Ile Tyr Asn Arg Asn
            20
```

What is claimed is:

1. A method of delivering a drug to a subject comprising administering to the subject a pharmaceutical composition comprising a therapeutically effective amount of a nucleic acid encoding a chimeric protein comprising (i) a first protein comprising the amino acid sequence of SEQ ID NO: 51, said amino acid sequence being capable of specifically binding to the gastro-intestinal receptor HPT1 (SEQ ID NO: 178), which comprises said first protein being fused via a covalent bond to a second protein, wherein the second protein acts as a drug; and (ii) a pharmaceutically acceptable carrier.

2. A method of delivering an active agent in vivo comprising administering to a subject a composition comprising an isolated protein comprising the amino acid sequence of SEQ ID NO: 51, said amino acid sequence being capable of specifically binding to the gastro-intestinal receptor HPT1 (SEQ ID NO: 178), wherein the isolated protein is bound to a material comprising an active agent selected from the group consisting of an antigen, imaging agent and drug.

3. A method of delivering a drug to a subject comprising administering to the subject a composition comprising an isolated protein comprising the amino acid sequence of SEQ ID NO: 51, said amino acid sequence being capable of specifically binding to the gastro-intestinal receptor HPT1 (SEQ ID NO: 178), wherein the isolated protein is covalently bound to a particle containing the drug.

4. A method of delivering a drug to a subject comprising administering to the subject a composition comprising an isolated protein comprising the amino acid sequence of SEQ ID NO: 51, said amino acid sequence being capable of specifically binding to the gastro-intestinal receptor HPT1 (SEQ ID NO: 178), wherein the isolated protein is covalently bound to the drug.

5. The method of claim 2 wherein the active agent is a drug.

6. The method of claim 2 wherein the material is a particle containing the active agent.

7. The method as in any one of claims 2 to 4 wherein the isolated protein consists essentially of the amino acid sequence of SEQ ID NO: 51.

8. The method as in any one of claims 2 to 4 wherein the isolated protein facilitates the transport of the active agent through human or animal gastro-intestinal tissue.

9. The method as in any one of claims 1 to 4 wherein the administration is oral.

10. The method as in any one of claims 1 to 4 wherein the subject is human.

* * * * *

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

At the end of the sequence listing below column 103, please insert the following sequence identifiers and sequences.

(2) INFORMATION FOR SEQ ID NO: 31:
  (i) SEQUENCE CHARACTERISTICS:
    (A) LENGTH: 38 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 31:
    Arg Trp Pro Ser Val Gly Tyr Lys Gly Asn Gly Ser Asp Thr Ile Asp
    1     5      10      15
    Val His Ser Asn Asp Ala Ser Thr Lys Arg Ser Leu Ile Tyr Asn His
      20      25      30
    Arg Arg Pro Leu Phe Pro
      35

(2) INFORMATION FOR SEQ ID NO: 32:
  (i) SEQUENCE CHARACTERISTICS:
    (A) LENGTH: 39 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 32:
    Arg Thr Phe Glu Asn Asp Gly Leu Gly Val Gly Arg Ser Ile Gln Lys
    1     5      10      15
    Lys Ser Asp Arg Trp Tyr Ala Ser His Asn Ile Arg Ser His Phe Ala
      20      25      30
    Ser Met Ser Pro Ala Gly Lys
      35

(2) INFORMATION FOR SEQ ID NO: 33:
  (i) SEQUENCE CHARACTERISTICS:

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(A) LENGTH: 44 amino acids
    (B) TYPE: amino acid
    (C) STRANDEDNESS: <Unknown>
    (D) TOPOLOGY: unknown
(ii) MOLECULE TYPE: peptide
(xi) SEQUENCE DESCRIPTION: SEQ ID NO: 33:
  Ser Tyr Cys Arg Val Lys Gly Gly Gly Glu Gly Gly His Thr Asp Ser
  1        5          10          15
  Asn Leu Ala Arg Ser Gly Cys Gly Lys Val Ala Arg Thr Ser Arg Leu
       20          25          30
  Gln His Ile Asn Pro Arg Ala Thr Pro Pro Ser Arg
     35          40

(2) INFORMATION FOR SEQ ID NO: 34:
  (i) SEQUENCE CHARACTERISTICS:
    (A) LENGTH: 39 amino acids
    (B) TYPE: amino acid
    (C) STRANDEDNESS: <Unknown>
    (D) TOPOLOGY: unknown
(ii) MOLECULE TYPE: peptide
(xi) SEQUENCE DESCRIPTION: SEQ ID NO: 34:
  Ser Trp Thr Arg Trp Gly Lys His Thr His Gly Gly Phe Val Asn Lys
  1        5          10          15
  Ser Pro Pro Gly Lys Asn Ala Thr Ser Pro Tyr Thr Asp Ala Gln Leu
       20          25          30
  Pro Ser Asp Gln Gly Pro Pro
     35

(2) INFORMATION FOR SEQ ID NO: 35:
  (i) SEQUENCE CHARACTERISTICS:
    (A) LENGTH: 44 amino acids
    (B) TYPE: amino acid
    (C) STRANDEDNESS: <Unknown>
    (D) TOPOLOGY: unknown
(ii) MOLECULE TYPE: peptide
(xi) SEQUENCE DESCRIPTION: SEQ ID NO: 35:
  Ser Gln Val Asp Ser Phe Arg Asn Ser Phe Arg Trp Tyr Glu Pro Ser
  1        5          10          15
  Arg Ala Leu Cys His Gly Cys Gly Lys Arg Asp Thr Ser Thr Thr Arg
       20          25          30
  Ile His Asn Ser Pro Ser Asp Ser Tyr Pro Thr Arg
     35          40

(2) INFORMATION FOR SEQ ID NO: 36:
  (i) SEQUENCE CHARACTERISTICS:

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
            (A) LENGTH: 39 amino acids
            (B) TYPE: amino acid
            (C) STRANDEDNESS: <Unknown>
            (D) TOPOLOGY: unknown
        (ii) MOLECULE TYPE: peptide
        (xi) SEQUENCE DESCRIPTION: SEQ ID NO: 36:
          Ser Phe Leu Arg Phe Gln Ser Pro Arg Phe Glu Asp Tyr Ser Arg Thr
          1           5              10             15
          Ile Ser Arg Leu Arg Asn Ala Thr Asn Pro Ser Asn Val Ser Asp Ala
                  20            25           30
          His Asn Asn Arg Ala Leu Ala
                 35

(2) INFORMATION FOR SEQ ID NO: 37:
        (i) SEQUENCE CHARACTERISTICS:
            (A) LENGTH: 39 amino acids
            (B) TYPE: amino acid
            (C) STRANDEDNESS: <Unknown>
            (D) TOPOLOGY: unknown
        (ii) MOLECULE TYPE: peptide
        (xi) SEQUENCE DESCRIPTION: SEQ ID NO: 37:
          Arg Ser Ile Thr Asp Gly Gly Ile Asn Glu Val Asp Leu Ser Ser Val
          1           5              10             15
          Ser Asn Val Leu Glu Asn Ala Asn Ser His Arg Ala Tyr Arg Lys His
                  20            25           30
          Arg Pro Thr Leu Lys Arg Pro
                 35

(2) INFORMATION FOR SEQ ID NO: 38:
        (i) SEQUENCE CHARACTERISTICS:
            (A) LENGTH: 44 amino acids
            (B) TYPE: amino acid
            (C) STRANDEDNESS: <Unknown>
            (D) TOPOLOGY: unknown
        (ii) MOLECULE TYPE: peptide
        (xi) SEQUENCE DESCRIPTION: SEQ ID NO: 38:
          Ser Ser Lys Val Ser Ser Pro Arg Asp Pro Thr Val Pro Arg Lys Gly
          1           5              10             15
          Gly Asn Val Asp Tyr Gly Cys Gly His Arg Ser Ser Ala Arg Met Pro
                  20            25           30
          Thr Ser Ala Leu Ser Ser Ile Thr Lys Cys Tyr Thr
                 35           40

(2) INFORMATION FOR SEQ ID NO: 39:
        (i) SEQUENCE CHARACTERISTICS:
            (A) LENGTH: 44 amino acids
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
            (B) TYPE: amino acid
            (C) STRANDEDNESS: <Unknown>
            (D) TOPOLOGY: unknown
        (ii) MOLECULE TYPE: peptide
        (xi) SEQUENCE DESCRIPTION: SEQ ID NO: 39:
          Arg Ala Ser Thr Gln Gly Gly Arg Gly Val Ala Pro Glu Phe Gly Ala
          1           5              10              15
          Ser Val Leu Gly Arg Gly Cys Gly Ser Ala Thr Tyr Tyr Thr Asn Ser
                   20              25              30
          Thr Ser Cys Lys Asp Ala Met Gly His Asn Tyr Ser
                   35              40

(2) INFORMATION FOR SEQ ID NO: 40:
        (i) SEQUENCE CHARACTERISTICS:
            (A) LENGTH: 39 amino acids
            (B) TYPE: amino acid
            (C) STRANDEDNESS: <Unknown>
            (D) TOPOLOGY: unknown
        (ii) MOLECULE TYPE: peptide
        (xi) SEQUENCE DESCRIPTION: SEQ ID NO: 40:
          Arg Trp Cys Glu Lys His Lys Phe Thr Ala Ala Arg Cys Ser Ala Gly
          1           5              10              15
          Ala Gly Phe Glu Arg Asp Ala Ser Arg Pro Pro Gln Pro Ala His Arg
                   20              25              30
          Asp Asn Thr Asn Arg Asn Ala
                   35

(2) INFORMATION FOR SEQ ID NO: 41:
        (i) SEQUENCE CHARACTERISTICS:
            (A) LENGTH: 39 amino acids
            (B) TYPE: amino acid
            (C) STRANDEDNESS: <Unknown>
            (D) TOPOLOGY: unknown
        (ii) MOLECULE TYPE: peptide
        (xi) SEQUENCE DESCRIPTION: SEQ ID NO: 41:
          Ser Phe Gln Val Tyr Pro Asp His Gly Leu Glu Arg His Ala Leu Asp
          1           5              10              15
          Gly Thr Gly Pro Leu Tyr Ala Met Pro Gly Arg Trp Ile Arg Ala Arg
                   20              25              30
          Pro Gln Asn Arg Asp Arg Gln
                   35

(2) INFORMATION FOR SEQ ID NO: 42:
        (i) SEQUENCE CHARACTERISTICS:
            (A) LENGTH: 38 amino acids
            (B) TYPE: amino acid
```

UNITED STATES PATENT AND TRADEMARK OFFICE
CERTIFICATE OF CORRECTION

PATENT NO.      : 7,053,177 B1
APPLICATION NO. : 09/079678
DATED           : May 30, 2006
INVENTOR(S)     : Vernon L. Alvarez et al.

It is certified that error appears in the above-identified patent and that said Letters Patent is hereby corrected as shown below:

```
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 42:
      Ser Arg Cys Thr Asp Asn Glu Gln Cys Pro Asp Thr Gly Thr Arg Ser
      1           5              10              15
      Arg Ser Val Ser Asn Ala Arg Tyr Phe Ser Ser Arg Leu Leu Lys Thr
            20              25              30
      His Ala Pro His Arg Pro
            35

(2) INFORMATION FOR SEQ ID NO: 43:
    (i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 43:
      Ser Ala Arg Asp Ser Gly Pro Ala Glu Asp Gly Ser Arg Ala Val Arg
      1           5              10              15
      Leu Asn Gly Val Glu Asn Ala Asn Thr Arg Lys Ser Ser Arg Ser Asn
            20              25              30
      Pro Arg Gly Arg Arg His Pro
            35

(2) INFORMATION FOR SEQ ID NO: 44:
    (i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 44:
      Ser Ser Ala Asp Ala Glu Lys Cys Ala Gly Ser Leu Leu Trp Trp Gly
      1           5              10              15
      Arg Gln Asn Asn Ser Gly Cys Gly Ser Pro Thr Lys Lys His Leu Lys
            20              25              30
      His Arg Asn Arg Ser Gln Thr Ser Ser Ser His
            35              40

(2) INFORMATION FOR SEQ ID NO: 45:
    (i) SEQUENCE CHARACTERISTICS:
        (A) LENGTH: 39 amino acids
        (B) TYPE: amino acid
        (C) STRANDEDNESS: <Unknown>
```

UNITED STATES PATENT AND TRADEMARK OFFICE
CERTIFICATE OF CORRECTION

PATENT NO. : 7,053,177 B1 Page 6 of 159
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (D) TOPOLOGY: unknown
    (ii) MOLECULE TYPE: peptide
    (xi) SEQUENCE DESCRIPTION: SEQ ID NO: 45:
      Arg Pro Lys Asn Val Ala Asp Ala Tyr Ser Ser Gln Asp Gly Ala Ala
      1               5              10             15
      Ala Glu Glu Thr Ser His Ala Ser Asn Ala Ala Arg Lys Ser Pro Lys
             20             25             30
      His Lys Pro Leu Arg Arg Pro
         35

(2) INFORMATION FOR SEQ ID NO: 46:
      (i) SEQUENCE CHARACTERISTICS:
         (A) LENGTH: 39 amino acids
         (B) TYPE: amino acid
         (C) STRANDEDNESS: <Unknown>
         (D) TOPOLOGY: unknown
     (ii) MOLECULE TYPE: peptide
     (xi) SEQUENCE DESCRIPTION: SEQ ID NO: 46:
       Arg Gly Ser Thr Gly Thr Ala Gly Gly Glu Arg Ser Gly Val Leu Asn
       1               5              10             15
       Leu His Thr Arg Asp Asn Ala Ser Gly Ser Gly Phe Lys Pro Trp Tyr
              20             25             30
       Pro Ser Asn Arg Gly His Lys
          35

(2) INFORMATION FOR SEQ ID NO: 47:
      (i) SEQUENCE CHARACTERISTICS:
         (A) LENGTH: 39 amino acids
         (B) TYPE: amino acid
         (C) STRANDEDNESS: <Unknown>
         (D) TOPOLOGY: unknown
     (ii) MOLECULE TYPE: peptide
     (xi) SEQUENCE DESCRIPTION: SEQ ID NO: 47:
       Arg Trp Gly Trp Glu Arg Ser Pro Ser Asp Tyr Asp Ser Asp Met Asp
       1               5              10             15
       Leu Gly Ala Arg Arg Tyr Ala Thr Arg Thr His Arg Ala Pro Pro Arg
              20             25             30
       Val Leu Lys Ala Pro Leu Pro
          35

(2) INFORMATION FOR SEQ ID NO: 48:
      (i) SEQUENCE CHARACTERISTICS:
         (A) LENGTH: 44 amino acids
         (B) TYPE: amino acid
         (C) STRANDEDNESS: <Unknown>
         (D) TOPOLOGY: unknown
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (ii) MOLECULE TYPE: peptide
    (xi) SEQUENCE DESCRIPTION: SEQ ID NO: 48:
      Arg Gly Trp Lys Cys Glu Gly Ser Gln Ala Ala Tyr Gly Asp Lys Asp
      1         5            10              15
      Ile Gly Arg Ser Arg Gly Cys Gly Ser Ile Thr Lys Asn Asn Thr Asn
              20            25          30
      His Ala His Pro Ser His Gly Ala Val Ala Lys Ile
              35          40

(2) INFORMATION FOR SEQ ID NO: 49:
    (i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 49:
      Ser Arg Glu Glu Ala Asn Trp Asp Gly Tyr Lys Arg Glu Met Ser His
      1         5            10              15
      Arg Ser Arg Phe Trp Asp Ala Thr His Leu Ser Arg Pro Arg Arg Pro
              20            25          30
      Ala Asn Ser Gly Asp Pro Asn
              35

(2) INFORMATION FOR SEQ ID NO: 50:
    (i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 50:
      Glu Trp Tyr Ser Trp Lys Arg Ser Ser Lys Ser Thr Gly Leu Gly Asp
      1         5            10              15
      Thr Ala Thr Arg Glu Gly Cys Gly Pro Ser Gln Ser Asp Gly Cys Pro
              20            25          30
      Tyr Asn Gly Arg Leu Thr Thr Val Lys Pro Arg Lys
              35          40

(2) INFORMATION FOR SEQ ID NO: 51:
    (i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown
    (ii) MOLECULE TYPE: peptide
```

UNITED STATES PATENT AND TRADEMARK OFFICE
CERTIFICATE OF CORRECTION

PATENT NO.        : 7,053,177 B1
APPLICATION NO.   : 09/079678
DATED             : May 30, 2006
INVENTOR(S)       : Vernon L. Alvarez et al.

It is certified that error appears in the above-identified patent and that said Letters Patent is hereby corrected as shown below:

```
(xi) SEQUENCE DESCRIPTION: SEQ ID NO: 51:
  Arg Glu Phe Ala Glu Arg Arg Leu Trp Gly Cys Asp Asp Leu Ser Trp
  1               5              10                  15
  Arg Leu Asp Ala Glu Gly Cys Gly Pro Thr Pro Ser Asn Arg Ala Val
          20              25              30
  Lys His Arg Lys Pro Arg Pro Arg Ser Pro Ala Leu
          35              40

(2) INFORMATION FOR SEQ ID NO: 52:
    (i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown
   (ii) MOLECULE TYPE: peptide
   (xi) SEQUENCE DESCRIPTION: SEQ ID NO: 52:
  Ser Asp His Ala Leu Gly Thr Asn Leu Arg Ser Asp Asn Ala Lys Glu
  1               5              10                  15
  Pro Gly Asp Tyr Asn Cys Cys Gly Asn Gly Asn Ser Thr Gly Arg Lys
          20              25              30
  Val Phe Asn Arg Arg Arg Pro Ser Ala Ile Pro Thr
          35              40

(2) INFORMATION FOR SEQ ID NO: 53:
    (i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown
   (ii) MOLECULE TYPE: peptide
   (xi) SEQUENCE DESCRIPTION: SEQ ID NO: 53:
  Arg His Ile Ser Glu Tyr Ser Phe Ala Asn Ser His Leu Met Gly Gly
  1               5              10                  15
  Glu Ser Lys Arg Lys Gly Cys Gly Ile Asn Gly Ser Phe Ser Pro Thr
          20              25              30
  Cys Pro Arg Ser Pro Thr Pro Ala Phe Arg Arg Thr
          35              40

(2) INFORMATION FOR SEQ ID NO: 54:
    (i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown
   (ii) MOLECULE TYPE: peptide
   (xi) SEQUENCE DESCRIPTION: SEQ ID NO: 54:
```

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

```
Ser Arg Glu Ser Gly Met Trp Gly Ser Trp Trp Arg Gly His Arg Leu
 1           5              10              15
Asn Ser Thr Gly Gly Asn Ala Asn Met Asn Ala Ser Leu Pro Pro Asp
        20              25              30
Pro Pro Val Ser Thr Pro
        35
```

(2) INFORMATION FOR SEQ ID NO: 55:
   (i) SEQUENCE CHARACTERISTICS:
      (A) LENGTH: 39 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 55:

```
Ser Thr Pro Pro Ser Arg Glu Ala Tyr Ser Arg Pro Tyr Ser Val Asp
 1           5              10              15
Ser Asp Ser Asp Thr Asn Ala Lys His Ser Ser His Asn Arg Arg Leu
        20              25              30
Arg Thr Arg Ser Arg Pro Asn
        35
```

(2) INFORMATION FOR SEQ ID NO: 56:
   (i) SEQUENCE CHARACTERISTICS:
      (A) LENGTH: 177 base pairs
      (B) TYPE: nucleic acid
      (C) STRANDEDNESS: single
      (D) TOPOLOGY: linear
   (ii) MOLECULE TYPE: DNA
   (xi) SEQUENCE DESCRIPTION: SEQ ID NO: 56:

```
  TCTCACTCCT CGAGATCCGG CGCTTATGAG AGTCCGGATG GTCGGGGGGG
TCGGAGCTAT    60
  GTGGGGGGCG GGGGTGGNTG TGGTAACATT GGTCGGAAGC ATAACCTGTG
GGGGCTGCGT   120
  ACCGCGTCGC CGGCCTGCTG GGACTCTAGA ATCGAAGGTC GCGCTAGACC TTCGAGA
177
```

(2) INFORMATION FOR SEQ ID NO: 57:
   (i) SEQUENCE CHARACTERISTICS:
      (A) LENGTH: 177 base pairs
      (B) TYPE: nucleic acid
      (C) STRANDEDNESS: single
      (D) TOPOLOGY: linear
   (ii) MOLECULE TYPE: DNA
   (xi) SEQUENCE DESCRIPTION: SEQ ID NO: 57:

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

TCTCACTCCT CGAGTCCTCG CTCTTTCTGG CCCGTTGTGT CCCGGCATGA GTCGTTTGGG 60
    ATCTCTAACT ATTTGGGNTG TGGTTATCGT ACATGTATCT CCGGCACGAT GACTAAGTCT 120
    AGCCCGATTT ACCCTCGGCA TTCGTCTAGA ATCGAAGGTC GCGCTAGACC TTCGAGA 177

(2) INFORMATION FOR SEQ ID NO: 58:
   (i) SEQUENCE CHARACTERISTICS:
     (A) LENGTH: 177 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 58:
    TCTCACTCCT CGAGTAGTAG CTCCGATTGG GGTGGTGTGC CTGGGAAGGT GGTTAGGGAG 60
    CGCTTTAAGG GGCGCGGTTG TGGTATTTCC ATCACCTCCG TGCTCACTGG GAAGCCCAAT 120
    CCGTGTCCGG AGCCTAAGGC GGCCTCTAGA ATCGAAGGTC GCGCTAGACC TTCGAGA 177

(2) INFORMATION FOR SEQ ID NO: 59:
   (i) SEQUENCE CHARACTERISTICS:
     (A) LENGTH: 177 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 59:
    TCTCACTCCT CGAGAGTTGG CCAGTGCACG GATTCTGATG TGCGGCGTCC TTGGGCCAGG 60
    TCTTGCGCTC ATCAGGGTTG TGGTGCGGGC ACTCGCAACT CGCACGGCTG CATCACCCGT 120
    CCTCTCCGCC AGGCTAGCGC TCATTCTAGA ATCGAAGGTC GCGCTAGACC TTCGAGA 177

(2) INFORMATION FOR SEQ ID NO: 60:
   (i) SEQUENCE CHARACTERISTICS:
     (A) LENGTH: 162 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 60:

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
    TCTCACTCCT CGAGCCACTC CGGTGGTATG AATAGGGCCT ACGGGGATGT
GTTTAGGGAG    60
    CTTCGTGATC GGTGGAACGC CACTTCCCAC CACACTCGCC CCACCCCTCA
GCTCCCCCGT   120
    GGGCCTAATT CTAGAATCGA AGGTCGCGCT AGACCTTCGA GA          162

(2) INFORMATION FOR SEQ ID NO: 61:
    (i) SEQUENCE CHARACTERISTICS:
        (A) LENGTH: 168 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 61:
    TCTCACTCCT CGAGTCCGTG CGGGGGGTCG TGGGGGCGTT TTATGCAGGG
TGGCCTTTTC    60
    GGCGGTAGGA CTGATGGTTG TGGTGCCCAT AGAAACCGCA CTTCTGCGTC
GTTAGAGCCC   120
    CCGAGCAGCG ACTACTCTAG AATCGAAGGT CGCGCTAGAC CTTCGAGA    168

(2) INFORMATION FOR SEQ ID NO: 62:
    (i) SEQUENCE CHARACTERISTICS:
        (A) LENGTH: 135 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 62:
    TCTCACTCCT CGAGGGGCGC CGCCGATCAG CGGCGGGGGT GGTCCGAGAA
CTTGGGGTTG    60
    CCTAGGGTGG GGTGGGACGC CATCGCTCAC AATAGCTATA CGTTCACCTC
GCGCCGCCCG   120
    CGCCCCCCCT CTAGA                                        135

(2) INFORMATION FOR SEQ ID NO: 63:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 63:
    TCTCACTCCT CGAGCGGTGG GGAGGTCAGC TCCTGGGGCC GCGTGAATGA
CCTCTGCGCT    60
    AGGGTGAGTT GGACTGGTTG TGGTACTGCT CGTTCCGCGC GTACCGACAA
CAAAGGCTTT   120
```

UNITED STATES PATENT AND TRADEMARK OFFICE
CERTIFICATE OF CORRECTION

PATENT NO.        : 7,053,177 B1
APPLICATION NO.   : 09/079678
DATED             : May 30, 2006
INVENTOR(S)       : Vernon L. Alvarez et al.

It is certified that error appears in the above-identified patent and that said Letters Patent is hereby corrected as shown below:

CTTCCTAAGC ACTCGTCACT CCGCTCTAGA ATCGAAGGTC GCGCTAGACC TTCGAGA 177

(2) INFORMATION FOR SEQ ID NO: 64:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO: 64:
    TCTCACTCCT CGAGTGATAG TGACGGGGAT CATTATGGGC TTCGGGGGGG GGTGCGTTGT 60
    TCGCTTCGTG ATAGGGGTTG TGGTCTGGCC CTGTCCACCG TCCATGCTGG TCCCCCCTCT 120
    TTTTACCCCA AGCTCTCCAG CCCCTCTAGA ATCGAAGGTC GCGCTAGACC TTCGAGA 177

(2) INFORMATION FOR SEQ ID NO: 65:
    (i) SEQUENCE CHARACTERISTICS:
        (A) LENGTH: 162 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO: 65:
    TCTCACTCCT CGAGGAGCTT GGGTAATTAT GGCGTCACCG GGACTGTGGA CGTGACGGTT 60
    TTGCCCATGC CTGGCCACGC CAACCACCTT GGTGTCTCCT CCGCCTCTAG CTCTGATCCT 120
    CCGCGGCGCT CTAGAATCGA AGGTCGCGCT AGACCTTCGA GA 162

(2) INFORMATION FOR SEQ ID NO: 66:
    (i) SEQUENCE CHARACTERISTICS:
        (A) LENGTH: 159 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO: 66:
    TCTCACTCCT CGAGAACTAC GACGGCTAAG GGGTGTCTTC TCGGAAGCTT CGGCGTTCTT 60
    AGTGGGTGCT CATTTACGCC AACCTCTCCA CCGCCCCACC TAGGATACCC CCCCCACTCC 120
    GTCAATTCTA GAATCGAAGG TCGCGCTAGA CCTTCGAGA 159

UNITED STATES PATENT AND TRADEMARK OFFICE
CERTIFICATE OF CORRECTION

| | | |
|---|---|---|
| PATENT NO. | : 7,053,177 B1 | Page 13 of 159 |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

(2) INFORMATION FOR SEQ ID NO: 67:
   (i) SEQUENCE CHARACTERISTICS:
      (A) LENGTH: 162 base pairs
      (B) TYPE: nucleic acid
      (C) STRANDEDNESS: single
      (D) TOPOLOGY: linear
   (ii) MOLECULE TYPE: DNA
   (xi) SEQUENCE DESCRIPTION: SEQ ID NO: 67:
    TCTCACTCCT CGAGCCCGAA GTTGTCCAGC GTGGGTGTTA TGACTAAGGT CACGGAGCTG   60
    CCCACGGAGG GGCCTAACGC CATTAGTATT CCGATCTCCG CGACCCTCGG CCCGCGCAAC   120
    CCGCTCCGCT CTAGAATCGA AGGTCGCGCT AGACCTTCGA GA   162

(2) INFORMATION FOR SEQ ID NO: 68:
   (i) SEQUENCE CHARACTERISTICS:
      (A) LENGTH: 162 base pairs
      (B) TYPE: nucleic acid
      (C) STRANDEDNESS: single
      (D) TOPOLOGY: linear
   (ii) MOLECULE TYPE: DNA
   (xi) SEQUENCE DESCRIPTION: SEQ ID NO: 68:
    TCTCACTCCT CGAGGTGGTG CGGCGCTGAG CTGTGCAACT CGGTGACTAA GAAGTTTCGC   60
    CCGGGCTGGC GGGATCACGC CAATCCCTCC ACCCATCATC GTACTCCCCC GCCCAGCCAG   120
    TCCAGCCCTT CTAGAATCGA AGGTCGCGCT AGACCTTCGA GA   162

(2) INFORMATION FOR SEQ ID NO: 69:
   (i) SEQUENCE CHARACTERISTICS:
      (A) LENGTH: 176 base pairs
      (B) TYPE: nucleic acid
      (C) STRANDEDNESS: single
      (D) TOPOLOGY: linear
   (ii) MOLECULE TYPE: DNA
   (xi) SEQUENCE DESCRIPTION: SEQ ID NO: 69:
    TCTCACTCCT CGAGGTGGTG CGGCGCTGAT GACCCGTGTG GTGCCAGTCG TTGGCGGGGG   60
    GGCAACAGCT TGTTTGGTTG TGGTCTTCGT TGTAGTGCGG CGCAGAGCAC CCCGAGTGGC   120
    AGGATCCATT CCACTTCGAC CAGCTCTAGA ATCGAAGGTG CGCTAGACCT TCGAGA   176

(2) INFORMATION FOR SEQ ID NO: 70:
   (i) SEQUENCE CHARACTERISTICS:
      (A) LENGTH: 162 base pairs

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 70:
       TCTCACTCCT CGAGTAAGTC CGGGGAGGGG GGTGACAGTA GCAGGGGCGA
GACGGGCTGG    60
       GCGAGGGTTC GGTCTCACGC CATGACTGCT GGCCGCTTTC GGTGGTACAA
CCAGTTGCCC   120
       TCTGATCGGT CTAGAATCGA AGGTCGCGCT AGACCTTCGA GA            162

(2) INFORMATION FOR SEQ ID NO: 71:
    (i) SEQUENCE CHARACTERISTICS:
        (A) LENGTH: 159 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 71:
       TCTCACTCCT CGAGGTCGAG CGCCAATAAT TGCGAGTGGA AGTCTGATTG
GATGCGCAGG    60
       GCCTGTATTG CTCGTTACGC CAACAGTTCG GGCCCCGCCC GCGCCGTCGA
CACTAAGGCC   120
       GCGCCCTCTA GAATCGAAGG TCGCGCTAGA CCTTCGAGA                 159

(2) INFORMATION FOR SEQ ID NO: 72:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 72:
       TCTCACTCCT CGAGTAAGTG GTCGTGGAGT TCGAGGTGGG GCTCCCCGCA
GGATAAGGTT    60
       GAGAAGACCA GGGCGGGTTG TGGTGGTAGT CCCAGCAGCA CCAATTGTCA
CCCCTACACC   120
       TTTGCCCCCC CCCCGCAAGC CGGCTCTAGA ATCGAAGGTC GCGCTAGACC TTCGAGA
177

(2) INFORMATION FOR SEQ ID NO: 73:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(ii) MOLECULE TYPE: DNA
    (xi) SEQUENCE DESCRIPTION: SEQ ID NO: 73:
     TCTCACTCCT CGAGTGGGTT CTGGGAGTTT AGCAGGGGGC TTTGGGATGG GGAGAACCGT  60
     AAGAGTGTCC GGTCGGGTTG TGGTTTTCGT GGCTCCTCTG CTCAGGGCCC GTGTCCGGTC  120
     ACGCCTGCCA CCATTGACAA ACACTCTAGA ATCGAAGGTC GCGCTAGACC TTCGAGA  177

(2) INFORMATION FOR SEQ ID NO: 74:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 74:
     TCTCACTCCT CGAGTGAGAG CGGGCGGTGC CGTAGCGTGA GCCGGTGGAT GACGACGTGG  60
     CAGACGCAGA AGGGCGGTTG TGGTTCCAAT GTTTCCCGCG GTTCGCCCCT CGACCCCTCT  120
     CACCAGACCG GGCATGCCAC TACTTCTAGA ATCGAAGGTC GCGCTAGACC TTCGAGA  177

(2) INFORMATION FOR SEQ ID NO: 75:
    (i) SEQUENCE CHARACTERISTICS:
        (A) LENGTH: 162 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 75:
     TCTCACTCCT CGAGGGAGTG GAGGTTTGCC GGGCCGCCGT TGGACCTGTG GGCGGGTCCG  60
     AGCTTGCCCT CTTTTAACGC CAGTTCCCAC CCTCGCGCCC TGCGCACCTA TTGGTCCCAG  120
     CGGCCCCGCT CTAGAATCGA AGGTCGCGCT AGACCTTCGA GA  162

(2) INFORMATION FOR SEQ ID NO: 76:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 76:

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
     TCTCACTCCT CGAGGATGGA GGACATCAAG AACTCGGGGT GGAGGGACTC
TTGTAGGTGG   60
     GGTGACCTGA GGCCTGGTTG TGGTAGCCGC CAGTGGTACC CCTCGAATAT
GCGTTCTAGC   120
     AGAGATTACC CCGCGGGGGG CCACTCTAGA ATCGAAGGTC GCGCTAGACC TTCGAGA
177

(2) INFORMATION FOR SEQ ID NO: 77:
    (i) SEQUENCE CHARACTERISTICS:
        (A) LENGTH: 152 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 77:
     TCTCACTCCT CGAGTCATCC GTGGTACAGG CATTGGAACC ATGGTGACTT
CTCTGGTTCG   60
     GGCCAGTCAC GCCACACCCC GCCGGAGAGC CCCCACCCCG GCCGCCCTAA
TGCCACCATT   120
     TCTAGAATCG AAGGTCGCGC TAGACCTTCG AG                    152

(2) INFORMATION FOR SEQ ID NO: 78:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 78:
     TCTCACTCCT CGAGATATAA GCACGATATC GGTTGCGATG CTGGGGTTGA
CAAGAAGTCG   60
     TCGTCTGTGC GTGGTGGTTG TGGTGCTCAT TNGTCGCCAC CCCGCGCCGG
CCGTGGTCCT   120
     CGCGGCACGA TGGTTAGCAG GCTTTCTAGA ATCGAAGGTC GCGCTAGACC TTCGAGA
177

(2) INFORMATION FOR SEQ ID NO: 79:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 79:
     TCTCACTCCT CGAGTCAGGG CTCCAAGCAG TGTATGCAGT ACCGCACCGG
TCGTTTGACG   60
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

GTGGGGTCTG AGTATGGTTG TGGTATGAAC CCCGCCCGCC ATGCCACGCC CGCTTATCCG 120
    GCGCGCCTGC TGCCACGCTA TCGCTCTAGA ATCGAAGGTC GCGCTAGACC TTCGAGA 177

(2) INFORMATION FOR SEQ ID NO: 80:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 80:
    TCTCACTCCT CGAGTGGGCG GACTACTAGT GAGATTTCTG GGCTCTGGGG TTGGGGTGAC 60
    GACCGGAGCG GTTATGGTTG GGGTAACACG CTCCGCCCCA ACTACATCCC TTATAGGCAG 120
    GCGACGAACA GGCATCGTTA TACGTCTAGA ATCGAAGGTC GCGCTAGACC TTCGAGA 177

(2) INFORMATION FOR SEQ ID NO: 81:
    (i) SEQUENCE CHARACTERISTICS:
        (A) LENGTH: 162 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 81:
    TCTCACTCCT CGAGGTGGAA TTGGACTGTC TTGCCCGCCA CTGGCGGCCA TTACTGGACG 60
    CGTTCGACGG ACTATCACGC CATTAACAAT CACAGGCCGA GCATCCCCCA CCAGCATCCG 120
    ACCCCTATCT CTAGAATCGA AGGTCGCGCT AGACCTTCGA GA 162

(2) INFORMATION FOR SEQ ID NO: 82:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 82:
    TCTCACTCCT CGAGTTGGTC GTCGTGGAAT TGGAGCTCTA AGACTACTCG TCTGGGCGAC 60
    AGGGCGACTC GGGAGGGTTG TGGTCCCAGC CAGTCTGATG GCTGTCCTTA TAACGGCCGC 120

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

CTTACGACCG TCAAGCCTCG CACGTCTAGA ATCGAAGGTC GCGCTAGACC TTCGAGA 177

(2) INFORMATION FOR SEQ ID NO: 83:
    (i) SEQUENCE CHARACTERISTICS:
        (A) LENGTH: 156 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 83:
    TCTCACTCCT CGAGTGGTAG TTTGAACGCA TGGCAACCGC GGTCATGGGT GGGGGGCGCG 60
    TTCCGGTCAC ACGCCAACAA TAACTTGAAC CCCAAGCCCA CCATGGTTAC TNGTCACCCT 120
    ACCTCTAGAA TCGAAGGTCG CGCTAGACCT TCGAGA 156

(2) INFORMATION FOR SEQ ID NO: 84:
    (i) SEQUENCE CHARACTERISTICS:
        (A) LENGTH: 178 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 84:
    TCTCACTCCT CGAGGTATTC GGGTTTGTCC CCGCGGGACA ACGGTCCCGC TTGTAGTCAG 60
    GAGGCTACCT TGGAGGGTTG TGGTGCGCAG AGGCTGATGT CCACCCGTCG CAAGGGCCGC 120
    AACTCCCGCC CCGGGTGGAC GCTCTCTAGA ATCGAAGGTC GCGCTAGACC CTTCGAGA 178

(2) INFORMATION FOR SEQ ID NO: 85:
    (i) SEQUENCE CHARACTERISTICS:
        (A) LENGTH: 162 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 85:
    TCTCACTCCT CGAGCGTGGG GAATGATAAG ACTAGCAGGC CGGTTTCCTT CTACGGGCGC 60
    GTTAGTGATC TGTGGAACGC CAGCTTGATG CCGAAGCGTA CTCCCAGCTC GAAGCGCCAC 120
    GATGATGGCT CTAGAATCGA AGGTCGCGCT AGACCTTCGA GA 162

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(2) INFORMATION FOR SEQ ID NO: 86:
   (i) SEQUENCE CHARACTERISTICS:
      (A) LENGTH: 162 base pairs
      (B) TYPE: nucleic acid
      (C) STRANDEDNESS: single
      (D) TOPOLOGY: linear
   (ii) MOLECULE TYPE: DNA
   (xi) SEQUENCE DESCRIPTION: SEQ ID NO: 86:
    TCTCACTCCT CGAGTACTCC CCCCAGTAGG GAGGCGTATA GTAGGCCCTA TAGTGTCGAT    60
    AGCGATTCGG ATACGAACGC CAAGCACAGC TCCCACAACC GCCGTNTGCG GACGCGCAGC   120
    CGCCCGAACT CTAGAATCGA AGGTCGCGCT AGACCTTCGA GA               162

(2) INFORMATION FOR SEQ ID NO: 87:
   (i) SEQUENCE CHARACTERISTICS:
      (A) LENGTH: 159 base pairs
      (B) TYPE: nucleic acid
      (C) STRANDEDNESS: single
      (D) TOPOLOGY: linear
   (ii) MOLECULE TYPE: DNA
   (xi) SEQUENCE DESCRIPTION: SEQ ID NO: 87:
    TCTCACTCCT CGAGATGGCC TAGTGTGGGT TACAAGGGTA ATGGCAGTGA CACTATTGAT    60
    GTTCACAGCA ATGACGCCAG TACTAAGAGG TCCCTCATCT ATAACCACCG CCGCCCCNTC   120
    TTTCCCTCTA GAATCGAAGG TCGCGCTAGA CCTTCGAGA               159

(2) INFORMATION FOR SEQ ID NO: 88:
   (i) SEQUENCE CHARACTERISTICS:
      (A) LENGTH: 162 base pairs
      (B) TYPE: nucleic acid
      (C) STRANDEDNESS: single
      (D) TOPOLOGY: linear
   (ii) MOLECULE TYPE: DNA
   (xi) SEQUENCE DESCRIPTION: SEQ ID NO: 88:
    TCTCACTCCT CGAGAACGTT TGAGAACGAC GGGCTGGGCG TCGGCCGGTC TATTCAGAAG    60
    AAGTCGGATA GGTGGTACGC CAGCCACAAC ATTCGTAGCC ATTTCGCGTC CATGTCTCCC   120
    GCTGGTAAGT CTAGAATCGA AGGTCGCGCT AGACCTTCGA GA             162

(2) INFORMATION FOR SEQ ID NO: 89:
   (i) SEQUENCE CHARACTERISTICS:
      (A) LENGTH: 160 base pairs
      (B) TYPE: nucleic acid

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (C) STRANDEDNESS: single
        (D) TOPOLOGY: linear
    (ii) MOLECULE TYPE: DNA
    (xi) SEQUENCE DESCRIPTION: SEQ ID NO: 89:
     TCTCACTCCT CGAGCTATTG TCGGGTTAAG GGTGGTGGGG AGGGGGGGCA
TACGGATTCC   60
     AATCTGGCTA GGTCGGGTTG TGGTAAGGTG GCCAGGACCA GCAGGCTTCA
GCATATCAAC   120
     CCGCGCGCTA CCCCCCCCTC CCGGTCTAGA ATCGAAGGTC              160

(2) INFORMATION FOR SEQ ID NO: 90:
    (i) SEQUENCE CHARACTERISTICS:
        (A) LENGTH: 162 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 90:
     TCTCACTCCT CGAGTTGGAC TCGGTGGGGC AAGCACANTC ATGGGGGGTT
TGTGAACAAG   60
     TCTCCCCCTG GGAAGAACGC CACGAGCCCC TACACCGACG CCCAGCTGCC
CAGTGATCAG   120
     GGTCCTCCCT CTAGAATCGA AGGTCGCGCT AGACCTTCGA GA           162

(2) INFORMATION FOR SEQ ID NO: 91:
    (i) SEQUENCE CHARACTERISTICS:
        (A) LENGTH: 177 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 91:
     TCTCACTCCT CGAGTCAGGT TGATTCGTTT CGTAATAGCT TTCGGTGGTA
TGAGCCGAGC   60
     AGGGCTCTGT GCCATGGTTG TGGTAAGCGC GACACCTCCA CCACTCGTAT
CCACAATAGC   120
     CCCAGCGACT CCTATCCTAC ACGCTCTAGA ATCGAAGGTC GCGCTAGACC TTCGAGA
177

(2) INFORMATION FOR SEQ ID NO: 92:
    (i) SEQUENCE CHARACTERISTICS:
        (A) LENGTH: 162 base pairs
        (B) TYPE: nucleic acid
        (C) STRANDEDNESS: single
        (D) TOPOLOGY: linear
    (ii) MOLECULE TYPE: DNA
```

UNITED STATES PATENT AND TRADEMARK OFFICE
CERTIFICATE OF CORRECTION

PATENT NO.        : 7,053,177 B1
APPLICATION NO.   : 09/079678
DATED             : May 30, 2006
INVENTOR(S)       : Vernon L. Alvarez et al.

It is certified that error appears in the above-identified patent and that said Letters Patent is hereby corrected as shown below:

(xi) SEQUENCE DESCRIPTION: SEQ ID NO: 92:
     TCTCACTCCT CGAGCTTTTT GCGGTTCCAG AGTCCGAGGT TCGAGGATTA CAGTAGGACG   60
     ATCTNTCGGT TGCGCAACGC CACGAACCCG AGTAATGTCT CCGATGCGCA CAATAACCGG   120
     GCCTTGGCCT CTAGAATCGA AGGTCGCGCT AGACCTTCGA GA            162

(2) INFORMATION FOR SEQ ID NO: 93:
   (i) SEQUENCE CHARACTERISTICS:
     (A) LENGTH: 162 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 93:
     TCTCACTCCT CGAGGAGCAT CACCGACGGG GGCATCAATG AGGTGGACCT GAGTAGTGTG   60
     TCGAACGTTC TTGAGAACGC CAACTCGCAT AGGGCCTACA GGAAGCATCG CCCGACCTTG   120
     AAGCGTCCTT CTAGAATCGA AGGTCGCGCT AGACCTTCGA GA            162

(2) INFORMATION FOR SEQ ID NO: 94:
   (i) SEQUENCE CHARACTERISTICS:
     (A) LENGTH: 177 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 94:
     TCTCACTCCT CGAGTTCGAA GGTGAGCAGC CCGAGGGATC CGACGGTCCC GCGGAAGGGC   60
     GGCAATGTTG ATTATGGTTG TGGTCACAGG TCTTCCGCCC GGATGCCTAC CTCCGCTCTG   120
     TCGTCGATCA CGAAGTGCTA CACTTCTAGA ATCGAAGGTC GCGCTAGACC TTCGAGA   177

(2) INFORMATION FOR SEQ ID NO: 95:
   (i) SEQUENCE CHARACTERISTICS:
     (A) LENGTH: 177 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 95:
     TCTCACTCCT CGAGAGCCAG TANGCAGGGC GGCCGGGGTG TTGCCCCTGA GTTTGGGGCG   60

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
     AGCGTTTTGG GTNGTGGTTG TGGTAGCGCC ACTTATTACA CGAACTCCAC
CAGCTGCAAG   120
     GATGCTATGG GCCACAACTA CTCGTCTAGA ATCGAAGGTC GCGNTAGACC TTCGAGA
177
```

(2) INFORMATION FOR SEQ ID NO: 96:
    (i) SEQUENCE CHARACTERISTICS:
        (A) LENGTH: 162 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 96:

```
     TCTCACTCCT CGAGATGGTG CGAGAAGCAC AAGTTTACGG CTGCGCGTTG
CAGCGCGGGG   60
     GCGGGTTTTG AGAGGGANGC CAGCCGTCCG CCCCAGCCTG CCCACCGGGA
TAATACCAAC   120
     CGTAATGCNT NTAGAATCGA AGGTCGCGCT AGACCTTCGA GA              162
```

(2) INFORMATION FOR SEQ ID NO: 97:
    (i) SEQUENCE CHARACTERISTICS:
        (A) LENGTH: 162 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 97:

```
     TCTCACTCCT CGAGTTTTCA GGTGTACCCG GACCATGGTC TGGAGAGGCA
TGCTTTGGAC   60
     GGGACGGGTC CGCTTTACGC CATGCCCGGC CGCTGGATTA GGGCGCGTCC
GCAGAACAGG   120
     GACCGCCAGT CTAGAATCGA AGGTCGCGCT AGACCTTCGA GA              162
```

(2) INFORMATION FOR SEQ ID NO: 98:
    (i) SEQUENCE CHARACTERISTICS:
        (A) LENGTH: 159 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 98:

```
     TCTCACTCCT CGAGCAGGTG TACGGACAAC GAGCAGTGCC CCGATACCGG
GANTAGGTCT   60
     CGTTCCGTTA GTAACGCCAG GTACTTTTCG AGCAGGTTGC TCAAGACTCA
CGCCCCCCAT   120
     CGCCCTTCTA GAATCGAAGG TCGCGCTAGA CCTTCGAGA                  159
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

(2) INFORMATION FOR SEQ ID NO: 99:
   (i) SEQUENCE CHARACTERISTICS:
     (A) LENGTH: 162 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 99:
    TCTCACTCCT CGAGTGCCAG GGATAGCGGG CCTGCGGAGG ATGGGTCCCG CGCCGTCCGG   60
    TTGAACGGGG TTGAGAACGC CAACACTAGG AAGTCCTCCC GCAGTAACCC GCGGGGTAGG   120
    CGCCATCCCT CTAGAATCGA AGGTCGCGCT AGACCTTCGA GA   162

(2) INFORMATION FOR SEQ ID NO: 100:
   (i) SEQUENCE CHARACTERISTICS:
     (A) LENGTH: 177 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 100:
    TCTCACTCCT CGAGTTCCGC CGATGCGGAG AAGTGTGCGG GCAGTCTGTT GTGGTGGGGT   60
    AGGCAGAACA ACTCCGGTTG TGGTTCGCCC ACGAAGAAGC ATCTGAAGCA CCGCAATCGC   120
    AGTCAGACCT CCTCTTCGTC CCACTCTAGA ATCGAAGGTC GCGCTAGACC TTCGAGA   177

(2) INFORMATION FOR SEQ ID NO: 101:
   (i) SEQUENCE CHARACTERISTICS:
     (A) LENGTH: 162 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 101:
    TCTCACTCCT CGAGACCGAA GAACGTGGCC GATGCTTATT CGTCTCAGGA CGGGGCGGCG   60
    GCCGAGGAGA CGTCTCACGC CAGTAATGCC GCGCGGAAGT CCCCTAAGCA CAAGCCCTTG   120
    AGGCGGCCTT CTAGAATCGA AGGTCGCGCT AGACCTTCGA GA   162

(2) INFORMATION FOR SEQ ID NO: 102:
   (i) SEQUENCE CHARACTERISTICS:

UNITED STATES PATENT AND TRADEMARK OFFICE
CERTIFICATE OF CORRECTION

PATENT NO.        : 7,053,177 B1
APPLICATION NO.   : 09/079678
DATED             : May 30, 2006
INVENTOR(S)       : Vernon L. Alvarez et al.

It is certified that error appears in the above-identified patent and that said Letters Patent is hereby corrected as shown below:

```
       (A) LENGTH: 162 base pairs
       (B) TYPE: nucleic acid
       (C) STRANDEDNESS: single
       (D) TOPOLOGY: linear
   (ii) MOLECULE TYPE: DNA
   (xi) SEQUENCE DESCRIPTION: SEQ ID NO: 102:
      TCTCACTCCT CGAGAGGCAG TACGGGGACG GCCGGCGGCG AGCGTTCCGG
GGTGCTCAAC   60
      CTGCACACCA GGGATAACGC CAGCGGCAGC GGTTTCAAAC CGTGGTACCC
TTCGAATCGG   120
      GGTCACAAGT CTAGAATCGA AGGTCGCGCT AGACCTTCGA GA                 162

(2) INFORMATION FOR SEQ ID NO: 103:
   (i) SEQUENCE CHARACTERISTICS:
       (A) LENGTH: 162 base pairs
       (B) TYPE: nucleic acid
       (C) STRANDEDNESS: single
       (D) TOPOLOGY: linear
   (ii) MOLECULE TYPE: DNA
   (xi) SEQUENCE DESCRIPTION: SEQ ID NO: 103:
      TCTCACTCCT CGAGGTGGGG GTGGGAGAGG AGTCCGTCCG ACTACGATTC
TGATATGGAC   60
      TTGGGGGCGA GGAGGTACGC CACCCGCACC CACCGCGCGC CCCCTCGCGT
CTTGAAGGCT   120
      CCCCTGCCCT CTAGAATCGA AGGTCGCGCT AGACCTTCGA GA                 162

(2) INFORMATION FOR SEQ ID NO: 104:
   (i) SEQUENCE CHARACTERISTICS:
       (A) LENGTH: 177 base pairs
       (B) TYPE: nucleic acid
       (C) STRANDEDNESS: single
       (D) TOPOLOGY: linear
   (ii) MOLECULE TYPE: DNA
   (xi) SEQUENCE DESCRIPTION: SEQ ID NO: 104:
      TCTCACTCCT CGAGGCACTG GAAGTGCGAG GGCTCTCAGG CTGCCTACGG
GGACAAGGAT   60
      ATCGGGAGGT CCAGGGGTTG TGGTTCCATT ACAAAGAATA ACACTAATCA
CGCCCATCCT   120
      AGCCACGGCG CCGTTGCTAA GATCTCTAGA ATCGAAGGTC GCGCTAGACC TTCGAGA
177

(2) INFORMATION FOR SEQ ID NO: 105:
   (i) SEQUENCE CHARACTERISTICS:
       (A) LENGTH: 162 base pairs
       (B) TYPE: nucleic acid
       (C) STRANDEDNESS: single
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(D) TOPOLOGY: linear
  (ii) MOLECULE TYPE: DNA
  (xi) SEQUENCE DESCRIPTION: SEQ ID NO: 105:
    TCTCACTCCT CGAGCCGCGA GGAGGCGAAC TGGGACGGCT ATAAGAGGGA GATGAGCCAC  60
    CGGAGTCGCT TTTGGGACGC CACCCACCTG TCCCGCCCTC GCCGCCCCGC TAACTCTGGT  120
    GACCCTAACT CTAGAATCGA AGGTCGCGCT AGACCTTCGA GA    162

(2) INFORMATION FOR SEQ ID NO: 106:
  (i) SEQUENCE CHARACTERISTICS:
    (A) LENGTH: 177 base pairs
    (B) TYPE: nucleic acid
    (C) STRANDEDNESS: single
    (D) TOPOLOGY: linear
  (ii) MOLECULE TYPE: DNA
  (xi) SEQUENCE DESCRIPTION: SEQ ID NO: 106:
    TCTCACTCNT CGAGAGAGTT CGCGGAGAGG AGGTTGTGGG GGTGTGATGA CCTGAGTTGG  60
    CGTCTCGACG CGGAGGGTTG TGGTCCCACT CCGAGCAATC GGGCCGTCAA GCATCGCAAG  120
    CCCCGCCCAC GCTCCCCCGC ACTCTCTAGA ATCGAAGGTC GCGCTAGACC TTCGAGA  177

(2) INFORMATION FOR SEQ ID NO: 107:
  (i) SEQUENCE CHARACTERISTICS:
    (A) LENGTH: 177 base pairs
    (B) TYPE: nucleic acid
    (C) STRANDEDNESS: single
    (D) TOPOLOGY: linear
  (ii) MOLECULE TYPE: DNA
  (xi) SEQUENCE DESCRIPTION: SEQ ID NO: 107:
    TCTCACTCNT NGAGTGATCA CGCGTTGGGG ACGAATCTGA GGTCTGACAA TGCCAAGGAG  60
    CCGGGTGATT ACAACTGTTG TGGTAACGGG AACTCTACCG GGCGAAAGGT TTTTAACCGT  120
    AGGCGCCCCT CCGCCATCCC CANTTCTAGA ATCGAAGGTC GCGCTAGACC TTCGAGA  177

(2) INFORMATION FOR SEQ ID NO: 108:
  (i) SEQUENCE CHARACTERISTICS:
    (A) LENGTH: 177 base pairs
    (B) TYPE: nucleic acid
    (C) STRANDEDNESS: single
    (D) TOPOLOGY: linear
  (ii) MOLECULE TYPE: DNA

UNITED STATES PATENT AND TRADEMARK OFFICE
CERTIFICATE OF CORRECTION

PATENT NO.         : 7,053,177 B1
APPLICATION NO.   : 09/079678
DATED              : May 30, 2006
INVENTOR(S)        : Vernon L. Alvarez et al.

It is certified that error appears in the above-identified patent and that said Letters Patent is hereby corrected as shown below:

(xi) SEQUENCE DESCRIPTION: SEQ ID NO: 108:
TCTCACTCCT CGAGGCATAT TTCTGAGTAT AGCTTTGCGA ATTCCCACTT GATGGGTGGC  60
GAGTCCAAGC GGAAGGGTTG TGGTATTAAC GGCTCCTTTT CTCCCACTTG TCCCCGCTCC  120
CCCACCCCAG CCTTCCGCCG CACCTCTAGA ATCGAAGGTC GCGCTAGACC TTCGAGA  177

(2) INFORMATION FOR SEQ ID NO: 109:
   (i) SEQUENCE CHARACTERISTICS:
     (A) LENGTH: 158 base pairs
     (B) TYPE: nucleic acid
     (C) STRANDEDNESS: single
     (D) TOPOLOGY: linear
   (ii) MOLECULE TYPE: DNA
   (xi) SEQUENCE DESCRIPTION: SEQ ID NO: 109:
TCTCACTCCT CGAGCCGGGA GAGCGGGATG TGGGGTAGTT GGTGGCGTGG TCACAGGTTG  60
AATTCCACGG GGGGTAACGC CAACATGAAT GCTAGTCTGC CCCCCGACCC CCCTGTTTCC  120
ACTCCGTCTA GAATCGAAGG TCGCGCTAGA CCTTCGAG  158

(2) INFORMATION FOR SEQ ID NO: 110:
   (i) SEQUENCE CHARACTERISTICS:
     (A) LENGTH: 708 amino acids
     (B) TYPE: amino acid
     (C) STRANDEDNESS: <Unknown>
     (D) TOPOLOGY: unknown
   (ii) MOLECULE TYPE: peptide
   (xi) SEQUENCE DESCRIPTION: SEQ ID NO: 110:
Met Gly Met Ser Lys Ser His Ser Phe Phe Gly Tyr Pro Leu Ser Ile
 1               5                  10                  15
Phe Phe Ile Val Val Asn Glu Phe Cys Glu Arg Phe Ser Tyr Tyr Gly
        20                  25                  30
Met Arg Ala Ile Leu Ile Leu Tyr Phe Thr Asn Phe Ile Ser Trp Asp
        35                  40                  45
Asp Asn Leu Ser Thr Ala Ile Tyr His Thr Phe Val Ala Leu Cys Tyr
        50                  55                  60
Leu Thr Pro Ile Leu Gly Ala Leu Ile Ala Asp Ser Trp Leu Gly Lys
 65              70                  75                  80
Phe Lys Thr Ile Val Ser Leu Ser Ile Val Tyr Thr Ile Gly Gln Ala
        85                  90                  95
Val Thr Ser Val Ser Ser Ile Asn Asp Leu Thr Asp His Asn His Asp
        100                 105                 110
Gly Thr Pro Asp Ser Leu Pro Val His Val Val Leu Ser Leu Ile Gly
         115                 120                 125

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
Leu Ala Leu Ile Ala Leu Gly Thr Gly Gly Ile Lys Pro Cys Val Ser
    130             135             140
Ala Phe Gly Gly Asp Gln Phe Glu Glu Gly Gln Glu Lys Gln Arg Asn
145             150             155             160
Arg Phe Phe Ser Ile Phe Tyr Leu Ala Ile Asn Ala Gly Ser Leu Leu
            165             170             175
Ser Thr Ile Ile Thr Pro Met Leu Arg Val Gln Gln Cys Gly Ile His
        180             185             190
Ser Lys Gln Ala Cys Tyr Pro Leu Ala Phe Gly Val Pro Ala Ala Leu
    195             200             205
Met Ala Val Ala Leu Ile Val Phe Val Leu Gly Ser Gly Met Tyr Lys
    210             215             220
Lys Phe Lys Pro Gln Gly Asn Ile Met Gly Lys Val Ala Lys Cys Ile
225             230             235             240
Gly Phe Ala Ile Lys Asn Arg Phe Arg His Arg Ser Lys Ala Phe Pro
            245             250             255
Lys Arg Glu His Trp Leu Asp Trp Ala Lys Glu Lys Tyr Asp Glu Arg
        260             265             270
Leu Ile Ser Gln Ile Lys Met Val Thr Arg Val Met Phe Leu Tyr Ile
    275             280             285
Pro Leu Pro Met Phe Trp Ala Leu Phe Asp Gln Gln Gly Ser Arg Trp
    290             295             300
Thr Leu Gln Ala Thr Thr Met Ser Gly Lys Ile Gly Ala Leu Glu Ile
305             310             315             320
Gln Pro Asp Gln Met Gln Thr Val Asn Ala Ile Leu Ile Val Ile Met
            325             330             335
Val Pro Ile Phe Asp Ala Val Leu Tyr Pro Leu Ile Ala Lys Cys Gly
        340             345             350
Phe Asn Phe Thr Ser Leu Lys Lys Met Ala Val Gly Met Val Leu Ala
    355             360             365
Ser Met Ala Phe Val Val Ala Ala Ile Val Gln Val Glu Ile Asp Lys
    370             375             380
Thr Leu Pro Val Phe Pro Lys Gly Asn Glu Val Gln Ile Lys Val Leu
385             390             395             400
Asn Ile Gly Asn Asn Thr Met Asn Ile Ser Leu Pro Gly Glu Met Val
            405             410             415
Thr Leu Gly Pro Met Ser Gln Thr Asn Ala Phe Met Thr Phe Asp Val
        420             425             430
Asn Lys Leu Thr Arg Ile Asn Ile Ser Ser Pro Gly Ser Pro Val Thr
    435             440             445
Ala Val Thr Asp Asp Phe Lys Gln Gly Gln Arg His Thr Leu Leu Val
    450             455             460
Trp Ala Pro Asn His Tyr Gln Val Val Lys Asp Gly Leu Asn Gln Lys
465             470             475             480
Pro Glu Lys Gly Glu Asn Gly Ile Arg Phe Val Asn Thr Phe Asn Glu
            485             490             495
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
            Leu Ile Thr Ile Thr Met Ser Gly Lys Val Tyr Ala Asn Ile Ser Ser
                500             505             510
            Tyr Asn Ala Ser Thr Tyr Gln Phe Phe Pro Ser Gly Ile Lys Gly Phe
                515             520             525
            Thr Ile Ser Ser Thr Glu Ile Pro Pro Gln Cys Gln Pro Asn Phe Asn
                530             535             540
            Thr Phe Tyr Leu Glu Phe Gly Ser Ala Tyr Thr Tyr Ile Val Gln Arg
            545             550             555             560
            Lys Asn Asp Ser Cys Pro Glu Val Lys Val Phe Glu Asp Ile Ser Ala
                565             570             575
            Asn Thr Val Asn Met Ala Leu Gln Ile Pro Gln Tyr Phe Leu Leu Thr
                580             585             590
            Cys Gly Glu Val Val Phe Ser Val Thr Gly Leu Glu Phe Ser Tyr Ser
                595             600             605
            Gln Ala Pro Ser Asn Met Lys Ser Val Leu Gln Ala Gly Trp Leu Leu
                610             615             620
            Thr Val Ala Val Gly Asn Ile Ile Val Leu Ile Val Ala Gly Ala Gly
            625             630             635             640
            Gln Phe Ser Lys Gln Trp Ala Glu Tyr Ile Leu Phe Ala Ala Leu Leu
                645             650             655
            Leu Val Val Cys Val Val Phe Ala Ile Met Ala Arg Phe Tyr Thr Tyr
                660             665             670
            Ile Asn Pro Ala Glu Ile Glu Ala Gln Phe Asp Glu Asp Glu Lys Lys
                675             680             685
            Asn Arg Leu Glu Lys Ser Asn Pro Tyr Phe Met Ser Gly Ala Asn Ser
                690             695             700
            Gln Lys Gln Met
            705

(2) INFORMATION FOR SEQ ID NO: 111:
        (i) SEQUENCE CHARACTERISTICS:
            (A) LENGTH: 22 base pairs
            (B) TYPE: nucleic acid
            (C) STRANDEDNESS: single
            (D) TOPOLOGY: linear
        (ii) MOLECULE TYPE: DNA
        (xi) SEQUENCE DESCRIPTION: SEQ ID NO: 111:
            TCCGGACTCT CATAAGCGCC GG                               22

(2) INFORMATION FOR SEQ ID NO: 112:
        (i) SEQUENCE CHARACTERISTICS:
            (A) LENGTH: 22 base pairs
            (B) TYPE: nucleic acid
            (C) STRANDEDNESS: single
            (D) TOPOLOGY: linear
        (ii) MOLECULE TYPE: DNA
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (xi) SEQUENCE DESCRIPTION: SEQ ID NO: 112:
            ACAACGGGCC AGAAAGAGCG AG                          22

(2) INFORMATION FOR SEQ ID NO: 113:
        (i) SEQUENCE CHARACTERISTICS:
            (A) LENGTH: 22 base pairs
            (B) TYPE: nucleic acid
            (C) STRANDEDNESS: single
            (D) TOPOLOGY: linear
        (ii) MOLECULE TYPE: DNA
        (xi) SEQUENCE DESCRIPTION: SEQ ID NO: 113:
            ACACCACCCC AATCGGAGCT AC                          22

(2) INFORMATION FOR SEQ ID NO: 114:
        (i) SEQUENCE CHARACTERISTICS:
            (A) LENGTH: 22 base pairs
            (B) TYPE: nucleic acid
            (C) STRANDEDNESS: single
            (D) TOPOLOGY: linear
        (ii) MOLECULE TYPE: DNA
        (xi) SEQUENCE DESCRIPTION: SEQ ID NO: 114:
            TCAGAATCCG TGCACTGGCC AA                          22

(2) INFORMATION FOR SEQ ID NO: 115:
        (i) SEQUENCE CHARACTERISTICS:
            (A) LENGTH: 22 base pairs
            (B) TYPE: nucleic acid
            (C) STRANDEDNESS: single
            (D) TOPOLOGY: linear
        (ii) MOLECULE TYPE: DNA
        (xi) SEQUENCE DESCRIPTION: SEQ ID NO: 115:
            GCCCTATTCA TACCACCGGA GT                          22

(2) INFORMATION FOR SEQ ID NO: 116:
        (i) SEQUENCE CHARACTERISTICS:
            (A) LENGTH: 22 base pairs
            (B) TYPE: nucleic acid
            (C) STRANDEDNESS: single
            (D) TOPOLOGY: linear
        (ii) MOLECULE TYPE: DNA
        (xi) SEQUENCE DESCRIPTION: SEQ ID NO: 116:
            CATCAGTCCT ACCGCCGAAA AG                          22

(2) INFORMATION FOR SEQ ID NO: 117:
        (i) SEQUENCE CHARACTERISTICS:
            (A) LENGTH: 22 base pairs
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 117:
        CGTATAGCTA TTGTGAGCGA TG                      22

(2) INFORMATION FOR SEQ ID NO: 118:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 118:
        ACGCGCGGAA CGAGCAGTAC CA                      22

(2) INFORMATION FOR SEQ ID NO: 119:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 119:
        CCATAATGAT CCCCGTCACT AT                      22

(2) INFORMATION FOR SEQ ID NO: 120:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 120:
        AGACACCCCT TAGCCGTCGT AG                      22

(2) INFORMATION FOR SEQ ID NO: 121:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 121:
        AGCTCCGTGA CCTTAGTCAT AA                      22
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(2) INFORMATION FOR SEQ ID NO: 122:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 122:
        TGCACAGCTC AGCGCCGCAC CA        22

(2) INFORMATION FOR SEQ ID NO: 123:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 123:
        ACGGGTCATC AGCGCCGCAC CA        22

(2) INFORMATION FOR SEQ ID NO: 124:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 124:
        TGTCACCCCC CTCCCCGGAC TT        22

(2) INFORMATION FOR SEQ ID NO: 125:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 125:
        ACTCGCAATT ATTGGCGCTC GA        22

(2) INFORMATION FOR SEQ ID NO: 126:
    (i) SEQUENCE CHARACTERISTICS:
        (A) LENGTH: 22 base pairs
        (B) TYPE: nucleic acid
        (C) STRANDEDNESS: single

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
        (D) TOPOLOGY: linear
    (ii) MOLECULE TYPE: DNA
    (xi) SEQUENCE DESCRIPTION: SEQ ID NO: 126:
     GTCTTCTCAA CCTTATCCTG CG                              22

(2) INFORMATION FOR SEQ ID NO: 127:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 127:
     AAAGCCCCCT GCTAAACTCC CA                              22

(2) INFORMATION FOR SEQ ID NO: 128:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 128:
     CTGCGTCTGC CACGTCGTCA TC                              22

(2) INFORMATION FOR SEQ ID NO: 129:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 129:
     GTTAAAAGAG GGCAAGCTCG GA                              22

(2) INFORMATION FOR SEQ ID NO: 130:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 130:
     CCGAGTTCTT GATGTCCTCC AT                              22

(2) INFORMATION FOR SEQ ID NO: 131:
```

UNITED STATES PATENT AND TRADEMARK OFFICE
CERTIFICATE OF CORRECTION

PATENT NO.         : 7,053,177 B1
APPLICATION NO.    : 09/079678
DATED              : May 30, 2006
INVENTOR(S)        : Vernon L. Alvarez et al.

It is certified that error appears in the above-identified patent and that said Letters Patent is hereby corrected as shown below:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 131:
      TCCAATGCCT GTACCACGGA TG                              22

(2) INFORMATION FOR SEQ ID NO: 132:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 132:
      TCGCAACCGA TATCGTGCTT AT                              22

(2) INFORMATION FOR SEQ ID NO: 133:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 133:
      TGCATACACT GCTTGGAGCC CT                              22

(2) INFORMATION FOR SEQ ID NO: 134:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 134:
      GAAATCTCAC TAGTAGTCCG CC                              22

(2) INFORMATION FOR SEQ ID NO: 135:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (xi) SEQUENCE DESCRIPTION: SEQ ID NO: 135:
        GCGGGCAAGA CAGTCCAATT CC                              22

(2) INFORMATION FOR SEQ ID NO: 136:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 136:
        GAGCTCCAAT TCCACGACGA CC                              22

(2) INFORMATION FOR SEQ ID NO: 137:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 137:
        GGTTGCCATG CGTTCAAACT AC                              22

(2) INFORMATION FOR SEQ ID NO: 138:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 138:
        TCCCGCGGGG ACAAACCCGA AT                              22

(2) INFORMATION FOR SEQ ID NO: 139:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 139:
        CTGCTAGTCT TATCATTCCC CA                              22

(2) INFORMATION FOR SEQ ID NO: 140:
    (i) SEQUENCE CHARACTERISTICS:
        (A) LENGTH: 22 base pairs
```

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

```
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 140:
        CTATCGACAC TATAGGGCCT AC                          22

(2) INFORMATION FOR SEQ ID NO: 141:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 141:
        TACCCTTGTA ACCCACACTA GG                          22

(2) INFORMATION FOR SEQ ID NO: 142:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 142:
        TTCTTCTGAA TAGACCGGCC GA                          22

(2) INFORMATION FOR SEQ ID NO: 143:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 143:
        CCACCACCCT TAACCCGACA AT                          22

(2) INFORMATION FOR SEQ ID NO: 144:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 144:
        AGGGGGAGAC TTGTTCACAA AC                          22
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(2) INFORMATION FOR SEQ ID NO: 145:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 145:
    CGGCTCATAC CACCGAAAGC TA					22

(2) INFORMATION FOR SEQ ID NO: 146:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 146:
    ATCGTCCTAC TGTAATCCTC GA					22

(2) INFORMATION FOR SEQ ID NO: 147:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 147:
    GACACACTAC TCAGGTCCAC CT					22

(2) INFORMATION FOR SEQ ID NO: 148:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 148:
    CCATAATCAA CATTGCCGCC CT					22

(2) INFORMATION FOR SEQ ID NO: 149:
    (i) SEQUENCE CHARACTERISTICS:
        (A) LENGTH: 22 base pairs
        (B) TYPE: nucleic acid
        (C) STRANDEDNESS: single

UNITED STATES PATENT AND TRADEMARK OFFICE
CERTIFICATE OF CORRECTION

PATENT NO.      : 7,053,177 B1
APPLICATION NO. : 09/079678
DATED           : May 30, 2006
INVENTOR(S)     : Vernon L. Alvarez et al.

It is certified that error appears in the above-identified patent and that said Letters Patent is hereby corrected as shown below:

```
       (D) TOPOLOGY: linear
   (ii) MOLECULE TYPE: DNA
   (xi) SEQUENCE DESCRIPTION: SEQ ID NO: 149:
        CAAAACGCTC GCCCCAAACT CA                         22

(2) INFORMATION FOR SEQ ID NO: 150:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO: 150:
        GTAAACTTGT GCTTCTCGCA CC                         22

(2) INFORMATION FOR SEQ ID NO: 151:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO: 151:
        CCATGGTCCG GGTACACCTG AA                         22

(2) INFORMATION FOR SEQ ID NO: 152:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO: 152:
        GTTACTAACG GAACGAGACC TA                         22

(2) INFORMATION FOR SEQ ID NO: 153:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO: 153:
        TGTTGGCGTT CTCAACCCCG TT                         22

(2) INFORMATION FOR SEQ ID NO: 154:
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
   (i) SEQUENCE CHARACTERISTICS:
       (A) LENGTH: 22 base pairs
       (B) TYPE: nucleic acid
       (C) STRANDEDNESS: single
       (D) TOPOLOGY: linear
  (ii) MOLECULE TYPE: DNA
  (xi) SEQUENCE DESCRIPTION: SEQ ID NO: 154:
    ACAACCGGAG TTGTTCTGCC TA                                22

(2) INFORMATION FOR SEQ ID NO: 155:
    (i) SEQUENCE CHARACTERISTICS:
       (A) LENGTH: 22 base pairs
       (B) TYPE: nucleic acid
       (C) STRANDEDNESS: single
       (D) TOPOLOGY: linear
   (ii) MOLECULE TYPE: DNA
   (xi) SEQUENCE DESCRIPTION: SEQ ID NO: 155:
    TAAGCATCGG CCACGTTCTT CG                                22

(2) INFORMATION FOR SEQ ID NO: 156:
    (i) SEQUENCE CHARACTERISTICS:
       (A) LENGTH: 22 base pairs
       (B) TYPE: nucleic acid
       (C) STRANDEDNESS: single
       (D) TOPOLOGY: linear
   (ii) MOLECULE TYPE: DNA
   (xi) SEQUENCE DESCRIPTION: SEQ ID NO: 156:
    TTATCCCTGG TGTGCAGGTT GA                                22

(2) INFORMATION FOR SEQ ID NO: 157:
    (i) SEQUENCE CHARACTERISTICS:
       (A) LENGTH: 22 base pairs
       (B) TYPE: nucleic acid
       (C) STRANDEDNESS: single
       (D) TOPOLOGY: linear
   (ii) MOLECULE TYPE: DNA
   (xi) SEQUENCE DESCRIPTION: SEQ ID NO: 157:
    TATCAGAATC GTAGTCGGAC GG                                22

(2) INFORMATION FOR SEQ ID NO: 158:
    (i) SEQUENCE CHARACTERISTICS:
       (A) LENGTH: 22 base pairs
       (B) TYPE: nucleic acid
       (C) STRANDEDNESS: single
       (D) TOPOLOGY: linear
   (ii) MOLECULE TYPE: DNA
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (xi) SEQUENCE DESCRIPTION: SEQ ID NO: 158:
        CTTTGTAATG GAACCACAAC CC                              22

(2) INFORMATION FOR SEQ ID NO: 159:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 159:
        CGGTGGCTCA TCTCCCTCTT AT                              22

(2) INFORMATION FOR SEQ ID NO: 160:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 160:
        ATCAGACTGG CTGGGACCAC AA                              22

(2) INFORMATION FOR SEQ ID NO: 161:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 161:
        CACAACCTCC TCTCCGCGAA CT                              22

(2) INFORMATION FOR SEQ ID NO: 162:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 162:
        AGATTCGTCC CCAACGCGTG AT                              22

(2) INFORMATION FOR SEQ ID NO: 163:
    (i) SEQUENCE CHARACTERISTICS:
        (A) LENGTH: 22 base pairs
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 163:
      GGGAATTCGC AAAGCTATAC TC                                   22

(2) INFORMATION FOR SEQ ID NO: 164:
    (i) SEQUENCE CHARACTERISTICS:
        (A) LENGTH: 22 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 164:
      CCCCGTGGAA TTCAACCTGT GA                                   22

(2) INFORMATION FOR SEQ ID NO: 165:
    (i) SEQUENCE CHARACTERISTICS:
        (A) LENGTH: 17 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 165:
      GTCGTCTTTC CAGACGT                                         17

(2) INFORMATION FOR SEQ ID NO: 166:
    (i) SEQUENCE CHARACTERISTICS:
        (A) LENGTH: 21 base pairs
        (B) TYPE: nucleic acid
        (C) STRANDEDNESS: single
        (D) TOPOLOGY: linear
    (ii) MOLECULE TYPE: DNA
    (xi) SEQUENCE DESCRIPTION: SEQ ID NO: 166:
      CTTGCATGCC TGCAGGTCGA C                                    21

(2) INFORMATION FOR SEQ ID NO: 167:
    (i) SEQUENCE CHARACTERISTICS:
        (A) LENGTH: 37 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 167:
      Arg Ile Ala Gly Leu Pro Trp Tyr Arg Cys Arg Thr Val Ala Phe Glu
```

UNITED STATES PATENT AND TRADEMARK OFFICE
CERTIFICATE OF CORRECTION

PATENT NO.        : 7,053,177 B1
APPLICATION NO.   : 09/079678
DATED             : May 30, 2006
INVENTOR(S)       : Vernon L. Alvarez et al.

It is certified that error appears in the above-identified patent and that said Letters Patent is hereby corrected as shown below:

```
         1           5          10          15
    Thr Gly Met Gln Asn Thr Gln Leu Cys Ser Thr Ile Val Gln Leu Ser
            20          25          30
    Phe Thr Pro Glu Glu
         35
```

(2) INFORMATION FOR SEQ ID NO: 168:
  (i) SEQUENCE CHARACTERISTICS:
    (A) LENGTH: 44 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 168:

```
    Arg Glu Phe Ala Glu Arg Arg Leu Trp Gly Cys Asp Asp Leu Ser Trp
         1           5          10          15
    Arg Leu Asp Ala Glu Gly Cys Gly Pro Thr Pro Ser Asn Arg Ala Val
            20          25          30
    Lys His Arg Lys Pro Arg Pro Arg Ser Pro Ala Leu
         35          40
```

(2) INFORMATION FOR SEQ ID NO: 169:
  (i) SEQUENCE CHARACTERISTICS:
    (A) LENGTH: 41 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 169:

```
    Ser Gly Ser His Ser Gly Gly Met Asn Arg Ala Tyr Gly Asp Val Phe
         1           5          10          15
    Arg Glu Leu Arg Asp Arg Trp Tyr Ala Thr Ser His His Thr Arg Pro
            20          25          30
    Thr Pro Gln Leu Pro Arg Gly Pro Asn
         35          40
```

(2) INFORMATION FOR SEQ ID NO: 170:
  (i) SEQUENCE CHARACTERISTICS:
    (A) LENGTH: 20 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 170:

```
    Ser Thr Pro Pro Ser Arg Glu Ala Tyr Ser Arg Pro Tyr Ser Val Asp
         1           5          10          15
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
    Ser Asp Ser Asp
         20

(2) INFORMATION FOR SEQ ID NO: 171:
    (i) SEQUENCE CHARACTERISTICS:
        (A) LENGTH: 29 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 171:
     Ser Thr Pro Pro Ser Arg Glu Ala Tyr Ser Arg Pro Tyr Ser Val Asp
     1           5              10              15
     Ser Asp Ser Asp Thr Asn Ala Lys His Ser Ser His Asn
         20              25

(2) INFORMATION FOR SEQ ID NO: 172:
    (i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 172:
     Thr Asn Ala Lys His Ser Ser His Asn Arg Arg Leu Arg Thr Arg Ser
     1           5              10              15
     Arg Pro Asn (2) INFORMATION FOR SEQ ID NO: 173:
    (i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 173:
     Thr Asn Ala Lys His Ser Ser His Asn
     1           5

(2) INFORMATION FOR SEQ ID NO: 174:
    (i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown
    (ii) MOLECULE TYPE: peptide
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (xi) SEQUENCE DESCRIPTION: SEQ ID NO: 174:
    Ser Ser His Asn Arg Arg Leu Arg Thr Arg Ser Arg Pro Asn
     1           5              10

(2) INFORMATION FOR SEQ ID NO: 175:
    (i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 175:
    Arg Arg Leu Arg Thr Arg Ser Arg Pro Asn
     1           5              10

(2) INFORMATION FOR SEQ ID NO: 176:
    (i) SEQUENCE CHARACTERISTICS:
        (A) LENGTH: 708 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 176:
    Met Gly Met Ser Lys Ser His Ser Phe Phe Gly Tyr Pro Leu Ser Ile
     1               5              10              15
    Phe Phe Ile Val Val Asn Glu Phe Cys Glu Arg Phe Ser Tyr Tyr Gly
                20              25              30
    Met Arg Ala Ile Leu Ile Leu Tyr Phe Thr Asn Phe Ile Ser Trp Asp
            35              40              45
    Asp Asn Leu Ser Thr Ala Ile Tyr His Thr Phe Val Ala Leu Cys Tyr
        50              55              60
    Leu Thr Pro Ile Leu Gly Ala Leu Ile Ala Asp Ser Trp Leu Gly Lys
    65              70              75              80
    Phe Lys Thr Ile Val Ser Leu Ser Ile Val Tyr Thr Ile Gly Gln Ala
                85              90              95
    Val Thr Ser Val Ser Ser Ile Asn Asp Leu Thr Asp His Asn His Asp
                100             105             110
    Gly Thr Pro Asp Ser Leu Pro Val His Val Val Leu Ser Leu Ile Gly
            115             120             125
    Leu Ala Leu Ile Ala Leu Gly Thr Gly Gly Ile Lys Pro Cys Val Ser
        130             135             140
    Ala Phe Gly Gly Asp Gln Phe Glu Glu Gly Gln Glu Lys Gln Arg Asn
    145             150             155             160
    Arg Phe Phe Ser Ile Phe Tyr Leu Ala Ile Asn Ala Gly Ser Leu Leu
                165             170             175
    Ser Thr Ile Ile Thr Pro Met Leu Arg Val Gln Gln Cys Gly Ile His
```

Page 43 of 159

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
              180             185             190
Ser Lys Gln Ala Cys Tyr Pro Leu Ala Phe Gly Val Pro Ala Ala Leu
       195             200             205
Met Ala Val Ala Leu Ile Val Phe Val Leu Gly Ser Gly Met Tyr Lys
       210             215             220
Lys Phe Lys Pro Gln Gly Asn Ile Met Gly Lys Val Ala Lys Cys Ile
 225             230             235             240
Gly Phe Ala Ile Lys Asn Arg Phe Arg His Arg Ser Lys Ala Phe Pro
               245             250             255
Lys Arg Glu His Trp Leu Asp Trp Ala Lys Glu Lys Tyr Asp Glu Arg
           260             265             270
Leu Ile Ser Gln Ile Lys Met Val Thr Arg Val Met Phe Leu Tyr Ile
         275             280             285
Pro Leu Pro Met Phe Trp Ala Leu Phe Asp Gln Gln Gly Ser Arg Trp
       290             295             300
Thr Leu Gln Ala Thr Thr Met Ser Gly Lys Ile Gly Ala Leu Glu Ile
 305             310             315             320
Gln Pro Asp Gln Met Gln Thr Val Asn Ala Ile Leu Ile Val Ile Met
             325             330             335
Val Pro Ile Phe Asp Ala Val Leu Tyr Pro Leu Ile Ala Lys Cys Gly
           340             345             350
Phe Asn Phe Thr Ser Leu Lys Lys Met Ala Val Gly Met Val Leu Ala
         355             360             365
Ser Met Ala Phe Val Val Ala Ala Ile Val Gln Val Glu Ile Asp Lys
       370             375             380
Thr Leu Pro Val Phe Pro Lys Gly Asn Glu Val Gln Ile Lys Val Leu
 385             390             395             400
Asn Ile Gly Asn Asn Thr Met Asn Ile Ser Leu Pro Gly Glu Met Val
             405             410             415
Thr Leu Gly Pro Met Ser Gln Thr Asn Ala Phe Met Thr Phe Asp Val
           420             425             430
Asn Lys Leu Thr Arg Ile Asn Ile Ser Ser Pro Gly Ser Pro Val Thr
         435             440             445
Ala Val Thr Asp Asp Phe Lys Gln Gly Gln Arg His Thr Leu Leu Val
       450             455             460
Trp Ala Pro Asn His Tyr Gln Val Val Lys Asp Gly Leu Asn Gln Lys
 465             470             475             480
Pro Glu Lys Gly Glu Asn Gly Ile Arg Phe Val Asn Thr Phe Asn Glu
             485             490             495
Leu Ile Thr Ile Thr Met Ser Gly Lys Val Tyr Ala Asn Ile Ser Ser
         500             505             510
Tyr Asn Ala Ser Thr Tyr Gln Phe Phe Pro Ser Gly Ile Lys Gly Phe
       515             520             525
Thr Ile Ser Ser Thr Glu Ile Pro Pro Gln Cys Gln Pro Asn Phe Asn
   530             535             540
Thr Phe Tyr Leu Glu Phe Gly Ser Ala Tyr Thr Tyr Ile Val Gln Arg
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
              545       550       555       560
     Lys Asn Asp Ser Cys Pro Glu Val Lys Val Phe Glu Asp Ile Ser Ala
              565       570       575
     Asn Thr Val Asn Met Ala Leu Gln Ile Pro Gln Tyr Phe Leu Leu Thr
              580       585       590
     Cys Gly Glu Val Val Phe Ser Val Thr Gly Leu Glu Phe Ser Tyr Ser
              595       600       605
     Gln Ala Pro Ser Asn Met Lys Ser Val Leu Gln Ala Gly Trp Leu Leu
              610       615       620
     Thr Val Ala Val Gly Asn Ile Ile Val Leu Ile Val Ala Gly Ala Gly
              625       630       635       640
     Gln Phe Ser Lys Gln Trp Ala Glu Tyr Ile Leu Phe Ala Ala Leu Leu
              645       650       655
     Leu Val Val Cys Val Val Phe Ala Ile Met Ala Arg Phe Tyr Thr Tyr
              660       665       670
     Ile Asn Pro Ala Glu Ile Glu Ala Gln Phe Asp Glu Asp Glu Lys Lys
              675       680       685
     Asn Arg Leu Glu Lys Ser Asn Pro Tyr Phe Met Ser Gly Ala Asn Ser
              690       695       700
     Gln Lys Gln Met
              705
```

(2) INFORMATION FOR SEQ ID NO: 177:
 (i) SEQUENCE CHARACTERISTICS:
  (A) LENGTH: 3345 base pairs
  (B) TYPE: nucleic acid
  (C) STRANDEDNESS: single
  (D) TOPOLOGY: linear
 (ii) MOLECULE TYPE: DNA
 (ix) FEATURE:
  (A) NAME/KEY: Coding Sequence
  (B) LOCATION: 88...2583
  (D) OTHER INFORMATION:
 (xi) SEQUENCE DESCRIPTION: SEQ ID NO: 177:
  GAATTCCGTC TCGACCACTG AATGGAAGAA AAGGACTTTT AACCACCATT TTGTGACTTA  60
  CAGAAAGGAA TTTGAATAAA GAAAACT ATG ATA CTT CAG GCC CAT CTT CAC TCC  114
                              Met Ile Leu Gln Ala His Leu His Ser
                                1               5
  CTG TGT CTT CTT ATG CTT TAT TTG GCA ACT GGA TAT GGC CAA GAG GGG  162
  Leu Cys Leu Leu Met Leu Tyr Leu Ala Thr Gly Tyr Gly Gln Glu Gly
       10              15                  20          25
  AAG TTT AGT GGA CCC CTG AAA CCC ATG ACA TTT TCT ATT TAT GAA GGC  210
  Lys Phe Ser Gly Pro Leu Lys Pro Met Thr Phe Ser Ile Tyr Glu Gly
           30              35              40

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
CAA GAA CCG AGT CAA ATT ATA TTC CAG TTT AAG GCC AAT CCT CCT GCT    258
Gln Glu Pro Ser Gln Ile Ile Phe Gln Phe Lys Ala Asn Pro Pro Ala
         45              50              55
GTG ACT TTT GAA CTA ACT GGG GAG ACA GAC AAC ATA TTT GTG ATA GAA    306
Val Thr Phe Glu Leu Thr Gly Glu Thr Asp Asn Ile Phe Val Ile Glu
         60              65              70
CGG GAG GGA CTT CTG TAT TAC AAC AGA GCC TTG GAC AGG GAA ACA AGA    354
Arg Glu Gly Leu Leu Tyr Tyr Asn Arg Ala Leu Asp Arg Glu Thr Arg
         75              80              85
TCT ACT CAC AAT CTC CAG GTT GCA GCC CTG GAC GCT AAT GGA ATT ATA    402
Ser Thr His Asn Leu Gln Val Ala Ala Leu Asp Ala Asn Gly Ile Ile
         90              95             100             105
GTG GAG GGT CCA GTC CCT ATC ACC ATA GAA GTG AAG GAC ATC AAC GAC    450
Val Glu Gly Pro Val Pro Ile Thr Ile Glu Val Lys Asp Ile Asn Asp
        110             115             120
AAT CGA CCC ACG TTT CTC CAG TCA AAG TAC GAA GGC TCA GTA AGG CAG    498
Asn Arg Pro Thr Phe Leu Gln Ser Lys Tyr Glu Gly Ser Val Arg Gln
        125             130             135
AAC TCT CGC CCA GGA AAG CCC TTC TTG TAT GTC AAT GCC ACA GAC CTG    546
Asn Ser Arg Pro Gly Lys Pro Phe Leu Tyr Val Asn Ala Thr Asp Leu
        140             145             150
GAT GAT CCG GCC ACT CCC AAT GGC CAG CTT TAT TAC CAG ATT GTC ATC    594
Asp Asp Pro Ala Thr Pro Asn Gly Gln Leu Tyr Tyr Gln Ile Val Ile
        155             160             165
CAG CTT CCC ATG ATC AAC AAT GTC ATG TAC TTT CAG ATC AAC AAC AAA    642
Gln Leu Pro Met Ile Asn Asn Val Met Tyr Phe Gln Ile Asn Asn Lys
170             175             180             185
ACG GGA GCC ATC TCT CTT ACC CGA GAG GGA TCT CAG GAA TTG AAT CCT    690
Thr Gly Ala Ile Ser Leu Thr Arg Glu Gly Ser Gln Glu Leu Asn Pro
        190             195             200
GCT AAG AAT CCT TCC TAT AAT CTG GTG ATC TCA GTG AAG GAC ATG GGA    738
Ala Lys Asn Pro Ser Tyr Asn Leu Val Ile Ser Val Lys Asp Met Gly
        205             210             215
GGC CAG AGT GAG AAT TCC TTC AGT GAT ACC ACA TCT GTG GAT ATC ATA    786
Gly Gln Ser Glu Asn Ser Phe Ser Asp Thr Thr Ser Val Asp Ile Ile
        220             225             230
GTG ACA GAG AAT ATT TGG AAA GCA CCA AAA CCT GTG GAG ATG GTG GAA    834
Val Thr Glu Asn Ile Trp Lys Ala Pro Lys Pro Val Glu Met Val Glu
        235             240             245
AAC TCA ACT GAT CCT CAC CCC ATC AAA ATC ACT CAG GTG CGG TGG AAT    882
Asn Ser Thr Asp Pro His Pro Ile Lys Ile Thr Gln Val Arg Trp Asn
250             255             260             265
GAT CCC GGT GCA CAA TAT TCC TTA GTT GAC AAA GAG AAG CTG CCA AGA    930
Asp Pro Gly Ala Gln Tyr Ser Leu Val Asp Lys Glu Lys Leu Pro Arg
        270             275             280
TTC CCA TTT TCA ATT GAC CAG GAA GGA GAT ATT TAC GTG ACT CAG CCC    978
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
Phe Pro Phe Ser Ile Asp Gln Glu Gly Asp Ile Tyr Val Thr Gln Pro
        285             290             295
TTG GAC CGA GAA GAA AAG GAT GCA TAT GTT TTT TAT GCA GTT GCA AAG   1026
Leu Asp Arg Glu Glu Lys Asp Ala Tyr Val Phe Tyr Ala Val Ala Lys
    300             305             310
GAT GAG TAC GGA AAA CCA CTT TCA TAT CCG CTG GAA ATT CAT GTA AAA   1074
Asp Glu Tyr Gly Lys Pro Leu Ser Tyr Pro Leu Glu Ile His Val Lys
    315             320             325
GTT AAA GAT ATT AAT GAT AAT CCA CCT ACA TGT CCG TCA CCA GTA ACC   1122
Val Lys Asp Ile Asn Asp Asn Pro Pro Thr Cys Pro Ser Pro Val Thr
330             335             340             345
GTA TTT GAG GTC CAG GAG AAT GAA CGA CTG GGT AAC AGT ATC GGG ACC   1170
Val Phe Glu Val Gln Glu Asn Glu Arg Leu Gly Asn Ser Ile Gly Thr
        350             355             360
CTT ACT GCA CAT GAC AGG GAT GAA GAA AAT ACT GCC AAC AGT TTT CTA   1218
Leu Thr Ala His Asp Arg Asp Glu Glu Asn Thr Ala Asn Ser Phe Leu
    365             370             375
AAC TAC AGG ATT GTG GAG CAA ACT CCC AAA CTT CCC ATG GAT GGA CTC   1266
Asn Tyr Arg Ile Val Glu Gln Thr Pro Lys Leu Pro Met Asp Gly Leu
    380             385             390
TTC CTA ATC CAA ACC TAT GCT GGA ATG TTA CAG TTA GCT AAA CAG TCC   1314
Phe Leu Ile Gln Thr Tyr Ala Gly Met Leu Gln Leu Ala Lys Gln Ser
    395             400             405
TTG AAG AAG CAA GAT ACT CCT CAG TAC AAC TTA ACG ATA GAG GTG TCT   1362
Leu Lys Lys Gln Asp Thr Pro Gln Tyr Asn Leu Thr Ile Glu Val Ser
410             415             420             425
GAC AAA GAT TTC AAG ACC CTT TGT TTT GTG CAA ATC AAC GTT ATT GAT   1410
Asp Lys Asp Phe Lys Thr Leu Cys Phe Val Gln Ile Asn Val Ile Asp
        430             435             440
ATC AAT GAT CAG ATC CCC ATC TTT GAA AAA TCA GAT TAT GGA AAC CTG   1458
Ile Asn Asp Gln Ile Pro Ile Phe Glu Lys Ser Asp Tyr Gly Asn Leu
    445             450             455
ACT CTT GCT GAA GAC ACA AAC ATT GGG TCC ACC ATC TTA ACC ATC CAG   1506
Thr Leu Ala Glu Asp Thr Asn Ile Gly Ser Thr Ile Leu Thr Ile Gln
    460             465             470
GCC ACT GAT GCT GAT GAG CCA TTT ACT GGG AGT TCT AAA ATT CTG TAT   1554
Ala Thr Asp Ala Asp Glu Pro Phe Thr Gly Ser Ser Lys Ile Leu Tyr
    475             480             485
CAT ATC ATA AAG GGA GAC AGT GAG GGA CGC CTG GGG GTT GAC ACA GAT   1602
His Ile Ile Lys Gly Asp Ser Glu Gly Arg Leu Gly Val Asp Thr Asp
490             495             500             505
CCC CAT ACC AAC ACC GGA TAT GTC ATA ATT AAA AAG CCT CTT GAT TTT   1650
Pro His Thr Asn Thr Gly Tyr Val Ile Ile Lys Lys Pro Leu Asp Phe
        510             515             520
GAA ACA GCA GCT GTT TCC AAC ATT GTG TTC AAA GCA GAA AAT CCT GAG   1698
Glu Thr Ala Ala Val Ser Asn Ile Val Phe Lys Ala Glu Asn Pro Glu
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
           525           530           535
CCT CTA GTG TTT GGT GTG AAG TAC AAT GCA AGT TCT TTT GCC AAG TTC   1746
Pro Leu Val Phe Gly Val Lys Tyr Asn Ala Ser Ser Phe Ala Lys Phe
        540           545           550
ACG CTT ATT GTG ACA GAT GTG AAT GAA GCA CCT CAA TTT TCC CAA CAC   1794
Thr Leu Ile Val Thr Asp Val Asn Glu Ala Pro Gln Phe Ser Gln His
     555           560           565
GTA TTC CAA GCG AAA GTC AGT GAG GAT GTA GCT ATA GGC ACT AAA GTG   1842
Val Phe Gln Ala Lys Val Ser Glu Asp Val Ala Ile Gly Thr Lys Val
 570           575           580           585
GGC AAT GTG ACT GCC AAG GAT CCA GAA GGT CTG GAC ATA AGC TAT TCA   1890
Gly Asn Val Thr Ala Lys Asp Pro Glu Gly Leu Asp Ile Ser Tyr Ser
           590           595           600
CTG AGG GGA GAC ACA AGA GGT TGG CTT AAA ATT GAC CAC GTG ACT GGT   1938
Leu Arg Gly Asp Thr Arg Gly Trp Leu Lys Ile Asp His Val Thr Gly
        605           610           615
GAG ATC TTT AGT GTG GCT CCA TTG GAC AGA GAA GCC GGA AGT CCA TAT   1986
Glu Ile Phe Ser Val Ala Pro Leu Asp Arg Glu Ala Gly Ser Pro Tyr
     620           625           630
CGG GTA CAA GTG GTG GCC ACA GAA GTA GGG GGG TCT TCC TTA AGC TCT   2034
Arg Val Gln Val Val Ala Thr Glu Val Gly Gly Ser Ser Leu Ser Ser
 635           640           645
GTG TCA GAG TTC CAC CTG ATC CTT ATG GAT GTG AAT GAC AAC CCT CCC   2082
Val Ser Glu Phe His Leu Ile Leu Met Asp Val Asn Asp Asn Pro Pro
650           655           660           665
AGG CTA GCC AAG GAC TAC ACG GGC TTG TTC TTC TGC CAT CCC CTC AGT   2130
Arg Leu Ala Lys Asp Tyr Thr Gly Leu Phe Phe Cys His Pro Leu Ser
        670           675           680
GCA CCT GGA AGT CTC ATT TTC GAG GCT ACT GAT GAT GAT CAG CAC TTA   2178
Ala Pro Gly Ser Leu Ile Phe Glu Ala Thr Asp Asp Asp Gln His Leu
     685           690           695
TTT CGG GGT CCC CAT TTT ACA TTT TCC CTC GGC AGT GGA AGC TTA CAA   2226
Phe Arg Gly Pro His Phe Thr Phe Ser Leu Gly Ser Gly Ser Leu Gln
 700           705           710
AAC GAC TGG GAA GTT TCC AAA ATC AAT GGT ACT CAT GCC CGA CTG TCT   2274
Asn Asp Trp Glu Val Ser Lys Ile Asn Gly Thr His Ala Arg Leu Ser
715           720           725
ACC AGG CAC ACA GAC TTT GAG GAG AGG GCG TAT GTC GTC TTG ATC CGC   2322
Thr Arg His Thr Asp Phe Glu Glu Arg Ala Tyr Val Val Leu Ile Arg
730           735           740           745
ATC AAT GAT GGG GGT CGG CCA CCC TTG GAA GGC ATT GTT TCT TTA CCA   2370
Ile Asn Asp Gly Gly Arg Pro Pro Leu Glu Gly Ile Val Ser Leu Pro
        750           755           760
GTT ACA TTC TGC AGT TGT GTG GAA GGA AGT TGT TTC CGG CCA GCA GGT   2418
Val Thr Phe Cys Ser Cys Val Glu Gly Ser Cys Phe Arg Pro Ala Gly
     765           770           775
```

UNITED STATES PATENT AND TRADEMARK OFFICE
CERTIFICATE OF CORRECTION

PATENT NO.         : 7,053,177 B1
APPLICATION NO.    : 09/079678
DATED              : May 30, 2006
INVENTOR(S)        : Vernon L. Alvarez et al.

It is certified that error appears in the above-identified patent and that said Letters Patent is hereby corrected as shown below:

```
   CAC CAG ACT GGG ATA CCC ACT GTG GGC ATG GCA GTT GGT ATA CTG CTG   2466
   His Gln Thr Gly Ile Pro Thr Val Gly Met Ala Val Gly Ile Leu Leu
       780             785             790
   ACC ACC CTT CTG GTG ATT GGT ATA ATT TTA GCA GTT GTG TTT ATC CGC   2514
   Thr Thr Leu Leu Val Ile Gly Ile Ile Leu Ala Val Val Phe Ile Arg
       795             800             805
   ATA AAG AAG GAT AAA GGC AAA GAT AAT GTT GAA AGT GCT CAA GCA TCT   2562
   Ile Lys Lys Asp Lys Gly Lys Asp Asn Val Glu Ser Ala Gln Ala Ser
       810             815             820             825
   GAA GTC AAA CCT CTG AGA AGC TGAATTTGAA AAGGAATGTT TGAATTTATA TAGC
2617
   Glu Val Lys Pro Leu Arg Ser
               830
   AAGTGCTATT TCAGCAACAA CCATCTCATC CTATTACTTT TCATCTAACG
TGCATTATAA 2677
   TTTTTTAAAC AGATATTCCC TCTTGTCCTT TAATATTTGC TAAATATTTC TTTTTTGAGG
2737
   TGGAGTCTTG CTCTGTCGCC CAGGCTGGAG TACAGTGGTG TGATCCCAGC
TCACTGCAAC 2797
   CTCCGCCTCC TGGGTTCACA TGATTCTCCT GCCTCAGCTT CCTAAGTAGC
TGGGTTTACA 2857
   GGCACCCACC ACCATGCCCA GCTAATTTTT GTATTTTTAA TAGAGACGGG
GTTTCGCCAT 2917
   TTGGCCAGGC TGGTCTTGAA CTCCTGACGT CAAGTGATCT GCCTGCCTTG
GTCTCCCAAT 2977
   ACAGGCATGA ACCACTGCAC CCACCTACTT AGATATTTCA TGTGCTATAG
ACATTAGAGA 3037
   GATTTTTCAT TTTTCCATGA CATTTTTCCT CTCTGCAAAT GGCTTAGCTA CTTGTGTTTT
3097
   TCCCTTTTGG GGCAAGACAG ACTCATTAAA TATTCTGTAC ATTTTTTCTT
TATCAAGGAG 3157
   ATATATCAGT GTTGTCTCAT AGAACTGCCT GGATTCCATT TATGTTTTTT CTGATTCCAT
3217
   CCTGTGTCCC CTTCATCCTT GACTCCTTTG GTATTTCACT GAATTTCAAA CATTTGTCAG
3277
   AGAAGAAAAA AGTGAGGACT CAGGAAAAAT AAATAAATAA AAGAACAGCC
TTTTGCGGCC 3337
   GCGAATTC                              3345
```

(2) INFORMATION FOR SEQ ID NO: 178:
   (i) SEQUENCE CHARACTERISTICS:
      (A) LENGTH: 832 amino acids
      (B) TYPE: amino acid
      (C) STRANDEDNESS: <Unknown>
      (D) TOPOLOGY: unknown
   (ii) MOLECULE TYPE: protein

UNITED STATES PATENT AND TRADEMARK OFFICE
CERTIFICATE OF CORRECTION

PATENT NO.        : 7,053,177 B1
APPLICATION NO.   : 09/079678
DATED             : May 30, 2006
INVENTOR(S)       : Vernon L. Alvarez et al.

It is certified that error appears in the above-identified patent and that said Letters Patent is hereby corrected as shown below:

```
(xi) SEQUENCE DESCRIPTION: SEQ ID NO: 178:
 Met Ile Leu Gln Ala His Leu His Ser Leu Cys Leu Leu Met Leu Tyr
  1               5                  10                  15
 Leu Ala Thr Gly Tyr Gly Gln Glu Gly Lys Phe Ser Gly Pro Leu Lys
              20                  25                  30
 Pro Met Thr Phe Ser Ile Tyr Glu Gly Gln Glu Pro Ser Gln Ile Ile
                  35                  40                  45
 Phe Gln Phe Lys Ala Asn Pro Pro Ala Val Thr Phe Glu Leu Thr Gly
              50                  55                  60
 Glu Thr Asp Asn Ile Phe Val Ile Glu Arg Glu Gly Leu Leu Tyr Tyr
  65                  70                  75                  80
 Asn Arg Ala Leu Asp Arg Glu Thr Arg Ser Thr His Asn Leu Gln Val
                      85                  90                  95
 Ala Ala Leu Asp Ala Asn Gly Ile Ile Val Glu Gly Pro Val Pro Ile
                 100                 105                 110
 Thr Ile Glu Val Lys Asp Ile Asn Asp Asn Arg Pro Thr Phe Leu Gln
             115                 120                 125
 Ser Lys Tyr Glu Gly Ser Val Arg Gln Asn Ser Arg Pro Gly Lys Pro
             130                 135                 140
 Phe Leu Tyr Val Asn Ala Thr Asp Leu Asp Asp Pro Ala Thr Pro Asn
 145                 150                 155                 160
 Gly Gln Leu Tyr Tyr Gln Ile Val Ile Gln Leu Pro Met Ile Asn Asn
                 165                 170                 175
 Val Met Tyr Phe Gln Ile Asn Asn Lys Thr Gly Ala Ile Ser Leu Thr
                 180                 185                 190
 Arg Glu Gly Ser Gln Glu Leu Asn Pro Ala Lys Asn Pro Ser Tyr Asn
                 195                 200                 205
 Leu Val Ile Ser Val Lys Asp Met Gly Gly Gln Ser Glu Asn Ser Phe
 210                 215                 220
 Ser Asp Thr Thr Ser Val Asp Ile Ile Val Thr Glu Asn Ile Trp Lys
 225                 230                 235                 240
 Ala Pro Lys Pro Val Glu Met Val Glu Asn Ser Thr Asp Pro His Pro
                 245                 250                 255
 Ile Lys Ile Thr Gln Val Arg Trp Asn Asp Pro Gly Ala Gln Tyr Ser
                 260                 265                 270
 Leu Val Asp Lys Glu Lys Leu Pro Arg Phe Pro Phe Ser Ile Asp Gln
             275                 280                 285
 Glu Gly Asp Ile Tyr Val Thr Gln Pro Leu Asp Arg Glu Glu Lys Asp
             290                 295                 300
 Ala Tyr Val Phe Tyr Ala Val Ala Lys Asp Glu Tyr Gly Lys Pro Leu
 305                 310                 315                 320
 Ser Tyr Pro Leu Glu Ile His Val Lys Val Lys Asp Ile Asn Asp Asn
                 325                 330                 335
 Pro Pro Thr Cys Pro Ser Pro Val Thr Val Phe Glu Val Gln Glu Asn
                 340                 345                 350
 Glu Arg Leu Gly Asn Ser Ile Gly Thr Leu Thr Ala His Asp Arg Asp
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        355             360             365
Glu Glu Asn Thr Ala Asn Ser Phe Leu Asn Tyr Arg Ile Val Glu Gln
        370             375             380
Thr Pro Lys Leu Pro Met Asp Gly Leu Phe Leu Ile Gln Thr Tyr Ala
    385             390             395             400
Gly Met Leu Gln Leu Ala Lys Gln Ser Leu Lys Lys Gln Asp Thr Pro
            405             410             415
Gln Tyr Asn Leu Thr Ile Glu Val Ser Asp Lys Asp Phe Lys Thr Leu
        420             425             430
Cys Phe Val Gln Ile Asn Val Ile Asp Ile Asn Asp Gln Ile Pro Ile
        435             440             445
Phe Glu Lys Ser Asp Tyr Gly Asn Leu Thr Leu Ala Glu Asp Thr Asn
        450             455             460
Ile Gly Ser Thr Ile Leu Thr Ile Gln Ala Thr Asp Ala Asp Glu Pro
    465             470             475             480
Phe Thr Gly Ser Ser Lys Ile Leu Tyr His Ile Ile Lys Gly Asp Ser
            485             490             495
Glu Gly Arg Leu Gly Val Asp Thr Asp Pro His Thr Asn Thr Gly Tyr
        500             505             510
Val Ile Ile Lys Lys Pro Leu Asp Phe Glu Thr Ala Ala Val Ser Asn
        515             520             525
Ile Val Phe Lys Ala Glu Asn Pro Glu Pro Leu Val Phe Gly Val Lys
        530             535             540
Tyr Asn Ala Ser Ser Phe Ala Lys Phe Thr Leu Ile Val Thr Asp Val
    545             550             555             560
Asn Glu Ala Pro Gln Phe Ser Gln His Val Phe Gln Ala Lys Val Ser
            565             570             575
Glu Asp Val Ala Ile Gly Thr Lys Val Gly Asn Val Thr Ala Lys Asp
        580             585             590
Pro Glu Gly Leu Asp Ile Ser Tyr Ser Leu Arg Gly Asp Thr Arg Gly
        595             600             605
Trp Leu Lys Ile Asp His Val Thr Gly Glu Ile Phe Ser Val Ala Pro
        610             615             620
Leu Asp Arg Glu Ala Gly Ser Pro Tyr Arg Val Gln Val Val Ala Thr
    625             630             635             640
Glu Val Gly Gly Ser Ser Leu Ser Ser Val Ser Glu Phe His Leu Ile
            645             650             655
Leu Met Asp Val Asn Asp Asn Pro Pro Arg Leu Ala Lys Asp Tyr Thr
        660             665             670
Gly Leu Phe Phe Cys His Pro Leu Ser Ala Pro Gly Ser Leu Ile Phe
        675             680             685
Glu Ala Thr Asp Asp Asp Gln His Leu Phe Arg Gly Pro His Phe Thr
    690             695             700
Phe Ser Leu Gly Ser Gly Ser Leu Gln Asn Asp Trp Glu Val Ser Lys
    705             710             715             720
Ile Asn Gly Thr His Ala Arg Leu Ser Thr Arg His Thr Asp Phe Glu
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
                725           730           735
   Glu Arg Ala Tyr Val Val Leu Ile Arg Ile Asn Asp Gly Gly Arg Pro
            740           745           750
   Pro Leu Glu Gly Ile Val Ser Leu Pro Val Thr Phe Cys Ser Cys Val
          755           760           765
   Glu Gly Ser Cys Phe Arg Pro Ala Gly His Gln Thr Gly Ile Pro Thr
        770           775           780
   Val Gly Met Ala Val Gly Ile Leu Leu Thr Thr Leu Leu Val Ile Gly
   785           790           795           800
   Ile Ile Leu Ala Val Val Phe Ile Arg Ile Lys Lys Asp Lys Gly Lys
              805           810           815
   Asp Asn Val Glu Ser Ala Gln Ala Ser Glu Val Lys Pro Leu Arg Ser
            820           825           830
```

(2) INFORMATION FOR SEQ ID NO: 179:
   (i) SEQUENCE CHARACTERISTICS:
      (A) LENGTH: 1827 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 179:

```
    Met Ala Arg Lys Lys Phe Ser Gly Leu Glu Ile Ser Leu Ile Val Leu
    1             5             10            15
    Phe Val Ile Val Thr Ile Ile Ala Ile Ala Leu Ile Val Val Leu Ala
              20            25            30
    Thr Lys Thr Pro Ala Val Asp Glu Ile Ser Asp Ser Thr Ser Thr Pro
            35            40            45
    Ala Thr Thr Arg Val Thr Thr Asn Pro Ser Asp Ser Gly Lys Cys Pro
         50            55            60
    Asn Val Leu Asn Asp Pro Val Asn Val Arg Ile Asn Cys Ile Pro Glu
    65            70            75            80
    Gln Phe Pro Thr Glu Gly Ile Cys Ala Gln Arg Gly Cys Cys Trp Arg
                85            90            95
    Pro Trp Asn Asp Ser Leu Ile Pro Trp Cys Phe Phe Val Asp Asn His
              100           105           110
    Gly Tyr Asn Val Gln Asp Met Thr Thr Thr Ser Ile Gly Val Glu Ala
         115           120           125
    Lys Leu Asn Arg Ile Pro Ser Pro Thr Leu Phe Gly Asn Asp Ile Asn
        130           135           140
    Ser Val Leu Phe Thr Thr Gln Asn Gln Thr Pro Asn Arg Phe Arg Phe
    145           150           155           160
    Lys Ile Thr Asp Pro Asn Asn Arg Arg Tyr Glu Val Pro His Gln Tyr
                165           170           175
    Val Lys Glu Phe Thr Gly Pro Thr Val Ser Asp Thr Leu Tyr Asp Val
              180           185           190
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
Lys Val Ala Gln Asn Pro Phe Ser Ile Gln Val Ile Arg Lys Ser Asn
        195                 200                 205
Gly Lys Thr Leu Phe Asp Thr Ser Ile Gly Pro Leu Val Tyr Ser Asp
    210                 215                 220
Gln Tyr Leu Gln Ile Ser Ala Arg Leu Pro Ser Asp Tyr Ile Tyr Gly
225                 230                 235                 240
Ile Gly Glu Gln Val His Lys Arg Phe Arg His Asp Leu Ser Trp Lys
            245                 250                 255
Thr Trp Pro Ile Phe Thr Arg Asp Gln Leu Pro Gly Asp Asn Asn Asn
        260                 265                 270
Asn Leu Tyr Gly His Gln Thr Phe Phe Met Cys Ile Glu Asp Thr Ser
    275                 280                 285
Gly Lys Ser Phe Gly Val Phe Leu Met Asn Ser Asn Ala Met Glu Ile
    290                 295                 300
Phe Ile Gln Pro Thr Pro Ile Val Thr Tyr Arg Val Thr Gly Gly Ile
305                 310                 315                 320
Leu Asp Phe Tyr Ile Leu Leu Gly Asp Thr Pro Glu Gln Val Val Gln
            325                 330                 335
Gln Tyr Gln Gln Leu Val Gly Leu Pro Ala Met Pro Ala Tyr Trp Asn
        340                 345                 350
Leu Gly Phe Gln Leu Ser Arg Trp Asn Tyr Lys Ser Leu Asp Val Val
    355                 360                 365
Lys Glu Val Val Arg Arg Asn Arg Glu Ala Gly Ile Pro Phe Asp Thr
    370                 375                 380
Gln Val Thr Asp Ile Asp Tyr Met Glu Asp Lys Lys Asp Phe Thr Tyr
385                 390                 395                 400
Asp Gln Val Ala Phe Asn Gly Leu Pro Gln Phe Val Gln Asp Leu His
            405                 410                 415
Asp His Gly Gln Lys Tyr Val Ile Ile Leu Asp Pro Ala Ile Ser Ile
        420                 425                 430
Gly Arg Arg Ala Asn Gly Thr Thr Tyr Ala Thr Tyr Glu Arg Gly Asn
    435                 440                 445
Thr Gln His Val Trp Ile Asn Glu Ser Asp Gly Ser Thr Pro Ile Ile
    450                 455                 460
Gly Glu Val Trp Pro Gly Leu Thr Val Tyr Pro Asp Phe Thr Asn Pro
465                 470                 475                 480
Asn Cys Ile Asp Trp Trp Ala Asn Glu Cys Ser Ile Phe His Gln Glu
            485                 490                 495
Val Gln Tyr Asp Gly Leu Trp Ile Asp Met Asn Glu Val Ser Ser Phe
        500                 505                 510
Ile Gln Gly Ser Thr Lys Gly Cys Asn Val Asn Lys Leu Asn Tyr Pro
    515                 520                 525
Pro Phe Thr Pro Asp Ile Leu Asp Lys Leu Met Tyr Ser Lys Thr Ile
    530                 535                 540
Cys Met Asp Ala Val Gln Asn Trp Gly Lys Gln Tyr Asp Val His Ser
545                 550                 555                 560
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

Leu Tyr Gly Tyr Ser Met Ala Ile Ala Thr Glu Gln Ala Val Gln Lys
        565                570              575
Val Phe Pro Asn Lys Arg Ser Phe Ile Leu Thr Arg Ser Thr Phe Ala
     580               585              590
Gly Ser Gly Arg His Ala Ala His Trp Leu Gly Asp Asn Thr Ala Ser
       595             600            605
Trp Glu Gln Met Glu Trp Ser Ile Thr Gly Met Leu Glu Phe Ser Leu
   610               615              620
Phe Gly Ile Pro Leu Val Gly Ala Asp Ile Cys Gly Phe Val Ala Glu
625               630              635           640
Thr Thr Glu Glu Leu Cys Arg Arg Trp Met Gln Leu Gly Ala Phe Tyr
     645               650              655
Pro Phe Ser Arg Asn His Asn Ser Asp Gly Tyr Glu His Gln Asp Pro
       660             665            670
Ala Phe Phe Gly Gln Asn Ser Leu Leu Val Lys Ser Ser Arg Gln Tyr
   675               680              685
Leu Thr Ile Arg Tyr Thr Leu Leu Pro Phe Leu Tyr Thr Leu Phe Tyr
     690              695            700
Lys Ala His Val Phe Gly Glu Thr Val Ala Arg Pro Val Leu His Glu
705               710              715           720
Phe Tyr Glu Asp Thr Asn Ser Trp Ile Glu Asp Thr Glu Phe Leu Trp
     725               730            735
Gly Pro Ala Leu Leu Ile Thr Pro Val Leu Lys Gln Gly Ala Asp Thr
       740             745            750
Val Ser Ala Tyr Ile Pro Asp Ala Ile Trp Tyr Asp Tyr Glu Ser Gly
     755               760            765
Ala Lys Arg Pro Trp Arg Lys Gln Arg Val Asp Met Tyr Leu Pro Ala
770               775              780
Asp Lys Ile Gly Leu His Leu Arg Gly Gly Tyr Ile Ile Pro Ile Gln
785               790              795           800
Glu Pro Asp Val Thr Thr Thr Ala Ser Arg Lys Asn Pro Leu Gly Leu
       805             810            815
Ile Val Ala Leu Gly Glu Asn Asn Thr Ala Lys Gly Asp Phe Phe Trp
     820               825            830
Asp Asp Gly Glu Thr Lys Asp Thr Ile Gln Asn Gly Asn Tyr Ile Leu
     835               840            845
Tyr Thr Phe Ser Val Ser Asn Asn Thr Leu Asp Ile Val Cys Thr His
     850               855            860
Ser Ser Tyr Gln Glu Gly Thr Thr Leu Ala Phe Gln Thr Val Lys Ile
865               870              875           880
Leu Gly Leu Thr Asp Ser Val Thr Glu Val Arg Val Ala Glu Asn Asn
       885             890            895
Gln Pro Met Asn Ala His Ser Asn Phe Thr Tyr Asp Ala Ser Asn Gln
       900             905            910
Val Leu Leu Ile Ala Asp Leu Lys Leu Asn Leu Gly Arg Asn Phe Ser
     915               920            925

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
Val Gln Trp Asn Gln Ile Phe Ser Glu Asn Glu Arg Phe Asn Cys Tyr
      930             935             940
Pro Asp Ala Asp Leu Ala Thr Glu Gln Lys Cys Thr Gln Arg Gly Cys
945             950             955             960
Val Trp Arg Thr Gly Ser Ser Leu Ser Lys Ala Pro Glu Cys Tyr Phe
          965             970             975
Pro Arg Gln Asp Asn Ser Tyr Ser Val Asn Ser Ala Arg Tyr Ser Ser
          980             985             990
Met Gly Ile Thr Ala Asp Leu Gln Leu Asn Thr Ala Asn Ala Arg Ile
      995            1000            1005
Lys Leu Pro Ser Asp Pro Ile Ser Thr Leu Arg Val Glu Val Lys Tyr
     1010            1015            1020
His Lys Asn Asp Met Leu Gln Phe Lys Ile Tyr Asp Pro Gln Lys Lys
1025            1030            1035            1040
Arg Tyr Glu Val Pro Val Pro Leu Asn Ile Pro Thr Thr Pro Ile Ser
          1045            1050            1055
Thr Tyr Glu Asp Arg Leu Tyr Asp Val Glu Ile Lys Glu Asn Pro Phe
          1060            1065            1070
Gly Ile Gln Ile Arg Arg Arg Ser Ser Gly Arg Val Ile Trp Asp Ser
          1075            1080            1085
Trp Leu Pro Gly Phe Ala Phe Asn Asp Gln Phe Ile Gln Ile Ser Thr
     1090            1095            1100
Arg Leu Pro Ser Glu Tyr Ile Tyr Gly Phe Gly Glu Val Glu His Thr
1105            1110            1115            1120
Ala Phe Lys Arg Asp Leu Asn Trp Asn Thr Trp Gly Met Phe Thr Arg
          1125            1130            1135
Asp Gln Pro Pro Gly Tyr Lys Leu Asn Ser Tyr Gly Phe His Pro Tyr
          1140            1145            1150
Tyr Met Ala Leu Glu Glu Gly Asn Ala His Gly Val Phe Leu Leu
     1155            1160            1165
Asn Ser Asn Ala Met Asp Val Thr Phe Gln Pro Thr Pro Ala Leu Thr
     1170            1175            1180
Tyr Arg Thr Val Gly Gly Ile Leu Asp Phe Tyr Met Phe Leu Gly Pro
1185            1190            1195            1200
Thr Pro Gln Val Ala Thr Lys Gln Tyr His Glu Val Ile Gly His Pro
          1205            1210            1215
Val Met Pro Ala Tyr Trp Ala Leu Gly Phe Gln Leu Cys Arg Tyr Gly
          1220            1225            1230
Tyr Ala Asn Thr Ser Glu Val Arg Glu Leu Tyr Asp Ala Met Val Ala
     1235            1240            1245
Ala Asn Ile Pro Tyr Asp Val Gln Tyr Thr Asp Ile Asp Tyr Met Glu
     1250            1255            1260
Arg Gln Leu Asp Phe Thr Ile Gly Glu Ala Phe Gln Asp Leu Pro Gln
1265            1270            1275            1280
Phe Val Asp Lys Ile Arg Gly Glu Gly Met Arg Tyr Ile Ile Ile Leu
          1285            1290            1295
```

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

```
Asp Pro Ala Ile Ser Gly Asn Glu Thr Lys Thr Tyr Pro Ala Phe Glu
        1300            1305            1310
Arg Gly Gln Gln Asn Asp Val Phe Val Lys Trp Pro Asn Thr Asn Asp
    1315            1320            1325
Ile Cys Trp Ala Lys Val Trp Pro Asp Leu Pro Asn Ile Thr Ile Asp
    1330            1335            1340
Lys Thr Leu Thr Glu Asp Glu Ala Val Asn Ala Ser Arg Ala His Val
1345            1350            1355            1360
Ala Phe Pro Asp Phe Phe Arg Thr Ser Thr Ala Glu Trp Trp Ala Arg
        1365            1370            1375
Glu Ile Val Asp Phe Tyr Asn Glu Lys Met Lys Phe Asp Gly Leu Trp
        1380            1385            1390
Ile Asp Met Asn Glu Pro Ser Ser Phe Val Asn Gly Thr Thr Thr Asn
    1395            1400            1405
Gln Cys Arg Asn Asp Glu Leu Asn Tyr Pro Pro Tyr Phe Pro Glu Leu
    1410            1415            1420
Thr Lys Arg Thr Asp Gly Leu His Phe Arg Thr Ile Cys Met Glu Ala
1425            1430            1435            1440
Glu Gln Ile Leu Ser Asp Gly Thr Ser Val Leu His Tyr Asp Val His
        1445            1450            1455
Asn Leu Tyr Gly Trp Ser Gln Met Lys Pro Thr His Asp Ala Leu Gln
        1460            1465            1470
Lys Thr Thr Gly Lys Arg Gly Ile Val Ile Ser Arg Ser Thr Tyr Pro
    1475            1480            1485
Thr Ser Gly Arg Trp Gly Gly His Trp Leu Gly Asp Asn Tyr Ala Arg
1490            1495            1500
Trp Asp Asn Met Asp Lys Ser Ile Ile Gly Met Met Glu Phe Ser Leu
1505            1510            1515            1520
Phe Gly Ile Ser Tyr Thr Gly Ala Asp Ile Cys Gly Phe Phe Asn Asn
        1525            1530            1535
Ser Glu Tyr His Leu Cys Thr Arg Trp Met Gln Leu Gly Ala Phe Tyr
        1540            1545            1550
Pro Tyr Ser Arg Asn His Asn Ile Ala Asn Thr Arg Arg Gln Asp Pro
    1555            1560            1565
Ala Ser Trp Asn Glu Thr Phe Ala Glu Met Ser Arg Asn Ile Leu Asn
    1570            1575            1580
Ile Arg Tyr Thr Leu Leu Pro Tyr Phe Tyr Thr Gln Met His Glu Ile
1585            1590            1595            1600
His Ala Asn Gly Gly Thr Val Ile Arg Pro Leu Leu His Glu Phe Phe
        1605            1610            1615
Asp Glu Lys Pro Thr Trp Asp Ile Phe Lys Gln Phe Leu Trp Gly Pro
    1620            1625            1630
Ala Phe Met Val Thr Pro Val Leu Glu Pro Tyr Val Gln Thr Val Asn
    1635            1640            1645
Ala Tyr Val Pro Asn Ala Arg Trp Phe Asp Tyr His Thr Gly Lys Asp
    1650            1655            1660
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
Ile Gly Val Arg Gly Gln Phe Gln Thr Phe Asn Ala Ser Tyr Asp Thr
1665          1670           1675           1680
Ile Asn Leu His Val Arg Gly Gly His Ile Leu Pro Cys Gln Glu Pro
         1685          1690           1695
Ala Gln Asn Thr Phe Tyr Ser Arg Gln Lys His Met Lys Leu Ile Val
         1700          1705           1710
Ala Ala Asp Asp Asn Gln Met Ala Gln Gly Ser Leu Phe Trp Asp Asp
         1715          1720           1725
Gly Glu Ser Ile Asp Thr Tyr Glu Arg Asp Leu Tyr Leu Ser Val Gln
         1730          1735           1740
Phe Asn Leu Asn Gln Thr Thr Leu Thr Ser Thr Ile Leu Lys Arg Gly
1745          1750           1755           1760
Tyr Ile Asn Lys Ser Glu Thr Arg Leu Gly Ser Leu His Val Trp Gly
         1765          1770           1775
Lys Gly Thr Thr Pro Val Asn Ala Val Thr Leu Thr Tyr Asn Gly Asn
         1780          1785           1790
Lys Asn Ser Leu Pro Phe Asn Glu Asp Thr Thr Asn Met Ile Leu Arg
         1795          1800           1805
Ile Asp Leu Thr Thr His Asn Val Thr Leu Glu Glu Pro Ile Glu Ile
         1810          1815           1820
Asn Trp Ser
1825
```

(2) INFORMATION FOR SEQ ID NO: 180:
    (i) SEQUENCE CHARACTERISTICS:
        (A) LENGTH: 2284 base pairs
        (B) TYPE: nucleic acid
        (C) STRANDEDNESS: single
        (D) TOPOLOGY: linear
    (ii) MOLECULE TYPE: DNA
    (ix) FEATURE:
        (A) NAME/KEY: Coding Sequence
        (B) LOCATION: 45...2099
        (D) OTHER INFORMATION:
    (xi) SEQUENCE DESCRIPTION: SEQ ID NO: 180:

```
GCCTTACTGC AGGAAGGCAC TCCGAAGACA TAAGTCGGTG AGAC ATG GCT GAA GAT   56
                                             Met Ala Glu Asp
                                              1
AAA AGC AAG AGA GAC TCC ATC GAG ATG AGT ATG AAG GGA TGC CAG ACA   104
Lys Ser Lys Arg Asp Ser Ile Glu Met Ser Met Lys Gly Cys Gln Thr
 5           10              15              20
AAC AAC GGG TTT GTC CAT AAT GAA GAC ATT CTG GAG CAG ACC CCG GAT   152
Asn Asn Gly Phe Val His Asn Glu Asp Ile Leu Glu Gln Thr Pro Asp
         25              30              35
CCA GGC AGC TCA ACA GAC AAC CTG AAG CAC AGC ACC AGG GGC ATC CTT   200
```

UNITED STATES PATENT AND TRADEMARK OFFICE
CERTIFICATE OF CORRECTION

| | | |
|---|---|---|
| PATENT NO. | : 7,053,177 B1 | Page 58 of 159 |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
    Pro Gly Ser Ser Thr Asp Asn Leu Lys His Ser Thr Arg Gly Ile Leu
             40               45              50
    GGC TCC CAG GAG CCC GAC TTC AAG GGC GTC CAG CCC TAT GCG GGG ATG   248
    Gly Ser Gln Glu Pro Asp Phe Lys Gly Val Gln Pro Tyr Ala Gly Met
             55              60              65
    CCC AAG GAG GTG CTG TTC CAG TTC TCT GGC CAG GCC CGC TAC CGC ATA   296
    Pro Lys Glu Val Leu Phe Gln Phe Ser Gly Gln Ala Arg Tyr Arg Ile
         70              75              80
    CCT CGG GAG ATC CTC TTC TGG CTC ACA GTG GCT TCT GTG CTG GTG CTC   344
    Pro Arg Glu Ile Leu Phe Trp Leu Thr Val Ala Ser Val Leu Val Leu
    85              90              95              100
    ATC GCG GCC ACC ATA GCC ATC ATT GCC CTC TCT CCA AAG TGC CTA GAC   392
    Ile Ala Ala Thr Ile Ala Ile Ile Ala Leu Ser Pro Lys Cys Leu Asp
                 105             110             115
    TGG TGG CAG GAG GGG CCC ATG TAC CAG ATC TAC CCA AGG TCT TTC AAG   440
    Trp Trp Gln Glu Gly Pro Met Tyr Gln Ile Tyr Pro Arg Ser Phe Lys
             120             125             130
    GAC AGT AAC AAG GAT GGG AAC GGA GAT CTG AAA GGT ATT CAA GAT AAA   488
    Asp Ser Asn Lys Asp Gly Asn Gly Asp Leu Lys Gly Ile Gln Asp Lys
         135             140             145
    CTG GAC TAC ATC ACA GCT TTA AAT ATA AAA ACT GTT TGG ATT ACT TCA   536
    Leu Asp Tyr Ile Thr Ala Leu Asn Ile Lys Thr Val Trp Ile Thr Ser
         150             155             160
    TTT TAT AAA TCG TCC CTT AAA GAT TTC AGA TAT GGT GTT GAA GAT TTC   584
    Phe Tyr Lys Ser Ser Leu Lys Asp Phe Arg Tyr Gly Val Glu Asp Phe
    165             170             175             180
    CGG GAA GTT GAT CCC ATT TTT GGA ACG ATG GAA GAT TTT GAG AAT CTG   632
    Arg Glu Val Asp Pro Ile Phe Gly Thr Met Glu Asp Phe Glu Asn Leu
             185             190             195
    GTT GCA GCC ATA CAT GAT AAA GGT TTA AAA TTA ATC ATC GAT TTC ATA   680
    Val Ala Ala Ile His Asp Lys Gly Leu Lys Leu Ile Ile Asp Phe Ile
         200             205             210
    CCA AAC CAC ACG AGT GAT AAA CAT ATT TGG TTT CAA TTG AGT CGG ACA   728
    Pro Asn His Thr Ser Asp Lys His Ile Trp Phe Gln Leu Ser Arg Thr
         215             220             225
    CGG ACA GGA AAA TAT ACT GAT TAT TAT ATC TGG CAT GAC TGT ACC CAT   776
    Arg Thr Gly Lys Tyr Thr Asp Tyr Tyr Ile Trp His Asp Cys Thr His
         230             235             240
    GAA AAT GGC AAA ACC ATT CCA CCC AAC AAC TGG TTA AGT GTG TAT GGA   824
    Glu Asn Gly Lys Thr Ile Pro Pro Asn Asn Trp Leu Ser Val Tyr Gly
    245             250             255             260
    AAC TCC AGT TGG CAC TTT GAC GAA GTG CGA AAC CAA TGT TAT TTT CAT   872
    Asn Ser Ser Trp His Phe Asp Glu Val Arg Asn Gln Cys Tyr Phe His
                 265             270             275
    CAG TTT ATG AAA GAG CAA CCT GAT TTA AAT TTC CGC AAT CCT GAT GTT   920
    Gln Phe Met Lys Glu Gln Pro Asp Leu Asn Phe Arg Asn Pro Asp Val
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
            280         285         290
   CAA GAA GAA ATA AAA GAA ATT TTA CGG TTC TGG CTC ACA AAG GGT GTT    968
   Gln Glu Glu Ile Lys Glu Ile Leu Arg Phe Trp Leu Thr Lys Gly Val
        295         300         305
   GAT GGT TTT AGT TTG GAT GCT GTT AAA TTC CTC CTA GAA GCA AAG CAC   1016
   Asp Gly Phe Ser Leu Asp Ala Val Lys Phe Leu Leu Glu Ala Lys His
        310         315         320
   CTG AGA GAT GAG ATC CAA GTA AAT AAG ACC CAA ATC CCG GAC ACG GTC   1064
   Leu Arg Asp Glu Ile Gln Val Asn Lys Thr Gln Ile Pro Asp Thr Val
    325         330         335         340
   ACA CAA TAC TCG GAG CTG TAC CAT GAC TTC ACC ACC ACG CAG GTG GGA   1112
   Thr Gln Tyr Ser Glu Leu Tyr His Asp Phe Thr Thr Thr Gln Val Gly
            345         350         355
   ATG CAC GAC ATT GTC CGC AGC TTC CGG CAG ACC ATG GAC CAA TAC AGC   1160
   Met His Asp Ile Val Arg Ser Phe Arg Gln Thr Met Asp Gln Tyr Ser
        360         365         370
   ACG GAG CCC GGC AGA TAC AGG TTC ATG GGG ACT GAA GCC TAT GCA GAG   1208
   Thr Glu Pro Gly Arg Tyr Arg Phe Met Gly Thr Glu Ala Tyr Ala Glu
        375         380         385
   AGT ATT GAC AGG ACC GTG ATG TAC TAT GGA TTG CCA TTT ATC CAA GAA   1256
   Ser Ile Asp Arg Thr Val Met Tyr Tyr Gly Leu Pro Phe Ile Gln Glu
        390         395         400
   GCT GAT TTT CCC TTC AAC AAT TAC CTC AGC ATG CTA GAC ACT GTT TCT   1304
   Ala Asp Phe Pro Phe Asn Asn Tyr Leu Ser Met Leu Asp Thr Val Ser
    405         410         415         420
   GGG AAC AGC GTG TAT GAG GTT ATC ACA TCC TGG ATG GAA AAC ATG CCA   1352
   Gly Asn Ser Val Tyr Glu Val Ile Thr Ser Trp Met Glu Asn Met Pro
        425         430         435
   GAA GGA AAA TGG CCT AAC TGG ATG ATT GGT GGA CCA GAC AGT TCA CGG   1400
   Glu Gly Lys Trp Pro Asn Trp Met Ile Gly Gly Pro Asp Ser Ser Arg
        440         445         450
   CTG ACT TCG CGT TTG GGG AAT CAG TAT GTC AAC GTG ATG AAC ATG CTT   1448
   Leu Thr Ser Arg Leu Gly Asn Gln Tyr Val Asn Val Met Asn Met Leu
        455         460         465
   CTT TTC ACA CTC CCT GGA ACT CCT ATA ACT TAC TAT GGA GAA GAA ATT   1496
   Leu Phe Thr Leu Pro Gly Thr Pro Ile Thr Tyr Tyr Gly Glu Glu Ile
        470         475         480
   GGA ATG GGA AAT ATT GTA GCC GCA AAT CTC AAT GAA AGC TAT GAT ATT   1544
   Gly Met Gly Asn Ile Val Ala Ala Asn Leu Asn Glu Ser Tyr Asp Ile
    485         490         495         500
   AAT ACC CTT CGC TCA AAG TCA CCA ATG CAG TGG GAC AAT AGT TCA AAT   1592
   Asn Thr Leu Arg Ser Lys Ser Pro Met Gln Trp Asp Asn Ser Ser Asn
            505         510         515
   GCT GGT TTT TCT GAA GCT AGT AAC ACC TGG TTA CCT ACC AAT TCA GAT   1640
   Ala Gly Phe Ser Glu Ala Ser Asn Thr Trp Leu Pro Thr Asn Ser Asp
        520         525         530
```

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

```
TAC CAC ACT GTG AAT GTT GAT GTC CAA AAG ACT CAG CCC AGA TCG GCT   1688
Tyr His Thr Val Asn Val Asp Val Gln Lys Thr Gln Pro Arg Ser Ala
        535             540             545
TTG AAG TTA TAT CAA GAT TTA AGT CTA CTT CAT GCC AAT GAG CTA CTC   1736
Leu Lys Leu Tyr Gln Asp Leu Ser Leu Leu His Ala Asn Glu Leu Leu
        550             555             560
CTC AAC AGG GGC TGG TTT TGC CAT TTG AGG AAT GAC AGC CAC TAT GTT   1784
Leu Asn Arg Gly Trp Phe Cys His Leu Arg Asn Asp Ser His Tyr Val
565             570             575             580
GTG TAC ACA AGA GAG CTG GAT GGC ATC GAC AGA ATC TTT ATC GTG GTT   1832
Val Tyr Thr Arg Glu Leu Asp Gly Ile Asp Arg Ile Phe Ile Val Val
            585             590             595
CTG AAT TTT GGA GAA TCA ACA CTG TTA AAT CTA CAT AAT ATG ATT TCG   1880
Leu Asn Phe Gly Glu Ser Thr Leu Leu Asn Leu His Asn Met Ile Ser
            600             605             610
GGC CTT CCC GCT AAA ATA AGA ATA AGG TTA AGT ACC AAT TCT GCC GAC   1928
Gly Leu Pro Ala Lys Ile Arg Ile Arg Leu Ser Thr Asn Ser Ala Asp
        615             620             625
AAA GGC AGT AAA GTT GAT ACA AGT GGC ATT TTT CTG GAC AAG GGA GAG   1976
Lys Gly Ser Lys Val Asp Thr Ser Gly Ile Phe Leu Asp Lys Gly Glu
        630             635             640
GGA CTC ATC TTT GAA CAC AAC ACG AAG AAT CTC CTT CAT CGC CAA ACA   2024
Gly Leu Ile Phe Glu His Asn Thr Lys Asn Leu Leu His Arg Gln Thr
645             650             655             660
GCT TTC AGA GAT AGA TGC TTT GTT TCC AAT CGA GCA TGC TAT TCC AGT   2072
Ala Phe Arg Asp Arg Cys Phe Val Ser Asn Arg Ala Cys Tyr Ser Ser
            665             670             675
GTA CTG AAC ATA CTG TAT ACC TCG TGT TAGGCACCTT TATGAAGAGA TGAAGAC  2126
Val Leu Asn Ile Leu Tyr Thr Ser Cys
        680             685
ACTGGCATTT CAGTGGGATT GTAAGCATTT GTAATAGCTT CATGTACAGC
ATGCTGCTTG   2186
GTGAACAATC ATTAATTCTT CGATATTTCT GTAGCTTGAA TGTAACCGCT
TTAAGAAAGG   2246
TTCTCAAATG TTTTGAAAAA AATAAAATGT TTAAAAGT                         2284
```

(2) INFORMATION FOR SEQ ID NO: 181:
   (i) SEQUENCE CHARACTERISTICS:
     (A) LENGTH: 685 amino acids
     (B) TYPE: amino acid
     (C) STRANDEDNESS: <Unknown>
     (D) TOPOLOGY: unknown
  (ii) MOLECULE TYPE: protein
  (xi) SEQUENCE DESCRIPTION: SEQ ID NO: 181:
  Met Ala Glu Asp Lys Ser Lys Arg Asp Ser Ile Glu Met Ser Met Lys

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
      1           5          10          15
   Gly Cys Gln Thr Asn Asn Gly Phe Val His Asn Glu Asp Ile Leu Glu
           20          25          30
   Gln Thr Pro Asp Pro Gly Ser Ser Thr Asp Asn Leu Lys His Ser Thr
           35          40          45
   Arg Gly Ile Leu Gly Ser Gln Glu Pro Asp Phe Lys Gly Val Gln Pro
           50          55          60
   Tyr Ala Gly Met Pro Lys Glu Val Leu Phe Gln Phe Ser Gly Gln Ala
   65          70          75          80
   Arg Tyr Arg Ile Pro Arg Glu Ile Leu Phe Trp Leu Thr Val Ala Ser
               85          90          95
   Val Leu Val Leu Ile Ala Ala Thr Ile Ala Ile Ile Ala Leu Ser Pro
              100         105         110
   Lys Cys Leu Asp Trp Trp Gln Glu Gly Pro Met Tyr Gln Ile Tyr Pro
              115         120         125
   Arg Ser Phe Lys Asp Ser Asn Lys Asp Gly Asn Gly Asp Leu Lys Gly
              130         135         140
   Ile Gln Asp Lys Leu Asp Tyr Ile Thr Ala Leu Asn Ile Lys Thr Val
   145         150         155         160
   Trp Ile Thr Ser Phe Tyr Lys Ser Ser Leu Lys Asp Phe Arg Tyr Gly
               165         170         175
   Val Glu Asp Phe Arg Glu Val Asp Pro Ile Phe Gly Thr Met Glu Asp
              180         185         190
   Phe Glu Asn Leu Val Ala Ala Ile His Asp Lys Gly Leu Lys Leu Ile
              195         200         205
   Ile Asp Phe Ile Pro Asn His Thr Ser Asp Lys His Ile Trp Phe Gln
              210         215         220
   Leu Ser Arg Thr Arg Thr Gly Lys Tyr Thr Asp Tyr Tyr Ile Trp His
   225         230         235         240
   Asp Cys Thr His Glu Asn Gly Lys Thr Ile Pro Pro Asn Asn Trp Leu
               245         250         255
   Ser Val Tyr Gly Asn Ser Ser Trp His Phe Asp Glu Val Arg Asn Gln
              260         265         270
   Cys Tyr Phe His Gln Phe Met Lys Glu Gln Pro Asp Leu Asn Phe Arg
              275         280         285
   Asn Pro Asp Val Gln Glu Glu Ile Lys Glu Ile Leu Arg Phe Trp Leu
              290         295         300
   Thr Lys Gly Val Asp Gly Phe Ser Leu Asp Ala Val Lys Phe Leu Leu
   305         310         315         320
   Glu Ala Lys His Leu Arg Asp Glu Ile Gln Val Asn Lys Thr Gln Ile
               325         330         335
   Pro Asp Thr Val Thr Gln Tyr Ser Glu Leu Tyr His Asp Phe Thr Thr
              340         345         350
   Thr Gln Val Gly Met His Asp Ile Val Arg Ser Phe Arg Gln Thr Met
              355         360         365
   Asp Gln Tyr Ser Thr Glu Pro Gly Arg Tyr Arg Phe Met Gly Thr Glu
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
              370           375           380
   Ala Tyr Ala Glu Ser Ile Asp Arg Thr Val Met Tyr Tyr Gly Leu Pro
       385           390           395           400
   Phe Ile Gln Glu Ala Asp Phe Pro Phe Asn Asn Tyr Leu Ser Met Leu
              405           410           415
   Asp Thr Val Ser Gly Asn Ser Val Tyr Glu Val Ile Thr Ser Trp Met
             420           425           430
   Glu Asn Met Pro Glu Gly Lys Trp Pro Asn Trp Met Ile Gly Gly Pro
              435           440           445
   Asp Ser Ser Arg Leu Thr Ser Arg Leu Gly Asn Gln Tyr Val Asn Val
          450           455           460
   Met Asn Met Leu Leu Phe Thr Leu Pro Gly Thr Pro Ile Thr Tyr Tyr
   465           470           475           480
   Gly Glu Glu Ile Gly Met Gly Asn Ile Val Ala Ala Asn Leu Asn Glu
              485           490           495
   Ser Tyr Asp Ile Asn Thr Leu Arg Ser Lys Ser Pro Met Gln Trp Asp
             500           505           510
   Asn Ser Ser Asn Ala Gly Phe Ser Glu Ala Ser Asn Thr Trp Leu Pro
          515           520           525
   Thr Asn Ser Asp Tyr His Thr Val Asn Val Asp Val Gln Lys Thr Gln
          530           535           540
   Pro Arg Ser Ala Leu Lys Leu Tyr Gln Asp Leu Ser Leu Leu His Ala
   545           550           555           560
   Asn Glu Leu Leu Leu Asn Arg Gly Trp Phe Cys His Leu Arg Asn Asp
              565           570           575
   Ser His Tyr Val Val Tyr Thr Arg Glu Leu Asp Gly Ile Asp Arg Ile
             580           585           590
   Phe Ile Val Val Leu Asn Phe Gly Glu Ser Thr Leu Leu Asn Leu His
          595           600           605
   Asn Met Ile Ser Gly Leu Pro Ala Lys Ile Arg Ile Arg Leu Ser Thr
          610           615           620
   Asn Ser Ala Asp Lys Gly Ser Lys Val Asp Thr Ser Gly Ile Phe Leu
   625           630           635           640
   Asp Lys Gly Glu Gly Leu Ile Phe Glu His Asn Thr Lys Asn Leu Leu
              645           650           655
   His Arg Gln Thr Ala Phe Arg Asp Arg Cys Phe Val Ser Asn Arg Ala
              660           665           670
   Cys Tyr Ser Ser Val Leu Asn Ile Leu Tyr Thr Ser Cys
              675           680           685
```

(2) INFORMATION FOR SEQ ID NO: 182:
   (i) SEQUENCE CHARACTERISTICS:
      (A) LENGTH: 54 amino acids
      (B) TYPE: amino acid
      (C) STRANDEDNESS: <Unknown>
      (D) TOPOLOGY: unknown

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
   (ii) MOLECULE TYPE: peptide
   (xi) SEQUENCE DESCRIPTION: SEQ ID NO: 182:
     Leu Val Pro Arg Gly Ser Pro Gly Ile Pro Gly Ser Arg Val Gly Gln
      1           5              10             15
     Cys Thr Asp Ser Asp Val Arg Arg Pro Trp Ala Arg Ser Cys Ala His
            20             25             30
     Gln Gly Cys Gly Ala Gly Thr Arg Asn Ser His Gly Cys Ile Thr Arg
            35             40             45
     Pro Leu Arg Gln Ala Ser
        50

(2) INFORMATION FOR SEQ ID NO: 183:
   (i) SEQUENCE CHARACTERISTICS:
       (A) LENGTH: 19 amino acids
       (B) TYPE: amino acid
       (C) STRANDEDNESS: <Unknown>
       (D) TOPOLOGY: unknown
   (ii) MOLECULE TYPE: peptide
   (xi) SEQUENCE DESCRIPTION: SEQ ID NO: 183:
     Ser Ala Arg Asp Ser Gly Pro Ala Glu Asp Gly Ser Arg Ala Val Arg
      1           5              10             15
     Leu Asn Gly (2) INFORMATION FOR SEQ ID NO: 184:
   (i) SEQUENCE CHARACTERISTICS:
       (A) LENGTH: 21 amino acids
       (B) TYPE: amino acid
       (C) STRANDEDNESS: <Unknown>
       (D) TOPOLOGY: unknown
   (ii) MOLECULE TYPE: peptide
   (xi) SEQUENCE DESCRIPTION: SEQ ID NO: 184:
     Asp Gly Ser Arg Ala Val Arg Leu Asn Gly Val Glu Asn Ala Asn Thr
      1           5              10             15
     Arg Lys Ser Ser Arg
            20

(2) INFORMATION FOR SEQ ID NO: 185:
   (i) SEQUENCE CHARACTERISTICS:
       (A) LENGTH: 19 amino acids
       (B) TYPE: amino acid
       (C) STRANDEDNESS: <Unknown>
       (D) TOPOLOGY: unknown
   (ii) MOLECULE TYPE: peptide
   (xi) SEQUENCE DESCRIPTION: SEQ ID NO: 185:
     Glu Asn Ala Asn Thr Arg Lys Ser Arg Ser Asn Pro Arg Gly Arg
      1           5              10             15
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

Arg His Pro (2) INFORMATION FOR SEQ ID NO: 186:
   (i) SEQUENCE CHARACTERISTICS:
      (A) LENGTH: 11 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 186:
   Thr Arg Lys Ser Ser Arg Ser Asn Pro Arg Gly
   1       5         10

(2) INFORMATION FOR SEQ ID NO: 187:
   (i) SEQUENCE CHARACTERISTICS:
      (A) LENGTH: 21 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 187:
   Ser Arg Pro Tyr Ser Val Asp Ser Asp Ser Asp Thr Asn Ala Lys His
   1       5        10        15
   Ser Ser His Asn Arg
      20

(2) INFORMATION FOR SEQ ID NO: 188:
   (i) SEQUENCE CHARACTERISTICS:
      (A) LENGTH: 19 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 188:
   Thr Asn Ala Lys His Ser Ser His Asn Arg Arg Leu Arg Thr Arg Ser
   1       5        10        15
   Arg Pro Asn (2) INFORMATION FOR SEQ ID NO: 189:
   (i) SEQUENCE CHARACTERISTICS:
      (A) LENGTH: 24 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 189:

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
  Arg Tyr Lys His Asp Ile Gly Cys Asp Ala Gly Val Asp Lys Lys Ser
   1               5              10                  15
  Ser Ser Val Arg Gly Gly Cys Gly
       20
```

(2) INFORMATION FOR SEQ ID NO: 190:
  (i) SEQUENCE CHARACTERISTICS:
    (A) LENGTH: 26 amino acids
    (B) TYPE: amino acid
    (C) STRANDEDNESS: <Unknown>
    (D) TOPOLOGY: linear
  (ii) MOLECULE TYPE: peptide
  (xi) SEQUENCE DESCRIPTION: SEQ ID NO: 190:

```
  Gly Cys Asp Ala Gly Val Asp Lys Lys Ser Ser Ser Val Arg Gly Gly
   1               5              10                  15
  Cys Gly Ala His Ser Ser Pro Pro Arg Ala
       20                  25
```

(2) INFORMATION FOR SEQ ID NO: 191:
  (i) SEQUENCE CHARACTERISTICS:
    (A) LENGTH: 21 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 191:

```
  Gly Ala His Ser Ser Pro Pro Arg Ala Gly Arg Gly Pro Arg Gly Thr
   1               5              10                  15
  Met Val Ser Arg Leu
       20
```

(2) INFORMATION FOR SEQ ID NO: 192:
  (i) SEQUENCE CHARACTERISTICS:
    (A) LENGTH: 10 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 192:

```
  Glu Asn Ala Asn Thr Arg Lys Ser Ser Arg
   1               5              10
```

(2) INFORMATION FOR SEQ ID NO: 193:
  (i) SEQUENCE CHARACTERISTICS:
    (A) LENGTH: 39 amino acids
    (B) TYPE: amino acid

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 193:
      Lys Lys Arg Ile Ala Gly Leu Pro Trp Tyr Arg Cys Arg Thr Val Ala
       1           5              10              15
      Phe Glu Thr Gly Met Gln Asn Thr Gln Leu Cys Ser Thr Ile Val Gln
              20              25              30
      Leu Ser Phe Thr Pro Glu Glu
              35

(2) INFORMATION FOR SEQ ID NO: 194:
    (i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 194:
      Arg Lys Ser Ser Arg Ser Asn Pro Arg Gly
       1           5              10

(2) INFORMATION FOR SEQ ID NO: 195:
    (i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 195:
      Ser Asn Pro Arg Gly Arg Arg His Pro
       1           5

(2) INFORMATION FOR SEQ ID NO: 196:
    (i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 196:
      Thr Asn Ala Lys His Ser Ser His Asn
       1           5

(2) INFORMATION FOR SEQ ID NO: 197:
    (i) SEQUENCE CHARACTERISTICS:
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

(A) LENGTH: 10 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 197:
   Ser Ser His Asn Arg Arg Leu Arg Thr Arg
    1       5         10

(2) INFORMATION FOR SEQ ID NO: 198:
  (i) SEQUENCE CHARACTERISTICS:
    (A) LENGTH: 10 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 198:
   Arg Arg Leu Arg Thr Arg Ser Arg Pro Asn
    1       5         10

(2) INFORMATION FOR SEQ ID NO: 199:
  (i) SEQUENCE CHARACTERISTICS:
    (A) LENGTH: 19 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 199:
   Arg Val Gly Gln Cys Thr Asp Ser Asp Val Arg Arg Pro Trp Ala Arg
    1       5         10          15
   Ser Cys Ala (2) INFORMATION FOR SEQ ID NO: 200:
  (i) SEQUENCE CHARACTERISTICS:
    (A) LENGTH: 21 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 200:
   Val Arg Arg Pro Trp Ala Arg Ser Cys Ala His Gln Gly Cys Gly Ala
    1       5         10          15
   Gly Thr Arg Asn Ser
       20

(2) INFORMATION FOR SEQ ID NO: 201:

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

(i) SEQUENCE CHARACTERISTICS:
      (A) LENGTH: 19 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 201:
    Gly Thr Arg Asn Ser His Gly Cys Ile Thr Arg Pro Leu Arg Gln Ala
    1        5          10         15
    Ser Gln His (2) INFORMATION FOR SEQ ID NO: 202:
   (i) SEQUENCE CHARACTERISTICS:
      (A) LENGTH: 40 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 202:
    Ser Thr Pro Pro Ser Arg Glu Ala Tyr Ser Arg Pro Tyr Ser Val Asp
    1        5          10         15
    Ser Asp Ser Asp Thr Met Ala Lys His Ser Ser His Asn Arg Arg Leu
       20          25         30
    Arg Thr Arg Ser Arg Pro Asn Gly
       35          40

(2) INFORMATION FOR SEQ ID NO: 203:
   (i) SEQUENCE CHARACTERISTICS:
      (A) LENGTH: 4 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 203:
    Tyr Ser Lys Val
    1

(2) INFORMATION FOR SEQ ID NO: 204:
   (i) SEQUENCE CHARACTERISTICS:
      (A) LENGTH: 4 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 204:
    Phe Pro His Leu

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

1

(2) INFORMATION FOR SEQ ID NO: 205:
  (i) SEQUENCE CHARACTERISTICS:
    (A) LENGTH: 4 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 205:
  Tyr Arg Gly Val
   1

(2) INFORMATION FOR SEQ ID NO: 206:
  (i) SEQUENCE CHARACTERISTICS:
    (A) LENGTH: 4 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 206:
  Tyr Gln Thr Ile
   1

(2) INFORMATION FOR SEQ ID NO: 207:
  (i) SEQUENCE CHARACTERISTICS:
    (A) LENGTH: 4 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 207:
  Thr Glu Gln Phe
   1

(2) INFORMATION FOR SEQ ID NO: 208:
  (i) SEQUENCE CHARACTERISTICS:
    (A) LENGTH: 4 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 208:
  Thr Glu Val Met
   1

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(2) INFORMATION FOR SEQ ID NO: 209:
  (i) SEQUENCE CHARACTERISTICS:
    (A) LENGTH: 4 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 209:
  Thr Ser Ala Phe
   1

(2) INFORMATION FOR SEQ ID NO: 210:
  (i) SEQUENCE CHARACTERISTICS:
    (A) LENGTH: 4 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 210:
  Tyr Thr Arg Phe
   1

(2) INFORMATION FOR SEQ ID NO: 211:
  (i) SEQUENCE CHARACTERISTICS:
    (A) LENGTH: 717 base pairs
    (B) TYPE: nucleic acid
    (C) STRANDEDNESS: single
    (D) TOPOLOGY: linear
  (ii) MOLECULE TYPE: DNA
  (ix) FEATURE:
    (A) NAME/KEY: Coding Sequence
    (B) LOCATION: 1...714
    (D) OTHER INFORMATION:
  (xi) SEQUENCE DESCRIPTION: SEQ ID NO: 211:

```
ATG TCC CCT ATA CTA GGT TAT TGG AAA ATT AAG GGC CTT GTG CAA CCC    48
Met Ser Pro Ile Leu Gly Tyr Trp Lys Ile Lys Gly Leu Val Gln Pro
  1               5                  10                  15
ACT CGA CTT CTT TTG GAA TAT CTT GAA GAA AAA TAT GAA GAG CAT TTG    96
Thr Arg Leu Leu Leu Glu Tyr Leu Glu Glu Lys Tyr Glu Glu His Leu
             20                  25                  30
TAT GAG CGC GAT GAA GGT GAT AAA TGG CGA AAC AAA AAG TTT GAA TTG   144
Tyr Glu Arg Asp Glu Gly Asp Lys Trp Arg Asn Lys Lys Phe Glu Leu
         35                  40                  45
GGT TTG GAG TTT CCC AAT CTT CCT TAT TAT ATT GAT GGT GAT GTT AAA   192
Gly Leu Glu Phe Pro Asn Leu Pro Tyr Tyr Ile Asp Gly Asp Val Lys
     50                  55                  60
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
TTA ACA CAG TCT ATG GCC ATC ATA CGT TAT ATA GCT GAC AAG CAC AAC   240
Leu Thr Gln Ser Met Ala Ile Ile Arg Tyr Ile Ala Asp Lys His Asn
 65              70              75              80
ATG TTG GGT GGT TGT CCA AAA GAG CGT GCA GAG ATT TCA ATG CTT GAA   288
Met Leu Gly Gly Cys Pro Lys Glu Arg Ala Glu Ile Ser Met Leu Glu
             85              90              95
GGA GCG GTT TTG GAT ATT AGA TAC GGT GTT TCG AGA ATT GCA TAT AGT   336
Gly Ala Val Leu Asp Ile Arg Tyr Gly Val Ser Arg Ile Ala Tyr Ser
        100             105             110
AAA GAC TTT GAA ACT CTC AAA GTT GAT TTT CTT AGC AAG CTA CCT GAA   384
Lys Asp Phe Glu Thr Leu Lys Val Asp Phe Leu Ser Lys Leu Pro Glu
        115             120             125
ATG CTG AAA ATG TTC GAA GAT CGT TTA TGT CAT AAA ACA TAT TTA AAT   432
Met Leu Lys Met Phe Glu Asp Arg Leu Cys His Lys Thr Tyr Leu Asn
    130             135             140
GGT GAT CAT GTA ACC CAT CCT GAC TTC ATG TTG TAT GAC GCT CTT GAT   480
Gly Asp His Val Thr His Pro Asp Phe Met Leu Tyr Asp Ala Leu Asp
145             150             155             160
GTT GTT TTA TAC ATG GAC CCA ATG TGC CTG GAT GCG TTC CCA AAA TTA   528
Val Val Leu Tyr Met Asp Pro Met Cys Leu Asp Ala Phe Pro Lys Leu
        165             170             175
GTT TGT TTT AAA AAA CGT ATT GAA GCT ATC CCA CAA ATT GAT AAG TAC   576
Val Cys Phe Lys Lys Arg Ile Glu Ala Ile Pro Gln Ile Asp Lys Tyr
        180             185             190
TTG AAA TCC AGC AAG TAT ATA GCA TGG CCT TTG CAG GGC TGG CAA GCC   624
Leu Lys Ser Ser Lys Tyr Ile Ala Trp Pro Leu Gln Gly Trp Gln Ala
        195             200             205
ACG TTT GGT GGT GGC GAC CAT CCT CCA AAA TCG GAT CTG GTT CCG CGT   672
Thr Phe Gly Gly Gly Asp His Pro Pro Lys Ser Asp Leu Val Pro Arg
    210             215             220
GGA TCC CCA GGA ATT CCC GGG TCG ACT CGA GCG GCC GCA TCG TGA       717
Gly Ser Pro Gly Ile Pro Gly Ser Thr Arg Ala Ala Ala Ser
225             230             235
```

(2) INFORMATION FOR SEQ ID NO: 212:
   (i) SEQUENCE CHARACTERISTICS:
      (A) LENGTH: 238 amino acids
      (B) TYPE: amino acid
      (C) STRANDEDNESS: <Unknown>
      (D) TOPOLOGY: unknown
  (ii) MOLECULE TYPE: protein
  (xi) SEQUENCE DESCRIPTION: SEQ ID NO: 212:

```
Met Ser Pro Ile Leu Gly Tyr Trp Lys Ile Lys Gly Leu Val Gln Pro
  1               5              10              15
Thr Arg Leu Leu Leu Glu Tyr Leu Glu Glu Lys Tyr Glu Glu His Leu
         20              25              30
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
    Tyr Glu Arg Asp Glu Gly Asp Lys Trp Arg Asn Lys Lys Phe Glu Leu
        35              40              45
    Gly Leu Glu Phe Pro Asn Leu Pro Tyr Tyr Ile Asp Gly Asp Val Lys
        50              55              60
    Leu Thr Gln Ser Met Ala Ile Ile Arg Tyr Ile Ala Asp Lys His Asn
    65              70              75              80
    Met Leu Gly Gly Cys Pro Lys Glu Arg Ala Glu Ile Ser Met Leu Glu
                85              90              95
    Gly Ala Val Leu Asp Ile Arg Tyr Gly Val Ser Arg Ile Ala Tyr Ser
                100             105             110
    Lys Asp Phe Glu Thr Leu Lys Val Asp Phe Leu Ser Lys Leu Pro Glu
        115             120             125
    Met Leu Lys Met Phe Glu Asp Arg Leu Cys His Lys Thr Tyr Leu Asn
        130             135             140
    Gly Asp His Val Thr His Pro Asp Phe Met Leu Tyr Asp Ala Leu Asp
    145             150             155             160
    Val Val Leu Tyr Met Asp Pro Met Cys Leu Asp Ala Phe Pro Lys Leu
                165             170             175
    Val Cys Phe Lys Lys Arg Ile Glu Ala Ile Pro Gln Ile Asp Lys Tyr
                180             185             190
    Leu Lys Ser Ser Lys Tyr Ile Ala Trp Pro Leu Gln Gly Trp Gln Ala
        195             200             205
    Thr Phe Gly Gly Gly Asp His Pro Pro Lys Ser Asp Leu Val Pro Arg
        210             215             220
    Gly Ser Pro Gly Ile Pro Gly Ser Thr Arg Ala Ala Ala Ser
    225             230             235

(2) INFORMATION FOR SEQ ID NO: 213:
    (i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 213:
     Met Ser Pro Ile Leu Gly Tyr Trp Lys Ile Lys Gly Leu Val Gln Pro
     1               5               10              15
     Thr Arg Leu Leu Leu Glu Tyr Leu Glu Glu Lys Tyr Glu Glu His Leu
            20              25              30
     Tyr Glu Arg Asp Glu Gly Asp Lys Trp Arg Asn Lys Lys Phe Glu Leu
        35              40              45
     Gly Leu Glu Phe Pro Asn Leu Pro Tyr Tyr Ile Asp Gly Asp Val Lys
        50              55              60
     Leu Thr Gln Ser Met Ala Ile Ile Arg Tyr Ile Ala Asp Lys His Asn
     65              70              75              80
     Met Leu Gly Gly Cys Pro Lys Glu Arg Ala Glu Ile Ser Met Leu Glu
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
                85              90              95
  Gly Ala Val Leu Asp Ile Arg Tyr Gly Val Ser Arg Ile Ala Tyr Ser
            100             105             110
  Lys Asp Phe Glu Thr Leu Lys Val Asp Phe Leu Ser Lys Leu Pro Glu
        115             120             125
  Met Leu Lys Met Phe Glu Asp Arg Leu Cys His Lys Thr Tyr Leu Asn
        130             135             140
  Gly Asp His Val Thr His Pro Asp Phe Met Leu Tyr Asp Ala Leu Asp
    145             150             155             160
  Val Val Leu Tyr Met Asp Pro Met Cys Leu Asp Ala Phe Pro Lys Leu
            165             170             175
  Val Cys Phe Lys Lys Arg Ile Glu Ala Ile Pro Gln Ile Asp Lys Tyr
        180             185             190
  Leu Lys Ser Ser Lys Tyr Ile Ala Trp Pro Leu Gln Gly Trp Gln Ala
            195             200             205
  Thr Phe Gly Gly Gly Asp His Pro Pro Lys Ser Asp Leu Val Pro Arg
        210             215             220
  Gly Ser Pro Gly Ile Pro Gly Ser Thr Arg Ala Ala Ala Ser Ser Gln
  225             230             235             240
  Gly Ser Lys Gln Cys Met Gln Tyr Arg Thr Gly Arg Leu Thr Val Gly
            245             250             255
  Ser Glu Tyr Gly Cys Gly Met Asn Pro Ala Arg His Ala Thr Pro Ala
        260             265             270
  Tyr Pro Ala Arg Leu Leu Pro Arg Tyr Arg
        275             280

(2) INFORMATION FOR SEQ ID NO: 214:
    (i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 214:
  Met Ser Pro Ile Leu Gly Tyr Trp Lys Ile Lys Gly Leu Val Gln Pro
  1           5               10              15
  Thr Arg Leu Leu Leu Glu Tyr Leu Glu Glu Lys Tyr Glu Glu His Leu
        20              25              30
  Tyr Glu Arg Asp Glu Gly Asp Lys Trp Arg Asn Lys Lys Phe Glu Leu
        35              40              45
  Gly Leu Glu Phe Pro Asn Leu Pro Tyr Tyr Ile Asp Gly Asp Val Lys
    50              55              60
  Leu Thr Gln Ser Met Ala Ile Ile Arg Tyr Ile Ala Asp Lys His Asn
  65              70              75              80
  Met Leu Gly Gly Cys Pro Lys Glu Arg Ala Glu Ile Ser Met Leu Glu
            85              90              95
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
    Gly Ala Val Leu Asp Ile Arg Tyr Gly Val Ser Arg Ile Ala Tyr Ser
            100             105             110
    Lys Asp Phe Glu Thr Leu Lys Val Asp Phe Leu Ser Lys Leu Pro Glu
            115             120             125
    Met Leu Lys Met Phe Glu Asp Arg Leu Cys His Lys Thr Tyr Leu Asn
            130             135             140
    Gly Asp His Val Thr His Pro Asp Phe Met Leu Tyr Asp Ala Leu Asp
    145             150             155             160
    Val Val Leu Tyr Met Asp Pro Met Cys Leu Asp Ala Phe Pro Lys Leu
            165             170             175
    Val Cys Phe Lys Lys Arg Ile Glu Ala Ile Pro Gln Ile Asp Lys Tyr
            180             185             190
    Leu Lys Ser Ser Lys Tyr Ile Ala Trp Pro Leu Gln Gly Trp Gln Ala
            195             200             205
    Thr Phe Gly Gly Asp His Pro Pro Lys Ser Asp Leu Val Pro Arg
            210             215             220
    Gly Ser Pro Gly Ile Pro Gly Ser Thr Arg Ala Ala Ala Ser Ser Asp
    225             230             235             240
    His Ala Leu Gly Thr Asn Leu Arg Ser Asp Asn Ala Lys Glu Pro Gly
            245             250             255
    Asp Tyr Asn Cys Cys Gly Asn Gly Asn Ser Thr Gly Arg Lys Val Phe
            260             265             270
    Asn Arg Arg Arg Pro Ser Ala Ile Pro Thr
            275             280

(2) INFORMATION FOR SEQ ID NO: 215:
    (i) SEQUENCE CHARACTERISTICS:
        (A) LENGTH: 279 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 215:
    Met Ser Pro Ile Leu Gly Tyr Trp Lys Ile Lys Gly Leu Val Gln Pro
    1           5               10              15
    Thr Arg Leu Leu Leu Glu Tyr Leu Glu Glu Lys Tyr Glu Glu His Leu
            20              25              30
    Tyr Glu Arg Asp Glu Gly Asp Lys Trp Arg Asn Lys Lys Phe Glu Leu
            35              40              45
    Gly Leu Glu Phe Pro Asn Leu Pro Tyr Tyr Ile Asp Gly Asp Val Lys
    50              55              60
    Leu Thr Gln Ser Met Ala Ile Ile Arg Tyr Ile Ala Asp Lys His Asn
    65              70              75              80
    Met Leu Gly Gly Cys Pro Lys Glu Arg Ala Glu Ile Ser Met Leu Glu
            85              90              95
    Gly Ala Val Leu Asp Ile Arg Tyr Gly Val Ser Arg Ile Ala Tyr Ser
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
            100         105         110
Lys Asp Phe Glu Thr Leu Lys Val Asp Phe Leu Ser Lys Leu Pro Glu
        115         120         125
Met Leu Lys Met Phe Glu Asp Arg Leu Cys His Lys Thr Tyr Leu Asn
    130         135         140
Gly Asp His Val Thr His Pro Asp Phe Met Leu Tyr Asp Ala Leu Asp
145         150         155         160
Val Val Leu Tyr Met Asp Pro Met Cys Leu Asp Ala Phe Pro Lys Leu
            165         170         175
Val Cys Phe Lys Lys Arg Ile Glu Ala Ile Pro Gln Ile Asp Lys Tyr
        180         185         190
Leu Lys Ser Ser Lys Tyr Ile Ala Trp Pro Leu Gln Gly Trp Gln Ala
        195         200         205
Thr Phe Gly Gly Gly Asp His Pro Pro Lys Ser Asp Leu Val Pro Arg
    210         215         220
Gly Ser Pro Gly Ile Pro Gly Ser Thr Arg Ala Ala Ala Ser Ser Pro
225         230         235         240
Cys Gly Gly Ser Trp Gly Arg Phe Met Gln Gly Gly Leu Phe Gly Gly
            245         250         255
Arg Thr Asp Gly Cys Gly Ala His Arg Asn Arg Thr Ser Ala Ser Leu
        260         265         270
Glu Pro Pro Ser Ser Asp Tyr
        275
```

(2) INFORMATION FOR SEQ ID NO: 216:
   (i) SEQUENCE CHARACTERISTICS:
      (A) LENGTH: 277 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 216:

```
Met Ser Pro Ile Leu Gly Tyr Trp Lys Ile Lys Gly Leu Val Gln Pro
1           5           10          15
Thr Arg Leu Leu Leu Glu Tyr Leu Glu Glu Lys Tyr Glu Glu His Leu
        20          25          30
Tyr Glu Arg Asp Glu Gly Asp Lys Trp Arg Asn Lys Lys Phe Glu Leu
    35          40          45
Gly Leu Glu Phe Pro Asn Leu Pro Tyr Tyr Ile Asp Gly Asp Val Lys
50          55          60
Leu Thr Gln Ser Met Ala Ile Ile Arg Tyr Ile Ala Asp Lys His Asn
65          70          75          80
Met Leu Gly Gly Cys Pro Lys Glu Arg Ala Glu Ile Ser Met Leu Glu
        85          90          95
Gly Ala Val Leu Asp Ile Arg Tyr Gly Val Ser Arg Ile Ala Tyr Ser
            100         105         110
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
   Lys Asp Phe Glu Thr Leu Lys Val Asp Phe Leu Ser Lys Leu Pro Glu
           115                 120                 125
   Met Leu Lys Met Phe Glu Asp Arg Leu Cys His Lys Thr Tyr Leu Asn
       130                 135                 140
   Gly Asp His Val Thr His Pro Asp Phe Met Leu Tyr Asp Ala Leu Asp
   145                 150                 155                 160
   Val Val Leu Tyr Met Asp Pro Met Cys Leu Asp Ala Phe Pro Lys Leu
               165                 170                 175
   Val Cys Phe Lys Lys Arg Ile Glu Ala Ile Pro Gln Ile Asp Lys Tyr
           180                 185                 190
   Leu Lys Ser Ser Lys Tyr Ile Ala Trp Pro Leu Gln Gly Trp Gln Ala
           195                 200                 205
   Thr Phe Gly Gly Gly Asp His Pro Pro Lys Ser Asp Leu Val Pro Arg
       210                 215                 220
   Gly Ser Pro Gly Ile Pro Gly Ser Thr Arg Ala Ala Ala Ser Arg Gly
   225                 230                 235                 240
   Ser Thr Gly Thr Ala Gly Gly Glu Arg Ser Gly Val Leu Asn Leu His
               245                 250                 255
   Thr Arg Asp Asn Ala Ser Gly Ser Gly Phe Lys Pro Trp Tyr Pro Ser
           260                 265                 270
   Asn Arg Gly His Lys
           275

(2) INFORMATION FOR SEQ ID NO: 217:
    (i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown
   (ii) MOLECULE TYPE: peptide
   (xi) SEQUENCE DESCRIPTION: SEQ ID NO: 217:
   Met Ser Pro Ile Leu Gly Tyr Trp Lys Ile Lys Gly Leu Val Gln Pro
   1               5                   10                  15
   Thr Arg Leu Leu Leu Glu Tyr Leu Glu Glu Lys Tyr Glu Glu His Leu
           20                  25                  30
   Tyr Glu Arg Asp Glu Gly Asp Lys Trp Arg Asn Lys Lys Phe Glu Leu
           35                  40                  45
   Gly Leu Glu Phe Pro Asn Leu Pro Tyr Tyr Ile Asp Gly Asp Val Lys
       50                  55                  60
   Leu Thr Gln Ser Met Ala Ile Ile Arg Tyr Ile Ala Asp Lys His Asn
   65                  70                  75                  80
   Met Leu Gly Gly Cys Pro Lys Glu Arg Ala Glu Ile Ser Met Leu Glu
               85                  90                  95
   Gly Ala Val Leu Asp Ile Arg Tyr Gly Val Ser Arg Ile Ala Tyr Ser
           100                 105                 110
   Lys Asp Phe Glu Thr Leu Lys Val Asp Phe Leu Ser Lys Leu Pro Glu
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
           115          120          125
  Met Leu Lys Met Phe Glu Asp Arg Leu Cys His Lys Thr Tyr Leu Asn
       130          135          140
  Gly Asp His Val Thr His Pro Asp Phe Met Leu Tyr Asp Ala Leu Asp
   145          150          155          160
  Val Val Leu Tyr Met Asp Pro Met Cys Leu Asp Ala Phe Pro Lys Leu
            165          170          175
      Val Cys Phe Lys Lys Arg Ile Glu Ala Ile Pro Gln Ile Asp Lys Tyr
           180          185          190
      Leu Lys Ser Ser Lys Tyr Ile Ala Trp Pro Leu Gln Gly Trp Gln Ala
           195          200          205
      Thr Phe Gly Gly Gly Asp His Pro Pro Lys Ser Asp Leu Val Pro Arg
          210          215          220
      Gly Ser Pro Gly Ile Pro Gly Ser Thr Arg Ala Ala Ala Ser Ser His
  225          230          235          240
  Ser Gly Gly Met Asn Arg Ala Tyr Gly Asp Val Phe Arg Glu Leu Arg
           245          250          255
  Asp Arg Trp Asn Ala Thr Ser His His Thr Arg Pro Thr Pro Gln Leu
           260          265          270
  Pro Arg Gly Pro Asn
       275

(2) INFORMATION FOR SEQ ID NO: 218:
    (i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown
   (ii) MOLECULE TYPE: peptide
   (xi) SEQUENCE DESCRIPTION: SEQ ID NO: 218:
   Met Ser Pro Ile Leu Gly Tyr Trp Lys Ile Lys Gly Leu Val Gln Pro
   1            5           10           15
   Thr Arg Leu Leu Leu Glu Tyr Leu Glu Glu Lys Tyr Glu Glu His Leu
           20           25           30
     Tyr Glu Arg Asp Glu Gly Asp Lys Trp Arg Asn Lys Lys Phe Glu Leu
           35           40           45
   Gly Leu Glu Phe Pro Asn Leu Pro Tyr Tyr Ile Asp Gly Asp Val Lys
       50           55           60
   Leu Thr Gln Ser Met Ala Ile Ile Arg Tyr Ile Ala Asp Lys His Asn
   65           70           75           80
   Met Leu Gly Gly Cys Pro Lys Glu Arg Ala Glu Ile Ser Met Leu Glu
            85           90           95
   Gly Ala Val Leu Asp Ile Arg Tyr Gly Val Ser Arg Ile Ala Tyr Ser
            100          105          110
   Lys Asp Phe Glu Thr Leu Lys Val Asp Phe Leu Ser Lys Leu Pro Glu
            115          120          125
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
    Met Leu Lys Met Phe Glu Asp Arg Leu Cys His Lys Thr Tyr Leu Asn
        130             135             140
    Gly Asp His Val Thr His Pro Asp Phe Met Leu Tyr Asp Ala Leu Asp
    145             150             155             160
    Val Val Leu Tyr Met Asp Pro Met Cys Leu Asp Ala Phe Pro Lys Leu
            165             170             175
    Val Cys Phe Lys Lys Arg Ile Glu Ala Ile Pro Gln Ile Asp Lys Tyr
        180             185             190
    Leu Lys Ser Ser Lys Tyr Ile Ala Trp Pro Leu Gln Gly Trp Gln Ala
        195             200             205
    Thr Phe Gly Gly Gly Asp His Pro Pro Lys Ser Asp Leu Val Pro Arg
        210             215             220
    Gly Ser Pro Gly Ile Pro Gly Ser Thr Arg Ala Ala Ala Ser Ser His
    225             230             235             240
    Ser Gly Gly Met Asn Arg Ala Tyr
            245
```

(2) INFORMATION FOR SEQ ID NO: 219:
     (i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown
     (ii) MOLECULE TYPE: peptide
     (xi) SEQUENCE DESCRIPTION: SEQ ID NO: 219:

```
    Met Ser Pro Ile Leu Gly Tyr Trp Lys Ile Lys Gly Leu Val Gln Pro
    1               5               10              15
    Thr Arg Leu Leu Leu Glu Tyr Leu Glu Glu Lys Tyr Glu Glu His Leu
            20              25              30
    Tyr Glu Arg Asp Glu Gly Asp Lys Trp Arg Asn Lys Lys Phe Glu Leu
            35              40              45
    Gly Leu Glu Phe Pro Asn Leu Pro Tyr Tyr Ile Asp Gly Asp Val Lys
        50              55              60
    Leu Thr Gln Ser Met Ala Ile Ile Arg Tyr Ile Ala Asp Lys His Asn
    65              70              75              80
    Met Leu Gly Gly Cys Pro Lys Glu Arg Ala Glu Ile Ser Met Leu Glu
            85              90              95
    Gly Ala Val Leu Asp Ile Arg Tyr Gly Val Ser Arg Ile Ala Tyr Ser
        100             105             110
    Lys Asp Phe Glu Thr Leu Lys Val Asp Phe Leu Ser Lys Leu Pro Glu
        115             120             125
    Met Leu Lys Met Phe Glu Asp Arg Leu Cys His Lys Thr Tyr Leu Asn
        130             135             140
    Gly Asp His Val Thr His Pro Asp Phe Met Leu Tyr Asp Ala Leu Asp
    145             150             155             160
    Val Val Leu Tyr Met Asp Pro Met Cys Leu Asp Ala Phe Pro Lys Leu
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
                165           170           175
   Val Cys Phe Lys Lys Arg Ile Glu Ala Ile Pro Gln Ile Asp Lys Tyr
            180           185           190
   Leu Lys Ser Ser Lys Tyr Ile Ala Trp Pro Leu Gln Gly Trp Gln Ala
            195           200           205
   Thr Phe Gly Gly Gly Asp His Pro Pro Lys Ser Asp Leu Val Pro Arg
            210           215           220
   Gly Ser Pro Gly Ile Pro Gly Ser Thr Arg Ala Ala Ala Ser Gly Asp
        225           230           235           240
   Val Phe Arg Glu Leu Arg Asp Arg
            245
```

(2) INFORMATION FOR SEQ ID NO: 220:
   (i) SEQUENCE CHARACTERISTICS:
      (A) LENGTH: 248 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 220:

```
   Met Ser Pro Ile Leu Gly Tyr Trp Lys Ile Lys Gly Leu Val Gln Pro
    1             5            10            15
   Thr Arg Leu Leu Leu Glu Tyr Leu Glu Glu Lys Tyr Glu Glu His Leu
            20            25            30
   Tyr Glu Arg Asp Glu Gly Asp Lys Trp Arg Asn Lys Lys Phe Glu Leu
            35            40            45
   Gly Leu Glu Phe Pro Asn Leu Pro Tyr Tyr Ile Asp Gly Asp Val Lys
            50            55            60
   Leu Thr Gln Ser Met Ala Ile Ile Arg Tyr Ile Ala Asp Lys His Asn
   65            70            75            80
   Met Leu Gly Gly Cys Pro Lys Glu Arg Ala Glu Ile Ser Met Leu Glu
            85            90            95
   Gly Ala Val Leu Asp Ile Arg Tyr Gly Val Ser Arg Ile Ala Tyr Ser
            100           105           110
   Lys Asp Phe Glu Thr Leu Lys Val Asp Phe Leu Ser Lys Leu Pro Glu
            115           120           125
   Met Leu Lys Met Phe Glu Asp Arg Leu Cys His Lys Thr Tyr Leu Asn
            130           135           140
   Gly Asp His Val Thr His Pro Asp Phe Met Leu Tyr Asp Ala Leu Asp
   145           150           155           160
   Val Val Leu Tyr Met Asp Pro Met Cys Leu Asp Ala Phe Pro Lys Leu
                165           170           175
   Val Cys Phe Lys Lys Arg Ile Glu Ala Ile Pro Gln Ile Asp Lys Tyr
            180           185           190
   Leu Lys Ser Ser Lys Tyr Ile Ala Trp Pro Leu Gln Gly Trp Gln Ala
            195           200           205
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
    Thr Phe Gly Gly Gly Asp His Pro Pro Lys Ser Asp Leu Val Pro Arg
        210             215             220
    Gly Ser Pro Gly Ile Pro Gly Ser Thr Arg Ala Ala Ala Ser Trp Asn
    225             230             235             240
    Ala Thr Ser His His Thr Arg Pro
            245

(2) INFORMATION FOR SEQ ID NO: 221:
    (i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 221:
    Met Ser Pro Ile Leu Gly Tyr Trp Lys Ile Lys Gly Leu Val Gln Pro
    1               5               10              15
    Thr Arg Leu Leu Leu Glu Tyr Leu Glu Glu Lys Tyr Glu Glu His Leu
            20              25              30
    Tyr Glu Arg Asp Glu Gly Asp Lys Trp Arg Asn Lys Lys Phe Glu Leu
                35              40              45
    Gly Leu Glu Phe Pro Asn Leu Pro Tyr Tyr Ile Asp Gly Asp Val Lys
        50              55              60
    Leu Thr Gln Ser Met Ala Ile Ile Arg Tyr Ile Ala Asp Lys His Asn
    65              70              75              80
    Met Leu Gly Gly Cys Pro Lys Glu Arg Ala Glu Ile Ser Met Leu Glu
            85              90              95
    Gly Ala Val Leu Asp Ile Arg Tyr Gly Val Ser Arg Ile Ala Tyr Ser
            100             105             110
    Lys Asp Phe Glu Thr Leu Lys Val Asp Phe Leu Ser Lys Leu Pro Glu
            115             120             125
    Met Leu Lys Met Phe Glu Asp Arg Leu Cys His Lys Thr Tyr Leu Asn
        130             135             140
    Gly Asp His Val Thr His Pro Asp Phe Met Leu Tyr Asp Ala Leu Asp
    145             150             155             160
    Val Val Leu Tyr Met Asp Pro Met Cys Leu Asp Ala Phe Pro Lys Leu
            165             170             175
    Val Cys Phe Lys Lys Arg Ile Glu Ala Ile Pro Gln Ile Asp Lys Tyr
        180             185             190
    Leu Lys Ser Ser Lys Tyr Ile Ala Trp Pro Leu Gln Gly Trp Gln Ala
            195             200             205
    Thr Phe Gly Gly Gly Asp His Pro Pro Lys Ser Asp Leu Val Pro Arg
        210             215             220
    Gly Ser Pro Gly Ile Pro Gly Ser Thr Arg Ala Ala Ala Ser Thr Pro
    225             230             235             240
    Gln Leu Pro Arg Gly Pro Asn
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

245

(2) INFORMATION FOR SEQ ID NO: 222:
  (i) SEQUENCE CHARACTERISTICS:
    (A) LENGTH: 258 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 222:

```
Met Ser Pro Ile Leu Gly Tyr Trp Lys Ile Lys Gly Leu Val Gln Pro
 1               5                  10                  15
Thr Arg Leu Leu Leu Glu Tyr Leu Glu Glu Lys Tyr Glu Glu His Leu
            20                  25                  30
Tyr Glu Arg Asp Glu Gly Asp Lys Trp Arg Asn Lys Lys Phe Glu Leu
        35                  40                  45
Gly Leu Glu Phe Pro Asn Leu Pro Tyr Tyr Ile Asp Gly Asp Val Lys
        50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
            85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
        130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
            165                 170                 175
Val Cys Phe Lys Lys Arg Ile Glu Ala Ile Pro Gln Ile Asp Lys Tyr
        180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
        210                 215                 220
Gly Ser Pro Gly Ile Pro Gly Ser Thr Arg Ala Ala Ala Ser Gly Asp
225                 230                 235                 240
Val Phe Arg Glu Leu Arg Asp Arg Trp Asn Ala Thr Ser His His Thr
            245                 250                 255
Arg Pro
```

(2) INFORMATION FOR SEQ ID NO: 223:
  (i) SEQUENCE CHARACTERISTICS:

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(A) LENGTH: 257 amino acids
    (B) TYPE: amino acid
    (C) STRANDEDNESS: <Unknown>
    (D) TOPOLOGY: unknown
(ii) MOLECULE TYPE: peptide
(xi) SEQUENCE DESCRIPTION: SEQ ID NO: 223:
 Met Ser Pro Ile Leu Gly Tyr Trp Lys Ile Lys Gly Leu Val Gln Pro
  1       5        10       15
 Thr Arg Leu Leu Leu Glu Tyr Leu Glu Glu Lys Tyr Glu Glu His Leu
        20        25        30
 Tyr Glu Arg Asp Glu Gly Asp Lys Trp Arg Asn Lys Lys Phe Glu Leu
      35        40        45
 Gly Leu Glu Phe Pro Asn Leu Pro Tyr Tyr Ile Asp Gly Asp Val Lys
    50        55        60
 Leu Thr Gln Ser Met Ala Ile Ile Arg Tyr Ile Ala Asp Lys His Asn
65        70        75        80
 Met Leu Gly Gly Cys Pro Lys Glu Arg Ala Glu Ile Ser Met Leu Glu
        85        90        95
 Gly Ala Val Leu Asp Ile Arg Tyr Gly Val Ser Arg Ile Ala Tyr Ser
        100       105       110
 Lys Asp Phe Glu Thr Leu Lys Val Asp Phe Leu Ser Lys Leu Pro Glu
      115       120       125
 Met Leu Lys Met Phe Glu Asp Arg Leu Cys His Lys Thr Tyr Leu Asn
    130       135       140
 Gly Asp His Val Thr His Pro Asp Phe Met Leu Tyr Asp Ala Leu Asp
145       150       155       160
 Val Val Leu Tyr Met Asp Pro Met Cys Leu Asp Ala Phe Pro Lys Leu
      165       170       175
 Val Cys Phe Lys Lys Arg Ile Glu Ala Ile Pro Gln Ile Asp Lys Tyr
      180       185       190
 Leu Lys Ser Ser Lys Tyr Ile Ala Trp Pro Leu Gln Gly Trp Gln Ala
    195       200       205
 Thr Phe Gly Gly Gly Asp His Pro Pro Lys Ser Asp Leu Val Pro Arg
    210       215       220
 Gly Ser Pro Gly Ile Pro Gly Ser Thr Arg Ala Ala Ala Ser Trp Asn
225       230       235       240
 Ala Thr Ser His His Thr Arg Pro Thr Pro Gln Leu Pro Arg Gly Pro
      245       250       255
 Asn (2) INFORMATION FOR SEQ ID NO: 224:
  (i) SEQUENCE CHARACTERISTICS:
    (A) LENGTH: 267 amino acids
    (B) TYPE: amino acid
    (C) STRANDEDNESS: <Unknown>
    (D) TOPOLOGY: unknown

UNITED STATES PATENT AND TRADEMARK OFFICE
CERTIFICATE OF CORRECTION

PATENT NO.         : 7,053,177 B1
APPLICATION NO. : 09/079678
DATED                  : May 30, 2006
INVENTOR(S)        : Vernon L. Alvarez et al.

It is certified that error appears in the above-identified patent and that said Letters Patent is hereby corrected as shown below:

```
(ii) MOLECULE TYPE: peptide
(xi) SEQUENCE DESCRIPTION: SEQ ID NO: 224:
  Met Ser Pro Ile Leu Gly Tyr Trp Lys Ile Lys Gly Leu Val Gln Pro
   1               5              10              15
  Thr Arg Leu Leu Leu Glu Tyr Leu Glu Glu Lys Tyr Glu Glu His Leu
          20              25              30
  Tyr Glu Arg Asp Glu Gly Asp Lys Trp Arg Asn Lys Lys Phe Glu Leu
          35              40              45
  Gly Leu Glu Phe Pro Asn Leu Pro Tyr Tyr Ile Asp Gly Asp Val Lys
     50              55              60
  Leu Thr Gln Ser Met Ala Ile Ile Arg Tyr Ile Ala Asp Lys His Asn
  65              70              75              80
  Met Leu Gly Gly Cys Pro Lys Glu Arg Ala Glu Ile Ser Met Leu Glu
             85              90              95
  Gly Ala Val Leu Asp Ile Arg Tyr Gly Val Ser Arg Ile Ala Tyr Ser
             100             105             110
  Lys Asp Phe Glu Thr Leu Lys Val Asp Phe Leu Ser Lys Leu Pro Glu
        115             120             125
  Met Leu Lys Met Phe Glu Asp Arg Leu Cys His Lys Thr Tyr Leu Asn
        130             135             140
  Gly Asp His Val Thr His Pro Asp Phe Met Leu Tyr Asp Ala Leu Asp
  145             150             155             160
  Val Val Leu Tyr Met Asp Pro Met Cys Leu Asp Ala Phe Pro Lys Leu
        165             170             175
  Val Cys Phe Lys Lys Arg Ile Glu Ala Ile Pro Gln Ile Asp Lys Tyr
        180             185             190
  Leu Lys Ser Ser Lys Tyr Ile Ala Trp Pro Leu Gln Gly Trp Gln Ala
          195             200             205
  Thr Phe Gly Gly Gly Asp His Pro Pro Lys Ser Asp Leu Val Pro Arg
     210             215             220
  Gly Ser Pro Gly Ile Pro Gly Ser Thr Arg Ala Ala Ala Ser Gly Asp
  225             230             235             240
  Val Phe Arg Glu Leu Arg Asp Arg Trp Asn Ala Thr Ser His His Thr
          245             250             255
  Arg Pro Thr Pro Gln Leu Pro Arg Gly Pro Asn
          260             265

(2) INFORMATION FOR SEQ ID NO: 225:
   (i) SEQUENCE CHARACTERISTICS:
       (A) LENGTH: 277 amino acids
       (B) TYPE: amino acid
       (C) STRANDEDNESS: <Unknown>
       (D) TOPOLOGY: unknown
  (ii) MOLECULE TYPE: peptide
  (xi) SEQUENCE DESCRIPTION: SEQ ID NO: 225:
   Met Ser Pro Ile Leu Gly Tyr Trp Lys Ile Lys Gly Leu Val Gln Pro
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
            1           5           10          15
    Thr Arg Leu Leu Leu Glu Tyr Leu Glu Glu Lys Tyr Glu Glu His Leu
               20          25          30
    Tyr Glu Arg Asp Glu Gly Asp Lys Trp Arg Asn Lys Lys Phe Glu Leu
               35          40          45
    Gly Leu Glu Phe Pro Asn Leu Pro Tyr Tyr Ile Asp Gly Asp Val Lys
               50          55          60
    Leu Thr Gln Ser Met Ala Ile Ile Arg Tyr Ile Ala Asp Lys His Asn
       65          70          75          80
    Met Leu Gly Gly Cys Pro Lys Glu Arg Ala Glu Ile Ser Met Leu Glu
               85          90          95
    Gly Ala Val Leu Asp Ile Arg Tyr Gly Val Ser Arg Ile Ala Tyr Ser
              100         105         110
    Lys Asp Phe Glu Thr Leu Lys Val Asp Phe Leu Ser Lys Leu Pro Glu
              115         120         125
    Met Leu Lys Met Phe Glu Asp Arg Leu Cys His Lys Thr Tyr Leu Asn
              130         135         140
    Gly Asp His Val Thr His Pro Asp Phe Met Leu Tyr Asp Ala Leu Asp
       145         150         155         160
    Val Val Leu Tyr Met Asp Pro Met Cys Leu Asp Ala Phe Pro Lys Leu
              165         170         175
    Val Cys Phe Lys Lys Arg Ile Glu Ala Ile Pro Gln Ile Asp Lys Tyr
              180         185         190
    Leu Lys Ser Ser Lys Tyr Ile Ala Trp Pro Leu Gln Gly Trp Gln Ala
              195         200         205
    Thr Phe Gly Gly Gly Asp His Pro Pro Lys Ser Asp Leu Val Pro Arg
              210         215         220
    Gly Ser Pro Gly Ile Pro Gly Ser Thr Arg Ala Ala Ala Ser Ser His
       225         230         235         240
    Ser Gly Gly Met Asn Arg Ala Tyr Gly Asp Val Phe Arg Glu Leu Arg
              245         250         255
    Asp Arg Trp Asn Ala Thr Ser Ala Ala Thr Arg Pro Thr Pro Gln Leu
              260         265         270
    Pro Arg Gly Pro Asn
              275
```

(2) INFORMATION FOR SEQ ID NO: 226:
   (i) SEQUENCE CHARACTERISTICS:
      (A) LENGTH: 277 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 226:

```
    Met Ser Pro Ile Leu Gly Tyr Trp Lys Ile Lys Gly Leu Val Gln Pro
            1           5           10          15
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
Thr Arg Leu Leu Leu Glu Tyr Leu Glu Glu Lys Tyr Glu Glu His Leu
        20              25              30
Tyr Glu Arg Asp Glu Gly Asp Lys Trp Arg Asn Lys Lys Phe Glu Leu
        35              40              45
Gly Leu Glu Phe Pro Asn Leu Pro Tyr Tyr Ile Asp Gly Asp Val Lys
        50              55              60
Leu Thr Gln Ser Met Ala Ile Ile Arg Tyr Ile Ala Asp Lys His Asn
    65              70              75              80
Met Leu Gly Gly Cys Pro Lys Glu Arg Ala Glu Ile Ser Met Leu Glu
            85              90              95
Gly Ala Val Leu Asp Ile Arg Tyr Gly Val Ser Arg Ile Ala Tyr Ser
            100             105             110
Lys Asp Phe Glu Thr Leu Lys Val Asp Phe Leu Ser Lys Leu Pro Glu
        115             120             125
Met Leu Lys Met Phe Glu Asp Arg Leu Cys His Lys Thr Tyr Leu Asn
        130             135             140
Gly Asp His Val Thr His Pro Asp Phe Met Leu Tyr Asp Ala Leu Asp
    145             150             155             160
Val Val Leu Tyr Met Asp Pro Met Cys Leu Asp Ala Phe Pro Lys Leu
            165             170             175
Val Cys Phe Lys Lys Arg Ile Glu Ala Ile Pro Gln Ile Asp Lys Tyr
            180             185             190
Leu Lys Ser Ser Lys Tyr Ile Ala Trp Pro Leu Gln Gly Trp Gln Ala
            195             200             205
Thr Phe Gly Gly Gly Asp His Pro Pro Lys Ser Asp Leu Val Pro Arg
        210             215             220
Gly Ser Pro Gly Ile Pro Gly Ser Thr Arg Ala Ala Ala Ser Ser Ala
    225             230             235             240
Arg Asp Ser Gly Pro Ala Glu Asp Gly Ser Arg Ala Val Arg Leu Asn
            245             250             255
Gly Val Glu Asn Ala Asn Thr Arg Lys Ser Ser Arg Ser Asn Pro Arg
        260             265             270
Gly Arg Arg His Pro
        275
```

(2) INFORMATION FOR SEQ ID NO: 227:
  (i) SEQUENCE CHARACTERISTICS:
    (A) LENGTH: 257 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 227:

```
Met Ser Pro Ile Leu Gly Tyr Trp Lys Ile Lys Gly Leu Val Gln Pro
1               5               10              15
Thr Arg Leu Leu Leu Glu Tyr Leu Glu Glu Lys Tyr Glu Glu His Leu
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
                    20              25              30
   Tyr Glu Arg Asp Glu Gly Asp Lys Trp Arg Asn Lys Lys Phe Glu Leu
              35              40              45
   Gly Leu Glu Phe Pro Asn Leu Pro Tyr Tyr Ile Asp Gly Asp Val Lys
          50              55              60
   Leu Thr Gln Ser Met Ala Ile Ile Arg Tyr Ile Ala Asp Lys His Asn
      65              70              75              80
   Met Leu Gly Gly Cys Pro Lys Glu Arg Ala Glu Ile Ser Met Leu Glu
                  85              90              95
   Gly Ala Val Leu Asp Ile Arg Tyr Gly Val Ser Arg Ile Ala Tyr Ser
              100             105             110
   Lys Asp Phe Glu Thr Leu Lys Val Asp Phe Leu Ser Lys Leu Pro Glu
              115             120             125
   Met Leu Lys Met Phe Glu Asp Arg Leu Cys His Lys Thr Tyr Leu Asn
          130             135             140
   Gly Asp His Val Thr His Pro Asp Phe Met Leu Tyr Asp Ala Leu Asp
      145             150             155             160
   Val Val Leu Tyr Met Asp Pro Met Cys Leu Asp Ala Phe Pro Lys Leu
                  165             170             175
   Val Cys Phe Lys Lys Arg Ile Glu Ala Ile Pro Gln Ile Asp Lys Tyr
              180             185             190
   Leu Lys Ser Ser Lys Tyr Ile Ala Trp Pro Leu Gln Gly Trp Gln Ala
                  195             200             205
   Thr Phe Gly Gly Gly Asp His Pro Pro Lys Ser Asp Leu Val Pro Arg
      210             215             220
   Gly Ser Pro Gly Ile Pro Gly Ser Thr Arg Ala Ala Ala Ser Ser Ala
      225             230             235             240
   Arg Asp Ser Gly Pro Ala Glu Asp Gly Ser Arg Ala Val Arg Leu Asn
              245             250             255
   Gly
```

(2) INFORMATION FOR SEQ ID NO: 228:
  (i) SEQUENCE CHARACTERISTICS:
    (A) LENGTH: 259 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 228:

```
   Met Ser Pro Ile Leu Gly Tyr Trp Lys Ile Lys Gly Leu Val Gln Pro
   1               5               10              15
   Thr Arg Leu Leu Leu Glu Tyr Leu Glu Glu Lys Tyr Glu Glu His Leu
              20              25              30
   Tyr Glu Arg Asp Glu Gly Asp Lys Trp Arg Asn Lys Lys Phe Glu Leu
              35              40              45
   Gly Leu Glu Phe Pro Asn Leu Pro Tyr Tyr Ile Asp Gly Asp Val Lys
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
         50              55              60
  Leu Thr Gln Ser Met Ala Ile Ile Arg Tyr Ile Ala Asp Lys His Asn
   65              70              75              80
  Met Leu Gly Gly Cys Pro Lys Glu Arg Ala Glu Ile Ser Met Leu Glu
              85              90              95
  Gly Ala Val Leu Asp Ile Arg Tyr Gly Val Ser Arg Ile Ala Tyr Ser
              100             105             110
  Lys Asp Phe Glu Thr Leu Lys Val Asp Phe Leu Ser Lys Leu Pro Glu
          115             120             125
  Met Leu Lys Met Phe Glu Asp Arg Leu Cys His Lys Thr Tyr Leu Asn
              130             135             140
  Gly Asp His Val Thr His Pro Asp Phe Met Leu Tyr Asp Ala Leu Asp
   145             150             155             160
  Val Val Leu Tyr Met Asp Pro Met Cys Leu Asp Ala Phe Pro Lys Leu
                  165             170             175
  Val Cys Phe Lys Lys Arg Ile Glu Ala Ile Pro Gln Ile Asp Lys Tyr
                  180             185             190
  Leu Lys Ser Ser Lys Tyr Ile Ala Trp Pro Leu Gln Gly Trp Gln Ala
              195             200             205
  Thr Phe Gly Gly Gly Asp His Pro Pro Lys Ser Asp Leu Val Pro Arg
       210             215             220
  Gly Ser Pro Gly Ile Pro Gly Ser Thr Arg Ala Ala Ala Ser Asp Gly
   225             230             235             240
  Ser Arg Ala Val Arg Leu Asn Gly Val Glu Asn Ala Asn Thr Arg Lys
                  245             250             255
  Ser Ser Arg (2) INFORMATION FOR SEQ ID NO: 229:
      (i) SEQUENCE CHARACTERISTICS:
          (A) LENGTH: 257 amino acids
          (B) TYPE: amino acid
          (C) STRANDEDNESS: <Unknown>
          (D) TOPOLOGY: unknown
      (ii) MOLECULE TYPE: peptide
      (xi) SEQUENCE DESCRIPTION: SEQ ID NO: 229:
    Met Ser Pro Ile Leu Gly Tyr Trp Lys Ile Lys Gly Leu Val Gln Pro
     1               5              10              15
    Thr Arg Leu Leu Leu Glu Tyr Leu Glu Glu Lys Tyr Glu Glu His Leu
            20              25              30
    Tyr Glu Arg Asp Glu Gly Asp Lys Trp Arg Asn Lys Lys Phe Glu Leu
            35              40              45
    Gly Leu Glu Phe Pro Asn Leu Pro Tyr Tyr Ile Asp Gly Asp Val Lys
         50              55              60
    Leu Thr Gln Ser Met Ala Ile Ile Arg Tyr Ile Ala Asp Lys His Asn
     65              70              75              80
    Met Leu Gly Gly Cys Pro Lys Glu Arg Ala Glu Ile Ser Met Leu Glu
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
                85          90          95
    Gly Ala Val Leu Asp Ile Arg Tyr Gly Val Ser Arg Ile Ala Tyr Ser
               100         105         110
    Lys Asp Phe Glu Thr Leu Lys Val Asp Phe Leu Ser Lys Leu Pro Glu
               115         120         125
    Met Leu Lys Met Phe Glu Asp Arg Leu Cys His Lys Thr Tyr Leu Asn
               130         135         140
    Gly Asp His Val Thr His Pro Asp Phe Met Leu Tyr Asp Ala Leu Asp
    145         150         155         160
    Val Val Leu Tyr Met Asp Pro Met Cys Leu Asp Ala Phe Pro Lys Leu
               165         170         175
    Val Cys Phe Lys Lys Arg Ile Glu Ala Ile Pro Gln Ile Asp Lys Tyr
               180         185         190
    Leu Lys Ser Ser Lys Tyr Ile Ala Trp Pro Leu Gln Gly Trp Gln Ala
               195         200         205
    Thr Phe Gly Gly Gly Asp His Pro Pro Lys Ser Asp Leu Val Pro Arg
               210         215         220
    Gly Ser Pro Gly Ile Pro Gly Ser Thr Arg Ala Ala Ala Ser Glu Asn
    225         230         235         240
    Ala Asn Thr Arg Lys Ser Ser Arg Ser Asn Pro Arg Gly Arg Arg His
               245         250         255
    Pro (2) INFORMATION FOR SEQ ID NO: 230:
    (i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 230:
    Met Ser Pro Ile Leu Gly Tyr Trp Lys Ile Lys Gly Leu Val Gln Pro
    1           5           10          15
    Thr Arg Leu Leu Leu Glu Tyr Leu Glu Glu Lys Tyr Glu Glu His Leu
                20          25          30
    Tyr Glu Arg Asp Glu Gly Asp Lys Trp Arg Asn Lys Lys Phe Glu Leu
               35          40          45
    Gly Leu Glu Phe Pro Asn Leu Pro Tyr Tyr Ile Asp Gly Asp Val Lys
        50          55          60
    Leu Thr Gln Ser Met Ala Ile Ile Arg Tyr Ile Ala Asp Lys His Asn
    65          70          75          80
    Met Leu Gly Gly Cys Pro Lys Glu Arg Ala Glu Ile Ser Met Leu Glu
                85          90          95
    Gly Ala Val Leu Asp Ile Arg Tyr Gly Val Ser Arg Ile Ala Tyr Ser
               100         105         110
    Lys Asp Phe Glu Thr Leu Lys Val Asp Phe Leu Ser Lys Leu Pro Glu
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
                115           120           125
     Met Leu Lys Met Phe Glu Asp Arg Leu Cys His Lys Thr Tyr Leu Asn
             130           135           140
     Gly Asp His Val Thr His Pro Asp Phe Met Leu Tyr Asp Ala Leu Asp
         145           150           155           160
     Val Val Leu Tyr Met Asp Pro Met Cys Leu Asp Ala Phe Pro Lys Leu
                 165           170           175
     Val Cys Phe Lys Lys Arg Ile Glu Ala Ile Pro Gln Ile Asp Lys Tyr
             180           185           190
     Leu Lys Ser Ser Lys Tyr Ile Ala Trp Pro Leu Gln Gly Trp Gln Ala
             195           200           205
     Thr Phe Gly Gly Gly Asp His Pro Pro Lys Ser Asp Leu Val Pro Arg
         210           215           220
     Gly Ser Pro Gly Ile Pro Gly Ser Thr Arg Ala Ala Ala Ser Glu Asn
     225           230           235           240
     Ala Asn Thr Arg Lys Ser Ser Arg
                 245
```

(2) INFORMATION FOR SEQ ID NO: 231:
   (i) SEQUENCE CHARACTERISTICS:
      (A) LENGTH: 248 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 231:

```
     Met Ser Pro Ile Leu Gly Tyr Trp Lys Ile Lys Gly Leu Val Gln Pro
     1           5           10          15
     Thr Arg Leu Leu Leu Glu Tyr Leu Glu Glu Lys Tyr Glu Glu His Leu
             20          25          30
     Tyr Glu Arg Asp Glu Gly Asp Lys Trp Arg Asn Lys Lys Phe Glu Leu
             35          40          45
     Gly Leu Glu Phe Pro Asn Leu Pro Tyr Tyr Ile Asp Gly Asp Val Lys
     50          55          60
     Leu Thr Gln Ser Met Ala Ile Ile Arg Tyr Ile Ala Asp Lys His Asn
     65          70          75          80
     Met Leu Gly Gly Cys Pro Lys Glu Arg Ala Glu Ile Ser Met Leu Glu
                 85          90          95
     Gly Ala Val Leu Asp Ile Arg Tyr Gly Val Ser Arg Ile Ala Tyr Ser
             100         105         110
     Lys Asp Phe Glu Thr Leu Lys Val Asp Phe Leu Ser Lys Leu Pro Glu
             115         120         125
     Met Leu Lys Met Phe Glu Asp Arg Leu Cys His Lys Thr Tyr Leu Asn
             130         135         140
     Gly Asp His Val Thr His Pro Asp Phe Met Leu Tyr Asp Ala Leu Asp
     145         150         155         160
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
   Val Val Leu Tyr Met Asp Pro Met Cys Leu Asp Ala Phe Pro Lys Leu
           165                 170                 175
   Val Cys Phe Lys Arg Ile Glu Ala Ile Pro Gln Ile Asp Lys Tyr
           180                 185                 190
   Leu Lys Ser Ser Lys Tyr Ile Ala Trp Pro Leu Gln Gly Trp Gln Ala
           195                 200                 205
   Thr Phe Gly Gly Gly Asp His Pro Pro Lys Ser Asp Leu Val Pro Arg
           210                 215                 220
   Gly Ser Pro Gly Ile Pro Gly Ser Thr Arg Ala Ala Ala Ser Arg Lys
       225                 230                 235             240
   Ser Ser Arg Ser Asn Pro Arg Gly
               245
```

(2) INFORMATION FOR SEQ ID NO: 232:
    (i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 232:

```
   Met Ser Pro Ile Leu Gly Tyr Trp Lys Ile Lys Gly Leu Val Gln Pro
    1               5                 10                  15
   Thr Arg Leu Leu Leu Glu Tyr Leu Glu Glu Lys Tyr Glu Glu His Leu
           20                  25                  30
   Tyr Glu Arg Asp Gly Asp Lys Trp Arg Asn Lys Lys Phe Glu Leu
           35                  40                  45
   Gly Leu Glu Phe Pro Asn Leu Pro Tyr Tyr Ile Asp Gly Asp Val Lys
           50                  55                  60
   Leu Thr Gln Ser Met Ala Ile Ile Arg Tyr Ile Ala Asp Lys His Asn
       65                  70                  75              80
   Met Leu Gly Gly Cys Pro Lys Glu Arg Ala Glu Ile Ser Met Leu Glu
               85                  90                  95
   Gly Ala Val Leu Asp Ile Arg Tyr Gly Val Ser Arg Ile Ala Tyr Ser
               100                 105                 110
   Lys Asp Phe Glu Thr Leu Lys Val Asp Phe Leu Ser Lys Leu Pro Glu
               115                 120                 125
   Met Leu Lys Met Phe Glu Asp Arg Leu Cys His Lys Thr Tyr Leu Asn
               130                 135                 140
   Gly Asp His Val Thr His Pro Asp Phe Met Leu Tyr Asp Ala Leu Asp
       145                 150                 155             160
   Val Val Leu Tyr Met Asp Pro Met Cys Leu Asp Ala Phe Pro Lys Leu
               165                 170                 175
   Val Cys Phe Lys Arg Ile Glu Ala Ile Pro Gln Ile Asp Lys Tyr
               180                 185                 190
   Leu Lys Ser Ser Lys Tyr Ile Ala Trp Pro Leu Gln Gly Trp Gln Ala
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
             195             200             205
    Thr Phe Gly Gly Gly Asp His Pro Pro Lys Ser Asp Leu Val Pro Arg
         210             215             220
    Gly Ser Pro Gly Ile Pro Gly Ser Thr Arg Ala Ala Ala Ser Ser Asn
    225             230             235             240
    Pro Arg Gly Arg Arg His Pro
                245

(2) INFORMATION FOR SEQ ID NO: 233:
    (i) SEQUENCE CHARACTERISTICS:
        (A) LENGTH: 249 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 233:
      Met Ser Pro Ile Leu Gly Tyr Trp Lys Ile Lys Gly Leu Val Gln Pro
      1           5              10              15
      Thr Arg Leu Leu Leu Glu Tyr Leu Glu Glu Lys Tyr Glu Glu His Leu
              20              25              30
      Tyr Glu Arg Asp Glu Gly Asp Lys Trp Arg Asn Lys Lys Phe Glu Leu
              35              40              45
      Gly Leu Glu Phe Pro Asn Leu Pro Tyr Tyr Ile Asp Gly Asp Val Lys
              50              55              60
      Leu Thr Gln Ser Met Ala Ile Ile Arg Tyr Ile Ala Asp Lys His Asn
      65              70              75              80
      Met Leu Gly Gly Cys Pro Lys Glu Arg Ala Glu Ile Ser Met Leu Glu
              85              90              95
      Gly Ala Val Leu Asp Ile Arg Tyr Gly Val Ser Arg Ile Ala Tyr Ser
              100             105             110
      Lys Asp Phe Glu Thr Leu Lys Val Asp Phe Leu Ser Lys Leu Pro Glu
              115             120             125
      Met Leu Lys Met Phe Glu Asp Arg Leu Cys His Lys Thr Tyr Leu Asn
              130             135             140
      Gly Asp His Val Thr His Pro Asp Phe Met Leu Tyr Asp Ala Leu Asp
      145             150             155             160
      Val Val Leu Tyr Met Asp Pro Met Cys Leu Asp Ala Phe Pro Lys Leu
              165             170             175
      Val Cys Phe Lys Lys Arg Ile Glu Ala Ile Pro Gln Ile Asp Lys Tyr
              180             185             190
      Leu Lys Ser Ser Lys Tyr Ile Ala Trp Pro Leu Gln Gly Trp Gln Ala
              195             200             205
      Thr Phe Gly Gly Gly Asp His Pro Pro Lys Ser Asp Leu Val Pro Arg
              210             215             220
      Gly Ser Pro Gly Ile Pro Gly Ser Thr Arg Ala Ala Ala Ser Thr Arg
      225             230             235             240
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
      Lys Ser Ser Arg Ser Asn Pro Arg Gly
                    245

(2) INFORMATION FOR SEQ ID NO: 234:
    (i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 234:
   Met Ser Pro Ile Leu Gly Tyr Trp Lys Ile Lys Gly Leu Val Gln Pro
    1               5                  10                  15
   Thr Arg Leu Leu Leu Glu Tyr Leu Glu Glu Lys Tyr Glu Glu His Leu
            20                  25                  30
   Tyr Glu Arg Asp Glu Gly Asp Lys Trp Arg Asn Lys Lys Phe Glu Leu
            35                  40                  45
   Gly Leu Glu Phe Pro Asn Leu Pro Tyr Tyr Ile Asp Gly Asp Val Lys
    50                  55                  60
   Leu Thr Gln Ser Met Ala Ile Ile Arg Tyr Ile Ala Asp Lys His Asn
    65                  70                  75                  80
   Met Leu Gly Gly Cys Pro Lys Glu Arg Ala Glu Ile Ser Met Leu Glu
                85                  90                  95
   Gly Ala Val Leu Asp Ile Arg Tyr Gly Val Ser Arg Ile Ala Tyr Ser
                100                 105                 110
   Lys Asp Phe Glu Thr Leu Lys Val Asp Phe Leu Ser Lys Leu Pro Glu
            115                 120                 125
   Met Leu Lys Met Phe Glu Asp Arg Leu Cys His Lys Thr Tyr Leu Asn
            130                 135                 140
   Gly Asp His Val Thr His Pro Asp Phe Met Leu Tyr Asp Ala Leu Asp
   145                 150                 155                 160
   Val Val Leu Tyr Met Asp Pro Met Cys Leu Asp Ala Phe Pro Lys Leu
                165                 170                 175
   Val Cys Phe Lys Lys Arg Ile Glu Ala Ile Pro Gln Ile Asp Lys Tyr
                180                 185                 190
   Leu Lys Ser Ser Lys Tyr Ile Ala Trp Pro Leu Gln Gly Trp Gln Ala
            195                 200                 205
   Thr Phe Gly Gly Gly Asp His Pro Pro Lys Ser Asp Leu Val Pro Arg
    210                 215                 220
   Gly Ser Pro Gly Ile Pro Gly Ser Thr Arg Ala Ala Ala Ser Ser Thr
   225                 230                 235                 240
   Pro Pro Ser Arg Glu Ala Tyr Ser Arg Pro Tyr Ser Val Asp Ser Asp
                245                 250                 255
   Ser Asp Thr Asn Ala Lys His Ser Ser His Asn Arg Arg Leu Arg Thr
                260                 265                 270
   Arg Ser Arg Pro Asn
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

275

(2) INFORMATION FOR SEQ ID NO: 235:
  (i) SEQUENCE CHARACTERISTICS:
    (A) LENGTH: 258 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 235:

```
Met Ser Pro Ile Leu Gly Tyr Trp Lys Ile Lys Gly Leu Val Gln Pro
 1               5                  10                  15
Thr Arg Leu Leu Leu Glu Tyr Leu Glu Glu Lys Tyr Glu Glu His Leu
            20                  25                  30
Tyr Glu Arg Asp Glu Gly Asp Lys Trp Arg Asn Lys Lys Phe Glu Leu
        35                  40                  45
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
    130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
Gly Ser Pro Gly Ile Pro Gly Ser Thr Arg Ala Ala Ala Ser Ser Thr
225                 230                 235                 240
Pro Pro Ser Arg Glu Ala Tyr Ser Arg Pro Tyr Ser Val Asp Ser Asp
                245                 250                 255
Ser Asp
```

(2) INFORMATION FOR SEQ ID NO: 236:
  (i) SEQUENCE CHARACTERISTICS:

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(A) LENGTH: 259 amino acids
    (B) TYPE: amino acid
    (C) STRANDEDNESS: <Unknown>
    (D) TOPOLOGY: unknown
 (ii) MOLECULE TYPE: peptide
 (xi) SEQUENCE DESCRIPTION: SEQ ID NO: 236:

```
Met Ser Pro Ile Leu Gly Tyr Trp Lys Ile Lys Gly Leu Val Gln Pro
 1               5                  10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
                35                  40                  45
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
    115                 120                 125
Met Leu Lys Met Phe Glu Asp Arg Leu Cys His Lys Thr Tyr Leu Asn
    130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
    180                 185                 190
Leu Lys Ser Ser Lys Tyr Ile Ala Trp Pro Leu Gln Gly Trp Gln Ala
    195                 200                 205
Thr Phe Gly Gly Gly Asp His Pro Pro Lys Ser Asp Leu Val Pro Arg
    210                 215                 220
Gly Ser Pro Gly Ile Pro Gly Ser Thr Arg Ala Ala Ala Ser Ser Arg
225                 230                 235                 240
Pro Tyr Ser Val Asp Ser Asp Ser Asp Thr Asn Ala Lys His Ser Ser
                245                 250                 255
His Asn Arg
```

(2) INFORMATION FOR SEQ ID NO: 237:
  (i) SEQUENCE CHARACTERISTICS:
    (A) LENGTH: 257 amino acids
    (B) TYPE: amino acid
    (C) STRANDEDNESS: <Unknown>
    (D) TOPOLOGY: unknown

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
   (ii) MOLECULE TYPE: peptide
   (xi) SEQUENCE DESCRIPTION: SEQ ID NO: 237:
    Met Ser Pro Ile Leu Gly Tyr Trp Lys Ile Lys Gly Leu Val Gln Pro
     1               5                   10                  15
    Thr Arg Leu Leu Leu Glu Tyr Leu Glu Glu Lys Tyr Glu Glu His Leu
             20                  25                  30
    Tyr Glu Arg Asp Glu Gly Asp Lys Trp Arg Asn Lys Lys Phe Glu Leu
              35                  40                  45
    Gly Leu Glu Phe Pro Asn Leu Pro Tyr Tyr Ile Asp Gly Asp Val Lys
             50                  55                  60
    Leu Thr Gln Ser Met Ala Ile Ile Arg Tyr Ile Ala Asp Lys His Asn
    65                  70                  75                  80
    Met Leu Gly Gly Cys Pro Lys Glu Arg Ala Glu Ile Ser Met Leu Glu
                 85                  90                  95
    Gly Ala Val Leu Asp Ile Arg Tyr Gly Val Ser Arg Ile Ala Tyr Ser
                100                 105                 110
    Lys Asp Phe Glu Thr Leu Lys Val Asp Phe Leu Ser Lys Leu Pro Glu
            115                 120                 125
    Met Leu Lys Met Phe Glu Asp Arg Leu Cys His Lys Thr Tyr Leu Asn
            130                 135                 140
    Gly Asp His Val Thr His Pro Asp Phe Met Leu Tyr Asp Ala Leu Asp
    145                 150                 155                 160
    Val Val Leu Tyr Met Asp Pro Met Cys Leu Asp Ala Phe Pro Lys Leu
                165                 170                 175
    Val Cys Phe Lys Lys Arg Ile Glu Ala Ile Pro Gln Ile Asp Lys Tyr
                180                 185                 190
    Leu Lys Ser Ser Lys Tyr Ile Ala Trp Pro Leu Gln Gly Trp Gln Ala
                195                 200                 205
    Thr Phe Gly Gly Gly Asp His Pro Pro Lys Ser Asp Leu Val Pro Arg
            210                 215                 220
    Gly Ser Pro Gly Ile Pro Gly Ser Thr Arg Ala Ala Ala Ser Thr Asn
    225                 230                 235                 240
    Ala Lys His Ser Ser His Asn Arg Arg Leu Arg Thr Arg Ser Arg Pro
                245                 250                 255
    Asn (2) INFORMATION FOR SEQ ID NO: 238:
    (i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 238:
     Met Ser Pro Ile Leu Gly Tyr Trp Lys Ile Lys Gly Leu Val Gln Pro
      1               5                   10                  15
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
    Thr Arg Leu Leu Leu Glu Tyr Leu Glu Glu Lys Tyr Glu Glu His Leu
         20            25            30
    Tyr Glu Arg Asp Glu Gly Asp Lys Trp Arg Asn Lys Lys Phe Glu Leu
         35            40            45
    Gly Leu Glu Phe Pro Asn Leu Pro Tyr Tyr Ile Asp Gly Asp Val Lys
         50            55            60
    Leu Thr Gln Ser Met Ala Ile Ile Arg Tyr Ile Ala Asp Lys His Asn
    65            70            75            80
    Met Leu Gly Gly Cys Pro Lys Glu Arg Ala Glu Ile Ser Met Leu Glu
             85            90            95
    Gly Ala Val Leu Asp Ile Arg Tyr Gly Val Ser Arg Ile Ala Tyr Ser
             100           105           110
    Lys Asp Phe Glu Thr Leu Lys Val Asp Phe Leu Ser Lys Leu Pro Glu
             115           120           125
    Met Leu Lys Met Phe Glu Asp Arg Leu Cys His Lys Thr Tyr Leu Asn
             130           135           140
    Gly Asp His Val Thr His Pro Asp Phe Met Leu Tyr Asp Ala Leu Asp
    145           150           155           160
    Val Val Leu Tyr Met Asp Pro Met Cys Leu Asp Ala Phe Pro Lys Leu
             165           170           175
    Val Cys Phe Lys Lys Arg Ile Glu Ala Ile Pro Gln Ile Asp Lys Tyr
             180           185           190
    Leu Lys Ser Ser Lys Tyr Ile Ala Trp Pro Leu Gln Gly Trp Gln Ala
             195           200           205
    Thr Phe Gly Gly Gly Asp His Pro Pro Lys Ser Asp Leu Val Pro Arg
             210           215           220
    Gly Ser Pro Gly Ile Pro Gly Ser Thr Arg Ala Ala Ala Ser Thr Asn
    225           230           235           240
    Ala Lys His Ser Ser His Asn
             245

(2) INFORMATION FOR SEQ ID NO: 239:
    (i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 239:
    Met Ser Pro Ile Leu Gly Tyr Trp Lys Ile Lys Gly Leu Val Gln Pro
    1             5             10            15
    Thr Arg Leu Leu Leu Glu Tyr Leu Glu Glu Lys Tyr Glu Glu His Leu
             20            25            30
    Tyr Glu Arg Asp Glu Gly Asp Lys Trp Arg Asn Lys Lys Phe Glu Leu
             35            40            45
    Gly Leu Glu Phe Pro Asn Leu Pro Tyr Tyr Ile Asp Gly Asp Val Lys
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
              50           55           60
   Leu Thr Gln Ser Met Ala Ile Ile Arg Tyr Ile Ala Asp Lys His Asn
    65           70           75           80
   Met Leu Gly Gly Cys Pro Lys Glu Arg Ala Glu Ile Ser Met Leu Glu
              85           90           95
   Gly Ala Val Leu Asp Ile Arg Tyr Gly Val Ser Arg Ile Ala Tyr Ser
             100          105          110
   Lys Asp Phe Glu Thr Leu Lys Val Asp Phe Leu Ser Lys Leu Pro Glu
             115          120          125
   Met Leu Lys Met Phe Glu Asp Arg Leu Cys His Lys Thr Tyr Leu Asn
             130          135          140
   Gly Asp His Val Thr His Pro Asp Phe Met Leu Tyr Asp Ala Leu Asp
    145          150          155          160
   Val Val Leu Tyr Met Asp Pro Met Cys Leu Asp Ala Phe Pro Lys Leu
             165          170          175
   Val Cys Phe Lys Lys Arg Ile Glu Ala Ile Pro Gln Ile Asp Lys Tyr
             180          185          190
   Leu Lys Ser Ser Lys Tyr Ile Ala Trp Pro Leu Gln Gly Trp Gln Ala
             195          200          205
   Thr Phe Gly Gly Gly Asp His Pro Pro Lys Ser Asp Leu Val Pro Arg
             210          215          220
   Gly Ser Pro Gly Ile Pro Gly Ser Thr Arg Ala Ala Ala Ser Ser Ser
    225          230          235          240
   His Asn Arg Arg Leu Arg Thr Arg
             245

(2) INFORMATION FOR SEQ ID NO: 240:
      (i) SEQUENCE CHARACTERISTICS:
          (A) LENGTH: 248 amino acids
          (B) TYPE: amino acid
          (C) STRANDEDNESS: <Unknown>
          (D) TOPOLOGY: unknown
     (ii) MOLECULE TYPE: peptide
     (xi) SEQUENCE DESCRIPTION: SEQ ID NO: 240:
       Met Ser Pro Ile Leu Gly Tyr Trp Lys Ile Lys Gly Leu Val Gln Pro
        1            5           10           15
       Thr Arg Leu Leu Leu Glu Tyr Leu Glu Glu Lys Tyr Glu Glu His Leu
                 20           25           30
       Tyr Glu Arg Asp Glu Gly Asp Lys Trp Arg Asn Lys Lys Phe Glu Leu
                 35           40           45
       Gly Leu Glu Phe Pro Asn Leu Pro Tyr Tyr Ile Asp Gly Asp Val Lys
        50           55           60
       Leu Thr Gln Ser Met Ala Ile Ile Arg Tyr Ile Ala Asp Lys His Asn
        65           70           75           80
       Met Leu Gly Gly Cys Pro Lys Glu Arg Ala Glu Ile Ser Met Leu Glu
                 85           90           95
```

Page 97 of 159

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

```
    Gly Ala Val Leu Asp Ile Arg Tyr Gly Val Ser Arg Ile Ala Tyr Ser
            100                 105                 110
    Lys Asp Phe Glu Thr Leu Lys Val Asp Phe Leu Ser Lys Leu Pro Glu
            115                 120                 125
    Met Leu Lys Met Phe Glu Asp Arg Leu Cys His Lys Thr Tyr Leu Asn
        130                 135                 140
    Gly Asp His Val Thr His Pro Asp Phe Met Leu Tyr Asp Ala Leu Asp
    145                 150                 155                 160
    Val Val Leu Tyr Met Asp Pro Met Cys Leu Asp Ala Phe Pro Lys Leu
            165                 170                 175
    Val Cys Phe Lys Lys Arg Ile Glu Ala Ile Pro Gln Ile Asp Lys Tyr
            180                 185                 190
    Leu Lys Ser Ser Lys Tyr Ile Ala Trp Pro Leu Gln Gly Trp Gln Ala
            195                 200                 205
    Thr Phe Gly Gly Gly Asp His Pro Pro Lys Ser Asp Leu Val Pro Arg
            210                 215                 220
    Gly Ser Pro Gly Ile Pro Gly Ser Thr Arg Ala Ala Ala Ser Arg Arg
    225                 230                 235                 240
    Leu Arg Thr Arg Ser Arg Pro Asn
                245

(2) INFORMATION FOR SEQ ID NO: 241:
    (i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 241:
    Met Ser Pro Ile Leu Gly Tyr Trp Lys Ile Lys Gly Leu Val Gln Pro
    1               5                   10                  15
    Thr Arg Leu Leu Leu Glu Tyr Leu Glu Lys Tyr Glu Glu His Leu
            20                  25                  30
    Tyr Glu Arg Asp Glu Gly Asp Lys Trp Arg Asn Lys Lys Phe Glu Leu
            35                  40                  45
    Gly Leu Glu Phe Pro Asn Leu Pro Tyr Tyr Ile Asp Gly Asp Val Lys
        50                  55                  60
    Leu Thr Gln Ser Met Ala Ile Ile Arg Tyr Ile Ala Asp Lys His Asn
    65                  70                  75                  80
    Met Leu Gly Gly Cys Pro Lys Glu Arg Ala Glu Ile Ser Met Leu Glu
            85                  90                  95
    Gly Ala Val Leu Asp Ile Arg Tyr Gly Val Ser Arg Ile Ala Tyr Ser
            100                 105                 110
    Lys Asp Phe Glu Thr Leu Lys Val Asp Phe Leu Ser Lys Leu Pro Glu
            115                 120                 125
    Met Leu Lys Met Phe Glu Asp Arg Leu Cys His Lys Thr Tyr Leu Asn
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        130         135         140
Gly Asp His Val Thr His Pro Asp Phe Met Leu Tyr Asp Ala Leu Asp
  145         150         155         160
Val Val Leu Tyr Met Asp Pro Met Cys Leu Asp Ala Phe Pro Lys Leu
        165         170         175
Val Cys Phe Lys Lys Arg Ile Glu Ala Ile Pro Gln Ile Asp Lys Tyr
        180         185         190
Leu Lys Ser Ser Lys Tyr Ile Ala Trp Pro Leu Gln Gly Trp Gln Ala
        195         200         205
Thr Phe Gly Gly Gly Asp His Pro Pro Lys Ser Asp Leu Val Pro Arg
        210         215         220
Gly Ser Pro Gly Ile Pro Gly Ser Thr Arg Ala Ala Ala Ser Arg Val
  225         230         235         240
Gly Gln Cys Thr Asp Ser Asp Val Arg Arg Pro Trp Ala Arg Ser Cys
            245         250         255
Ala His Gln Gly Cys Gly Ala Gly Thr Arg Asn Ser His Gly Cys Ile
        260         265         270
Thr Arg Pro Leu Arg Gln Ala Ser Ala His
        275         280
```

(2) INFORMATION FOR SEQ ID NO: 242:
   (i) SEQUENCE CHARACTERISTICS:
     (A) LENGTH: 257 amino acids
     (B) TYPE: amino acid
     (C) STRANDEDNESS: <Unknown>
     (D) TOPOLOGY: unknown
  (ii) MOLECULE TYPE: peptide
  (xi) SEQUENCE DESCRIPTION: SEQ ID NO: 242:

```
Met Ser Pro Ile Leu Gly Tyr Trp Lys Ile Lys Gly Leu Val Gln Pro
 1           5          10          15
Thr Arg Leu Leu Leu Glu Tyr Leu Glu Glu Lys Tyr Glu Glu His Leu
        20          25          30
Tyr Glu Arg Asp Glu Gly Asp Lys Trp Arg Asn Lys Lys Phe Glu Leu
        35          40          45
Gly Leu Glu Phe Pro Asn Leu Pro Tyr Tyr Ile Asp Gly Asp Val Lys
   50          55          60
Leu Thr Gln Ser Met Ala Ile Ile Arg Tyr Ile Ala Asp Lys His Asn
65          70          75          80
Met Leu Gly Gly Cys Pro Lys Glu Arg Ala Glu Ile Ser Met Leu Glu
            85          90          95
Gly Ala Val Leu Asp Ile Arg Tyr Gly Val Ser Arg Ile Ala Tyr Ser
        100         105         110
Lys Asp Phe Glu Thr Leu Lys Val Asp Phe Leu Ser Lys Leu Pro Glu
        115         120         125
Met Leu Lys Met Phe Glu Asp Arg Leu Cys His Lys Thr Tyr Leu Asn
        130         135         140
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
  Gly Asp His Val Thr His Pro Asp Phe Met Leu Tyr Asp Ala Leu Asp
  145                 150                 155                 160
  Val Val Leu Tyr Met Asp Pro Met Cys Leu Asp Ala Phe Pro Lys Leu
              165                 170                 175
  Val Cys Phe Lys Lys Arg Ile Glu Ala Ile Pro Gln Ile Asp Lys Tyr
              180                 185                 190
  Leu Lys Ser Ser Lys Tyr Ile Ala Trp Pro Leu Gln Gly Trp Gln Ala
              195                 200                 205
  Thr Phe Gly Gly Gly Asp His Pro Pro Lys Ser Asp Leu Val Pro Arg
              210                 215                 220
  Gly Ser Pro Gly Ile Pro Gly Ser Thr Arg Ala Ala Ala Ser Arg Val
  225                 230                 235                 240
  Gly Gln Cys Thr Asp Ser Asp Val Arg Arg Pro Trp Ala Arg Ser Cys
              245                 250                 255
  Ala
```

(2) INFORMATION FOR SEQ ID NO: 243:
   (i) SEQUENCE CHARACTERISTICS:
      (A) LENGTH: 259 amino acids
      (B) TYPE: amino acid
      (C) STRANDEDNESS: <Unknown>
      (D) TOPOLOGY: unknown
  (ii) MOLECULE TYPE: peptide
  (xi) SEQUENCE DESCRIPTION: SEQ ID NO: 243:

```
  Met Ser Pro Ile Leu Gly Tyr Trp Lys Ile Lys Gly Leu Val Gln Pro
  1               5                   10                  15
  Thr Arg Leu Leu Leu Glu Tyr Leu Glu Glu Lys Tyr Glu Glu His Leu
              20                  25                  30
  Tyr Glu Arg Asp Glu Gly Asp Lys Trp Arg Asn Lys Lys Phe Glu Leu
              35                  40                  45
  Gly Leu Glu Phe Pro Asn Leu Pro Tyr Tyr Ile Asp Gly Asp Val Lys
  50                  55                  60
  Leu Thr Gln Ser Met Ala Ile Ile Arg Tyr Ile Ala Asp Lys His Asn
  65                  70                  75                  80
  Met Leu Gly Gly Cys Pro Lys Glu Arg Ala Glu Ile Ser Met Leu Glu
              85                  90                  95
  Gly Ala Val Leu Asp Ile Arg Tyr Gly Val Ser Arg Ile Ala Tyr Ser
              100                 105                 110
  Lys Asp Phe Glu Thr Leu Lys Val Asp Phe Leu Ser Lys Leu Pro Glu
              115                 120                 125
  Met Leu Lys Met Phe Glu Asp Arg Leu Cys His Lys Thr Tyr Leu Asn
              130                 135                 140
  Gly Asp His Val Thr His Pro Asp Phe Met Leu Tyr Asp Ala Leu Asp
  145                 150                 155                 160
  Val Val Leu Tyr Met Asp Pro Met Cys Leu Asp Ala Phe Pro Lys Leu
              165                 170                 175
```

UNITED STATES PATENT AND TRADEMARK OFFICE
CERTIFICATE OF CORRECTION

PATENT NO.        : 7,053,177 B1
APPLICATION NO.   : 09/079678
DATED             : May 30, 2006
INVENTOR(S)       : Vernon L. Alvarez et al.

It is certified that error appears in the above-identified patent and that said Letters Patent is hereby corrected as shown below:

```
    Val Cys Phe Lys Lys Arg Ile Glu Ala Ile Pro Gln Ile Asp Lys Tyr
            180             185             190
    Leu Lys Ser Ser Lys Tyr Ile Ala Trp Pro Leu Gln Gly Trp Gln Ala
            195             200             205
    Thr Phe Gly Gly Gly Asp His Pro Pro Lys Ser Asp Leu Val Pro Arg
            210             215             220
    Gly Ser Pro Gly Ile Pro Gly Ser Thr Arg Ala Ala Ala Ser Val Arg
        225             230             235             240
    Arg Pro Trp Ala Arg Ser Cys Ala His Gln Gly Cys Gly Ala Gly Thr
            245             250             255
    Arg Asn Ser (2) INFORMATION FOR SEQ ID NO: 244:
    (i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 244:
    Met Ser Pro Ile Leu Gly Tyr Trp Lys Ile Lys Gly Leu Val Gln Pro
    1               5               10              15
    Thr Arg Leu Leu Leu Glu Tyr Leu Glu Glu Lys Tyr Glu Glu His Leu
            20              25              30
    Tyr Glu Arg Asp Glu Gly Asp Lys Trp Arg Asn Lys Lys Phe Glu Leu
            35              40              45
    Gly Leu Glu Phe Pro Asn Leu Pro Tyr Tyr Ile Asp Gly Asp Val Lys
        50              55              60
    Leu Thr Gln Ser Met Ala Ile Ile Arg Tyr Ile Ala Asp Lys His Asn
    65              70              75              80
    Met Leu Gly Gly Cys Pro Lys Glu Arg Ala Glu Ile Ser Met Leu Glu
            85              90              95
    Gly Ala Val Leu Asp Ile Arg Tyr Gly Val Ser Arg Ile Ala Tyr Ser
            100             105             110
    Lys Asp Phe Glu Thr Leu Lys Val Asp Phe Leu Ser Lys Leu Pro Glu
            115             120             125
    Met Leu Lys Met Phe Glu Asp Arg Leu Cys His Lys Thr Tyr Leu Asn
            130             135             140
    Gly Asp His Val Thr His Pro Asp Phe Met Leu Tyr Asp Ala Leu Asp
    145             150             155             160
    Val Val Leu Tyr Met Asp Pro Met Cys Leu Asp Ala Phe Pro Lys Leu
            165             170             175
    Val Cys Phe Lys Lys Arg Ile Glu Ala Ile Pro Gln Ile Asp Lys Tyr
            180             185             190
    Leu Lys Ser Ser Lys Tyr Ile Ala Trp Pro Leu Gln Gly Trp Gln Ala
            195             200             205
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    Thr Phe Gly Gly Gly Asp His Pro Pro Lys Ser Asp Leu Val Pro Arg
        210             215             220
    Gly Ser Pro Gly Ile Pro Gly Ser Thr Arg Ala Ala Ala Ser Gly Thr
        225             230             235             240
    Arg Asn Ser His Gly Cys Ile Thr Arg Pro Leu Arg Gln Ala Ser Gln
                    245             250             255
    His
```

(2) INFORMATION FOR SEQ ID NO: 245:
   (i) SEQUENCE CHARACTERISTICS:
      (A) LENGTH: 282 amino acids
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 245:

```
    Met Ser Pro Ile Leu Gly Tyr Trp Lys Ile Lys Gly Leu Val Gln Pro
     1               5              10              15
    Thr Arg Leu Leu Leu Glu Tyr Leu Glu Glu Lys Tyr Glu Glu His Leu
            20              25              30
    Tyr Glu Arg Asp Glu Gly Asp Lys Trp Arg Asn Lys Lys Phe Glu Leu
            35              40              45
    Gly Leu Glu Phe Pro Asn Leu Pro Tyr Tyr Ile Asp Gly Asp Val Lys
        50              55              60
    Leu Thr Gln Ser Met Ala Ile Ile Arg Tyr Ile Ala Asp Lys His Asn
    65              70              75              80
    Met Leu Gly Gly Cys Pro Lys Glu Arg Ala Glu Ile Ser Met Leu Glu
                85              90              95
    Gly Ala Val Leu Asp Ile Arg Tyr Gly Val Ser Arg Ile Ala Tyr Ser
                100             105             110
    Lys Asp Phe Glu Thr Leu Lys Val Asp Phe Leu Ser Lys Leu Pro Glu
            115             120             125
    Met Leu Lys Met Phe Glu Asp Arg Leu Cys His Lys Thr Tyr Leu Asn
        130             135             140
    Gly Asp His Val Thr His Pro Asp Phe Met Leu Tyr Asp Ala Leu Asp
    145             150             155             160
    Val Val Leu Tyr Met Asp Pro Met Cys Leu Asp Ala Phe Pro Lys Leu
                165             170             175
    Val Cys Phe Lys Lys Arg Ile Glu Ala Ile Pro Gln Ile Asp Lys Tyr
                180             185             190
    Leu Lys Ser Ser Lys Tyr Ile Ala Trp Pro Leu Gln Gly Trp Gln Ala
            195             200             205
    Thr Phe Gly Gly Asp His Pro Pro Lys Ser Asp Leu Val Pro Arg
        210             215             220
    Gly Ser Pro Gly Ile Pro Gly Ser Thr Arg Ala Ala Ala Ser Arg Tyr
        225             230             235             240
```

Page 102 of 159

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    Lys His Asp Ile Gly Cys Asp Ala Gly Val Asp Lys Lys Ser Ser Ser
            245                 250                 255
    Val Arg Gly Gly Cys Gly Ala His Ser Ser Pro Pro Arg Ala Gly Arg
            260                 265                 270
    Gly Pro Arg Gly Thr Met Val Ser Arg Leu
            275                 280

(2) INFORMATION FOR SEQ ID NO: 246:
    (i) SEQUENCE CHARACTERISTICS:
        (A) LENGTH: 262 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 246:
    Met Ser Pro Ile Leu Gly Tyr Trp Lys Ile Lys Gly Leu Val Gln Pro
    1                   5                   10                  15
    Thr Arg Leu Leu Leu Glu Tyr Leu Glu Glu Lys Tyr Glu Glu His Leu
                20                  25                  30
    Tyr Glu Arg Asp Glu Gly Asp Lys Trp Arg Asn Lys Lys Phe Glu Leu
            35                  40                  45
    Gly Leu Glu Phe Pro Asn Leu Pro Tyr Tyr Ile Asp Gly Asp Val Lys
        50                  55                  60
    Leu Thr Gln Ser Met Ala Ile Ile Arg Tyr Ile Ala Asp Lys His Asn
    65                  70                  75                  80
    Met Leu Gly Gly Cys Pro Lys Glu Arg Ala Glu Ile Ser Met Leu Glu
                85                  90                  95
    Gly Ala Val Leu Asp Ile Arg Tyr Gly Val Ser Arg Ile Ala Tyr Ser
            100                 105                 110
    Lys Asp Phe Glu Thr Leu Lys Val Asp Phe Leu Ser Lys Leu Pro Glu
        115                 120                 125
    Met Leu Lys Met Phe Glu Asp Arg Leu Cys His Lys Thr Tyr Leu Asn
    130                 135                 140
    Gly Asp His Val Thr His Pro Asp Phe Met Leu Tyr Asp Ala Leu Asp
    145                 150                 155                 160
    Val Val Leu Tyr Met Asp Pro Met Cys Leu Asp Ala Phe Pro Lys Leu
            165                 170                 175
    Val Cys Phe Lys Lys Arg Ile Glu Ala Ile Pro Gln Ile Asp Lys Tyr
        180                 185                 190
    Leu Lys Ser Ser Lys Tyr Ile Ala Trp Pro Leu Gln Gly Trp Gln Ala
        195                 200                 205
    Thr Phe Gly Gly Gly Asp His Pro Pro Lys Ser Asp Leu Val Pro Arg
        210                 215                 220
    Gly Ser Pro Gly Ile Pro Gly Ser Thr Arg Ala Ala Ala Ser Arg Tyr
    225                 230                 235                 240
    Lys His Asp Ile Gly Cys Asp Ala Gly Val Asp Lys Lys Ser Ser Ser
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
                    245             250             255
    Val Arg Gly Gly Cys Gly
            260

(2) INFORMATION FOR SEQ ID NO: 247:
    (i) SEQUENCE CHARACTERISTICS:
        (A) LENGTH: 264 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 247:
    Met Ser Pro Ile Leu Gly Tyr Trp Lys Ile Lys Gly Leu Val Gln Pro
    1               5               10              15
    Thr Arg Leu Leu Leu Glu Tyr Leu Glu Glu Lys Tyr Glu Glu His Leu
            20              25              30
    Tyr Glu Arg Asp Glu Gly Asp Lys Trp Arg Asn Lys Lys Phe Glu Leu
            35              40              45
    Gly Leu Glu Phe Pro Asn Leu Pro Tyr Tyr Ile Asp Gly Asp Val Lys
            50              55              60
    Leu Thr Gln Ser Met Ala Ile Ile Arg Tyr Ile Ala Asp Lys His Asn
    65              70              75              80
    Met Leu Gly Gly Cys Pro Lys Glu Arg Ala Glu Ile Ser Met Leu Glu
            85              90              95
    Gly Ala Val Leu Asp Ile Arg Tyr Gly Val Ser Arg Ile Ala Tyr Ser
            100             105             110
    Lys Asp Phe Glu Thr Leu Lys Val Asp Phe Leu Ser Lys Leu Pro Glu
            115             120             125
    Met Leu Lys Met Phe Glu Asp Arg Leu Cys His Lys Thr Tyr Leu Asn
            130             135             140
    Gly Asp His Val Thr His Pro Asp Phe Met Leu Tyr Asp Ala Leu Asp
    145             150             155             160
    Val Val Leu Tyr Met Asp Pro Met Cys Leu Asp Ala Phe Pro Lys Leu
            165             170             175
    Val Cys Phe Lys Lys Arg Ile Glu Ala Ile Pro Gln Ile Asp Lys Tyr
            180             185             190
    Leu Lys Ser Ser Lys Tyr Ile Ala Trp Pro Leu Gln Gly Trp Gln Ala
            195             200             205
    Thr Phe Gly Gly Gly Asp His Pro Pro Lys Ser Asp Leu Val Pro Arg
            210             215             220
    Gly Ser Pro Gly Ile Pro Gly Ser Thr Arg Ala Ala Ala Ser Gly Cys
    225             230             235             240
    Asp Ala Gly Val Asp Lys Lys Ser Ser Val Arg Gly Gly Cys Gly
                245             250             255
    Ala His Ser Ser Pro Pro Arg Ala
            260
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(2) INFORMATION FOR SEQ ID NO: 248:
  (i) SEQUENCE CHARACTERISTICS:
    (A) LENGTH: 259 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 248:

Met Ser Pro Ile Leu Gly Tyr Trp Lys Ile Lys Gly Leu Val Gln Pro
 1     5      10      15
Thr Arg Leu Leu Leu Glu Tyr Leu Glu Glu Lys Tyr Glu Glu His Leu
    20      25      30
Tyr Glu Arg Asp Glu Gly Asp Lys Trp Arg Asn Lys Lys Phe Glu Leu
    35      40      45
Gly Leu Glu Phe Pro Asn Leu Pro Tyr Tyr Ile Asp Gly Asp Val Lys
    50      55      60
Leu Thr Gln Ser Met Ala Ile Ile Arg Tyr Ile Ala Asp Lys His Asn
65      70      75      80
Met Leu Gly Gly Cys Pro Lys Glu Arg Ala Glu Ile Ser Met Leu Glu
    85      90      95
Gly Ala Val Leu Asp Ile Arg Tyr Gly Val Ser Arg Ile Ala Tyr Ser
    100     105     110
Lys Asp Phe Glu Thr Leu Lys Val Asp Phe Leu Ser Lys Leu Pro Glu
    115     120     125
Met Leu Lys Met Phe Glu Asp Arg Leu Cys His Lys Thr Tyr Leu Asn
    130     135     140
Gly Asp His Val Thr His Pro Asp Phe Met Leu Tyr Asp Ala Leu Asp
145     150     155     160
Val Val Leu Tyr Met Asp Pro Met Cys Leu Asp Ala Phe Pro Lys Leu
    165     170     175
Val Cys Phe Lys Lys Arg Ile Glu Ala Ile Pro Gln Ile Asp Lys Tyr
    180     185     190
Leu Lys Ser Ser Lys Tyr Ile Ala Trp Pro Leu Gln Gly Trp Gln Ala
    195     200     205
Thr Phe Gly Gly Gly Asp His Pro Pro Lys Ser Asp Leu Val Pro Arg
    210     215     220
Gly Ser Pro Gly Ile Pro Gly Ser Thr Arg Ala Ala Ala Ser Gly Ala
225     230     235     240
His Ser Ser Pro Pro Arg Ala Gly Arg Gly Pro Arg Gly Thr Met Val
    245     250     255
Ser Arg Leu (2) INFORMATION FOR SEQ ID NO: 249:
  (i) SEQUENCE CHARACTERISTICS:
    (A) LENGTH: 44 amino acids

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
      (B) TYPE: amino acid
      (C) STRANDEDNESS: <Unknown>
      (D) TOPOLOGY: unknown
   (ii) MOLECULE TYPE: peptide
   (xi) SEQUENCE DESCRIPTION: SEQ ID NO: 249:
     Ser Gly Ser Pro Pro Cys Cys Cys Ser Trp Gly Arg Phe Met Gln Gly
     1               5                  10                 15
     Gly Leu Phe Gly Gly Arg Thr Asp Gly Cys Gly Ala His Arg Asn Arg
             20                 25                 30
     Thr Ser Ala Ser Leu Glu Pro Pro Ser Ser Asp Tyr
             35                 40

(2) INFORMATION FOR SEQ ID NO: 250:
    (i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown
   (ii) MOLECULE TYPE: peptide
   (xi) SEQUENCE DESCRIPTION: SEQ ID NO: 250:
     Ser His Ser Gly Gly Met Asn Arg Ala Tyr Gly Asp Val Phe Arg Glu
     1               5                  10                 15
     Leu Arg Asp Arg Trp Asn Ala Thr Ser His His Thr Arg Pro Thr Pro
             20                 25                 30
     Gln Leu Pro Arg Gly Pro Asn Ser
             35                 40

(2) INFORMATION FOR SEQ ID NO: 251:
    (i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown
   (ii) MOLECULE TYPE: peptide
   (xi) SEQUENCE DESCRIPTION: SEQ ID NO: 251:
     Asp Thr Asn Ala Lys His Ser Ser His Asn Arg Arg Leu Arg Thr Arg
     1               5                  10                 15
     Ser Arg Pro Asn Gly
             20

(2) INFORMATION FOR SEQ ID NO: 252:
    (i) SEQUENCE CHARACTERISTICS:
        (A) LENGTH: 23 amino acids
        (B) TYPE: amino acid
        (C) STRANDEDNESS: <Unknown>
        (D) TOPOLOGY: unknown
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (ii) MOLECULE TYPE: peptide
   (xi) SEQUENCE DESCRIPTION: SEQ ID NO: 252:
     Cys Gly Ala Gly Thr Arg Asn Ser His Gly Cys Ile Thr Arg Pro Leu
      1           5               10              15
     Arg Gln Ala Ser Ala His Gly
              20

(2) INFORMATION FOR SEQ ID NO: 253:
    (i) SEQUENCE CHARACTERISTICS:
       (A) LENGTH: 11 amino acids
       (B) TYPE: amino acid
       (C) STRANDEDNESS: <Unknown>
       (D) TOPOLOGY: unknown
   (ii) MOLECULE TYPE: peptide
   (ix) FEATURE:
       (A) NAME/KEY: Modified Site
       (B) LOCATION: 1
       (D) OTHER INFORMATION: "Xaa=Ser or Thr"
   (xi) SEQUENCE DESCRIPTION: SEQ ID NO: 253:
     Xaa Thr Xaa Xaa Ser Xaa Xaa Xaa Asn Xaa Arg
      1           5               10

(2) INFORMATION FOR SEQ ID NO: 254:
    (i) SEQUENCE CHARACTERISTICS:
       (A) LENGTH: 8 amino acids
       (B) TYPE: amino acid
       (C) STRANDEDNESS: <Unknown>
       (D) TOPOLOGY: unknown
   (ii) MOLECULE TYPE: peptide
   (ix) FEATURE:
       (A) NAME/KEY: Modified Site
       (B) LOCATION: 2
       (D) OTHER INFORMATION: "Xaa=Ser, Ala or Gly"
   (xi) SEQUENCE DESCRIPTION: SEQ ID NO: 254:
     Asp Xaa Asp Xaa Arg Arg Xaa Xaa
      1           5

(2) INFORMATION FOR SEQ ID NO: 255:
    (i) SEQUENCE CHARACTERISTICS:
       (A) LENGTH: 10 amino acids
       (B) TYPE: amino acid
       (C) STRANDEDNESS: <Unknown>
       (D) TOPOLOGY: unknown
   (ii) MOLECULE TYPE: peptide
   (ix) FEATURE:
       (A) NAME/KEY: Modified Site
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(B) LOCATION: 7
    (D) OTHER INFORMATION: "Xaa=Ala or Phe"
  (xi) SEQUENCE DESCRIPTION: SEQ ID NO: 255:
  Val Arg Ser Gly Cys Gly Xaa Xaa Ser Ser
   1       5      10

(2) INFORMATION FOR SEQ ID NO: 256:
  (i) SEQUENCE CHARACTERISTICS:
    (A) LENGTH: 11 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 256:
  Asn Thr Arg Lys Ser Ser Arg Ser Asn Pro Arg
   1       5      10

(2) INFORMATION FOR SEQ ID NO: 257:
  (i) SEQUENCE CHARACTERISTICS:
    (A) LENGTH: 11 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 257:
  Ser Thr Lys Arg Ser Leu Ile Tyr Asn His Arg
   1       5      10

(2) INFORMATION FOR SEQ ID NO: 258:
  (i) SEQUENCE CHARACTERISTICS:
    (A) LENGTH: 10 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 258:
  Ser Thr Gly Arg Lys Val Phe Asn Arg Arg
   1       5      10

(2) INFORMATION FOR SEQ ID NO: 259:
  (i) SEQUENCE CHARACTERISTICS:
    (A) LENGTH: 11 amino acids
    (B) TYPE: amino acid
    (C) STRANDEDNESS: <Unknown>
    (D) TOPOLOGY: unknown
  (ii) MOLECULE TYPE: peptide

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (xi) SEQUENCE DESCRIPTION: SEQ ID NO: 259:
    Thr Asn Ala Lys His Ser Ser His Asn Arg Arg
     1         5          10

(2) INFORMATION FOR SEQ ID NO: 260:
    (i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 260:
    Asp Ser Asp Val Arg Arg Pro Trp
     1         5

(2) INFORMATION FOR SEQ ID NO: 261:
    (i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 261:
    Ala Ala Asp Gln Arg Arg Gly Trp
     1         5

(2) INFORMATION FOR SEQ ID NO: 262:
    (i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 262:
    Asp Gly Arg Gly Gly Arg Ser Tyr
     1         5

(2) INFORMATION FOR SEQ ID NO: 263:
    (i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown
    (ii) MOLECULE TYPE: peptide
    (xi) SEQUENCE DESCRIPTION: SEQ ID NO: 263:
    Arg Val Arg Ser
```

UNITED STATES PATENT AND TRADEMARK OFFICE
CERTIFICATE OF CORRECTION

PATENT NO.      : 7,053,177 B1
APPLICATION NO. : 09/079678
DATED           : May 30, 2006
INVENTOR(S)     : Vernon L. Alvarez et al.

It is certified that error appears in the above-identified patent and that said Letters Patent is hereby corrected as shown below:

1

(2) INFORMATION FOR SEQ ID NO: 264:
  (i) SEQUENCE CHARACTERISTICS:
    (A) LENGTH: 12 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 264:
    Ser Val Arg Ser Gly Cys Gly Phe Arg Gly Ser Ser
    1     5      10

(2) INFORMATION FOR SEQ ID NO: 265:
  (i) SEQUENCE CHARACTERISTICS:
    (A) LENGTH: 11 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 265:
    Ser Val Arg Gly Gly Cys Gly Ala His Ser Ser
    1     5      10

(2) INFORMATION FOR SEQ ID NO: 266:
  (i) SEQUENCE CHARACTERISTICS:
    (A) LENGTH: 37 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 2...2
    (D) OTHER INFORMATION: Xaa=Lys(dns)
  (xi) SEQUENCE DESCRIPTION: SEQ ID NO: 266:
    Cys Xaa Phe Ile Thr Lys Ala Leu Gly Ile Ser Tyr Gly Arg Lys Lys
    1     5      10        15
    Arg Arg Gln Arg Arg Arg Pro Pro Gln Gly Ser Gln Thr His Gln Val
       20        25       30
    Ser Leu Ser Lys Gln
      35

(2) INFORMATION FOR SEQ ID NO: 267:
  (i) SEQUENCE CHARACTERISTICS:
    (A) LENGTH: 18 amino acids

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Ac-Cys
   (xi) SEQUENCE DESCRIPTION: SEQ ID NO: 267:
    Xaa Leu Asn Gly Gly Val Lys Met Tyr Val Glu Ser Val Asp Arg Tyr
    1           5             10              15
    Val Cys (2) INFORMATION FOR SEQ ID NO: 268:
   (i) SEQUENCE CHARACTERISTICS:
      (A) LENGTH: 22 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Ac-Cys
   (xi) SEQUENCE DESCRIPTION: SEQ ID NO: 268:
    Xaa Leu Asn Gly Gly Val Lys Phe Ile Thr Cys Met Tyr Val Glu Ser
    1           5             10              15
    Val Asp Arg Tyr Val Cys
            20

(2) INFORMATION FOR SEQ ID NO: 269:
   (i) SEQUENCE CHARACTERISTICS:
      (A) LENGTH: 21 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 2...2
      (D) OTHER INFORMATION: Xaa=Lys(dns)
   (xi) SEQUENCE DESCRIPTION: SEQ ID NO: 269:
    Cys Xaa Arg Leu Asn Gly Gly Val Ser Met Tyr Val Glu Ser Val Asp
    1           5             10              15
    Arg Tyr Val Cys Arg
            20
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(2) INFORMATION FOR SEQ ID NO: 270:
  (i) SEQUENCE CHARACTERISTICS:
    (A) LENGTH: 40 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=biotin-Lys(dns)
  (xi) SEQUENCE DESCRIPTION: SEQ ID NO: 270:
  Xaa Ser Ala Arg Asp Ser Gly Pro Ala Glu Asp Gly Ser Arg Ala Val
  1      5         10         15
  Arg Leu Asn Gly Val Glu Asn Ala Asn Thr Arg Lys Ser Ser Arg Ser
       20        25        30
  Asn Pro Arg Gly Arg Arg His Pro
     35        40

(2) INFORMATION FOR SEQ ID NO: 271:
  (i) SEQUENCE CHARACTERISTICS:
    (A) LENGTH: 45 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=biotin-Lys(dns)
  (xi) SEQUENCE DESCRIPTION: SEQ ID NO: 271:
  Xaa Ser Ser Ala Asp Ala Glu Lys Cys Ala Gly Ser Leu Leu Trp Trp
  1      5         10         15
  Gly Arg Gln Asn Asn Ser Gly Cys Gly Ser Pro Thr Lys Lys His Leu
       20        25        30
  Lys His Arg Asn Arg Ser Gln Thr Ser Ser Ser Ser His
     35        40        45

(2) INFORMATION FOR SEQ ID NO: 272:
  (i) SEQUENCE CHARACTERISTICS:
    (A) LENGTH: 45 amino acids
    (B) TYPE: amino acid
    (C) STRANDEDNESS: single
    (D) TOPOLOGY: unknown
  (ii) MOLECULE TYPE: peptide

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
   (ix) FEATURE:
      (A) NAME/KEY: Other
      (B) LOCATION: 1...1
      (D) OTHER INFORMATION: Xaa=biotin-Lys(dns)
   (xi) SEQUENCE DESCRIPTION: SEQ ID NO: 272:
    Xaa Arg Glu Phe Ala Glu Arg Arg Leu Trp Gly Cys Asp Asp Leu Ser
     1           5              10              15
    Trp Arg Leu Asp Ala Glu Gly Cys Gly Pro Thr Pro Ser Asn Arg Ala
             20              25              30
    Val Lys His Arg Lys Pro Arg Pro Arg Ser Pro Ala Leu
         35              40              45

(2) INFORMATION FOR SEQ ID NO: 273:
   (i) SEQUENCE CHARACTERISTICS:
      (A) LENGTH: 41 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=biotin-Ser
   (xi) SEQUENCE DESCRIPTION: SEQ ID NO: 273:
    Xaa Gly Ser His Ser Gly Gly Met Asn Arg Ala Tyr Gly Asp Val Phe
     1           5              10              15
    Arg Glu Leu Arg Asp Arg Trp Tyr Ala Thr Ser His His Thr Arg Pro
             20              25              30
    Thr Pro Gln Leu Pro Arg Gly Pro Asn
         35              40

(2) INFORMATION FOR SEQ ID NO: 274:
   (i) SEQUENCE CHARACTERISTICS:
      (A) LENGTH: 42 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 274:
    Xaa Ser Gly Ser His Ser Gly Gly Met Asn Arg Ala Tyr Gly Asp Val
     1           5              10              15
    Phe Arg Glu Leu Arg Asp Arg Trp Tyr Ala Thr Ser His His Thr Arg
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
            20              25          30
   Pro Thr Pro Gln Leu Pro Arg Gly Pro Asn
       35          40

(2) INFORMATION FOR SEQ ID NO: 275:
   (i) SEQUENCE CHARACTERISTICS:
       (A) LENGTH: 40 amino acids
       (B) TYPE: amino acid
       (C) STRANDEDNESS: single
       (D) TOPOLOGY: unknown
   (ii) MOLECULE TYPE: peptide
   (ix) FEATURE:
       (A) NAME/KEY: Other
       (B) LOCATION: 1...1
       (D) OTHER INFORMATION: Xaa=biotin-Lys(dns)
   (xi) SEQUENCE DESCRIPTION: SEQ ID NO: 275:
     Xaa Ser His Ser Gly Gly Met Asn Arg Ala Tyr Gly Asp Val Phe Arg
      1           5              10              15
     Glu Leu Arg Asp Arg Trp Asn Ala Thr Ser His His Thr Arg Pro Thr
              20              25          30
     Pro Gln Leu Pro Arg Gly Pro Asn
         35          40

(2) INFORMATION FOR SEQ ID NO: 276:
   (i) SEQUENCE CHARACTERISTICS:
       (A) LENGTH: 41 amino acids
       (B) TYPE: amino acid
       (C) STRANDEDNESS: single
       (D) TOPOLOGY: unknown
   (ii) MOLECULE TYPE: peptide
   (ix) FEATURE:
       (A) NAME/KEY: Other
       (B) LOCATION: 1...1
       (D) OTHER INFORMATION: Xaa=Lys(dns)
   (xi) SEQUENCE DESCRIPTION: SEQ ID NO: 276:
     Xaa Ser His Ser Gly Gly Met Asn Arg Ala Tyr Gly Asp Val Phe Arg
      1           5              10              15
     Glu Leu Arg Asp Arg Trp Asn Ala Thr Ser His His Thr Arg Pro Thr
              20              25          30
     Pro Gln Leu Pro Arg Gly Pro Asn Ser
         35          40

(2) INFORMATION FOR SEQ ID NO: 277:
   (i) SEQUENCE CHARACTERISTICS:
       (A) LENGTH: 45 amino acids
       (B) TYPE: amino acid
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 277:
    Xaa Ser Gln Gly Ser Lys Gln Cys Met Gln Tyr Arg Thr Gly Arg Leu
     1           5              10              15
    Thr Val Gly Ser Glu Tyr Gly Cys Gly Met Asn Pro Ala Arg His Ala
            20              25              30
    Thr Pro Ala Tyr Pro Ala Arg Leu Leu Pro Arg Tyr Arg
            35              40              45

(2) INFORMATION FOR SEQ ID NO: 278:
    (i) SEQUENCE CHARACTERISTICS:
        (A) LENGTH: 45 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 278:
    Xaa Arg Val Gly Gln Cys Thr Asp Ser Asp Val Arg Arg Pro Trp Ala
     1           5              10              15
    Arg Ser Cys Ala His Gln Gly Cys Gly Ala Gly Thr Arg Asn Ser His
            20              25              30
    Gly Cys Ile Thr Arg Pro Leu Arg Gln Ala Ser Ala His
            35              40              45

(2) INFORMATION FOR SEQ ID NO: 279:
    (i) SEQUENCE CHARACTERISTICS:
        (A) LENGTH: 24 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=biotin-Lys(dns)
    (xi) SEQUENCE DESCRIPTION: SEQ ID NO: 279:
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    Xaa Ser Gly Ser Gly Arg Val Gly Gln Cys Thr Asp Ser Asp Val Arg
     1           5              10             15
    Arg Pro Trp Ala Arg Ser Cys Ala
              20
```

(2) INFORMATION FOR SEQ ID NO: 280:
   (i) SEQUENCE CHARACTERISTICS:
      (A) LENGTH: 20 amino acids
      (B) TYPE: amino acid
      (C) STRANDEDNESS: single
      (D) TOPOLOGY: unknown
  (ii) MOLECULE TYPE: peptide
  (ix) FEATURE:
      (A) NAME/KEY: Other
      (B) LOCATION: 1...1
      (D) OTHER INFORMATION: Xaa=Lys(dns)
  (xi) SEQUENCE DESCRIPTION: SEQ ID NO: 280:

```
    Xaa Arg Val Gly Gln Cys Thr Asp Ser Asp Val Arg Arg Pro Trp Ala
     1           5              10             15
    Arg Ser Cys Ala
              20
```

(2) INFORMATION FOR SEQ ID NO: 281:
   (i) SEQUENCE CHARACTERISTICS:
      (A) LENGTH: 41 amino acids
      (B) TYPE: amino acid
      (C) STRANDEDNESS: single
      (D) TOPOLOGY: unknown
  (ii) MOLECULE TYPE: peptide
  (ix) FEATURE:
      (A) NAME/KEY: Other
      (B) LOCATION: 1...1
      (D) OTHER INFORMATION: Xaa=Lys(dns)
  (xi) SEQUENCE DESCRIPTION: SEQ ID NO: 281:

```
    Xaa Ser Thr Pro Pro Ser Arg Glu Ala Tyr Ser Arg Pro Tyr Ser Val
     1           5              10             15
    Asp Ser Asp Ser Asp Thr Asn Ala Lys His Ser Ser His Asn Arg Arg
              20             25             30
    Leu Arg Thr Arg Ser Arg Pro Asn Gly
              35             40
```

(2) INFORMATION FOR SEQ ID NO: 282:
   (i) SEQUENCE CHARACTERISTICS:
      (A) LENGTH: 40 amino acids
      (B) TYPE: amino acid
      (C) STRANDEDNESS: single

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
    (D) TOPOLOGY: unknown
(ii) MOLECULE TYPE: peptide
(ix) FEATURE:
    (A) NAME/KEY: Other
    (B) LOCATION: 1...1
    (D) OTHER INFORMATION: Xaa=Lys(dns)
(xi) SEQUENCE DESCRIPTION: SEQ ID NO: 282:
  Xaa Arg Gly Ser Thr Gly Thr Ala Gly Gly Glu Arg Ser Gly Val Leu
   1               5                  10                  15
  Asn Leu His Thr Arg Asp Asn Ala Ser Gly Ser Gly Phe Lys Pro Trp
              20                  25                  30
  Tyr Pro Ser Asn Arg Gly His Lys
          35                  40

(2) INFORMATION FOR SEQ ID NO: 283:
    (i) SEQUENCE CHARACTERISTICS:
        (A) LENGTH: 20 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 283:
     Xaa Ser Gly Ser Gly Leu Tyr Ala Asn Pro Gly Met Tyr Ser Arg Leu
      1               5                  10                  15
     His Ser Pro Ala
                 20

(2) INFORMATION FOR SEQ ID NO: 284:
    (i) SEQUENCE CHARACTERISTICS:
        (A) LENGTH: 20 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=biotin-Lys(dns)
   (xi) SEQUENCE DESCRIPTION: SEQ ID NO: 284:
     Xaa Ser Gly Ser Gly Leu Tyr Ala Asn Pro Gly Met Tyr Ser Arg Leu
      1               5                  10                  15
     His Ser Pro Ala
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

20

(2) INFORMATION FOR SEQ ID NO: 285:
  (i) SEQUENCE CHARACTERISTICS:
    (A) LENGTH: 45 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 285:
  Xaa Ser Asp His Ala Leu Gly Thr Asn Leu Arg Ser Asp Asn Ala Lys
   1       5         10         15
  Glu Pro Gly Asp Tyr Asn Cys Cys Gly Asn Gly Asn Ser Thr Gly Arg
        20         25         30
  Lys Val Phe Asn Arg Arg Arg Pro Ser Ala Ile Pro Thr
    35         40         45

(2) INFORMATION FOR SEQ ID NO: 286:
  (i) SEQUENCE CHARACTERISTICS:
    (A) LENGTH: 42 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 286:
  Xaa Ser Pro Cys Gly Gly Ser Trp Gly Arg Phe Met Gln Gly Gly Leu
   1       5         10         15
  Phe Gly Gly Arg Thr Asp Gly Cys Gly Ala His Arg Asn Arg Thr Ser
        20         25         30
  Ala Ser Leu Glu Pro Pro Ser Ser Asp Tyr
    35         40

(2) INFORMATION FOR SEQ ID NO: 287:
  (i) SEQUENCE CHARACTERISTICS:
    (A) LENGTH: 45 amino acids
    (B) TYPE: amino acid
    (C) STRANDEDNESS: single
    (D) TOPOLOGY: unknown

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 287:
      Xaa Arg Tyr Lys His Asp Ile Gly Cys Asp Ala Gly Val Asp Lys Lys
      1               5                   10                  15
      Ser Ser Ser Val Arg Gly Gly Cys Gly Ala His Ser Ser Pro Pro Arg
              20                  25              30
      Ala Gly Arg Gly Pro Arg Gly Thr Met Val Ser Arg Leu
          35              40              45

(2) INFORMATION FOR SEQ ID NO: 288:
    (i) SEQUENCE CHARACTERISTICS:
        (A) LENGTH: 42 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 288:
      Xaa Ser Ala Arg Asp Ser Gly Pro Ala Glu Asp Gly Ser Arg Ala Val
      1               5                   10                  15
      Arg Leu Asn Gly Val Glu Asn Ala Asn Thr Arg Lys Ser Ser Arg Ser
              20                  25              30
      Asn Pro Arg Gly Arg Arg His Pro Gly Gly
          35              40

(2) INFORMATION FOR SEQ ID NO: 289:
    (i) SEQUENCE CHARACTERISTICS:
        (A) LENGTH: 40 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 289:
      Xaa Ser Lys Ser Gly Glu Gly Gly Asp Ser Ser Arg Gly Glu Thr Gly
      1               5                   10                  15
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    Trp Ala Arg Val Arg Ser His Ala Met Thr Ala Gly Arg Phe Arg Trp
         20                  25                  30
    Tyr Asn Gln Leu Pro Ser Asp Arg
         35                  40
```

(2) INFORMATION FOR SEQ ID NO: 290:
   (i) SEQUENCE CHARACTERISTICS:
      (A) LENGTH: 41 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 290:

```
    Xaa Ser Glu Ala Asn Leu Asp Gly Arg Lys Ser Arg Tyr Ser Ser Pro
     1            5                  10                  15
    Arg Arg Asn Ser Ser Thr Arg Pro Arg Thr Ser Pro Asn Ser Val His
         20                  25                  30
    Ala Arg Tyr Pro Ser Thr Asp His Asp
         35                  40
```

(2) INFORMATION FOR SEQ ID NO: 291:
   (i) SEQUENCE CHARACTERISTICS:
      (A) LENGTH: 44 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Modified Base
      (B) LOCATION: 1...1
      (D) OTHER INFORMATION: Xaa=biotin-S
   (xi) SEQUENCE DESCRIPTION: SEQ ID NO: 291:

```
    Xaa Gly Ser Gly Ser Thr Pro Pro Ser Arg Glu Ala Tyr Ser Arg Pro
     1            5                  10                  15
    Tyr Ser Val Asp Ser Asp Ser Asp Thr Asn Ala Lys His Ser Ser His
         20                  25                  30
    Asn Arg Arg Leu Arg Thr Arg Ser Arg Pro Asn Gly
         35                  40
```

(2) INFORMATION FOR SEQ ID NO: 292:
   (i) SEQUENCE CHARACTERISTICS:
      (A) LENGTH: 23 amino acids

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 292:
     Xaa Arg Val Gly Gln Cys Thr Asp Ser Asp Val Arg Arg Pro Trp Ala
      1         5             10              15
     Arg Ser Cys Ala His Gln Gly
              20

(2) INFORMATION FOR SEQ ID NO: 293:
    (i) SEQUENCE CHARACTERISTICS:
        (A) LENGTH: 24 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 293:
     Xaa Cys Gly Ala Gly Thr Arg Asn Ser His Gly Cys Ile Thr Arg Pro
      1         5             10              15
     Leu Arg Gln Ala Ser Ala His Gly
              20

(2) INFORMATION FOR SEQ ID NO: 294:
    (i) SEQUENCE CHARACTERISTICS:
        (A) LENGTH: 21 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 294:
     Xaa Glu Asn Ala Asn Thr Arg Lys Ser Ser Arg Ser Asn Pro Arg Gly
      1         5             10              15
     Arg Arg His Pro Gly
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
                      20

(2) INFORMATION FOR SEQ ID NO: 295:
    (i) SEQUENCE CHARACTERISTICS:
        (A) LENGTH: 12 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 295:
     Xaa Thr Arg Lys Ser Ser Arg Ser Asn Pro Arg Gly
      1           5              10

(2) INFORMATION FOR SEQ ID NO: 296:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 296:
     Xaa Glu Asn Ala Asn Thr Arg Lys Ser Ser Arg Ser Asn Pro Arg Gly
      1           5              10             15

(2) INFORMATION FOR SEQ ID NO: 297:
    (i) SEQUENCE CHARACTERISTICS:
        (A) LENGTH: 17 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 297:
     Xaa Thr Arg Lys Ser Ser Arg Ser Asn Pro Arg Gly Arg Arg His Pro
      1           5              10             15
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

Gly (2) INFORMATION FOR SEQ ID NO: 298:
  (i) SEQUENCE CHARACTERISTICS:
    (A) LENGTH: 20 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 298:
  Xaa Thr Asn Ala Lys His Ser Ser His Asn Arg Arg Leu Arg Thr Arg
   1      5          10         15
  Ser Arg Pro Asn
     20

(2) INFORMATION FOR SEQ ID NO: 299:
  (i) SEQUENCE CHARACTERISTICS:
    (A) LENGTH: 16 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 299:
  Xaa Thr Asn Ala Lys His Ser Ser His Asn Arg Arg Leu Arg Thr Arg
   1      5          10         15

(2) INFORMATION FOR SEQ ID NO: 300:
  (i) SEQUENCE CHARACTERISTICS:
    (A) LENGTH: 15 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 300:

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

```
  Xaa Ser Ser His Asn Arg Arg Leu Arg Thr Arg Ser Arg Pro Asn
   1       5          10          15
```

(2) INFORMATION FOR SEQ ID NO: 301:
   (i) SEQUENCE CHARACTERISTICS:
      (A) LENGTH: 11 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 301:

```
  Xaa Ser Ser His Asn Arg Arg Leu Arg Thr Arg
   1       5          10
```

(2) INFORMATION FOR SEQ ID NO: 302:
   (i) SEQUENCE CHARACTERISTICS:
      (A) LENGTH: 22 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 302:

```
  Xaa Val Arg Arg Pro Trp Ala Arg Ser Cys Ala His Gln Gly Cys Gly
   1       5          10          15
  Ala Gly Thr Arg Asn Ser
          20
```

(2) INFORMATION FOR SEQ ID NO: 303:
   (i) SEQUENCE CHARACTERISTICS:
      (A) LENGTH: 15 amino acids
      (B) TYPE: amino acid
      (C) STRANDEDNESS: single
      (D) TOPOLOGY: linear
   (ii) MOLECULE TYPE: None
   (ix) FEATURE:
      (A) NAME/KEY: Other
      (B) LOCATION: 1...1
      (D) OTHER INFORMATION: Xaa=Lys(dns)

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

(xi) SEQUENCE DESCRIPTION: SEQ ID NO: 303:
    Xaa Cys Thr Asp Ser Asp Val Arg Arg Pro Trp Ala Arg Ser Cys
     1     5       10        15

(2) INFORMATION FOR SEQ ID NO: 304:
   (i) SEQUENCE CHARACTERISTICS:
     (A) LENGTH: 41 amino acids
     (B) TYPE: amino acid
     (C) STRANDEDNESS: single
     (D) TOPOLOGY: unknown
  (ii) MOLECULE TYPE: peptide
  (ix) FEATURE:
     (A) NAME/KEY: Other
     (B) LOCATION: 1...1
     (D) OTHER INFORMATION: Xaa=Lys(dns)
  (xi) SEQUENCE DESCRIPTION: SEQ ID NO: 304:
    Xaa Ser Arg Ala Asn Thr Asp Gly Arg Lys Ser Arg Tyr Ser Ser Pro
     1     5       10        15
    Arg Arg Asn Ser Ser Thr Glu Pro Arg Leu Ser Pro Asn Ser Val His
       20       25       30
    Ala Arg Tyr Pro Ser Thr Asp His Asp
      35       40

(2) INFORMATION FOR SEQ ID NO: 305:
   (i) SEQUENCE CHARACTERISTICS:
     (A) LENGTH: 11 amino acids
     (B) TYPE: amino acid
     (C) STRANDEDNESS: single
     (D) TOPOLOGY: unknown
  (ii) MOLECULE TYPE: peptide
  (ix) FEATURE:
     (A) NAME/KEY: Other
     (B) LOCATION: 1...1
     (D) OTHER INFORMATION: Xaa=Lys(dns)
  (xi) SEQUENCE DESCRIPTION: SEQ ID NO: 305:
    Xaa Glu Asn Ala Asn Thr Arg Lys Ser Ser Arg
     1     5       10

(2) INFORMATION FOR SEQ ID NO: 306:
   (i) SEQUENCE CHARACTERISTICS:
     (A) LENGTH: 11 amino acids
     (B) TYPE: amino acid
     (C) STRANDEDNESS: single
     (D) TOPOLOGY: unknown
  (ii) MOLECULE TYPE: peptide
  (ix) FEATURE:

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 306:
       Xaa Ser Asn Pro Arg Gly Arg Arg His Pro Gly
        1           5              10

(2) INFORMATION FOR SEQ ID NO: 307:
     (i) SEQUENCE CHARACTERISTICS:
        (A) LENGTH: 6 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 307:
       Xaa Glu Asn Ala Asn Thr
        1           5

(2) INFORMATION FOR SEQ ID NO: 308:
     (i) SEQUENCE CHARACTERISTICS:
        (A) LENGTH: 7 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 308:
       Xaa Ala Asn Thr Arg Lys Ser
        1           5

(2) INFORMATION FOR SEQ ID NO: 309:
     (i) SEQUENCE CHARACTERISTICS:
        (A) LENGTH: 6 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) LOCATION: 1...1
        (D) OTHER INFORMATION: Xaa=Lys(dns)
    (xi) SEQUENCE DESCRIPTION: SEQ ID NO: 309:
     Xaa Thr Arg Lys Ser Ser
      1           5

(2) INFORMATION FOR SEQ ID NO: 310:
    (i) SEQUENCE CHARACTERISTICS:
        (A) LENGTH: 6 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 310:
     Xaa Arg Lys Ser Ser Arg
      1           5

(2) INFORMATION FOR SEQ ID NO: 311:
    (i) SEQUENCE CHARACTERISTICS:
        (A) LENGTH: 7 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 311:
     Xaa Lys Ser Ser Arg Ser Asn
      1           5

(2) INFORMATION FOR SEQ ID NO: 312:
    (i) SEQUENCE CHARACTERISTICS:
        (A) LENGTH: 8 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
        (D) OTHER INFORMATION: Xaa=Lys(dns)
    (xi) SEQUENCE DESCRIPTION: SEQ ID NO: 312:
     Xaa Ser Ser Arg Ser Asn Pro Gly
       1           5

(2) INFORMATION FOR SEQ ID NO: 313:
    (i) SEQUENCE CHARACTERISTICS:
        (A) LENGTH: 7 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 313:
     Xaa Arg Ser Asn Pro Arg Gly
       1           5

(2) INFORMATION FOR SEQ ID NO: 314:
    (i) SEQUENCE CHARACTERISTICS:
        (A) LENGTH: 6 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 314:
     Xaa Ser Asn Pro Arg Gly
       1           5

(2) INFORMATION FOR SEQ ID NO: 315:
    (i) SEQUENCE CHARACTERISTICS:
        (A) LENGTH: 7 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (xi) SEQUENCE DESCRIPTION: SEQ ID NO: 315:
      Xaa Pro Arg Gly Arg Arg His
       1             5

(2) INFORMATION FOR SEQ ID NO: 316:
    (i) SEQUENCE CHARACTERISTICS:
        (A) LENGTH: 6 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 316:
      Xaa Arg Arg His Pro Gly
       1             5

(2) INFORMATION FOR SEQ ID NO: 317:
    (i) SEQUENCE CHARACTERISTICS:
        (A) LENGTH: 7 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 317:
      Xaa Lys Ser Ser Arg Gly Asn
       1             5

(2) INFORMATION FOR SEQ ID NO: 318:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 318:
```

UNITED STATES PATENT AND TRADEMARK OFFICE
CERTIFICATE OF CORRECTION

PATENT NO.        : 7,053,177 B1
APPLICATION NO.   : 09/079678
DATED             : May 30, 2006
INVENTOR(S)       : Vernon L. Alvarez et al.

It is certified that error appears in the above-identified patent and that said Letters Patent is hereby corrected as shown below:

```
    Xaa Lys Thr Ser Glu Arg Ser Gln Pro Arg Gly Arg Arg Gln Pro Gly
    1           5           10              15
```

(2) INFORMATION FOR SEQ ID NO: 319:
   (i) SEQUENCE CHARACTERISTICS:
      (A) LENGTH: 17 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 319:

```
    Xaa Thr Arg Lys Ser Ser Arg Ser Asn Pro Arg Gly Arg Arg His Pro
    1           5           10              15
    Gly
```

(2) INFORMATION FOR SEQ ID NO: 320:
   (i) SEQUENCE CHARACTERISTICS:
      (A) LENGTH: 17 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 320:

```
    Xaa Thr Arg Lys Ser Ser Arg Ser Asn Pro Arg Gly Arg Arg His Pro
    1           5           10              15
    Gly
```

(2) INFORMATION FOR SEQ ID NO: 321:
   (i) SEQUENCE CHARACTERISTICS:
      (A) LENGTH: 10 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

(xi) SEQUENCE DESCRIPTION: SEQ ID NO: 321:
    Xaa Thr Asn Ala Lys His Ser Ser His Asn
     1      5        10

(2) INFORMATION FOR SEQ ID NO: 322:
  (i) SEQUENCE CHARACTERISTICS:
    (A) LENGTH: 11 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 322:
    Xaa Arg Arg Leu Arg Thr Arg Ser Arg Pro Asn
     1      5        10

(2) INFORMATION FOR SEQ ID NO: 323:
  (i) SEQUENCE CHARACTERISTICS:
    (A) LENGTH: 9 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 323:
    Xaa Arg Arg Leu Arg Thr Arg Ser Arg
     1      5

(2) INFORMATION FOR SEQ ID NO: 324:
  (i) SEQUENCE CHARACTERISTICS:
    (A) LENGTH: 7 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 324:

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

```
    Xaa Arg Arg Leu Arg Thr Arg
     1           5
```

(2) INFORMATION FOR SEQ ID NO: 325:
   (i) SEQUENCE CHARACTERISTICS:
      (A) LENGTH: 11 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 325:

```
    Xaa Arg Arg Leu Arg Thr Arg Ser Arg Pro Asn
     1           5                  10
```

(2) INFORMATION FOR SEQ ID NO: 326:
   (i) SEQUENCE CHARACTERISTICS:
      (A) LENGTH: 27 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 326:

```
    Xaa Ser Asp His Ala Leu Gly Thr Asn Leu Arg Ser Asp Asn Ala Lys
     1           5                  10                  15
    Glu Pro Gly Asp Tyr Asn Cys Cys Gly Asn Gly
              20                  25
```

(2) INFORMATION FOR SEQ ID NO: 327:
   (i) SEQUENCE CHARACTERISTICS:
      (A) LENGTH: 28 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(xi) SEQUENCE DESCRIPTION: SEQ ID NO: 327:
      Xaa Gly Asp Tyr Asn Cys Cys Gly Asn Gly Asn Ser Thr Gly Arg Lys
      1         5          10           15
      Val Phe Asn Arg Arg Arg Pro Ser Ala Ile Pro Thr
            20          25

(2) INFORMATION FOR SEQ ID NO: 328:
   (i) SEQUENCE CHARACTERISTICS:
      (A) LENGTH: 20 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 328:
      Xaa Ser Asp His Ala Leu Gly Thr Asn Leu Arg Ser Asp Asn Ala Lys
      1         5          10           15
      Glu Pro Gly Cys
            20

(2) INFORMATION FOR SEQ ID NO: 329:
   (i) SEQUENCE CHARACTERISTICS:
      (A) LENGTH: 14 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 329:
      Xaa Gly Asp Tyr Asn Cys Cys Gly Asn Gly Asn Ser Thr Gly
      1         5          10

(2) INFORMATION FOR SEQ ID NO: 330:
   (i) SEQUENCE CHARACTERISTICS:
      (A) LENGTH: 15 amino acids
      (B) TYPE: amino acid
      (C) STRANDEDNESS: single
      (D) TOPOLOGY: unknown
   (ii) MOLECULE TYPE: peptide
   (ix) FEATURE:

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 330:
     Xaa Arg Lys Val Phe Asn Arg Arg Arg Pro Ser Ala Ile Pro Thr
      1           5              10             15

(2) INFORMATION FOR SEQ ID NO: 331:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
   (ii) MOLECULE TYPE: peptide
   (ix) FEATURE:
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 331:
     Xaa Arg Lys Val Phe Asn Arg Arg Arg Pro Ser
      1           5              10

(2) INFORMATION FOR SEQ ID NO: 332:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
   (ii) MOLECULE TYPE: peptide
   (ix) FEATURE:
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 332:
     Xaa Asn Arg Arg Arg Pro Ser Ala Ile Pro Thr
      1           5              10

(2) INFORMATION FOR SEQ ID NO: 333:
    (i) SEQUENCE CHARACTERISTICS:
        (A) LENGTH: 7 amino acids
        (B) TYPE: amino acid
        (C) STRANDEDNESS: single
        (D) TOPOLOGY: unknown
   (ii) MOLECULE TYPE: peptide
   (ix) FEATURE:
        (A) NAME/KEY: Other
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) LOCATION: 1...1
        (D) OTHER INFORMATION: Xaa=Lys(dns)
     (xi) SEQUENCE DESCRIPTION: SEQ ID NO: 333:
      Xaa Asn Arg Arg Arg Pro Ser
       1          5

(2) INFORMATION FOR SEQ ID NO: 334:
     (i) SEQUENCE CHARACTERISTICS:
        (A) LENGTH: 40 amino acids
        (B) TYPE: amino acid
        (C) STRANDEDNESS: single
        (D) TOPOLOGY: unknown
     (ii) MOLECULE TYPE: peptide
     (xi) SEQUENCE DESCRIPTION: SEQ ID NO: 334:
      Ser Thr Pro Pro Ser Arg Glu Ala Tyr Ser Arg Pro Tyr Ser Val Asp
       1          5              10             15
      Ser Asp Ser Asp Thr Asn Ala Lys His Ser Ser His Asn Arg Arg Leu
             20             25             30
      Arg Thr Arg Ser Arg Pro Asn Gly
           35            40

(2) INFORMATION FOR SEQ ID NO: 335:
     (i) SEQUENCE CHARACTERISTICS:
        (A) LENGTH: 44 amino acids
        (B) TYPE: amino acid
        (C) STRANDEDNESS: single
        (D) TOPOLOGY: unknown
     (ii) MOLECULE TYPE: peptide
     (xi) SEQUENCE DESCRIPTION: SEQ ID NO: 335:
      Ser Asp His Ala Leu Gly Thr Asn Leu Arg Ser Asp Asn Ala Lys Glu
       1          5              10             15
      Pro Gly Asp Tyr Asn Cys Cys Gly Asn Gly Asn Ser Thr Gly Arg Lys
             20             25             30
      Val Phe Asn Arg Arg Arg Pro Ser Ala Ile Pro Thr
           35            40

(2) INFORMATION FOR SEQ ID NO: 336:
     (i) SEQUENCE CHARACTERISTICS:
        (A) LENGTH: 30 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
        (D) OTHER INFORMATION: Xaa=Lys(dns)
     (xi) SEQUENCE DESCRIPTION: SEQ ID NO: 336:
       Xaa Ser Asp His Ala Leu Gly Thr Asn Leu Arg Ser Asp Asn Ala Lys
       1               5                  10                  15
       Glu Pro Gly Asp Tyr Asn Cys Cys Gly Asn Gly Asn Ser Thr
                   20                  25                  30

(2) INFORMATION FOR SEQ ID NO: 337:
      (i) SEQUENCE CHARACTERISTICS:
         (A) LENGTH: 30 amino acids
         (B) TYPE: amino acid
         (C) STRANDEDNESS: single
         (D) TOPOLOGY: unknown
     (ii) MOLECULE TYPE: peptide
     (ix) FEATURE:
         (A) NAME/KEY: Other
         (B) LOCATION: 1...1
         (D) OTHER INFORMATION: Xaa=Lys(dns)
     (xi) SEQUENCE DESCRIPTION: SEQ ID NO: 337:
       Xaa Asn Leu Arg Ser Asp Asn Ala Lys Glu Pro Gly Asp Tyr Asn Cys
       1               5                  10                  15
       Cys Gly Asn Gly Asn Ser Thr Gly Arg Lys Val Phe Asn Arg
                   20                  25                  30

(2) INFORMATION FOR SEQ ID NO: 338:
      (i) SEQUENCE CHARACTERISTICS:
         (A) LENGTH: 28 amino acids
         (B) TYPE: amino acid
         (C) STRANDEDNESS: single
         (D) TOPOLOGY: unknown
     (ii) MOLECULE TYPE: peptide
     (ix) FEATURE:
         (A) NAME/KEY: Other
         (B) LOCATION: 1...1
         (D) OTHER INFORMATION: Xaa=Lys(dns)
     (xi) SEQUENCE DESCRIPTION: SEQ ID NO: 338:
       Xaa Pro Gly Asp Tyr Asn Cys Cys Gly Asn Gly Asn Ser Thr Gly Arg
       1               5                  10                  15
       Lys Val Phe Asn Arg Arg Pro Ser Ala Ile Pro Thr
                   20                  25

(2) INFORMATION FOR SEQ ID NO: 339:
      (i) SEQUENCE CHARACTERISTICS:
         (A) LENGTH: 11 amino acids
         (B) TYPE: amino acid
         (C) STRANDEDNESS: single
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 339:
     Xaa Ala Ser His Asn Arg Arg Leu Arg Thr Arg
      1           5                  10

(2) INFORMATION FOR SEQ ID NO: 340:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 340:
     Xaa Ser Ala His Asn Arg Arg Leu Arg Thr Arg
      1           5                  10

(2) INFORMATION FOR SEQ ID NO: 341:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 341:
     Xaa Ser Ser Ala Asn Arg Arg Leu Arg Thr Arg
      1           5                  10

(2) INFORMATION FOR SEQ ID NO: 342:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 342:
      Xaa Ser Ser His Ala Arg Arg Leu Arg Thr Arg
       1           5               10

(2) INFORMATION FOR SEQ ID NO: 343:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 343:
      Xaa Ser Ser His Asn Ala Arg Leu Arg Thr Arg
       1           5               10

(2) INFORMATION FOR SEQ ID NO: 344:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 344:
      Xaa Ser Ser His Asn Arg Ala Leu Arg Thr Arg
       1           5               10

(2) INFORMATION FOR SEQ ID NO: 345:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
    (ii) MOLECULE TYPE: peptide
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 345:
     Xaa Ser Ser His Asn Arg Arg Ala Arg Thr Arg
      1           5              10

(2) INFORMATION FOR SEQ ID NO: 346:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 346:
     Xaa Ser Ser His Asn Arg Arg Leu Ala Thr Arg
      1           5              10

(2) INFORMATION FOR SEQ ID NO: 347:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 347:
     Xaa Ser Ser His Asn Arg Arg Leu Arg Ala Arg
      1           5              10

(2) INFORMATION FOR SEQ ID NO: 348:
    (i) SEQUENCE CHARACTERISTICS:
        (A) LENGTH: 11 amino acids
        (B) TYPE: amino acid
        (C) STRANDEDNESS: single
        (D) TOPOLOGY: unknown
    (ii) MOLECULE TYPE: peptide
    (ix) FEATURE:
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 348:
      Xaa Ser Ser His Asn Arg Arg Leu Arg Thr Ala
       1         5              10

(2) INFORMATION FOR SEQ ID NO: 349:
      (i) SEQUENCE CHARACTERISTICS:
        (A) LENGTH: 10 amino acids
        (B) TYPE: amino acid
        (C) STRANDEDNESS: single
        (D) TOPOLOGY: unknown
     (ii) MOLECULE TYPE: peptide
     (xi) SEQUENCE DESCRIPTION: SEQ ID NO: 349:
       Ser Ser His Asn Arg Arg Leu Arg Thr Arg
        1         5              10

(2) INFORMATION FOR SEQ ID NO: 350:
      (i) SEQUENCE CHARACTERISTICS:
        (A) LENGTH: 41 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 350:
       Xaa Gly Arg Asn His Asp Val Val Ser Ser Asn Thr His Lys Ser Tyr
        1         5              10              15
       Arg Ser Pro Arg Ser Ala Ser Tyr Pro Arg Leu Ser Asn Asp Arg Thr
            20              25              30
       Asp Arg Thr Glu Pro Ala Pro Ser Ser
            35              40

(2) INFORMATION FOR SEQ ID NO: 351:
      (i) SEQUENCE CHARACTERISTICS:
        (A) LENGTH: 20 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) LOCATION: 1...1
        (D) OTHER INFORMATION: Xaa=Lys(dns)
    (xi) SEQUENCE DESCRIPTION: SEQ ID NO: 351:
     Xaa Arg Asn Thr Arg Asn Lys Thr Ser Arg Leu Ser Ala Asn Pro His
      1           5              10              15
     Arg Ser His Arg
              20

(2) INFORMATION FOR SEQ ID NO: 352:
    (i) SEQUENCE CHARACTERISTICS:
        (A) LENGTH: 20 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 20...20
        (D) OTHER INFORMATION: Xaa=Lys(dns)
    (xi) SEQUENCE DESCRIPTION: SEQ ID NO: 352:
     Thr Asn Ala Lys His Ser Ser His Asn Arg Arg Leu Arg Thr Arg Ser
      1           5              10              15
     Arg Pro Asn Xaa
              20

(2) INFORMATION FOR SEQ ID NO: 353:
    (i) SEQUENCE CHARACTERISTICS:
        (A) LENGTH: 10 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 10...10
        (D) OTHER INFORMATION: Xaa=Lys(dns)
    (xi) SEQUENCE DESCRIPTION: SEQ ID NO: 353:
     Arg Arg Leu Arg Thr Arg Ser Arg Lys Xaa
      1           5              10

(2) INFORMATION FOR SEQ ID NO: 354:
    (i) SEQUENCE CHARACTERISTICS:
        (A) LENGTH: 21 amino acids
        (B) TYPE: amino acid
        (C) STRANDEDNESS: single
        (D) TOPOLOGY: unknown
```

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

(ii) MOLECULE TYPE: peptide
    (ix) FEATURE:
       (A) NAME/KEY: Other
       (B) LOCATION: 1...1
       (D) OTHER INFORMATION: Xaa=Lys(dns)
    (xi) SEQUENCE DESCRIPTION: SEQ ID NO: 354:
     Xaa Ser Asp His Ala Leu Gly Thr Asn Leu Arg Ser Asp Asn Ala Lys
      1        5          10         15
     Glu Pro Gly Asp Tyr
        20

(2) INFORMATION FOR SEQ ID NO: 355:
    (i) SEQUENCE CHARACTERISTICS:
       (A) LENGTH: 21 amino acids
       (B) TYPE: amino acid
       (C) STRANDEDNESS: single
       (D) TOPOLOGY: unknown
    (ii) MOLECULE TYPE: peptide
    (ix) FEATURE:
       (A) NAME/KEY: Other
       (B) LOCATION: 1...1
       (D) OTHER INFORMATION: Xaa=Lys(dns)
    (xi) SEQUENCE DESCRIPTION: SEQ ID NO: 355:
     Xaa Ser Asp Asn Ala Lys Glu Pro Gly Asp Tyr Asn Cys Cys Gly Asn
      1        5          10         15
     Gly Asn Ser Thr Gly
        20

(2) INFORMATION FOR SEQ ID NO: 356:
    (i) SEQUENCE CHARACTERISTICS:
       (A) LENGTH: 16 amino acids
       (B) TYPE: amino acid
       (C) STRANDEDNESS: single
       (D) TOPOLOGY: unknown
    (ii) MOLECULE TYPE: peptide
    (ix) FEATURE:
       (A) NAME/KEY: Other
       (B) LOCATION: 1...1
       (D) OTHER INFORMATION: Xaa=Lys(dns)
    (xi) SEQUENCE DESCRIPTION: SEQ ID NO: 356:
     Xaa Ser Asp His Ala Leu Gly Thr Asn Leu Arg Ser Asp Asn Ala Lys
      1        5          10         15

(2) INFORMATION FOR SEQ ID NO: 357:
    (i) SEQUENCE CHARACTERISTICS:
       (A) LENGTH: 16 amino acids

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 357:
      Xaa Glu Pro Gly Asp Tyr Asn Cys Cys Gly Asn Gly Asn Ser Thr Gly
       1        5            10            15

(2) INFORMATION FOR SEQ ID NO: 358:
     (i) SEQUENCE CHARACTERISTICS:
        (A) LENGTH: 15 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 358:
      Xaa Pro Gly Asp Tyr Asn Cys Cys Gly Asn Gly Asn Ser Thr Gly
       1        5            10            15

(2) INFORMATION FOR SEQ ID NO: 359:
     (i) SEQUENCE CHARACTERISTICS:
        (A) LENGTH: 11 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 359:
      Xaa Pro Gly Asp Tyr Asn Cys Cys Gly Asn Gly
       1        5            10

(2) INFORMATION FOR SEQ ID NO: 360:
     (i) SEQUENCE CHARACTERISTICS:
        (A) LENGTH: 11 amino acids
        (B) TYPE: amino acid
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (C) STRANDEDNESS: single
        (D) TOPOLOGY: unknown
   (ii) MOLECULE TYPE: peptide
   (vi) ORIGINAL SOURCE:
        (A) ORGANISM: MEMORY
        (B) STRAIN: DISPLAY MEMORY
   (ix) FEATURE:
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 360:
    Xaa Asn Cys Cys Gly Asn Gly Asn Ser Thr Gly
     1           5              10

(2) INFORMATION FOR SEQ ID NO: 361:
    (i) SEQUENCE CHARACTERISTICS:
        (A) LENGTH: 18 amino acids
        (B) TYPE: amino acid
        (C) STRANDEDNESS: single
        (D) TOPOLOGY: unknown
   (ii) MOLECULE TYPE: peptide
   (ix) FEATURE:
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 361:
    Xaa Lys Thr Arg Lys Ser Ser Arg Ser Asn Pro Arg Gly Arg Arg His
     1           5              10             15
    Pro Gly (2) INFORMATION FOR SEQ ID NO: 362:
    (i) SEQUENCE CHARACTERISTICS:
        (A) LENGTH: 18 amino acids
        (B) TYPE: amino acid
        (C) STRANDEDNESS: single
        (D) TOPOLOGY: unknown
   (ii) MOLECULE TYPE: peptide
   (ix) FEATURE:
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 362:
    Xaa Lys Thr Arg Lys Ser Ser Arg Ser Asn Pro Arg Gly Arg Arg His
     1           5              10             15
    Pro Gly
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
(2) INFORMATION FOR SEQ ID NO: 363:
    (i) SEQUENCE CHARACTERISTICS:
        (A) LENGTH: 17 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 363:
      Xaa Lys Thr Asn Ala Lys His Ser Ser His Asn Arg Arg Leu Arg Thr
       1           5              10              15
      Arg (2) INFORMATION FOR SEQ ID NO: 364:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 364:
      Xaa Thr Asn Ala Lys His Ser Ser Cys Asn Arg Arg Cys Arg Thr Arg
       1           5              10              15

(2) INFORMATION FOR SEQ ID NO: 365:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 365:
      Xaa Thr Asn Ala Lys His Ser Ser Cys Asn Arg Arg Leu Arg Cys Arg
       1           5              10              15
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(2) INFORMATION FOR SEQ ID NO: 366:
  (i) SEQUENCE CHARACTERISTICS:
    (A) LENGTH: 16 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 366:
    Xaa Ala Asn Ala Lys His Ser Ser His Asn Arg Arg Leu Arg Thr Arg
     1      5      10      15

(2) INFORMATION FOR SEQ ID NO: 367:
  (i) SEQUENCE CHARACTERISTICS:
    (A) LENGTH: 16 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 367:
    Xaa Thr Ala Ala Lys Asn Ser Ser His Asn Arg Arg Leu Arg Thr Arg
     1      5      10      15

(2) INFORMATION FOR SEQ ID NO: 368:
  (i) SEQUENCE CHARACTERISTICS:
    (A) LENGTH: 16 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 368:
    Xaa Thr Asn Gly Lys Asn Ser Ser His Asn Arg Arg Leu Arg Thr Arg
     1      5      10      15

(2) INFORMATION FOR SEQ ID NO: 369:

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(i) SEQUENCE CHARACTERISTICS:
      (A) LENGTH: 16 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 369:
    Xaa Thr Asn Ala Lys Ala Ser Ser His Asn Arg Arg Leu Arg Thr Arg
     1       5          10          15

(2) INFORMATION FOR SEQ ID NO: 370:
   (i) SEQUENCE CHARACTERISTICS:
      (A) LENGTH: 16 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 370:
    Xaa Thr Asn Ala Lys His Ala Ser His Asn Arg Arg Leu Arg Thr Arg
     1       5          10          15

(2) INFORMATION FOR SEQ ID NO: 371:
   (i) SEQUENCE CHARACTERISTICS:
      (A) LENGTH: 16 amino acids
      (B) TYPE: amino acid
      (C) STRANDEDNESS: single
      (D) TOPOLOGY: unknown
   (ii) MOLECULE TYPE: peptide
   (ix) FEATURE:
      (A) NAME/KEY: Other
      (B) LOCATION: 1...1
      (D) OTHER INFORMATION: Xaa=Lys(dns)
   (xi) SEQUENCE DESCRIPTION: SEQ ID NO: 371:
    Xaa Thr Asn Ala Lys His Ser Ala His Asn Arg Arg Leu Arg Thr Arg
     1       5          10          15

(2) INFORMATION FOR SEQ ID NO: 372:
   (i) SEQUENCE CHARACTERISTICS:

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

(A) LENGTH: 16 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 372:
  Xaa Thr Asn Ala Lys His Ser Ser Ala Asn Arg Arg Leu Arg Thr Arg
   1      5         10         15

(2) INFORMATION FOR SEQ ID NO: 373:
  (i) SEQUENCE CHARACTERISTICS:
    (A) LENGTH: 16 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 373:
  Xaa Thr Asn Ala Lys His Ser Ser His Ala Arg Arg Leu Arg Thr Arg
   1      5         10         15

(2) INFORMATION FOR SEQ ID NO: 374:
  (i) SEQUENCE CHARACTERISTICS:
    (A) LENGTH: 16 amino acids
    (B) TYPE: amino acid
    (C) STRANDEDNESS: single
    (D) TOPOLOGY: unknown
  (ii) MOLECULE TYPE: peptide
  (ix) FEATURE:
    (A) NAME/KEY: Other
    (B) LOCATION: 1...1
    (D) OTHER INFORMATION: Xaa=Lys(dns)
  (xi) SEQUENCE DESCRIPTION: SEQ ID NO: 374:
  Xaa Thr Asn Ala Lys His Ser Ser His Asn Ala Arg Leu Arg Thr Arg
   1      5         10         15

(2) INFORMATION FOR SEQ ID NO: 375:
  (i) SEQUENCE CHARACTERISTICS:
    (A) LENGTH: 16 amino acids

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 375:
     Xaa Thr Asn Ala Lys His Ser Ser His Asn Arg Ala Leu Arg Thr Arg
      1           5              10             15

(2) INFORMATION FOR SEQ ID NO: 376:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 376:
     Xaa Thr Asn Ala Lys His Ser Ser His Asn Arg Arg Ala Arg Thr Arg
      1           5              10             15

(2) INFORMATION FOR SEQ ID NO: 377:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 377:
     Xaa Thr Asn Ala Lys His Ser Ser His Asn Arg Arg Leu Ala Thr Arg
      1           5              10             15

(2) INFORMATION FOR SEQ ID NO: 378:
    (i) SEQUENCE CHARACTERISTICS:
        (A) LENGTH: 16 amino acids
        (B) TYPE: amino acid
```

UNITED STATES PATENT AND TRADEMARK OFFICE
CERTIFICATE OF CORRECTION

PATENT NO.      : 7,053,177 B1
APPLICATION NO. : 09/079678
DATED           : May 30, 2006
INVENTOR(S)     : Vernon L. Alvarez et al.

It is certified that error appears in the above-identified patent and that said Letters Patent is hereby corrected as shown below:

```
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 378:
     Xaa Thr Asn Ala Lys His Ser Ser His Asn Arg Arg Leu Arg Ala Arg
      1           5          10              15

(2) INFORMATION FOR SEQ ID NO: 379:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 379:
     Xaa Thr Asn Ala Lys His Ser Ser His Asn Arg Arg Leu Arg Thr Ala
      1           5          10              15

(2) INFORMATION FOR SEQ ID NO: 380:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 380:
     Xaa Thr Asn Ala Lys His Ser Ser His Asn Arg Arg Leu Arg Thr Arg
      1           5          10              15

(2) INFORMATION FOR SEQ ID NO: 381:
    (i) SEQUENCE CHARACTERISTICS:
        (A) LENGTH: 17 amino acids
        (B) TYPE: amino acid
        (C) STRANDEDNESS: single
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 381:
     Xaa Lys Thr Asn Ala Lys His Ser Ser His Asn Arg Arg Leu Arg Thr
      1           5              10              15
     Arg (2) INFORMATION FOR SEQ ID NO: 382:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 382:
     Xaa Thr Asn Ala Lys His Ser Ser His Asn Arg Arg Leu Arg Thr Arg
      1           5              10              15

(2) INFORMATION FOR SEQ ID NO: 383:
    (i) SEQUENCE CHARACTERISTICS:
        (A) LENGTH: 12 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 383:
     Xaa Lys Ser Ser His Asn Arg Arg Leu Arg Thr Arg
      1           5              10

(2) INFORMATION FOR SEQ ID NO: 384:
    (i) SEQUENCE CHARACTERISTICS:
        (A) LENGTH: 12 amino acids
        (B) TYPE: amino acid
        (C) STRANDEDNESS: single
```

UNITED STATES PATENT AND TRADEMARK OFFICE
CERTIFICATE OF CORRECTION

| | | |
|---|---|---|
| PATENT NO. | : 7,053,177 B1 | |
| APPLICATION NO. | : 09/079678 | |
| DATED | : May 30, 2006 | |
| INVENTOR(S) | : Vernon L. Alvarez et al. | |

It is certified that error appears in the above-identified patent and that said Letters Patent is hereby corrected as shown below:

```
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 384:
     Xaa Lys Ser Ser His Asn Arg Arg Leu Arg Thr Arg
      1           5             10

(2) INFORMATION FOR SEQ ID NO: 385:
    (i) SEQUENCE CHARACTERISTICS:
        (A) LENGTH: 12 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 385:
     Xaa Lys Thr Asn Ala Lys His Ser Ser His Asn Arg
      1           5             10

(2) INFORMATION FOR SEQ ID NO: 386:
    (i) SEQUENCE CHARACTERISTICS:
        (A) LENGTH: 12 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 386:
     Xaa Lys Thr Asn Ala Lys His Ser Ser His Asn Arg
      1           5             10

(2) INFORMATION FOR SEQ ID NO: 387:
    (i) SEQUENCE CHARACTERISTICS:
        (A) LENGTH: 16 amino acids
        (B) TYPE: amino acid
        (C) STRANDEDNESS: single
        (D) TOPOLOGY: unknown
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

(ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 387:
     Xaa Thr Asn Ala Lys His Ser Ser His Asn Arg Arg Leu Arg Thr Arg
      1        5         10        15

(2) INFORMATION FOR SEQ ID NO: 388:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 388:
     Xaa Ala Gly Asp Tyr Asn Cys Cys Gly Asn Gly Asn Ser Thr Gly
      1        5         10        15

(2) INFORMATION FOR SEQ ID NO: 389:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 389:
     Xaa Pro Ala Asp Tyr Asn Cys Cys Gly Asn Gly Asn Ser Thr Gly
      1        5         10        15

(2) INFORMATION FOR SEQ ID NO: 390:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
    (ii) MOLECULE TYPE: peptide

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 390:
     Xaa Pro Gly Ala Tyr Asn Cys Cys Gly Asn Gly Asn Ser Thr Gly
      1           5          10             15

(2) INFORMATION FOR SEQ ID NO: 391:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
   (ii) MOLECULE TYPE: peptide
   (ix) FEATURE:
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 391:
     Xaa Pro Gly Asp Ala Asn Cys Cys Gly Asn Gly Asn Ser Thr Gly
      1           5          10             15

(2) INFORMATION FOR SEQ ID NO: 392:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
   (ii) MOLECULE TYPE: peptide
   (ix) FEATURE:
        (A) NAME/KEY: Other
        (B) LOCATION: 1...1
        (D) OTHER INFORMATION: Xaa=Lys(dns)
   (xi) SEQUENCE DESCRIPTION: SEQ ID NO: 392:
     Xaa Pro Gly Asp Tyr Ala Cys Cys Gly Asn Gly Asn Ser Thr Gly
      1           5          10             15

(2) INFORMATION FOR SEQ ID NO: 393:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
   (ii) MOLECULE TYPE: peptide
   (ix) FEATURE:
```

UNITED STATES PATENT AND TRADEMARK OFFICE
CERTIFICATE OF CORRECTION

PATENT NO.       : 7,053,177 B1
APPLICATION NO.  : 09/079678
DATED            : May 30, 2006
INVENTOR(S)      : Vernon L. Alvarez et al.

It is certified that error appears in the above-identified patent and that said Letters Patent is hereby corrected as shown below:

```
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 393:
      Xaa Pro Gly Asp Tyr Asn Ala Cys Gly Asn Gly Asn Ser Thr Gly
       1           5            10           15

(2) INFORMATION FOR SEQ ID NO: 394:
     (i) SEQUENCE CHARACTERISTICS:
        (A) LENGTH: 15 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 394:
      Xaa Pro Gly Asp Tyr Asn Cys Ala Gly Asn Gly Asn Ser Thr Gly
       1           5            10           15

(2) INFORMATION FOR SEQ ID NO: 395:
     (i) SEQUENCE CHARACTERISTICS:
        (A) LENGTH: 15 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
     (xi) SEQUENCE DESCRIPTION: SEQ ID NO: 395:
      Xaa Pro Gly Asp Tyr Asn Cys Cys Ala Asn Gly Asn Ser Thr Gly
       1           5            10           15

(2) INFORMATION FOR SEQ ID NO: 396:
     (i) SEQUENCE CHARACTERISTICS:
        (A) LENGTH: 15 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
```

UNITED STATES PATENT AND TRADEMARK OFFICE
CERTIFICATE OF CORRECTION

PATENT NO. : 7,053,177 B1
APPLICATION NO. : 09/079678
DATED : May 30, 2006
INVENTOR(S) : Vernon L. Alvarez et al.

It is certified that error appears in the above-identified patent and that said Letters Patent is hereby corrected as shown below:

```
        (B) LOCATION: 1...1
        (D) OTHER INFORMATION: Xaa=Lys(dns)
    (xi) SEQUENCE DESCRIPTION: SEQ ID NO: 396:
     Xaa Pro Gly Asp Tyr Asn Cys Cys Gly Ala Gly Asn Ser Thr Gly
      1         5            10          15

(2) INFORMATION FOR SEQ ID NO: 397:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 397:
     Xaa Pro Gly Asp Tyr Asn Cys Cys Gly Asn Ala Asn Ser Thr Gly
      1         5            10          15

(2) INFORMATION FOR SEQ ID NO: 398:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 398:
     Xaa Pro Gly Asp Tyr Asn Cys Cys Gly Asn Gly Ala Ser Thr Gly
      1         5            10          15

(2) INFORMATION FOR SEQ ID NO: 399:
    (i) SEQUENCE CHARACTERISTICS:
        (A) LENGTH: 15 amino acids
        (B) TYPE: amino acid
        (C) STRANDEDNESS: single
        (D) TOPOLOGY: unknown
    (ii) MOLECULE TYPE: peptide
    (ix) FEATURE:
        (A) NAME/KEY: Other
        (B) LOCATION: 1...1
```

UNITED STATES PATENT AND TRADEMARK OFFICE
CERTIFICATE OF CORRECTION

| | |
|---|---|
| PATENT NO. | : 7,053,177 B1 |
| APPLICATION NO. | : 09/079678 |
| DATED | : May 30, 2006 |
| INVENTOR(S) | : Vernon L. Alvarez et al. |

It is certified that error appears in the above-identified patent and that said Letters Patent is hereby corrected as shown below:

```
        (D) OTHER INFORMATION: Xaa=Lys(dns)
    (xi) SEQUENCE DESCRIPTION: SEQ ID NO: 399:
     Xaa Pro Gly Asp Tyr Asn Cys Cys Gly Asn Gly Asn Ala Thr Gly
      1           5           10          15

(2) INFORMATION FOR SEQ ID NO: 400:
     (i) SEQUENCE CHARACTERISTICS:
        (A) LENGTH: 15 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 400:
     Xaa Pro Gly Asp Tyr Asn Cys Cys Gly Asn Gly Asn Ser Ala Gly
      1           5           10          15

(2) INFORMATION FOR SEQ ID NO: 401:
     (i) SEQUENCE CHARACTERISTICS:
        (A) LENGTH: 15 amino acids
        (B) TYPE: amino acid
        (C) STRANDEDNESS: single
        (D) TOPOLOGY: unknown
     (ii) MOLECULE TYPE: peptide
     (ix) FEATURE:
        (A) NAME/KEY: Other
        (B) LOCATION: 1...1
        (D) OTHER INFORMATION: Xaa=Lys(dns)
    (xi) SEQUENCE DESCRIPTION: SEQ ID NO: 401:
     Xaa Pro Gly Asp Tyr Asn Cys Cys Gly Asn Gly Asn Ser Thr Ala
      1           5           10          15

(2) INFORMATION FOR SEQ ID NO: 402:
     (i) SEQUENCE CHARACTERISTICS:
        (A) LENGTH: 15 amino acids
        (B) TYPE: amino acid
        (C) STRANDEDNESS: single
        (D) TOPOLOGY: unknown
     (ii) MOLECULE TYPE: peptide
    (xi) SEQUENCE DESCRIPTION: SEQ ID NO: 402:
     Thr Asn Ala Lys His Ser Ser His Asn Arg Arg Leu Arg Thr Arg
      1           5           10          15
```

UNITED STATES PATENT AND TRADEMARK OFFICE
CERTIFICATE OF CORRECTION

PATENT NO.         : 7,053,177 B1
APPLICATION NO.    : 09/079678
DATED              : May 30, 2006
INVENTOR(S)        : Vernon L. Alvarez et al.

It is certified that error appears in the above-identified patent and that said Letters Patent is hereby corrected as shown below:

(2) INFORMATION FOR SEQ ID NO: 403:
  (i) SEQUENCE CHARACTERISTICS:
    (A) LENGTH: 14 amino acids
    (B) TYPE: amino acid
    (C) STRANDEDNESS: single
    (D) TOPOLOGY: unknown
  (ii) MOLECULE TYPE: peptide
  (xi) SEQUENCE DESCRIPTION: SEQ ID NO: 403:
   Pro Gly Asp Tyr Asn Cys Cys Gly Asn Cys Asn Ser Thr Gly
    1       5          10

(2) INFORMATION FOR SEQ ID NO: 404:
  (i) SEQUENCE CHARACTERISTICS:
    (A) LENGTH: 40 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 404:
   Ser Ala Arg Asp Ser Gly Pro Ala Glu Asp Gly Ser Arg Ala Val Arg
    1      5        10         15
   Leu Asn Gly Val Glu Asn Ala Asn Thr Arg Lys Ser Ser Arg Ser Asn
     20       25       30
   Pro Arg Gly Arg Arg His Pro Gly
     35       40

(2) INFORMATION FOR SEQ ID NO: 405:
  (i) SEQUENCE CHARACTERISTICS:
    (A) LENGTH: 19 amino acids
    (B) TYPE: amino acid
    (C) STRANDEDNESS: <Unknown>
    (D) TOPOLOGY: unknown
  (ii) MOLECULE TYPE: peptide
  (xi) SEQUENCE DESCRIPTION: SEQ ID NO: 405:
   Gly Thr Arg Asn Ser His Gly Cys Ile Thr Arg Pro Leu Arg Gln Ala
    1      5        10         15
   Ser Ala His (2) INFORMATION FOR SEQ ID NO: 406:
  (i) SEQUENCE CHARACTERISTICS:
    (A) LENGTH: 21 amino acids
    (B) TYPE: amino acid
    (C) STRANDEDNESS: <Unknown>
    (D) TOPOLOGY: unknown
  (ii) MOLECULE TYPE: peptide
  (ix) FEATURE:

UNITED STATES PATENT AND TRADEMARK OFFICE
CERTIFICATE OF CORRECTION

PATENT NO. : 7,053,177 B1 Page 159 of 159
APPLICATION NO. : 09/079678
DATED : May 30, 2006

It is certified that error appears in the above-identified patent and that said Letters Patent is hereby corrected as shown below:

(A) NAME/KEY: Other
    (B) LOCATION: 1...1
    (D) OTHER INFORMATION: Xaa=Lys(dns)
 (xi) SEQUENCE DESCRIPTION: SEQ ID NO: 406:
  Xaa Arg Val Gly Gln Cys Thr Asp Ser Asp Val Arg Arg Pro Trp Ala
  1     5          10         15
  Arg Ser Cys Ala His
      20

(2) INFORMATION FOR SEQ ID NO: 407:
  (i) SEQUENCE CHARACTERISTICS:
    (A) LENGTH: 23 amino acids
    (B) TYPE: amino acid
    (C) STRANDEDNESS: single
    (D) TOPOLOGY: unknown
 (ii) MOLECULE TYPE: peptide
 (ix) FEATURE:
    (A) NAME/KEY: Other
    (B) LOCATION: 1...1
    (D) OTHER INFORMATION: Xaa=Lys(dns)
 (xi) SEQUENCE DESCRIPTION: SEQ ID NO: 407:
  Xaa Cys Gly Ala Gly Thr Arg Asn Ser His Gly Cys Ile Thr Arg Pro
  1     5          10         15
  Leu Arg Gln Ala Ser Ala His
      20

Signed and Sealed this

Eighth Day of April, 2008

JON W. DUDAS
*Director of the United States Patent and Trademark Office*